US012016910B2

(12) United States Patent
Chene et al.

(10) Patent No.: US 12,016,910 B2
(45) Date of Patent: Jun. 25, 2024

(54) ANTIGENIC PEPTIDES FOR PREVENTION AND TREATMENT OF CANCER

(71) Applicant: ENTEROME S.A., Paris (FR)

(72) Inventors: Laurent Chene, Neuville aux Bois (FR); Christophe Bonny, Paris (FR); Francesco Strozzi, Paris (FR)

(73) Assignee: ENTEROME S.A., Paris (FR)

( * ) Notice: Subject to any disclaimer, the term of this patent is extended or adjusted under 35 U.S.C. 154(b) by 722 days.

(21) Appl. No.: 17/043,192

(22) PCT Filed: Apr. 11, 2019

(86) PCT No.: PCT/EP2019/059329
§ 371 (c)(1),
(2) Date: Sep. 29, 2020

(87) PCT Pub. No.: WO2019/197567
PCT Pub. Date: Oct. 17, 2019

(65) Prior Publication Data
US 2021/0113678 A1 Apr. 22, 2021

(30) Foreign Application Priority Data
Apr. 11, 2018 (EP) .................................... 18305444
Oct. 9, 2018 (WO) ................. PCT/EP2018/077512

(51) Int. Cl.
A61K 39/00 (2006.01)
A61P 35/00 (2006.01)

(52) U.S. Cl.
CPC . *A61K 39/001119* (2018.08); *A61K 39/00115* (2018.08); *A61K 39/001152* (2018.08); *A61K 39/001154* (2018.08); *A61P 35/00* (2018.01); *A61K 2039/55566* (2013.01)

(58) Field of Classification Search
CPC ...... A61K 2039/55566; A61K 39/0011; A61P 35/00
See application file for complete search history.

(56) References Cited

U.S. PATENT DOCUMENTS

| 2007/0087411 A1 | 4/2007 | Sharma et al. |
| 2008/0166374 A1 | 7/2008 | Debinski et al. |
| 2011/0110955 A1 | 5/2011 | Debinski et al. |
| 2012/0052080 A1 | 3/2012 | Okada |
| 2014/0141044 A1 | 5/2014 | Bhatt et al. |
| 2018/0078627 A1 | 3/2018 | Zeng et al. |
| 2018/0133339 A1 | 5/2018 | Derouazi et al. |
| 2019/0388532 A1 | 12/2019 | Chene et al. |
| 2020/0025774 A1 | 1/2020 | Chene et al. |
| 2020/0113983 A1 | 4/2020 | Chene et al. |
| 2020/0256877 A1 | 8/2020 | Chene et al. |
| 2021/0106652 A1 | 4/2021 | Chene et al. |
| 2022/0323561 A1 | 10/2022 | Chene et al. |

FOREIGN PATENT DOCUMENTS

| CN | 1954217 A | 4/2007 |
| CN | 104774261 A | 7/2015 |
| EP | 2189471 A1 | 5/2010 |
| JP | 2003524016 A | 8/2003 |
| WO | WO-1995021862 | 8/1995 |
| WO | WO-1995021862 A1 | 8/1995 |
| WO | WO-2001000225 | 1/2001 |
| WO | WO-2001000225 A1 | 1/2001 |
| WO | WO-2001/058479 A1 | 8/2001 |
| WO | WO-2001062776 | 8/2001 |
| WO | WO-2001062776 A1 | 8/2001 |
| WO | WO-2003/092717 A1 | 11/2003 |
| WO | WO-2004031211 | 4/2004 |
| WO | WO-2004031211 A2 | 4/2004 |
| WO | WO-2004067023 A2 | 8/2004 |
| WO | WO-2006034334 A2 | 3/2006 |
| WO | WO-2008073463 A2 | 6/2008 |
| WO | WO-2010/018136 A1 | 2/2010 |
| WO | 2010/129033 A3 | 3/2011 |
| WO | WO-2011140284 A2 | 11/2011 |
| WO | WO-2012027379 A2 | 3/2012 |
| WO | WO-2013135553 A1 | 9/2013 |
| WO | WO-2013142477 A1 | 9/2013 |
| WO | WO-2013148147 A1 | 10/2013 |
| WO | WO-2013173411 A1 | 11/2013 |
| WO | WO-2014088432 A1 | 6/2014 |
| WO | WO-2014089375 A1 | 6/2014 |
| WO | WO-2017203526 A1 | 11/2017 |
| WO | WO-2019072871 A2 | 4/2019 |

(Continued)

OTHER PUBLICATIONS

Fichtner-Feigl et al., "IL-13 signaling through the IL-13alpha2 receptor is involved in induction of TGF-beta1 production and fibrosis," Nature Medicine, 12(1): 99-106 (2006).
Hirsova et al., "Emerging Roles of T Cells in the Pathogenesis of Nonalcoholic Steatohepatitis and Hepatocellular Carcinoma," Front. Endocrinol. 12(760860): 1-14 (2021).
Office action issued in U.S. Appl. No. 17/043,197 dated Jun. 1, 2023.
U.S. Appl. No. 17/823,117, filed Aug. 30, 2022.
U.S. Appl. No. 17/929,063, filed Sep. 1, 2022.
U.S. Appl. No. 16/338,953, filed Apr. 2, 2019.
U.S. Appl. No. 16/338,954, filed Apr. 2, 2019.

(Continued)

*Primary Examiner* — Bao Q Li
(74) *Attorney, Agent, or Firm* — Harness Dickey & Pierce P.L.C.

(57) ABSTRACT

The present invention relates to antigen-based immunotherapy, in particular cancer immunotherapy. In particular, the present invention provides antigenic peptides, which are distinct from, but have amino acid similarity to, fragments of human tumor antigens. The present invention further provides immunogenic compounds, nanoparticles, cells and pharmaceutical compositions comprising such antigenic peptides and nucleic acids encoding such antigenic peptides.

30 Claims, 11 Drawing Sheets
Specification includes a Sequence Listing.

(56) References Cited

FOREIGN PATENT DOCUMENTS

| WO | WO-2021074389 A1 | 4/2021 |
|---|---|---|
| WO | WO-2021094562 A2 | 5/2021 |

OTHER PUBLICATIONS

U.S. Appl. No. 16/338,955, filed Apr. 2, 2019.
U.S. Appl. No. 16/753,657, filed Apr. 3, 2020.
U.S. Appl. No. 17/043,197, filed Sep. 29, 2020.
U.S. Appl. No. 17/768,757, filed Apr. 13, 2022.
Office Action from corresponding U.S. Appl. No. 16/338,953 dated Nov. 23, 2021.
Office Action from corresponding U.S. Appl. No. 16/338,955 dated Oct. 8, 2021.
Office Action from corresponding U.S. Appl. No. 16/338,955 dated May 20, 2022.
Baylot, V., et al., "Chapter 13: TCTP Has a Crucial Role in the Different Stages of Prostate Cancer Malignant Progression," Springer International Publishing AG, 2017, p. 255-261.
Badri, H., et al., "Optimization of radiation dosing schedules for proneural glioblastoma," J. Math. Biol., 72: 1301-1336 (2016).
Office Action from corresponding Russian Application No. 2020135927 dated Jun. 16, 2023.
Parkhurst et al., "Improved Induction of Melanoma-Reactive CTL with Peptides from the Melanoma Antigen gp100 Modified at HLA-A*0201-Binding Residues," The American Association of Immunologists, 1996, 157(6): 2539-2548.
Rodeberg, David et al., "Recognition of Six-Transmembrane Epithelial Antigen of the Prostate-Expressing Tumor Cells by Peptide Antigen-Induced Cytotoxic T Lymphocytes," Clinical Cancer Research, 2005, 11(12): 4545-4552.
Tourdot, Sophie et al., "A general strategy to enhance immunogenicity of low-affinity HLA-A2.1-associated peptides: implication in the identification of cryptic tumor epitopes," European Journal of Immunology, 2000, 30(1): 3411-3421.
Vertuani, Simona et al., "Improved Immunogenicity of an Immunodominant Epitope of the Her-2/neu Protooncogene by Alterations of MHC Contact Residues," Journal of Immunology, 2004, 172(6): 3501-3508.
Nakashima, Hideyuki et al., "IL-13 receptor-directed cancer vaccines and immunotherapy," Immunotherapy, 2012, 4(4): 443-451.
Nakashima, Hideyuki et al., "A Novel Combination Immunotherapy for Cancer by IL-13R α2-Targeted DNA Vaccine and Immunotoxin in Murine Tumor Models," The Journal of Immunology, 2011, 187(10): 4935-4946.
International Search Report and Written Opinion issued in PCT/EP2017/075673, dated Apr. 30, 2018, 17 pgs.
International Search Report and Written Opinion issued in PCT/EP2017/075676, dated Jun. 15, 2018, 18 pgs.
Office Action from corresponding U.S. Appl. No. 16/338,955 dated May 14, 2021.
Office Action issued in corresponding CN Appln. No. 201780074779.3 dated Oct. 14, 2022.
Search Report issued in corresponding CN Appln. No. 201780074779.3 dated Oct. 8, 2022.
Office action issued in corresponding U.S. Appl. No. 16/338,954 dated Mar. 3, 2022.
Restriction requirement issued in corresponding U.S. Appl. No. 16/338,954 dated Jun. 24, 2022.
Notice of Allowance issued in corresponding U.S. Appl. No. 16/338,954 dated Dec. 1, 2022.
Restriction Requirement issued in corresponding U.S. Appl. No. 16/338,953 dated Apr. 5, 2021.
Notice of Allowance issued in corresponding U.S. Appl. No. 16/338,953 dated Mar. 2, 2022.
Notice of Allowance issued in corresponding U.S. Appl. No. 16/338,953 dated Apr. 5, 2022.
Notice of Allowance issued in corresponding U.S. Appl. No. 16/338,953 dated Jun. 15, 2022.
Restriction Requirement issued in corresponding U.S. Appl. No. 16/338,955 dated Mar. 9, 2021.
Notice of Allowance issued in corresponding U.S. Appl. No. 16/338,955 dated Aug. 8, 2022.
Notice of Allowance issued in corresponding U.S. Appl. No. 16/338,955 dated Aug. 31, 2022.
Office Action issued in corresponding RU Appln. No. 2020135927 dated Nov. 3, 2022.
Baryšnikov A. Û, "The Interation of Tumor and Immune System of the Organism," Praktičeskaâ Onkologiâ [Practical Oncology] 4(3), p. 127-130 (2003).
Dhanik, et al. "In-silico discovery of cancer-specific peptide-HLA complexes for targeted therapy," BCM Bioinformatics 17:286 (2016), 14 pages.
Xiao et al., "Peptide-Based Treatment: A Promising Cancer Therapy," Journal of Immunology Research, Vo. 2015, Article ID 761820, 13 pages.
International Search Report from PCT Application No. PCT/EP2018/077515 dated May 6, 2019.
Written Opinion from PCT Application No. PCT/EP2018/077515 dated May 6, 2019.
Eguchi, J., et al., "Identification of Interleukin-13 Receptor α2 Peptide Analogues Capable of Inducing Improved Antiglioma CTL Responses," Cancer Res. 66(11): 5883-5891 (2006).
Fikes, John, "The Rational Design of T-Cell Epitopes With Enhanced Immunogenicity," Handbook of Cancer Vaccines, Humana Press, pp. 11-17 (2004).
Noedominguez-Romero, A., et al., "Variable epitope library carrying heavily mutated survivin-derived CTL epitope variants as a new class of efficient vaccine immunogen tested in a mouse model of breat cancer," Human Vaccines & Immunotherapeutics, 10(11): 3201-3213 (2014).
Scardino, A., et al., "HER-2/neu and hTERT Cryptic Epitopes as Novel Targets for Broad Spectrum Tumor Immunotherapy," The Journal of Immunology, 168(11): 5900-5906 (2000).
Buhrman, J.D., and Slansky, J.E., "Improving T cell responses to modified peptides in tumor vaccines," Immunol Res 55: 34-47 (2013).
Database UniParc XP-002777567 (2017).
Database UniParc XP-002777566 (2016).
Database UniParc XP-002777565 (2016).
Database UniParc XP-002777564 (2016).
Database UniParc XP-002790579 (2013).
Database UniParc (Online) Apr. 6, 2016 (Apr. 6, 2016), XP002777564, Database accession No. UPI0008B57C7B abstract.
Database UniParc [Online] Jun. 4, 2016 (Jun. 4, 2016), XP002777565, Database accession No. UPI000ADDED27 abstract.
Database UniParc [Online] Nov. 6, 2017 (Nov. 6, 2017), XP002777567, Database accession No. UPI000B513427 abstract.
Database UniParc [Online] Apr. 6, 2016 (Apr. 6, 2016), XP002777566, Database accession No. UPI000AFC0494 abstract.
International Search Report and Written Opinion issued in PCT/EP2017/075683, dated Apr. 4, 2018, 20 pages.
International Search Report and Written Opinion issued in PCT/EP2017/075673, dated Apr. 30, 2018, 17 pgs.
International Search Report and Written Opinion issued in PCT/EP2017/075676, dated Jun. 15, 2018, 18 pgs.
Cuzick, J., et al., "Tamoxifen for prevention of breast cancer: extended long-term follow-up of the IBIS-I breast cancer prevention trial," Lancet Oncol, 16(1): 67-75 (2015).
Carter, J., "Conjugation of Peptides to Carrier Proteins via Glutaraldehyde," The Protein Protocols Handbook, 117: 679-687 (1996).
Shah, R., et al., "Pathogenesis, prevention, diagnosis and treatment of breast cancer," World J Clin Oncol, 5(3): 283-298 (2014).
Ma, W., et al., "PLGA nanoparticle-mediated delivery of tumor antigenic peptides elicits effective immune responses," International Journal of Nanomedicine, 7: 1475-1487 (2012).
Office Action from corresponding U.S. Appl. No. 16/338,953 dated Jul. 20, 2021.
Huarte, E., et al., "Enhancing Immunogenicity of a CTL Epitope from Carcinoembryonic Antigen by Selective Amino Acid Replacements", Clinical Cancer Research, 8: 2336-2344 (2002).

(56) References Cited

OTHER PUBLICATIONS

Accession No. C2MB65, version 17, Heavy metal efflux pump, CzcA family, Database Uniprot [online], (2016).
Accession No. F4KLC2, version 28, Acriflavin resistance protein, Database Uniprot [online] (2016).
International Search Report from PCT Application No. PCT/EP2019/059319 dated Dec. 17, 2019.
Written Opinion from PCT Application No. PCT/EP2019/059319 dated Dec. 17, 2019.
Andrews, A., et al., "IL-13 receptor alpha 2: A regulator of IL-13 and IL-4 signal transduction in primary human fibroblasts," Journal of Allergy and Clinical Immuno., 118(4): 858-865, (2006).
International Search Report from PCT Application No. PCT/EP2019/059329 dated Oct. 28, 2019.
Written Opinion from PCT Application No. PCT/EP2019/059329 dated Oct. 28, 2019.
Database UniParc XP-002794914 (2017).
Yokomine, K., et al., "The forkhead box M1 transcription factor as a candidate of target for anti-cancer immunotherapy," Int. J. Cancer, 126: 2153-2163 (2010).
International Search Report from corresponding PCT Application No. PCT/EP2020/079226 dated Mar. 19, 2021.
Written Opinion from corresponding PCT Application No. PCT/EP2020/079226 dated Mar. 19, 2021.
Papewalis, C., et al., "Chromogranin A as potential target for immunotherapy of malignant pheochromocytoma," Molecular and Cellular Endocrinology, 335: 569-77 (2011).
Dosset et al. (2012). Universal cancer peptide-based therapeutic vaccine breaks tolerance against telomerase and eradicates established tumor. Clinical Cancer Res. 8(22):6284-95.
Flugel and Fischer. (2014). Simian Virus Tumor Antigen: A virus-specific and preexisting and preexisting cell protein. Journal of the National Cancer Institute. 55:4.
Restriction Requirement issued in U.S. Appl. No. 16/753,657 dated Aug. 9, 2023.
Office Action issued in U.S. Appl. No. 17/929,063 dated Nov. 9, 2023.
Office Action issued in Chinese Application No. CN201880065726.X dated Jan. 20, 2023.
Search Report issued in Chinese Application No. 201880065726.X dated Jan. 17, 2023.
Attallah et al. (2016) Interferon-gamma is associated with hepatic dysfunction in fibrosis, cirrhosis, and hepatocellular carcinoma. J Immunoassay Immunochem, 37(6): 597-610.
Tian et al. (2020). Small and mighty: adaptation of superphylum Patescibacteria to groundwater environment drives their genome simplicity. Microbiome, 8:51.
Cania et al. (2019). A long-term field experiment demonstrates the influence of tillage on the bacterial potential to produce soil structure-stabilizing agents such as exopolysaccharides and lipopolysaccharides. Envrionmental Microbiome, 14:1.
Dill et al. (2011). Physical limits of cells and proteomes. PNAS, 108(44):17876.
Aglietta et al. (2009). Reduced-intensity allogeneic hematopietic stem cell transplantation in metastatic colorectal cancer as a novel adoptive cell therapy approach. The European group for blood and marrow transplantation experience. Biol Blood Marrow Transplant, 15:326.

A

B

A

B

A

B

ANTIGENIC PEPTIDES FOR PREVENTION AND TREATMENT OF CANCER

The present invention relates to the field of cancer therapy, more particularly by immunotherapeutic methods. In particular, the present invention provides various peptides, which are useful in cancer immunotherapy.

Cancer is one of the leading causes of death across the world. According to the World Health Organization (WHO), in 2012 only, 14 million new cases and 8.2 million cancer-related deaths were reported worldwide, and it is expected that the number of new cancer cases will rise by about 70% within the next two decades. So far, more than 60% of world's total new annual cases occur in Africa, Asia and Central and South America. These regions also account for 70% of the world's cancer deaths. Among men, the five most common sites of cancer are lung, prostate, colorectum, stomach and liver; while in women, those are breast, colorectum, lung, cervix, and stomach.

Cancer has long been managed with surgery, radiation therapy, cytotoxic chemotherapy, and endocrine manipulation, which are typically combined in sequential order so as to best control the disease. However, major limitations to the true efficacy of these standard therapies are their imprecise specificity which leads to the collateral damage of normal tissues incurred with treatment, a low cure rate, and intrinsic drug resistance.

In the last years, there has been a tremendous increase in the development of cancer therapies due notably to great advances in the expression profiling of tumors and normal cells, and recent researches and first clinical results in immunotherapy, or molecular targeted therapy, have started to change our perception of this disease.

Promising anticancer immunotherapies have now become a reality and evidences that the host immune system can recognize tumor antigens have led to the development of anticancer drugs which are now approved by regulatory agencies as the US Food and Drug Administration (FDA) and European Medicines Agency (EMA). Various therapeutic approaches include, among others, adoptive transfer of ex vivo expanded tumor-infiltrating lymphocytes (TIL), cancer cell vaccines, immunostimulatory cytokines and variants thereof, Pattern recognition receptor (PRR) agonists, and immunomodulatory monoclonal antibodies targeting tumor antigens or immune checkpoints (Galuzzi et al., Classification of current anticancer immunotherapies. Oncotarget. 2014 Dec. 30; 5(24):12472-508).

Unfortunately, a significant percentage of patients can still present an intrinsic resistance to some of these immunotherapies or even acquire resistance during the course of treatment. For example, the three-year survival rate has been reported to be around 20% with the anti-CTLA-4 antibody Ipilumumab in unresectable or metastatic melanoma (Snyder et al., Genetic basis for clinical response to CTLA-4 blockade in melanoma. N Engl J Med. 2014 Dec. 4; 371 (23):2189-2199; Schadendorf et al., Pooled Analysis of Long-Term Survival Data From Phase II and Phase III Trials of Ipilimumab in Unresectable or Metastatic Melanoma. J Clin Oncol. 2015 Jun. 10; 33(17):1889-94), while the three-year survival rate with another checkpoint inhibitor, Nivolumab targeting PD-1, has been reported to be of 44% in renal cell carcinoma (RCC) and 18% in non-small-cell lung carcinoma (NSCLC) (Mc Dermott et al., Survival, Durable Response, and Long-Term Safety in Patients With Previously Treated Advanced Renal Cell Carcinoma Receiving Nivolumab. J Clin Oncol. 2015 Jun. 20; 33(18):2013-20; Gettinger et al., Overall Survival and Long-Term Safety of Nivolumab (Anti-Programmed Death 1 Antibody, BMS-936558, ONO-4538) in Patients With Previously Treated Advanced Non-Small-Cell Lung Cancer. J Clin Oncol. 2015 Jun. 20; 33(18):2004-12). Fundamental drug resistance thus represents a fixed barrier to the efficacy of these immunotherapies. It is thus clear that a different approach to cancer treatment is needed to break this barrier.

Absence of response in a large number of subjects treated with these immunotherapies might be associated with a deficient anti-tumor immune response (as defect in antigen presentation by antigen-presenting cells (APC) or antigen recognition by T cells). In other words, positive response to immunotherapy correlates with the ability of the immune system to develop specific lymphocytes subsets able to recognize MHC class I-restricted antigens that are expressed by human cancer cells (Kvistborg et al., Human cancer regression antigens. Curr Opin Immunol. 2013 April; 25(2): 284-90). This hypothesis is strongly supported by data demonstrating that response to adoptive transfer of tumor-infiltrating lymphocytes (TIL), is directly correlated with the numbers of $CD8^+$ T-cells transfused to the patient (Besser et al., Adoptive transfer of tumor-infiltrating lymphocytes in patients with metastatic melanoma: intent-to-treat analysis and efficacy after failure to prior immunotherapies. Clin Cancer Res. 2013 Sep. 1; 19(17):4792-800). A potent anti-tumoral response will thus depend on the presentation of immunoreactive peptides and the presence of a sufficient number of reactive cells "trained" to recognize these antigens.

Tumor antigen-based vaccination represent a unique approach to cancer therapy that has gained considerable interest as it can enlist the patient's own immune system to recognize, attack and destroy tumors, in a specific and durable manner. Tumor cells are indeed known to express a large number of peptide antigens susceptible to be recognized by the immune system. Vaccines based on such antigens thus provide great opportunities not only to improve patient's overall survival but also for the monitoring of immune responses and the preparation of GMP-grade product thanks to the low toxicity and low molecular weight of tumor antigens. Examples of tumor antigens include, among others, by-products of proteins transcribed from normally silent genes or overexpressed genes and from proteins expressed by oncovirus (Kvistborg et al., Human cancer regression antigens. Curr Opin Immunol. 2013 April; 25(2):284-90), and neo-antigens, resulting from point mutations of cellular proteins. The later are of particular interest as they have been shown to be directly associated with increased overall survival in patient treated with CTLA-4 inhibitors (Snyder et al., Genetic basis for clinical response to CTLA-4 blockade in melanoma. N Engl J Med. 2014 Dec. 4; 371(23):2189-2199; Brown et al., Neo-antigens predicted by tumor genome meta-analysis correlate with increased patient survival. Genome Res. 2014 May; 24(5):743-50).

Nevertheless, the number of human tumor antigens on which cancer vaccines can be developed is limited. In particular, antigens derived from mutated or modified self-proteins may induce immune tolerance and/or undesired autoimmunity side effects.

There is thus a need in the art to identify alternative cancer therapeutics, which can overcome the limitations encountered in this field.

The invention has for objective to meet the aforementioned needs. This object is achieved by means of the subject-matter set out below, in particular in the items provided by the present invention and in the appended claims.

ITEMS OF THE INVENTION

The present invention provides in particular the following items:
1. An antigenic peptide comprising or consisting of an amino acid sequence as set forth in any one of SEQ ID NOs 1-580 and 861-887.
2. The antigenic peptide according to item 1 comprising or consisting of an amino acid sequence as set forth in any one of SEQ ID NOs 1-580.
3. The antigenic peptide according to item 1 comprising or consisting of an amino acid sequence as set forth in any one of SEQ ID NOs 861-887.
4. The antigenic peptide according to item 1 or 2 comprising or consisting of an amino acid sequence as set forth in any one of SEQ ID NOs 1-160, 162-253 and 255-580.
5. The antigenic peptide according to item 2 or 4, wherein the antigenic peptide comprises or consists of an amino acid sequence as set forth in any one of SEQ ID NOs 30, 31, 32, 87, 97, 145, 193, 194, 220, 221, 255, 521 and 524.
6. The antigenic peptide according to any one of items 1-5, wherein the antigenic peptide comprises or consists of an amino acid sequence as set forth in any one of SEQ ID NOs 30, 31, 32, 87, 97, 193, 194, 220, 255, 521 and 524.
7. The antigenic peptide according to any one of items 1-6, wherein the antigenic peptide comprises or consists of an amino acid sequence as set forth in any one of SEQ ID NOs 30, 31, 32, 87, 97, 194, 220, 255, 521 and 524.
8. The antigenic peptide according to any one of items 1-7, wherein the antigenic peptide comprises or consists of an amino acid sequence as set forth in any one of SEQ ID NOs 30, 32, 87, 97, and 194.
9. The antigenic peptide according to item 1 or 2, wherein the antigenic peptide comprises or consists of an amino acid sequence as set forth in any one of SEQ ID NOs 30, 32, 194, 220, 254 or 255.
10. An immunogenic compound comprising the antigenic peptide according to any one of items 1-9.
11. The immunogenic compound according to item 10, wherein the antigenic peptide is linked to a carrier molecule.
12. The immunogenic compound according to item 11, wherein the carrier molecule is a carrier protein or a carrier peptide.
13. The immunogenic compound according to any one of items 10-12, comprising or consisting of a polypeptide of formula (I)

PepNt-CORE-PepCt       (I)

wherein:
    "PepNt" consists of a polypeptide having a length varying from 0 to 500 amino acid residues and is located at the N-terminal end of the polypeptide of formula (I);
    CORE consists of an antigenic peptide as defined in any one of items 1-6; and
    "PepCt" consists of a polypeptide having a length varying from 0 to 500 amino acid residues and is located at the C-terminal end of the polypeptide of formula (I).
14. A nanoparticle loaded with
    at least one of the antigenic peptides according to any one of items 1-9, or
    at least one of the immunogenic compounds according to any one of items 10-13; and, optionally, with an adjuvant.
15. A cell loaded with the antigenic peptide according to any one of items 1-9 or with the immunogenic compound according to any one of items 10-13.
16. The cell according to item 15, wherein said cell is an antigen presenting cell (APC), preferably a dendritic cell.
17. A nucleic acid encoding the antigenic peptide according to any one of items 1-9, the polypeptide of formula (I) as defined in item 13, or the immunogenic compound according to any one of items 10-13, wherein the immunogenic compound is a peptide or a protein.
18. The nucleic acid according to item 17, wherein the nucleic acid is a DNA molecule or an RNA molecule; preferably selected from genomic DNA; cDNA; siRNA; rRNA; mRNA; antisense DNA; antisense RNA; ribozyme; complementary RNA and/or DNA sequences; RNA and/or DNA sequences with or without expression elements, regulatory elements, and/or promoters; a vector; and combinations thereof.
19. A host cell comprising the nucleic acid according to item 17 or 18.
20. The host cell according to item 19, wherein the nucleic acid is a vector.
21. The host cell according to item 19 or 20, wherein the host cell is a bacterial cell, preferably a gut bacterial cell.
22. A pharmaceutical composition comprising
    the antigenic peptide according to any one of items 1-9,
    the immunogenic compound according to any one of items 10-13,
    the nanoparticle according to item 14,
    the cell according to item 15 or 16,
    the nucleic acid according to item 17 or 18, and/or
    the host cell according to any one of items 19-21,
    and, optionally, one or more pharmaceutically acceptable excipients or carriers.
23. The pharmaceutical composition according to item 22, further comprising one or more immunostimulatory agents.
24. The pharmaceutical composition according to item 23, wherein the immunostimulatory agent is selected from the group consisting of immuno-adjuvants and antigen-presenting cells.
25. The pharmaceutical composition according to item 24, wherein the antigen-presenting cell is a dendritic cell.
26. The pharmaceutical composition according to any one of items 22-25, wherein the composition comprises
    (i) at least two distinct antigenic peptides according to any one of items 1-9;
    (ii) at least two distinct immunogenic compounds according to any one of items 10-13;
    (iii) at least two distinct nanoparticles according to item 14; and/or
    (iv) at least two distinct nucleic acids according to item 17 or 18.
27. A kit comprising
    the antigenic peptide according to any one of items 1-9,
    the immunogenic compound according to any one of items 10-13,
    the nanoparticle according to item 14,
    the cell according to item 15 or 16,
    the nucleic acid according to item 17 or 18,
    the host cell according to any one of items 19-21, and/or the pharmaceutical composition according to any one of items 22-26.
28. The kit according to item 27 further comprising a package insert or instruction leaflet with directions to prevent or to treat a cancer by using the antigenic peptide, the immunogenic compound, the nanoparticle, the cell, the nucleic acid, the host cell, and/or the pharmaceutical composition.
29. The kit according to item 27 or 28, wherein the kit comprises at least two distinct antigenic peptides according to any one of items 1-9.
30. The kit according to item 27 or 28, wherein the kit comprises at least two distinct immunogenic compounds according to any one of items 10-13.
31. The kit according to item 27 or 28, wherein the kit comprises at least two distinct nanoparticles according to item 14.
32. The kit according to item 27 or 28, wherein the kit comprises at least two distinct nucleic acids according to item 15 or 16.
33. The antigenic peptide according to any one of items 1-9,
the immunogenic compound according to any one of items 10-13,
the nanoparticle according to item 14,
the cell according to item 15 or 16,
the nucleic acid according to item 17 or 18,
the host cell according to any one of items 19-21,
the pharmaceutical composition according to any one of items 22-26, or
the kit according to any one of items 27-32
for use in the prevention and/or treatment of a cancer.
34. The antigenic peptide, the immunogenic compound, the nanoparticle, the cell, the nucleic acid, the host cell, the pharmaceutical composition or the kit for use according to item 33, wherein the cancer is selected from glioma, kidney cancer, skin cancer, in particular melanoma, lung cancer, ovarian cancer, breast cancer, colorectal cancer, liver cancer, pancreatic cancer, head and neck cancer, urothelial cancer and prostate cancer.
35. A combination of at least two distinct antigenic peptides according to any one of items 1-9 for use in the prevention and/or treatment of a cancer.
36. A combination of at least two distinct immunogenic compounds according to any one of items 10-13 for use in the prevention and/or treatment of a cancer.
37. A combination of at least two distinct nanoparticles according to item 14 for use in the prevention and/or treatment of a cancer.
38. A combination of at least two distinct nucleic acids according to item 17 or 18 for use in the prevention and/or treatment of a cancer.
39. The combination for use according to any one of items 35-38, wherein the at least two distinct components are comprised in distinct compositions.
40. The combination for use according to any one of items 35-38, wherein the at least two distinct components are comprised in the same composition.
41. The combination for use according to any one of items 35-39, wherein the at least two distinct components are administered via distinct routes of administration.
42. The combination for use according to any one of items 35-40, wherein the at least two distinct components are administered via the same route of administration.
43. The combination for use according to any one of items 35-39, 41 and 42 wherein the at least two distinct components are administered consecutively.
44. The combination for use according to any one of items 35-42 wherein the at least two distinct components are administered at about the same time.
45. A method for preventing and/or treating a cancer or initiating, enhancing or prolonging an anti-tumor-response in a subject in need thereof comprising administering to the subject
the antigenic peptide according to any one of items 1-9,
the immunogenic compound according to any one of items 10-13,
the nanoparticle according to item 14,
the cell according to item 15 or 16,
the nucleic acid according to item 17 or 18,
the host cell according to any one of items 19-21,
the pharmaceutical composition according to any one of items 22-26, and/or the combination as defined in any one of items 35-44.
46. The method according to item 45, wherein the cancer is selected from glioma, kidney cancer, skin cancer, in particular melanoma, lung cancer, ovarian cancer, breast cancer, colorectal cancer, liver cancer, pancreatic cancer, head and neck cancer, urothelial cancer and prostate cancer.
47. A peptide-MHC (pMHC) multimer comprising the antigenic peptide according to any one of items 1-9.

The invention, and in particular the items outlined above, are described in more detail below.

DEFINITIONS

Unless otherwise defined herein, scientific and technical terms used in the present application shall have the meanings that are commonly understood by those of ordinary skill in the art. Further, unless otherwise required by context, nomenclatures used herein, and techniques of cell and tissue culture are those well-known and commonly used in the art.

Such techniques are fully explained in the literature, such as Owen et al. (Kuby Immunology, $7^{th}$, edition, 2013—W. H. Freeman) and Sambrook et al. (Molecular cloning: A laboratory manual 4th edition, Cold Spring Harbor Laboratory Press—Cold Spring Harbor, NY, USA, 2012).

Nevertheless, with respect to the use of different terms throughout the current specification, the following definitions more particularly apply.

The terms "peptide", "polypeptide", "protein" and variations of these terms refer to peptides, oligopeptides, polypeptides, or proteins comprising at least two amino acids joined to each other preferably by a normal peptide bond, or, alternatively, by a modified peptide bond, such as for example in the cases of isosteric peptides. The term "(poly) peptide" refers to a peptide and/or to a polypeptide. In particular, the terms "peptide", "polypeptide" and "protein" refer to a sequential chain of amino acids of any length linked together via peptide bonds (—NHCO—). Peptides, polypeptides and proteins can play a structural and/or functional role in a cell in vitro and/or in vivo. The terms "peptide", "polypeptide", "protein" preferably encompass amino acids chains in size ranging from 2 to at least about 1000 amino acid residues. The term "peptide" preferably encompasses herein amino acid chains in size of less than about 30 amino acids, while the terms "polypeptide" and "protein" preferably encompass amino acid chains in size of at least 30 amino acids. The terms "polypeptide" and "protein" are used herein interchangeably. In a preferred embodiment, the terms "peptide", "polypeptide", "protein" also include "peptidomimetics" which are defined as peptide analogs containing non-peptidic structural elements, which peptides are capable of mimicking or antagonizing the biological action(s) of a natural parent peptide. A peptidomimetic lacks classical peptide characteristics such as enzymatically scissile peptide bonds. In particular, a peptide, polypeptide or protein can comprise amino acids other than the 20 amino acids defined by the genetic code in addition to these amino acids, or it can be composed of amino acids other than the 20 amino acids defined by the genetic code. In particular, a peptide, polypeptide or protein in the context of the present invention can equally be composed of amino acids modified by natural processes, such as post-translational maturation processes or by chemical processes, which are well known to a person skilled in the art. Such modifications are fully detailed in the literature. These modifications can appear anywhere in the polypeptide: in the peptide skeleton, in the amino acid chain or even at the carboxy- or amino-terminal ends. In particular, a peptide or polypeptide can be branched following an ubiquitination or be cyclic with or without branching. This type of modification can be the result of natural or synthetic post-translational processes that are well known to a person skilled in the art. The terms "peptide", "polypeptide", "protein" in the context of the present invention in particular also include modified peptides, polypeptides and proteins. For example, peptide, polypeptide or protein modifications can include acetylation, acylation, ADP-ribosylation, amidation, covalent fixation of a nucleotide or of a nucleotide derivative, covalent fixation of a lipid or of a lipidic derivative, the covalent fixation of a phosphatidylinositol, covalent or non-covalent cross-linking, cyclization, disulfide bond formation, demethylation, glycosylation including pegylation, hydroxylation, iodization, methylation, myristoylation, oxidation, proteolytic processes, phosphorylation, prenylation, racemization, seneloylation, sulfatation, amino acid addition such as arginylation or ubiquitination. Such modifications are fully detailed in the literature (Proteins Structure and Molecular Properties (1993) 2nd Ed., T. E. Creighton, New York; Post-translational Covalent Modifications of Proteins (1983) B. C. Johnson, Ed., Academic Press, New York; Seifter et al. (1990) Analysis for protein modifications and nonprotein cofactors, Meth. Enzymol. 182: 626-646 and Rattan et al., (1992) Protein Synthesis: Post-translational Modifications and Aging, Ann NY Acad Sci, 663: 48-62). Accordingly, the terms "peptide", "polypeptide", "protein" preferably include for example lipopeptides, lipoproteins, glycopeptides, glycoproteins and the like.

In a preferred embodiment, a (poly)peptide or protein is a "classical" (poly)peptide or protein, whereby a "classical" (poly)peptide or protein is typically composed of amino acids selected from the 20 amino acids defined by the genetic code, linked to each other by a normal peptide bond.

As well-known in the art, peptides, polypeptides and proteins can be encoded by nucleic acids. The terms "nucleic acid", "nucleic acid molecule", "nucleic acid sequence", "polynucleotide", "nucleotide sequence" are used herein interchangeable and refer to a precise succession of natural nucleotides (e.g., A, T, G, C and U), or synthetic nucleotides, i.e. to a chain of at least two nucleotides. In particular, the terms "nucleic acid", "nucleic acid molecule", "nucleic acid sequence", "polynucleotide", "nucleotide sequence" refer to DNA or RNA. Nucleic acids preferably comprise single stranded, double stranded or partially double stranded DNA or RNA, preferably selected from genomic DNA (gDNA), complementary DNA (cDNA), ribosomal DNA (rDNA), and the transcription product of said DNA, such as RNA. Preferred examples of nucleic acids include ribosomal RNA (rRNA), messenger RNA (mRNA); antisense DNA, antisense RNA; complementary RNA and/or DNA sequences, ribozyme, (complementary) RNA/DNA sequences with or without expression elements, a vector; a mini-gene, gene fragments, regulatory elements, promoters, and combinations thereof. Further preferred examples of nucleic acid (molecules) and/or polynucleotides include, e.g., a recombinant polynucleotide, a vector, an oligonucleotide, an RNA molecule such as an rRNA, an mRNA, or a transfer RNA (tRNA), or a DNA molecule as described above. It is thus preferred that the nucleic acid (molecule) is a DNA molecule or an RNA molecule; preferably selected from gDNA; cDNA; rRNA; mRNA; antisense DNA; antisense RNA; complementary RNA and/or DNA sequences; RNA and/or DNA sequences with or without expression elements, regulatory elements, and/or promoters; a vector; and combinations thereof. It is within the skill of the person in the art to determine nucleotide sequences which can encode a specific amino acid sequence.

The (poly)peptides and/or nucleic acids according to the invention may be prepared by any known method in the art including, but not limited to, any synthetic method, any recombinant method, any ex vivo generation method and the like, and any combination thereof. Such techniques are fully explained in the literature as mentioned above.

The term "antigenic peptide" as used herein refers to a peptide, which is prone to induce/elicit, increase, prolong or maintain an immune response in a subject to whom it is administered. In particular, the antigenic peptide is a sequence variant of (a fragment/epitope of) a (human) tumor antigen. In other words, the antigenic peptide is preferably distinct from (a fragment/epitope of) a (human) tumor antigen, but it has preferably amino acid similarity with (a fragment/epitope of) the (human) tumor antigen. Preferably, the immune response induced/elicited, increased, prolonged or maintained by the antigenic peptide (also) targets the respective (fragment/epitope of) a (human) tumor antigen.

As used herein, the term "tumor antigen" comprises tumor-specific antigens and tumor-associated antigens. In general, the term "tumor antigen" or "tumor protein" designates herein an antigenic substance produced in tumor cells, and sometimes also in normal cells, and which can trigger an immune response upon administration in a subject. In humans, those have been classified according to their expression pattern, function or genetic origin, and include without limitation, overexpressed self-antigens (such as HER2/neu and its variant dHER2, p53, Wilm's Tumor 1, Ephrin receptor, Proteinase-3, Mucin-1, Mesothelin, EGFR, CD20); cancer-testis (CT) antigens (such as MAGE-1, BAGE, GAGE, NY-ESO-1); mutational antigens, also known as neo-antigens (such as mutants from MUM-1, bcr-abl, ras, b-raf, p53, CDK-4, CDC127, beta-catenin, alpha-actenin-4); tissue-specific differentiation antigens (such as the melanoma antigens Melan A/MART-1, tyrosinase, TRP1/pg75, TRP2, gp100 and gangliosides GM3, GM2, GD2 and GD3; the prostate cancer antigens PSMA, PSA and PAP); viral antigens which are expressed by oncoviruses (such as HPV, EBV); oncofetal antigens (such as alpha-fetoprotein AFP and carcinoembryonic antigen CEA); and universal antigens (telomerase, hTERT, survivin, mdm-2, CYP-1B1) (Srinivasan and Wolchok, Tumor antigens for cancer immunotherapy: therapeutic potential of xenogeneic DNA vaccines. J Trans Med. 2004 Apr. 16; 2(1):12). Accordingly, human tumor antigens are well-known in the art. For instance, the Interleukin-13 receptor subunit alpha-2 (IL-13Rα2 or IL13RA2) is a membrane bound protein that in humans is encoded by the IL13RA2 gene. In a non-exhaustive manner, IL13RA2 has been reported as a potential immunotherapy target (see Beard et al.; Clin Cancer Res; 72(11); 2012). The high expression of IL13RA2 has further been associated with invasion, liver metastasis and poor prognosis in colorectal cancer (Barderas et al.; Cancer Res; 72(11); 2012). In particular, the antigenic peptides according to the present invention are preferably sequence variants of (an epitope/fragment of) the tumor antigens shown in Table 1B and may be used in particular in the disease outlined for the respective tumor antigen in Table 1B.

The term "microbiota", as used herein, refers to commensal microorganisms found in and on all multicellular organisms studied to date from plants to animals. In particular, microbiota have been found to be crucial for immunologic, hormonal and metabolic homeostasis of their host. Microbiota include bacteria, archaea, protists, fungi and viruses. Accordingly, a "microbiota sequence variant" is a sequence variant of a reference sequence (in particular an epitope/a fragment of a human tumor antigen), which occurs in microbiota (e.g., it may be contained in a microbiota protein). A "sequence variant" typically shares, in particular over the whole length of the sequence, at least 50% sequence identity with a reference sequence, namely, a fragment/epitope of a (reference) tumor antigen. Preferably, the sequence variant shares at least 60%, preferably at least 70%, preferably at least 75%, more preferably at least 80%, even more preferably at least 85%, still more preferably at least 90%, particularly preferably at least 95%, and most preferably at least 99% sequence identity with the reference sequence, namely, a fragment/epitope of a (reference) tumor antigen. Sequence identity may be calculated as known in the art, in particular as described below. Preferably, a sequence variant preserves the specific function of the reference sequence, for example its function as tumor epitope and/or its ability to elicit or maintain an immune response. The microbiota sequence variant is preferably selected from the group consisting of bacterial sequence variants, archaea sequence variants, protist sequence variants, fungi sequence variants and viral sequence variants. More preferably, the microbiota sequence variant is a bacterial sequence variant.

Anatomically, microbiota reside on or within any of a number of tissues and biofluids, including the skin, conjunctiva, mammary glands, vagina, placenta, seminal fluid, uterus, ovarian follicles, lung, saliva, oral cavity (in particular oral mucosa), and the gastrointestinal tract, in particular the gut. In the context of the present invention the microbiota sequence variant is preferably a sequence variant of microbiota of the gastrointestinal tract (microorganisms residing in the gastrointestinal tract), more preferably a sequence variant of microbiota of the gut (microorganisms residing in the gut). Accordingly, it is most preferred that the microbiota sequence variant is a (human) gut bacterial sequence variant (i.e. a sequence variant of bacteria residing in the (human) gut).

While microbiota can be found in and on many multicellular organisms (all multicellular organisms studied to date from plants to animals), microbiota found in and on human are preferred. Such microbiota are referred to herein as "human microbiota" (wherein the term human refers specifically to the localization/residence of the microbiota). Within the context of the present invention, the microbiota sequence variant is a human microbiota sequence variant.

The term "immunogenic compound" refers to a compound comprising an antigenic peptide according to the present invention. An "immunogenic compound" is able to induce/elicit, increase, prolong or maintain an immune response against said antigenic peptide in a subject to whom it is administered. In some embodiments, immunogenic compounds comprise at least one antigenic peptide, or alternatively at least one compound comprising such an antigenic peptide, linked to a protein, such as a carrier protein.

A "carrier protein" is usually a protein, which is able to transport a cargo, such as the antigenic peptide according to the present invention. For example, the carrier protein may transport its cargo across a membrane. In the context of the present invention, a carrier protein in particular (also) encompasses a peptide or a polypeptide that is able to elicit an immune response against the antigenic peptide that is linked thereto. Carrier proteins are known in the art.

Alternatively such carrier peptide or polypeptide may be co-administered in the form of immune adjuvant.

Preferably, the antigenic peptide as described herein may be co-administrated or linked, for example by covalent or non-covalent bond, to a protein/peptide having immuno-adjuvant properties, such as providing stimulation of CD4+ Th1 cells. While the antigenic peptide as described herein preferably binds to MHC class I, CD4+ helper epitopes may be additionally used to provide an efficient immune response. Th1 helper cells are able to sustain efficient dendritic cell (DC) activation and specific CTL activation by secreting interferon-gamma (IFN-γ), tumor necrosis factor-alpha (TNF-α) and interleukin-2 (IL-2) and enhancing expression of costimulatory signal on DCs and T cells (Galaine et al., Interest of Tumor-Specific CD4 T Helper 1 Cells for Therapeutic Anticancer Vaccine. Vaccines (Basel). 2015 Jun. 30; 3(3):490-502).

For example, the adjuvant peptide/protein may preferably be distinct from the antigenic peptide according to the present invention. Preferably, the adjuvant peptide/protein is capable of recalling immune memory or provides a non-specific help or could be a specific helper peptide. Several helper peptides have been described in the literature for providing a nonspecific T cell help, such as tetanus helper peptide, keyhole limpet hemocyanin peptide or PADRE peptide (Adotevi et al., Targeting antitumor CD4 helper T cells with universal tumor-reactive helper peptides derived from telomerase for cancer vaccine. Hum Vaccin Immunother. 2013 May; 9(5):1073-7, Slingluff C L, The present and future of peptide vaccines for cancer: single or multiple, long or short, alone or in combination? Cancer J. 2011 September-October; 17(5):343-50). Accordingly, tetanus helper peptide, keyhole limpet hemocyanin peptide and PADRE peptide are preferred examples of such adjuvant peptide/proteins. In particular, the antigenic peptide as described herein, or a polypeptide comprising the said antigenic peptide, may be linked, for example by covalent or non-covalent bond, to the HHD-DR3 peptide of sequence MAKTIAYDEEARRGLERGLN (SEQ ID NO: 856). This peptide represents another example of a helper peptide (having immuno-adjuvant properties), which is preferred in the context of the present invention. Another preferred example is h-pAg T13L (sequence: TPPAYRPPNAPIL; SEQ ID NO: 860; Bhasin M, Singh H, Raghava GP (2003) MHCBN: a comprehensive database of MHC binding and non-binding peptides. Bioinformatics 19: 665-666). Further examples of preferred helper peptides include the UCP2 peptide (for example as described in WO 2013/135553 A1 or in Dosset M, Godet Y, Vauchy C, Beziaud L, Lone Y C, Sedlik C, Liard C, Levionnois E, Clerc B, Sandoval F, Daguindau E, Wain-Hobson S, Tartour E, Langlade-Demoyen P, Borg C, Adotevi O: Universal cancer peptide-based therapeutic vaccine breaks tolerance against telomerase and eradicates established tumor. Clin Cancer Res. 2012 Nov. 15; 18(22):6284-95. doi: 10.1158/1078-0432.CCR-12-0896. Epub 2012 Oct. 2) and the BIRC5 peptide (for example as described in EP2119726 A1 or in Widenmeyer M, Griesemann H, Stevanovie S, Feyerabend S, Klein R, Attig S, Hennenlotter J, Wernet D, Kuprash D V, Sazykin A Y, Pascolo S, Stenzl A, Gouttefangeas C, Rammensee H G: Promiscuous survivin peptide induces robust CD4+ T-cell responses in the majority of vaccinated cancer patients. Int J Cancer. 2012 Jul. 1; 131(1):140-9. doi: 10.1002/ijc.26365. Epub 2011 Sep. 14). The most preferred helper peptide is the UCP2 peptide (amino acid sequence: KSVWSKLQSIGIRQH; SEQ ID NO: 859, for example as described in WO 2013/135553 A1 or in Dosset et al., Clin Cancer Res. 2012 Nov. 15; 18(22):6284-95.

As used herein, the term "immunogenic composition" refers to a composition that is able to elicit, induce, increase, prolong or maintain an immune response, in particular which elicits, induces, increases, prolongs or maintains an immune response, when it is administered to a mammal, and especially when it is administered to a human individual. Preferably, an immunogenic composition further comprises one or more immuno-adjuvant substances.

By "pharmaceutically acceptable excipient or carrier", it is meant herein a compound of pharmaceutical grade which improves the delivery, stability or bioavailability of an active agent, and can be metabolized by, and is non-toxic to, a subject to whom it is administered. Preferred excipients and carriers according to the invention include any of the excipients or carriers commonly used in pharmaceutical products, such as, for example, water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Pharmaceutically acceptable excipients or carriers may further comprise minor amounts of auxiliary substances such as wetting or emulsifying agents, or preservatives.

By "vaccine", it is meant herein a composition capable of stimulating the immune system of a living organism so that protection against a harmful antigen is provided, either through prophylaxis or through therapy. Prophylactic vaccines are preferred. Preferably, a vaccine or a vaccine composition further comprises one or more immuno-adjuvant substances.

According to the different aspects and embodiments of the invention described herein, a "subject" or "host" preferably refers to a mammal, and most preferably to a human being. Said subject may have, been suspected of having, or be at risk of developing cancer.

The term "cancer", as used herein, refers to a malignant neoplasm. In particular, the term "cancer" refers herein to any member of a class of diseases or disorders that are characterized by uncontrolled division of cells and the ability of these cells to invade other tissues, either by direct growth into adjacent tissue through invasion or by implantation into distant sites by metastasis. Metastasis is defined as the stage in which cancer cells are transported through the bloodstream or lymphatic system. It encompasses, among others, esophageal cancer, gastric cancer, duodenal cancer, small intestinal cancer, appendiceal cancer, large bowel cancer, colon cancer, rectum cancer, colorectal cancer, anal cancer, pancreatic cancer, liver cancer, gallbladder cancer, spleen cancer, renal cancer, bladder cancer, prostatic cancer, testicular cancer, uterine cancer, endometrial cancer, ovarian cancer, vaginal cancer, vulvar cancer, breast cancer, pulmonary cancer, thyroid cancer, thymus cancer, brain cancer, nervous system cancer, gliomas, oral cavity cancer, skin cancer, blood cancer, lymphomas, eye cancer, bone cancer, bone marrow cancer, muscle cancer, etc. . . . . In the context of the present invention, melanoma, head and neck, breast, colorectal or renal cancer (such as clear cell renal cell carcinoma) are preferred.

As used herein, the term "preventing", "prevention", "prophylaxis" or "prevent" generally means to avoid or minimize the onset or development of a disease or condition before its onset, while the term "treating, "treatment" or "treat" encompasses reducing, ameliorating or curing a disease or condition (or symptoms of a disease or condition) after its onset. The term "preventing" encompasses "reducing the likelihood of occurrence of" or "reducing the likelihood of reoccurrence".

An "effective amount" or "effective dose" as used herein is an amount which provides the desired effect. For therapeutic purposes, an effective amount is an amount sufficient to provide a beneficial or desired clinical result. The preferred effective amount for a given application can be easily determined by the skilled person taking into consideration, for example, the size, age, weight of the subject, the type of disease/disorder to be prevented or treated, and the amount of time since the disease/disorder began. In the context of the present invention, in terms of prevention or treatment, an effective amount of the composition is an amount that is sufficient to induce a humoral and/or cell-mediated immune response directed against the disease/disorder.

Throughout this specification and the claims which follow, unless the context requires otherwise, the term "comprise", and variations such as "comprises" and "comprising", will be understood to imply the inclusion of a stated member, integer or step but not the exclusion of any other non-stated member, integer or step. The term "consist of" is a particular embodiment of the term "comprise", wherein any other non-stated member, integer or step is excluded. In the context of the present invention, the term "comprise" encompasses the term "consist of". The term "comprising" thus encompasses "including" as well as "consisting" e.g., a composition "comprising" X may consist exclusively of X or may include something additional e.g., X+Y.

The terms "a" and "an" and "the" and similar reference used in the context of describing the invention (especially in the context of the claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. No language in the specification should be construed as indicating any non-claimed element essential to the practice of the invention.

The word "substantially" does not exclude "completely" e.g., a composition which is "substantially free" from Y may be completely free from Y. Where necessary, the word "substantially" may be omitted from the definition of the invention.

The term "about" in relation to a numerical value x means x±10%.

Additional definitions are provided throughout the specification.

The present invention may be understood more readily by reference to the following detailed description, including preferred embodiments of the invention, and examples included herein.

DETAILED DESCRIPTION

Although the present invention is described in detail below, it is to be understood that this invention is not limited to the particular methodologies, protocols and reagents described herein as these may vary. It is also to be understood that the terminology used herein is not intended to limit the scope of the present invention which will be limited only by the appended claims. Unless defined otherwise, all technical and scientific terms used herein have the same meanings as commonly understood by one of ordinary skill in the art.

In the following, the elements of the present invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise.

The present inventors have identified a set of antigenic peptides that can be used to induce a specific immune response against tumor cells. Those antigenic peptides are distinct from, but have amino acid similarity to, (fragments of) human tumor antigens, as shown in Table 1A and Table 1B.

In particular, the antigenic peptides according to the present invention are comprised in polypeptides and proteins produced by commensal bacteria from the human gut.

Accordingly, the antigenic peptides according to the present invention are not human sequences, but bacterial sequences. Without wishing to be bound by any particular theory, the inventors believe that the human immune repertoire contains T-cell clones that are reactive against bacterial peptides (comprised in proteins produced by commensal bacteria from the gut), which have amino acid similarity to fragments of human tumor antigens. In particular, the antigenic peptides according to the present invention can elicit a stronger immune response than the corresponding human peptides, since T cells able to recognize strictly human peptides have been depleted as recognizing self-antigens during maturation, which is not the case for the antigenic peptides according to the present invention. This may explain why the antigenic peptides described herein are able to induce an immune response, and especially a T-cell response, when these peptides are administered to a (human) individual.

Accordingly, the inventors believe that proteins produced by commensal bacteria from the gut are able to "mimic" tumor antigens, and can be used for triggering a specific immune response against tumor cells. These findings provide further evidence that commensal bacteria may contribute to tumor cells eradication.

The antigenic peptides disclosed herein can be prepared using well known techniques. For example, the peptides can be prepared synthetically, by recombinant DNA technology or chemical synthesis. Peptides disclosed herein can be synthesized individually or as longer polypeptides comprising two or more peptides (e.g., two or more peptides or a peptide and a non-peptide). The antigenic peptides can be isolated i.e., purified to be substantially free of other naturally occurring host cell proteins and fragments thereof, e.g., at least about 70%, 80% or 90% purified. Preferably, the antigenic peptides according to the present invention are isolated antigenic peptides.

Antigenic Peptides According to the Present Invention

In a first aspect the present invention provides an antigenic peptide comprising or consisting of an amino acid sequence as set forth in any one of SEQ ID NOs 1-580 and 861-887. Preferably, the antigenic peptide comprises or consists of an amino acid sequence as set forth in any one of SEQ ID NOs 1-580. It is also preferred that the antigenic peptide comprises or consists of an amino acid sequence as set forth in any one of SEQ ID NOs 861-887.

Accordingly, the invention relates to antigenic peptides having amino acid similarity with a tumor antigen. The expression "having amino acid similarity with a tumor antigen" as used herein, refers in particular to a sequence variant of fragments of a (reference) human tumor antigen, such as IL13RA2 or the other exemplified human tumor antigens described below in Tables 1A and 1B. A "sequence variant" typically shares, in particular over the whole length of the sequence, at least 50% sequence identity with a reference sequence, namely, a fragment of a (reference) tumor antigen. Preferably, the sequence variant shares at least 60%, preferably at least 70%, preferably at least 75%, more preferably at least 80%, even more preferably at least 85%, still more preferably at least 90%, particularly preferably at least 95%, and most preferably at least 99% sequence identity with the reference sequence, namely, a fragment of a (reference) tumor antigen. Sequence identity may be calculated as known in the art, in particular as described below. Preferably, a sequence variant preserves the specific function of the reference sequence, for example its function as tumor epitope and/or its ability to elicit or maintain an immune response. In particular, an amino acid sequence variant has an altered sequence in which one or more of the amino acids in the reference sequence is mutated, e.g. deleted or substituted, or one or more amino acids are inserted into the sequence of the reference amino acid sequence. For example, variant sequences which are at least 90% identical have no more than 10 alterations, i.e. any combination of deletions, insertions or substitutions, per 100 amino acids of the reference sequence.

Methods for comparing the identity (similarity) of two or more sequences are well known in the art. The percentage to which two sequences are identical can, e.g., be determined using a mathematical algorithm. A preferred, but not limiting, example of a mathematical algorithm which can be used is the algorithm of Karlin et al. (1993), PNAS USA, 90:5873-5877. Such an algorithm is integrated in the BLAST family of programs, e.g. BLAST or NBLAST program (see also Altschul et al., 1990, J. Mol. Biol. 215, 403-410 or Altschul et al. (1997), Nucleic Acids Res, 25:3389-3402), accessible through the home page of the NCBI at world wide web site ncbi.nlm.nih.gov) and FASTA (Pearson (1990), Methods Enzymol. 783, 63-98; Pearson and Lipman (1988), Proc. Natl. Acad. Sci. U.S.A. 85, 2444-2448). Sequences which are identical to other sequences to a certain extent can be identified by these programmes. Furthermore, programs available in the Wisconsin Sequence Analysis Package, version 9.1 (Devereux et al., 1984, Nucleic Acids Res., 387-395), for example the programs BESTFIT and GAP, may also be used to determine the % identity between two polynucleotides and the % identity between two (poly)peptide sequences. BESTFIT uses the "local homology" algorithm of Smith and Waterman (1981), J. Mol. Biol. 147, 195-197 and finds the best single region of similarity between two sequences.

The "fragment" of the (reference) tumor antigen, which typically serves as reference sequence, preferably comprises at least seven, more preferably at least eight and most preferably (at least) nine amino acids or ten amino acids. It is understood that the "fragment" of the (reference) tumor antigen (protein) is not the full-length tumor antigen (protein). Accordingly, the "fragment" of the (reference) tumor antigen may have a maximum length of 95%, 90%, 85%, 80%, 75%, 70%, 65%, 60%, 55%, 50%, 45%, 40%, 35%, 30%, 25%, 20%, 19%, 18%, 17%, 16%, 15%, 14%, 13%, 12%, 11%, 10%, 9%, 8%, 7%, 6%, 5%, 4%, 3%, 2% or 1% of the full-length (reference) tumor antigen. In some embodiments, the length of the fragment of the (reference) tumor antigen does not exceed 50% of the length of the (full-length) (reference) tumor antigen. In other embodiments, the length of the fragment of the (reference) tumor antigen does not exceed 20% or 10% of the length of the (full-length) (reference) tumor antigen.

In general, the antigenic peptide according to the present invention may be of any length. Preferably, the length of the antigenic peptide according to the present invention does not exceed 350 amino acids. For example, the maximum length of the antigenic peptide according to the present invention may be 300 or 250 amino acids. More preferably, the maximum length of the antigenic peptide according to the present invention does not exceed 200 amino acids, e.g., not more than 190, 180, 170, 160, 150, 140, 130, 120, 110, 100, 95, 90, 85, 80, 75, 70, 65, 60, 55, 50, 45, 40, 35, 30, 29, 28, 27, 26, 25, 24, 23, 22, 21, 20, 19, 18, 17, 16, 15, 14 or 13 amino acids. In particular, the length of the antigenic peptides according to the present invention is preferably at most 30 or 25 amino acids, more preferably at most 20 or 15 amino acids, with smaller molecules of 10 or 9 amino acids in length being even more preferred. In particular, the antigenic peptides are not the full-length proteins produced by commensal bacteria from the gut from which the antigenic peptides are derived from.

In more general, the present invention provides an antigenic peptide, which comprises or consists of a microbiota sequence variant of a fragment of a human tumor antigen. The human tumor antigen may be selected from the group consisting of ACPP, ANKRD30A, AREG, ASCL1, ASCL2, BIRC5, CA9, CCNA1, CCND1, CDH17, CDH6, CDKN2A, CEACAM5, CHI3L1, CHI3L2, COL11A1, CT83, CTCFL, DCT, DMRTA2, EGFR, ERBB2, ERG, ESR1, EZH2, FAP, FLT1, FOXM1, FSIP1, GAL3ST1, GPR143, HES6, IL13RA2, KISS1R, KLHDC8A, KLHL14, KLK4, KRT81, LEMD1, LRRC15, MAGEA1, MAGEA10, MAGEA11, MAGEA12, MAGEA4, MLANA, NKX2-1, NPTX2, PAGE3, PAX2, PCDHB16, PIWIL1, PMEL, PRAME, PTHLH, SEMG1, SERHL2, SLC45A3, SLC6A3, SNX31, SOX11, SPINK1, STEAP1, TBL1Y, TDRD1, TOP2A, TPTE, TRPM8, TYMS, TYR, UPK2, VCAM1, WFDC2, WT1, ZEB1, ZNF165, and ZNF280A.

In particular, the present invention provides an antigenic peptide, which is a microbiota sequence variant of a fragment of a human tumor antigen, wherein the fragment of the human tumor antigen may comprise or consist of any one of SEQ ID NOs 580-858 and 888-895. Table 1A below provides an overview over the antigenic peptides according to the present inventions with their amino acid sequences and SEQ ID NOs and with the corresponding fragment/epitope of a human tumor antigen (also referred to herein as "human reference peptide"). Table 1A also provides information to which tumor antigen each antigenic peptide according to the present invention relates. SEQ ID NOs 1 to 580 and 861 to 887 refer to antigenic peptides according to the present invention.

TABLE 1A

Antigenic peptides according to the invention

| Tumor antigen | Sequence human reference peptide | SEQ ID NO. human reference peptide | Sequence antigenic peptide | SEQ ID NO. antigenic peptide |
|---|---|---|---|---|
| ACPP | FLFLLFFWL | 581 | VLFLLFFPV | 1 |
| ACPP | SLSLGFLFL | 582 | SMSLGFLSV | 2 |
| ACPP | SLSLGFLFL | 582 | FLSLGFLAV | 3 |
| ACPP | LSLGFLFLL | 583 | LLLGFLFLI | 4 |
| ANKRD30A | YTSNDSYIV | 584 | YLSNDSYRV | 5 |
| ANKRD30A | ILIDSGADI | 585 | GLIDSGAFL | 6 |
| ANKRD30A | ILIDSGADI | 585 | LLIDSGALV | 7 |
| ANKRD30A | ILIDSGADI | 585 | RLIDSGATV | 8 |
| ANKRD30A | SLFESSAKI | 586 | KLFESSAAL | 9 |
| ANKRD30A | SLFESSAKI | 586 | TLFESSAFA | 10 |
| ANKRD30A | SLTPLLLSI | 587 | MLTPLLLGL | 11 |
| ANKRD30A | SLTPLLLSI | 587 | YLTPLLLIL | 12 |
| ANKRD30A | SLTPLLLSI | 587 | IMTPLLLPV | 13 |
| ANKRD30A | SLTPLLLSI | 587 | FMTPLLLCL | 14 |

TABLE 1A-continued

Antigenic peptides according to the invention

| Tumor antigen | Sequence human reference peptide | SEQ ID NO. human reference peptide | Sequence antigenic peptide | SEQ ID NO. antigenic peptide |
|---|---|---|---|---|
| ANKRD30A | SLTPLLLSI | 587 | FLTPLLLWL | 15 |
| AREG | MSAVILTAV | 588 | WMAVILTAL | 16 |
| AREG | MSAVILTAV | 588 | VLAVILTAV | 17 |
| AREG | ALAAIAAFM | 589 | VLAAIAAGV | 18 |
| AREG | ALAAIAAFM | 589 | LLAAIAAFL | 19 |
| AREG | ALAAIAAFM | 589 | KLAAIAAAV | 20 |
| AREG | ALAAIAAFM | 589 | ILAAIAAAV | 21 |
| AREG | ALAAIAAFM | 589 | GMAAIAAFL | 22 |
| AREG | ALAAIAAFM | 589 | FLAAIAAVL | 23 |
| AREG | ALAAIAAFM | 589 | ALAAIAALV | 24 |
| ASCL1 | VSAAFQAGV | 590 | ALAAFQAGL | 25 |
| ASCL2 | KLVNLGFQA | 591 | SLVNLGFSL | 26 |
| ASCL2 | KLVNLGFQA | 591 | GLVNLGFAL | 27 |
| ASCL2 | ELLDFSSWL | 592 | QLLDFSSSL | 28 |
| ASCL2 | ELLDFSSWL | 592 | ILLDFSSVV | 29 |
| BIRC5 | LTLGEFLKL | 593 | YTLGEFLYI | 30 |
| BIRC5 | LTLGEFLKL | 593 | GLLGEFLQI | 31 |
| BIRC5 | LTLGEFLKL | 593 | FMLGEFLKL | 32 |
| CA9 | AAGDILALV | 594 | VLGDILALL | 33 |
| CA9 | AAGDILALV | 594 | KVGDILALV | 34 |
| CA9 | ALVFGLLFA | 595 | NLVFGLLPV | 35 |
| CA9 | ALVFGLLFA | 595 | FLVFGLLGL | 36 |
| CA9 | ALVFGLLFA | 595 | ALVFGLLRV | 37 |
| CA9 | FQYEGSLTT | 596 | GVYEGSLTV | 38 |
| CA9 | HLSTAFARV | 597 | VLSTAFALV | 39 |
| CA9 | HLSTAFARV | 597 | GLSTAFAAV | 40 |
| CA9 | HLSTAFARV | 597 | ALSTAFAVV | 41 |
| CA9 | LSLLLLVPV | 598 | MLLLLLVPV | 42 |
| CA9 | LSLLLLVPV | 598 | LLLLLLVPV | 43 |
| CA9 | LSLLLLVPV | 598 | AILLLLVPV | 44 |
| CA9 | QLLLSLLLL | 599 | YLLLSLLRL | 45 |
| CA9 | QLLLSLLLL | 599 | FLLLSLLTL | 46 |
| CA9 | QLLLSLLLL | 599 | ALLLSLLPL | 47 |
| CA9 | VQLLLSLLL | 600 | RLLLLSLLV | 48 |
| CA9 | VQLLLSLLL | 600 | KLLLLSLLL | 49 |
| CA9 | VQLLLSLLL | 600 | FLLLLSLLI | 50 |
| CCNA1 | NLAKYVAEL | 601 | RLAKYVALV | 51 |

TABLE 1A-continued

Antigenic peptides according to the invention

| Tumor antigen | Sequence human reference peptide | SEQ ID NO. human reference peptide | Sequence antigenic peptide | SEQ ID NO. antigenic peptide |
|---|---|---|---|---|
| CCNA1 | LIAAAAFCL | 602 | LIAAAAFTV | 52 |
| CCNA1 | LIAAAAFCL | 602 | GMAAAAFCL | 53 |
| CCNA1 | LIAAAAFCL | 602 | GLAAAAFCI | 54 |
| CCNA1 | LIAAAAFCL | 602 | FLAAAAFCL | 55 |
| CCND1 | LLNDRVLRA | 603 | WLNDRVLQL | 56 |
| CDH17 | GILLTTLLV | 604 | KLLLTTLLV | 57 |
| CDH17 | ILAVVFIRI | 605 | GMAVVFINV | 58 |
| CDH17 | ILAVVFIRI | 605 | GMAVVFIEV | 59 |
| CDH17 | ILLTTLLVI | 606 | LLLTTLLAV | 60 |
| CDH17 | ILLTTLLVI | 606 | ALLTTLLLV | 61 |
| CDH17 | ILLTTLLVI | 606 | ALLTTLLGL | 62 |
| CDH17 | LVIGIILAV | 607 | KIIGIILAV | 63 |
| CDH6 | ALVAILLCI | 608 | YLVAILLLV | 64 |
| CDH6 | ALVAILLCI | 608 | TLVAILLNV | 65 |
| CDH6 | ALVAILLCI | 608 | MLVAILLAV | 66 |
| CDH6 | ALVAILLCI | 608 | LLVAILLSV | 67 |
| CDH6 | ALVAILLCI | 608 | FLVAILLNL | 68 |
| CDH6 | ALVAILLCI | 608 | AMVAILLNI | 69 |
| CDH6 | ALVAILLCI | 608 | ALVAILLAI | 70 |
| CDH6 | EMSDVGTFV | 609 | LLSDVGTLL | 71 |
| CDH6 | EMSTYLLPV | 610 | FLSTYLLPM | 72 |
| CDH6 | FLLEEYTGS | 611 | ALLEEYTGI | 73 |
| CDH6 | ILLCIVILL | 612 | SLLCIVIGL | 74 |
| CDH6 | ILLCIVILL | 612 | ILLCIVIGL | 75 |
| CDH6 | LLVTVVLFA | 613 | MLVTVVLTV | 76 |
| CDH6 | LLVTVVLFA | 613 | MLVTVVLLV | 77 |
| CDH6 | LLVTVVLFA | 613 | LLVTVVLPV | 78 |
| CDH6 | LLVTVVLFA | 613 | LLVTVVLAV | 79 |
| CDH6 | LLVTVVLFA | 613 | KLVTVVLAV | 80 |
| CDH6 | LLVTVVLFA | 613 | ILVTVVLGI | 81 |
| CDKN2A | AVALVLMLL | 614 | LMALVLMLV | 82 |
| CEACAM5 | LLTFWNPPT | 615 | GLTFWNPNV | 83 |
| CHI3L1 | KQLLLSAAL | 616 | FMLLLSAAA | 84 |
| CHI3L1 | KQLLLSAAL | 616 | FLLLLSAAL | 85 |
| CHI3L1 | LLLSAALSA | 617 | YLLSAALTL | 86 |
| CHI3L1 | LLLSAALSA | 617 | YLLSAALTI | 87 |

TABLE 1A-continued

Antigenic peptides according to the invention

| Tumor antigen | Sequence human reference peptide | SEQ ID NO. human reference peptide | Sequence antigenic peptide | SEQ ID NO. antigenic peptide |
|---|---|---|---|---|
| CHI3L1 | LLLSAALSA | 617 | VLLSAALLL | 88 |
| CHI3L1 | LLLSAALSA | 617 | VLLSAALFL | 89 |
| CHI3L1 | LLLSAALSA | 617 | SLLSAALTV | 90 |
| CHI3L1 | LLLSAALSA | 617 | RLLSAALAL | 91 |
| CHI3L1 | LLLSAALSA | 617 | LMLSAALLL | 92 |
| CHI3L1 | LLLSAALSA | 617 | LMLSAALCV | 93 |
| CHI3L1 | LLLSAALSA | 617 | LMLSAALAV | 94 |
| CHI3L1 | LLLSAALSA | 617 | LLLSAALWV | 95 |
| CHI3L1 | LLLSAALSA | 617 | LLLSAALTV | 96 |
| CHI3L1 | LLLSAALSA | 617 | LLLSAALSV | 97 |
| CHI3L1 | LLLSAALSA | 617 | LLLSAALMI | 98 |
| CHI3L1 | LLLSAALSA | 617 | LLLSAALLL | 99 |
| CHI3L1 | LLLSAALSA | 617 | LLLSAALCV | 100 |
| CHI3L1 | LLLSAALSA | 617 | LLLSAALAL | 101 |
| CHI3L1 | LLLSAALSA | 617 | KLLSAALSV | 102 |
| CHI3L1 | LLLSAALSA | 617 | ILLSAALLL | 103 |
| CHI3L1 | LLLSAALSA | 617 | ILLSAALGI | 104 |
| CHI3L1 | LLLSAALSA | 617 | FLLSAALVV | 105 |
| CHI3L1 | LLLSAALSA | 617 | FLLSAALIL | 106 |
| CHI3L1 | LLLSAALSA | 617 | ALLSAALML | 107 |
| CHI3L1 | LLLSAALSA | 617 | ALLSAALLV | 108 |
| CHI3L1 | LLLSAALSA | 617 | ALLSAALLL | 109 |
| CHI3L1 | QLAGAMVWA | 618 | YMAGAMVQL | 110 |
| CHI3L1 | QLAGAMVWA | 618 | RMAGAMVPV | 111 |
| CHI3L1 | QLAGAMVWA | 618 | RLAGAMVDV | 112 |
| CHI3L1 | SQTGFVVLV | 619 | MMTGFVVLM | 113 |
| CHI3L1 | TLASSETGV | 620 | YLASSETHV | 114 |
| CHI3L2 | ILLSIGGYL | 621 | SMLSIGGYV | 115 |
| CHI3L2 | HLIYSFASI | 622 | LLIYSFARV | 116 |
| CHI3L2 | VLIHELAEA | 623 | KLIHELAEV | 117 |
| CHI3L2 | VLIHELAEA | 623 | ILIHELAHI | 118 |
| CHI3L2 | SLWAGVVVL | 624 | HLWAGVVLV | 119 |
| COL11A1 | WLWDFTVTT | 625 | RLWDFTVGV | 120 |
| CT83 | LLASSILCA | 626 | VLASSILYI | 121 |
| CT83 | LLASSILCA | 626 | SLASSILQL | 122 |
| CT83 | LLASSILCA | 626 | ALASSILQL | 123 |
| CTCFL | KLAVSLAET | 627 | FLAVSLAPL | 124 |

TABLE 1A-continued

Antigenic peptides according to the invention

| Tumor antigen | Sequence human reference peptide | SEQ ID NO. human reference peptide | Sequence antigenic peptide | SEQ ID NO. antigenic peptide |
|---|---|---|---|---|
| DCT | ALVGLFVLL | 628 | ILVGLFVPV | 125 |
| DCT | ALVGLFVLL | 628 | ILVGLEVAV | 126 |
| DCT | GLFVLLAFL | 629 | YLFVLLAGI | 127 |
| DCT | GLFVLLAFL | 629 | SLFVLLAAV | 128 |
| DCT | GLFVLLAFL | 629 | KLFVLLALV | 129 |
| DCT | SVYDFFVWL | 630 | GIYDFFVKV | 130 |
| DCT | VVMGTLVAL | 631 | TIMGTLVSV | 131 |
| DCT | VVMGTLVAL | 631 | RVMGTLVGI | 132 |
| DMRTA2 | GTAEGLALA | 632 | TLAEGLALA | 133 |
| DMRTA2 | GLAAGLGPA | 633 | FLAAGLGQV | 134 |
| EGFR | ALESILHRI | 634 | VLESILHPV | 135 |
| EGFR | ALESILHRI | 634 | RMESILHEV | 136 |
| EGFR | ALLAALCPA | 635 | ALLAALCYV | 137 |
| EGFR | ALLALLAAL | 636 | YLLALLAWL | 138 |
| EGFR | ALLALLAAL | 636 | VLLALLAEV | 139 |
| EGFR | ALLALLAAL | 636 | SLLALLAFV | 140 |
| EGFR | ALLALLAAL | 636 | RLLALLASV | 141 |
| EGFR | ALLALLAAL | 636 | RLLALLAAV | 142 |
| EGFR | ALLALLAAL | 636 | LLLALLAPV | 143 |
| EGFR | ALLALLAAL | 636 | ALLALLASV | 144 |
| EGFR | ILDEAYVMA | 637 | ILDEAYVRV | 145 |
| EGFR | LLLLLVVAL | 638 | ALLLLVVGV | 146 |
| EGFR | MVGALLLLL | 639 | GLGALLLLV | 147 |
| EGFR | NLQEILHGA | 640 | YMQEILHRL | 148 |
| EGFR | SLAVVSLNI | 641 | TLAVVSLAV | 149 |
| EGFR | SLAVVSLNI | 641 | LLAVVSLFV | 150 |
| ERBB2 | AVVGILLVV | 642 | YLVGILLVL | 151 |
| ERBB2 | AVVGILLVV | 642 | KVVGILLPI | 152 |
| ERBB2 | AVVGILLVV | 642 | ILVGILLVV | 153 |
| ERBB2 | AVVGILLVV | 642 | FVVGILLQV | 154 |
| ERBB2 | ILDEAYVMA | 643 | ILDEAYVRV | 155 |
| ERBB2 | LLALLPPGA | 644 | LLALLPPEV | 156 |
| ERBB2 | LLALLPPGA | 644 | LLALLPPEL | 157 |
| ERBB2 | LLALLPPGA | 644 | AMALLPPEV | 158 |
| ERBB2 | LLALLPPGA | 644 | ALALLPPPV | 159 |
| ERBB2 | SIISAVVGI | 645 | ILISAVVGL | 160 |

TABLE 1A-continued

Antigenic peptides according to the invention

| Tumor antigen | Sequence human reference peptide | SEQ ID NO. human reference peptide | Sequence antigenic peptide | SEQ ID NO. antigenic peptide |
|---|---|---|---|---|
| ERBB2 | VVLGVVEGI | 646 | IVLGVVFGV | 161 |
| ERBB2 | VVLGVVFGI | 646 | IILGVVFGL | 162 |
| ERG | FLLELLSDS | 647 | YLLELLSAL | 163 |
| ERG | QLWQFLLEL | 857 | IMWQFLLEL | 164 |
| ESR1 | ALLDAEPPI | 648 | YLLDAEPQL | 165 |
| ESR1 | KITDTLIHL | 649 | KLTDTLIPL | 166 |
| ESR1 | KITDTLIHL | 649 | KLTDTLIEL | 167 |
| ESR1 | KLLFAPNLL | 650 | YLLFAPNAV | 168 |
| ESR1 | KLLFAPNLL | 650 | FLLFAPNSA | 169 |
| ESR1 | LLDAEPPIL | 651 | YLDAEPPAV | 170 |
| ESR1 | LLNSGVYTF | 652 | TLNSGVYLI | 171 |
| ESR1 | LLNSGVYTF | 652 | KMNSGVYVI | 172 |
| ESR1 | LMIGLVWRS | 653 | LLIGLVWSL | 173 |
| ESR1 | PLYDLLLEM | 654 | YLYDLLLTV | 174 |
| ESR1 | PLYDLLLEM | 654 | VLYDLLLEV | 175 |
| ESR1 | PLYDLLLEM | 654 | TLYDLLLSL | 176 |
| ESR1 | PLYDLLLEM | 654 | QLYDLLLVA | 177 |
| ESR1 | PLYDLLLEM | 654 | QLYDLLLSL | 178 |
| ESR1 | PLYDLLLEM | 654 | GLYDLLLRI | 179 |
| ESR1 | PLYDLLLEM | 654 | AVYDLLLEV | 180 |
| ESR1 | PLYDLLLEM | 654 | ALYDLLLEV | 181 |
| ESR1 | QLLLILSHI | 655 | VLLLILSGV | 182 |
| ESR1 | QLLLILSHI | 655 | VLLLILSEV | 183 |
| ESR1 | QLLLILSHI | 655 | SLLLILSFV | 184 |
| ESR1 | QLLLILSHI | 655 | MLLLILSYL | 185 |
| ESR1 | QLLLILSHI | 655 | ILLLILSGI | 186 |
| ESR1 | QLLLILSHI | 655 | FLLLILSLL | 187 |
| ESR1 | QLLLILSHI | 655 | FLLLILSFL | 188 |
| ESR1 | RLAQLLLIL | 656 | SLAQLLLAI | 189 |
| ESR1 | RLAQLLLIL | 656 | MLAQLLLTV | 190 |
| ESR1 | TLIHLMAKA | 657 | KLIHLMAAV | 191 |
| ESR1 | VLDKITDTL | 658 | FLDKITDLV | 192 |
| EZH2 | FMVEDETVL | 659 | FLVEDETVI | 193 |
| EZH2 | SMFRVLIGT | 660 | AVFRVLIPV | 194 |
| FAP | ATSAVLALL | 661 | LLSAVLALV | 195 |
| FAP | ATSAVLALL | 661 | LLSAVLALA | 196 |
| FAP | ATSAVLALL | 661 | GISAVLALV | 197 |

TABLE 1A-continued

Antigenic peptides according to the invention

| Tumor antigen | Sequence human reference peptide | SEQ ID NO. human reference peptide | Sequence antigenic peptide | SEQ ID NO. antigenic peptide |
|---|---|---|---|---|
| FAP | TGWAGGFFV | 662 | NLWAGGFFL | 198 |
| FAP | VLALLVMCI | 663 | YLALLVMLL | 199 |
| FAP | VLALLVMCI | 663 | LLALLVMAV | 200 |
| FAP | VLALLVMCI | 663 | ALALLVMAV | 201 |
| FLT1 | ALLSCLLLT | 664 | TMLSCLLHL | 202 |
| FLT1 | ALLSCLLLT | 664 | MLLSCLLFM | 203 |
| FLT1 | ALLSCLLLT | 664 | LLLSCLLPL | 204 |
| FLT1 | ALLSCLLLT | 664 | LLLSCLLHL | 205 |
| FLT1 | ALLSCLLLT | 664 | ILLSCLLLL | 206 |
| FLT1 | ALLSCLLLT | 664 | FLLSCLLCL | 207 |
| FLT1 | ALLSCLLLT | 664 | ALLSCLLML | 208 |
| FLT1 | CVAATLFWL | 665 | YVAATLFAL | 209 |
| FLT1 | EMYSEIPEI | 666 | YLYSEIPDI | 210 |
| FLT1 | KMASTLVVA | 667 | YMASTLVHL | 211 |
| FLT1 | KMASTLVVA | 667 | QMASTLVYL | 212 |
| FLT1 | SIFDKIYST | 668 | YQFDKIYSI | 213 |
| FLT1 | TLFWLLLTL | 669 | MMFWLLLVV | 214 |
| FLT1 | VLLWEIFSL | 670 | GMLWEIFGV | 215 |
| FLT1 | WLKDGLPAT | 671 | AMKDGLPEV | 216 |
| FOXM1 | ILLDISFPG | 672 | TLLDISFAA | 217 |
| FOXM1 | ILLDISFPG | 672 | NMLDISFYL | 218 |
| FOXM1 | ILLDISFPG | 672 | WLLDISFPL | 861 |
| FOXM1 | ILLDISFPG | 672 | HLLDISFPA | 862 |
| FOXM1 | ILLDISFPG | 672 | ELLDISFPA | 863 |
| FOXM1 | ILLDISFPG | 672 | VLLDISFEL | 864 |
| FOXM1 | ILLDISFPG | 672 | VLLDISFKV | 865 |
| FOXM1 | ILLDISFPG | 672 | IMLDISFLL | 866 |
| FOXM1 | LLDISFPGL | 673 | ILDISFPLV | 219 |
| FOXM1 | LLDISFPGL | 673 | LLDISFPSL | 867 |
| FOXM1 | LMDLSTTPL | 674 | LMDLSTTEV | 220 |
| FOXM1 | LMDLSTTPL | 674 | LMDLSTTNV | 868 |
| FOXM1 | RVSSYLVPI | 675 | RLSSYLVEI | 221 |
| FOXM1 | RVSSYLVPI | 675 | MVSSYLVEV | 222 |
| FOXM1 | RVSSYLVPI | 675 | KVSSYLVEV | 223 |
| FOXM1 | RVSSYLVPI | 675 | MLSSYLVPI | 869 |
| FOXM1 | RVSSYLVPI | 675 | LLSSYLVPI | 870 |

TABLE 1A-continued

Antigenic peptides according to the invention

| Tumor antigen | Sequence human reference peptide | SEQ ID NO. human reference peptide | Sequence antigenic peptide | SEQ ID NO. antigenic peptide |
|---|---|---|---|---|
| FOXM1 | RVSSYLVPI | 675 | FVSSYLVPT | 871 |
| FOXM1 | SLSKILLDI | 676 | ILSKILLFA | 224 |
| FOXM1 | SQLSYSQEV | 677 | YQLSYSQMV | 225 |
| FOXM1 | SQLSYSQEV | 677 | KLLSYSQEL | 226 |
| FOXM1 | WAAELPFPA | 678 | KIAELPFPL | 227 |
| FOXM1 | NLSLHDMFV | 888 | SLSLHDMFL | 872 |
| FOXM1 | KMKPLLPRV | 889 | KLKPLLPWI | 873 |
| FOXM1 | KMKPLLPRV | 889 | KLKPLLPFL | 874 |
| FOXM1 | YLVPIQFPV | 890 | KVVPIQFPV | 875 |
| FOXM1 | YLVPIQFPV | 890 | KIVPIQFPI | 876 |
| FOXM1 | YMAMIQFAI | 891 | YQAMIQFLI | 877 |
| FSIP1 | LLNESETKV | 679 | YLNESETVL | 228 |
| FSIP1 | RLVELLKDL | 680 | MLVELLKKV | 229 |
| FSIP1 | RLVELLKDL | 680 | KLVELLKLL | 230 |
| FSIP1 | RLVELLKDL | 680 | ALVELLKPL | 231 |
| GAL3ST1 | GLASTTPEA | 681 | FLASTTPTA | 232 |
| GAL3ST1 | RMAREVAAL | 682 | SLAREVAAV | 233 |
| GAL3ST1 | RMAREVAAL | 682 | GMAREVAAV | 234 |
| GPR143 | FLLSLAFYG | 683 | WLLSLAFLL | 235 |
| GPR143 | FLLSLAFYG | 683 | SLLSLAFSA | 236 |
| GPR143 | FLLSLAFYG | 683 | LLLSLAFIL | 237 |
| GPR143 | ILNPAQGFL | 684 | KLNPAQGYV | 238 |
| GPR143 | MAWGLATLL | 685 | KLWGLATLI | 239 |
| GPR143 | RLALGLLQL | 686 | VLALGLLAV | 240 |
| GPR143 | RLALGLLQL | 686 | SLALGLLQV | 241 |
| GPR143 | RLALGLLQL | 686 | SLALGLLLV | 242 |
| GPR143 | RLALGLLQL | 686 | MLALGLLEV | 243 |
| GPR143 | RLALGLLQL | 686 | GLALGLLFV | 244 |
| GPR143 | RLALGLLQL | 686 | GLALGLLAV | 245 |
| GPR143 | RLALGLLQL | 686 | FLALGLLFL | 246 |
| GPR143 | RLALGLLQL | 686 | ALALGLLMV | 247 |
| HES6 | RLLLAGAEV | 687 | VLLLAGAYV | 248 |
| IL13RA2 | CLYTFLIST | 688 | YLYTFLIVL | 249 |
| IL13RA2 | CLYTFLIST | 688 | GMYTFLIPM | 250 |
| IL13RA2 | CLYTFLIST | 688 | GLYTFLIPM | 251 |
| IL13RA2 | FLISTTFGC | 689 | FLISTTFAA | 252 |
| IL13RA2 | VLLDTNYNL | 690 | ILLDTNYEI | 253 |

TABLE 1A-continued

Antigenic peptides according to the invention

| Tumor antigen | Sequence human reference peptide | SEQ ID NO. human reference peptide | Sequence antigenic peptide | SEQ ID NO. antigenic peptide |
|---|---|---|---|---|
| IL13RA2 | WLPFGFILI | 691 | FLPFGFILV | 254 |
| IL13RA2 | WLPFGFILIL | 692 | FLPFGFILPV | 255 |
| IL13RA2 | WLPFGFILIL | 692 | FMPFGFILPI | 878 |
| IL13RA2 | WLPFGFILIL | 692 | FMPFGFILGV | 879 |
| IL13RA2 | FLISTTFGCT | 892 | FLISTTFTIN | 880 |
| IL13RA2 | FLISTTFGCT | 892 | FMISTTFMRL | 881 |
| IL13RA2 | FLISTTFGCT | 892 | QMISTTFGNV | 882 |
| IL13RA2 | YLYLQWQPPL | 893 | WLYLQWQPSV | 883 |
| IL13RA2 | GVLLDTNYNL | 894 | FVLLDTNYEI | 884 |
| IL13RA2 | GVLLDTNYNL | 894 | FILLDTNYEI | 885 |
| IL13RA2 | FQLQNIVKPL | 895 | YELQNIVLPI | 886 |
| IL13RA2 | FQLQNIVKPL | 895 | FMLQNIVKNL | 887 |
| KISS1R | ALYLLPLLA | 693 | MLYLLPLSL | 256 |
| KISS1R | ALYLLPLLA | 693 | MLYLLPLAL | 257 |
| KISS1R | ALYLLPLLA | 693 | LLYLLPLFL | 258 |
| KISS1R | FALYNLLAL | 694 | SMLYNLLAL | 259 |
| KISS1R | FALYNLLAL | 694 | AMLYNLLAL | 260 |
| KISS1R | FALYNLLAL | 694 | ALLYNLLAL | 261 |
| KISS1R | QLFLVLQAL | 695 | ILFLVLQRV | 262 |
| KISS1R | RLVAAVVLL | 696 | YLVAAVVLL | 263 |
| KISS1R | VLAERAGAV | 697 | YLAERAGHV | 264 |
| KISS1R | WLVPLFFAA | 698 | ILVPLFFTL | 265 |
| KISS1R | WLVPLFFAA | 698 | GLVPLFFAL | 266 |
| KISS1R | WLVPLFFAA | 698 | FLVPLFFVV | 267 |
| KISS1R | WLVPLFFAA | 698 | FLVPLFFLL | 268 |
| KISS1R | WLVPLFFAA | 698 | ALVPLFFAL | 269 |
| KISS1R | YLLPLLATC | 699 | YMLPLLAGA | 270 |
| KISS1R | YLLPLLATC | 699 | YLLPLLALA | 271 |
| KISS1R | YLLPLLATC | 699 | WLLPLLAVV | 272 |
| KISS1R | YLLPLLATC | 699 | WLLPLLACL | 273 |
| KISS1R | YLLPLLATC | 699 | WLLPLLAAL | 274 |
| KISS1R | YLLPLLATC | 699 | TLLPLLAAV | 275 |
| KISS1R | YLLPLLATC | 699 | TLLPLLAAA | 276 |
| KISS1R | YLLPLLATC | 699 | SLLPLLAGV | 277 |
| KISS1R | YLLPLLATC | 699 | RLLPLLAVL | 278 |
| KISS1R | YLLPLLATC | 699 | RLLPLLAAI | 279 |

TABLE 1A-continued

Antigenic peptides according to the invention

| Tumor antigen | Sequence human reference peptide | SEQ ID NO. human reference peptide | Sequence antigenic peptide | SEQ ID NO. antigenic peptide |
|---|---|---|---|---|
| KISS1R | YLLPLLATC | 699 | QLLPLLAYV | 280 |
| KISS1R | YLLPLLATC | 699 | LLLPLLAGL | 281 |
| KISS1R | YLLPLLATC | 699 | LLLPLLADL | 282 |
| KISS1R | YLLPLLATC | 699 | LLLPLLAAA | 283 |
| KISS1R | YLLPLLATC | 699 | HVLPLLATV | 284 |
| KISS1R | YLLPLLATC | 699 | HLLPLLAEV | 285 |
| KISS1R | YLLPLLATC | 699 | GLLPLLAKI | 286 |
| KISS1R | YLLPLLATC | 699 | GILPLLATV | 287 |
| KLHDC8A | GLSDAVEAL | 700 | YLSDAVEAV | 288 |
| KLHDC8A | MLREAAMGI | 701 | ILREAAMPV | 289 |
| KLHL14 | ALIPAPELV | 702 | FLIPAPESL | 290 |
| KLHL14 | NLLHGLNLL | 703 | FLLHGLNLM | 291 |
| KLHL14 | YVSSLPQPL | 704 | YMSSLPQGL | 292 |
| KLK4 | YLILGVAGS | 705 | YMILGVAMI | 293 |
| KLK4 | YLILGVAGS | 705 | VLILGVAAV | 294 |
| KLK4 | YLILGVAGS | 705 | SLILGVAAV | 295 |
| KLK4 | YLILGVAGS | 705 | ILILGVAGI | 296 |
| KRT81 | NMDCIIAEI | 706 | LLDCIIAFL | 297 |
| LEMD1 | AVLGIFIIV | 707 | LILGIFISV | 298 |
| LEMD1 | KLAVLGIFI | 708 | YLAVLGISL | 299 |
| LRRC15 | AIAAIVIGI | 709 | VLAAIVIGV | 300 |
| LRRC15 | ALACSLAAC | 710 | LLACSLAML | 301 |
| LRRC15 | IVIGIVALA | 711 | FVIGIVALV | 302 |
| LRRC15 | RIVAVPTPL | 712 | YVVAVPTPV | 303 |
| LRRC15 | RIVAVPTPL | 712 | YIVAVPTPV | 304 |
| LRRC15 | RIVAVPTPL | 712 | FIVAVPTPI | 305 |
| LRRC15 | SLKELSPGI | 713 | MLKELSPEL | 306 |
| LRRC15 | SLKELSPGI | 713 | FLKELSPGL | 307 |
| MAGEA1 | KVADLVGFL | 714 | FVADLVGHV | 308 |
| MAGEA1 | LVLGTLEEV | 858 | SLLGTLEEL | 309 |
| MAGEA10 | GMLSDVQSM | 715 | VMLSDVQSV | 310 |
| MAGEA10 | GMLSDVQSM | 715 | RLLSDVQGL | 311 |
| MAGEA10 | ILILILSIV | 716 | SLILILSSV | 312 |
| MAGEA10 | ILILILSIV | 716 | KLILILSYL | 313 |
| MAGEA11 | AMDAIFGSL | 717 | ALDAIFGGV | 314 |
| MAGEA11 | GLITKAEML | 718 | FLITKAEEL | 315 |
| MAGEA11 | GTLEELPAA | 719 | SLLEELPAL | 316 |

TABLE 1A-continued

Antigenic peptides according to the invention

| Tumor antigen | Sequence human reference peptide | SEQ ID NO. human reference peptide | Sequence antigenic peptide | SEQ ID NO. antigenic peptide |
|---|---|---|---|---|
| MAGEA11 | GTLEELPAA | 719 | MTLEELPFL | 317 |
| MAGEA11 | KVLEYIANA | 720 | IILEYIALL | 318 |
| MAGEA12 | QLVEGIEVV | 721 | YMVFGIEGI | 319 |
| MAGEA4 | AVSSSSPLV | 722 | SLSSSSPLV | 320 |
| MAGEA4 | KVDELAHFL | 723 | KLDELAHFL | 321 |
| MAGEA4 | KVLEHVVRV | 724 | FVLEHVVPL | 322 |
| MLANA | VILGVLLLI | 725 | YLLGVLLLL | 323 |
| MLANA | VILGVLLLI | 725 | YILGVLLTA | 324 |
| MLANA | VILGVLLLI | 725 | MLLGVLLLL | 325 |
| MLANA | VILGVLLLI | 725 | MILGVLLFL | 326 |
| MLANA | VILGVLLLI | 725 | LMLGVLLLA | 327 |
| MLANA | VILGVLLLI | 725 | LLLGVLLLL | 328 |
| MLANA | VILGVLLLI | 725 | KLLGVLLLV | 329 |
| MLANA | VILGVLLLI | 725 | IILGVLLAV | 330 |
| MLANA | VILGVLLLI | 725 | FILGVLLSL | 331 |
| MLANA | VILGVLLLI | 725 | ALLGVLLLL | 332 |
| MLANA | VILGVLLLI | 725 | ALLGVLLLA | 333 |
| MLANA | VILGVLLLI | 725 | AILGVLLLV | 334 |
| NKX2-1 | MTAAGVPQL | 726 | ILAAGVPEL | 335 |
| NKX2-1 | SVSDILSPL | 727 | YVSDILSYV | 336 |
| NKX2-1 | SVSDILSPL | 727 | YISDILSYV | 337 |
| NKX2-1 | SVSDILSPL | 727 | VISDILSFL | 338 |
| NKX2-1 | SVSDILSPL | 727 | SMSDILSRL | 339 |
| NKX2-1 | SVSDILSPL | 727 | FVSDILSAA | 340 |
| NPTX2 | ALLAASVAL | 728 | WLLAASVTV | 341 |
| NPTX2 | ALLAASVAL | 728 | ILLAASVLV | 342 |
| NPTX2 | ALLAASVAL | 728 | FLLAASVMM | 343 |
| NPTX2 | ALLAASVAL | 728 | ALLAASVLV | 344 |
| NPTX2 | LLAASVALA | 729 | LLAASVALL | 345 |
| NPTX2 | LLAASVALA | 729 | LLAASVAGV | 346 |
| NPTX2 | LLAASVALA | 729 | ILAASVAAV | 347 |
| NPTX2 | LLAASVALA | 729 | GLAASVAPV | 348 |
| NPTX2 | QLLRKVAEL | 730 | ALLRKVAEV | 349 |
| NPTX2 | TLPELYAFT | 731 | SLPELYAWI | 350 |
| NPTX2 | YLYGKIKKT | 732 | ILYGKIKYL | 351 |
| PAGE3 | QVLGLAAYL | 733 | MLLGLAAFL | 352 |

TABLE 1A-continued

Antigenic peptides according to the invention

| Tumor antigen | Sequence human reference peptide | SEQ ID NO. human reference peptide | Sequence antigenic peptide | SEQ ID NO. antigenic peptide |
|---|---|---|---|---|
| PAGE3 | QVLGLAAYL | 733 | GLLGLAAFL | 353 |
| PAGE3 | QVLGLAAYL | 733 | ALLGLAAFL | 354 |
| PAX2 | GLDEVKSSL | 734 | YLDEVKSLV | 355 |
| PAX2 | GLDEVKSSL | 734 | YLDEVKSLI | 356 |
| PAX2 | GLDEVKSSL | 734 | YLDEVKSIL | 357 |
| PAX2 | GLDEVKSSL | 734 | LLDEVKSLV | 358 |
| PCDHB16 | FVLLSLSGA | 735 | FILLSLSPV | 359 |
| PCDHB16 | SLFLFSVLL | 736 | RLFLFSVLV | 360 |
| PCDHB16 | SLTVYLVVA | 737 | ALTVYLVYL | 361 |
| PCDHB16 | VLLFVAVRL | 738 | RLLEVAVPI | 362 |
| PCDHB16 | VLLFVAVRL | 738 | RLLFVAVGL | 363 |
| PCDHB16 | VLLFVAVRL | 738 | FLLFVAVSV | 364 |
| PCDHB16 | VSSLFLFSV | 739 | FISLFLFSV | 365 |
| PIWIL1 | SIAGEVASI | 740 | LIAGFVALV | 366 |
| PMEL | ILLVLMAVV | 741 | YLLVLMASI | 367 |
| PMEL | LIVGILLVL | 742 | YLVGILLVL | 368 |
| PMEL | LIVGILLVL | 742 | KIVGILLGI | 369 |
| PMEL | LIVGILLVL | 742 | KIVGILLAV | 370 |
| PMEL | LIVGILLVL | 742 | ILVGILLVV | 371 |
| PMEL | LIVGILLVL | 742 | GIVGILLNV | 372 |
| PMEL | LIVGILLVL | 742 | GIVGILLAV | 373 |
| PMEL | LMAVVLASL | 743 | LLAVVLAFV | 374 |
| PMEL | LMAVVLASL | 743 | LLAVVLAAV | 375 |
| PMEL | PLLDGTATL | 744 | GVLDGTATV | 376 |
| PMEL | SLADTNSLA | 745 | ALADTNSYV | 377 |
| PMEL | SLADTNSLA | 745 | ALADTNSYL | 378 |
| PMEL | VLQAAIPLT | 746 | AMQAAIPML | 379 |
| PRAME | AVLDGLDVL | 747 | IVLDGLDLV | 380 |
| PRAME | AVLDGLDVL | 747 | AVLDGLDPV | 381 |
| PRAME | QLLALLPSL | 748 | YLLALLPLL | 382 |
| PRAME | QLLALLPSL | 748 | YLLALLPIL | 383 |
| PRAME | QLLALLPSL | 748 | QLLALLPGV | 384 |
| PRAME | QLLALLPSL | 748 | LLLALLPTV | 385 |
| PRAME | RLRELLCEL | 749 | FLRELLCQL | 386 |
| PRAME | VLYPVPLES | 750 | LLYPVPLGV | 387 |
| PTHLH | AVFLLSYAV | 751 | ALFLLSYTV | 388 |
| SEMG1 | FVLSLLLIL | 752 | YVLSLLLTL | 389 |

TABLE 1A-continued

Antigenic peptides according to the invention

| Tumor antigen | Sequence human reference peptide | SEQ ID NO. human reference peptide | Sequence antigenic peptide | SEQ ID NO. antigenic peptide |
|---|---|---|---|---|
| SEMG1 | FVLSLLLIL | 752 | VLLSLLLIV | 390 |
| SEMG1 | FVLSLLLIL | 752 | SLLSLLLIL | 391 |
| SEMG1 | FVLSLLLIL | 752 | RLLSLLLVL | 392 |
| SEMG1 | FVLSLLLIL | 752 | LVLSLLLLV | 393 |
| SEMG1 | FVLSLLLIL | 752 | KLLSLLLVL | 394 |
| SEMG1 | FVLSLLLIL | 752 | ILLSLLLVL | 395 |
| SEMG1 | FVLSLLLIL | 752 | FTLSLLLTL | 396 |
| SEMG1 | FVLSLLLIL | 752 | ALLSLLLIL | 397 |
| SEMG1 | IIFVLSLLL | 753 | VLFVLSLFL | 398 |
| SEMG1 | IIFVLSLLL | 753 | ILFVLSLQL | 399 |
| SEMG1 | LILEKQAAV | 754 | LLLEKQAEV | 400 |
| SERHL2 | LISELKLAV | 755 | VLSELKLAV | 401 |
| SERHL2 | RAIEHVLQV | 756 | RMIEHVLTV | 402 |
| SERHL2 | SSFDRLIPL | 757 | QIFDRLIPI | 403 |
| SERHL2 | SSFDRLIPL | 757 | GVFDRLIPI | 404 |
| SERHL2 | TLKEQFQFV | 758 | YLKEQFQTL | 405 |
| SLC45A3 | AILDSAFLL | 759 | SLLDSAFLL | 406 |
| SLC45A3 | AISLVFSLV | 760 | MLSLVFSLI | 407 |
| SLC45A3 | AISLVFSLV | 760 | LMSLVFSLV | 408 |
| SLC45A3 | ALQILPYTL | 761 | WMQILPYQV | 409 |
| SLC45A3 | ALTGFTFSA | 762 | MMTGFTFGV | 410 |
| SLC45A3 | AQLLLVNLL | 763 | MLLLLVNLV | 411 |
| SLC45A3 | CLFGLLTLI | 764 | VLFGLLTFL | 412 |
| SLC45A3 | CLFGLLTLI | 764 | QLFGLLTDV | 413 |
| SLC45A3 | CLFGLLTLI | 764 | FLFGLLTMI | 414 |
| SLC45A3 | CLFGLLTLI | 764 | FLFGLLTDA | 415 |
| SLC45A3 | GILLSLFLI | 765 | TLLLSLFLL | 416 |
| SLC45A3 | GILLSLFLI | 765 | FILLSLFML | 417 |
| SLC45A3 | GLLPPPPAL | 766 | ILLPPPPVV | 418 |
| SLC45A3 | GLLTLIFLT | 767 | VLLTLIFAL | 419 |
| SLC45A3 | GLLTLIFLT | 767 | RLLTLIFTL | 420 |
| SLC45A3 | GLLTLIFLT | 767 | QLLTLIFYL | 421 |
| SLC45A3 | GLLTLIFLT | 767 | LLLTLIFPI | 422 |
| SLC45A3 | GLLTLIFLT | 767 | FLLTLIFSL | 423 |
| SLC45A3 | GLVAIYFAT | 768 | VMVAIYFTL | 424 |
| SLC45A3 | NLGALLPRL | 769 | LLGALLPAV | 425 |

TABLE 1A-continued

Antigenic peptides according to the invention

| Tumor antigen | Sequence human reference peptide | SEQ ID NO. human reference peptide | Sequence antigenic peptide | SEQ ID NO. antigenic peptide |
|---|---|---|---|---|
| SLC45A3 | NLGALLPRL | 769 | ILGALLPLL | 426 |
| SLC45A3 | SVAAFPVAA | 770 | SVAAFPVTV | 427 |
| SLC6A3 | FLLSLFCVT | 771 | LLLSLFCLI | 428 |
| SLC6A3 | FLLSLFCVT | 771 | KLLSLFCTL | 429 |
| SLC6A3 | FLLSLFCVT | 771 | FLLSLFCIA | 430 |
| SLC6A3 | FSLGVGFGV | 772 | ILLGVGFGI | 431 |
| SLC6A3 | FSLGVGFGV | 772 | ALLGVGFGI | 432 |
| SLC6A3 | GLIDEFQLL | 773 | RLIDEFQSV | 433 |
| SLC6A3 | GMESVITGL | 774 | FLESVITTV | 434 |
| SLC6A3 | ILFGVLIEA | 775 | GLFGVLIGV | 435 |
| SLC6A3 | ILFGVLIEA | 775 | AMFGVLISV | 436 |
| SLC6A3 | KIDFLLSVI | 776 | FIDFLLSEV | 437 |
| SLC6A3 | LLFMVIAGM | 777 | GLFMVIAGV | 438 |
| SLC6A3 | LLFMVIAGM | 777 | FLFMVIAFA | 439 |
| SLC6A3 | LVPYLLFMV | 778 | HLPYLLFLL | 440 |
| SLC6A3 | QLTACLVLV | 779 | TLTACLVGV | 441 |
| SNX31 | MISEKMVKL | 780 | MLSEKMVQL | 442 |
| SOX11 | LMFDLSLNF | 781 | NLFDLSLVA | 443 |
| SOX11 | LMFDLSLNF | 781 | GLFDLSLRV | 444 |
| SOX11 | LMFDLSLNF | 781 | ALFDLSLPI | 445 |
| SOX17 | ALPAVMAGL | 782 | TLPAVMAEV | 446 |
| SOX17 | GLAEPQAAA | 783 | LLAEPQASL | 447 |
| SOX17 | GLAEPQAAA | 783 | ILAEPQALV | 448 |
| SOX17 | GLAEPQAAA | 783 | FIAEPQAAL | 449 |
| SPINK1 | GIFLLSALA | 784 | LLFLLSALL | 450 |
| STEAP1 | ASLTFLYTL | 785 | KMLTFLYTA | 451 |
| STEAP1 | AVLHAIYSL | 786 | AVLHAIYGV | 452 |
| STEAP1 | FFFAVLHAI | 787 | HLFAVLHAV | 453 |
| STEAP1 | GVIAAIVQL | 788 | SVIAAIVLV | 454 |
| STEAP1 | GVIAAIVQL | 788 | FVIAAIVCV | 455 |
| STEAP1 | GVIAAIVQL | 788 | FIIAAIVAV | 456 |
| STEAP1 | GVIAAIVQL | 788 | AVIAAIVGV | 457 |
| STEAP1 | KIAAIIASL | 789 | YIAAIIAEA | 458 |
| STEAM | KIAAIIASL | 789 | FVAAIIASL | 459 |
| STEAP1 | KIAAIIASL | 789 | FIAAIIAPI | 460 |
| STEAP1 | LIFKSILFL | 790 | GLFKSILFL | 461 |
| STEAP1 | LLLGTIHAL | 791 | MLLGTIHGV | 462 |

TABLE 1A-continued

Antigenic peptides according to the invention

| Tumor antigen | Sequence human reference peptide | SEQ ID NO. human reference peptide | Sequence antigenic peptide | SEQ ID NO. antigenic peptide |
|---|---|---|---|---|
| STEAP1 | LLSFFFAVL | 792 | LLSFFFAML | 463 |
| STEAP1 | LLSFFFAVL | 792 | LLSFFFAAL | 464 |
| STEAP1 | LLSFFFAVL | 792 | FLSFFFAAM | 465 |
| STEAP1 | MIAVFLPIV | 793 | FLAVFLPVL | 466 |
| STEAP1 | SLLLGTIHA | 794 | SLLLGTILV | 467 |
| STEAP1 | SLLLGTIHA | 794 | ILLLGTILL | 468 |
| TBL1Y | SLSLIVAVI | 795 | RLSLIVALV | 469 |
| TBL1Y | SLSLIVAVI | 795 | RLSLIVAFV | 470 |
| TDRD1 | IISPNLFYA | 796 | MISPNLFRV | 471 |
| TDRD1 | LLDHVLIEM | 797 | LLDHVLIAV | 472 |
| TDRD1 | VLIDEHLVL | 798 | RLIDEHLVV | 473 |
| TDRD1 | YSSEVLEYM | 799 | TLSEVLEYL | 474 |
| TOP2A | ILLRPDTYI | 800 | FLLRPDTFL | 475 |
| TOP2A | LMMTIINLA | 801 | LMMTIINQV | 476 |
| TOP2A | LMMTIINLA | 801 | LLMTIINQV | 477 |
| TOP2A | LMMTIINLA | 801 | FLMTIINQV | 478 |
| TOP2A | QLAGSVAEM | 802 | RLAGSVAGV | 479 |
| TOP2A | QLAGSVAEM | 802 | KLAGSVAGV | 480 |
| TOP2A | SLMMTIINL | 803 | LLMMTIITV | 481 |
| TOP2A | TMLSSLARL | 804 | AMLSSLAGV | 482 |
| TOP2A | YIFTMLSSL | 805 | YVFTMLSAV | 483 |
| TPTE | DLAGVIIEL | 806 | YLAGVIILI | 484 |
| TPTE | DLAGVIIEL | 806 | MLAGVIIYI | 485 |
| TPTE | DLAGVIIEL | 806 | MLAGVIIGI | 486 |
| TPTE | DLAGVIIEL | 806 | LLAGVIITI | 487 |
| TPTE | DLAGVIIEL | 806 | LLAGVIIGI | 488 |
| TPTE | DLAGVIIEL | 806 | GLAGVIITI | 489 |
| TPTE | DLAGVIIEL | 806 | GLAGVIIAV | 490 |
| TPTE | FGLFGVFLV | 807 | VMLFGVFMV | 491 |
| TPTE | FGLFGVFLV | 807 | VLLFGVFLV | 492 |
| TPTE | FGLFGVFLV | 807 | ILLFGVFMV | 493 |
| TPTE | FGLFGVFLV | 807 | FILFGVFML | 494 |
| TPTE | GLFGVFLVL | 808 | VLFGVFLGV | 495 |
| TPTE | GLFGVFLVL | 808 | GMFGVFLTL | 496 |
| TPTE | GLFGVFLVL | 808 | FLFGVFLAM | 497 |
| TPTE | ILDTAIIVI | 809 | VLDTAIIYI | 498 |

TABLE 1A-continued

Antigenic peptides according to the invention

| Tumor antigen | Sequence human reference peptide | SEQ ID NO. human reference peptide | Sequence antigenic peptide | SEQ ID NO. antigenic peptide |
|---|---|---|---|---|
| TPTE | ILDTAIIVI | 809 | KLDTAIIHV | 499 |
| TPTE | IVSSFAFGL | 810 | LISSFAFLV | 500 |
| TPTE | IVSSFAFGL | 810 | LISSFAFLL | 501 |
| TPTE | RLLRLIILL | 811 | FMLRLIINL | 502 |
| TPTE | SLAIALFFL | 812 | ALAIALFPV | 503 |
| TPTE | YFWLHTSFI | 813 | ALWLHTSFA | 504 |
| TRPM8 | AMFGYTVGT | 814 | TMFGYTVFL | 505 |
| TRPM8 | FIAGIVFRL | 815 | YLAGIVFTL | 506 |
| TRPM8 | FLLLFAYVL | 816 | LMLLFAYYL | 507 |
| TRPM8 | LLFAYVLLM | 817 | YLFAYVLIV | 508 |
| TRPM8 | LLFAYVLLM | 817 | TLFAYVLGL | 509 |
| TRPM8 | LLLFAYVLL | 818 | GLLFAYVEV | 510 |
| TRPM8 | LVLYSLVFV | 819 | KILYSLVEV | 511 |
| TRPM8 | NILLVNLLV | 820 | FLLLVNLLV | 512 |
| TRPM8 | QIADVIASL | 821 | VIADVIALL | 513 |
| TRPM8 | QIADVIASL | 821 | QIADVIAFL | 514 |
| TRPM8 | QIADVIASL | 821 | LVADVIASV | 515 |
| TRPM8 | QIADVIASL | 821 | LIADVIALL | 516 |
| TRPM8 | VLYSLVFVL | 822 | LLYSLVFFL | 517 |
| TRPM8 | YLVKINTKA | 823 | FLVKINTNI | 518 |
| TYMS | FLDSLGFST | 824 | KLDSLGFTL | 519 |
| TYMS | FLDSLGFST | 824 | KLDSLGFSL | 520 |
| TYMS | FLDSLGFST | 824 | FLDSLGFSL | 521 |
| TYMS | SLRDEFPLL | 825 | FMRDEFPDV | 522 |
| TYMS | SLRDEFPLL | 825 | FLRDEFPEA | 523 |
| TYMS | VLEELLWEI | 826 | SMEELLWFV | 524 |
| TYR | ALLAGLVSL | 827 | YLLAGLVLL | 525 |
| TYR | ALLAGLVSL | 827 | YLLAGLVLI | 526 |
| TYR | AMVGAVLTA | 828 | WLVGAVLTL | 527 |
| TYR | AMVGAVLTA | 828 | LLVGAVLTV | 528 |
| TYR | AMVGAVLTA | 828 | ALVGAVLTV | 529 |
| TYR | AMVGAVLTA | 828 | ALVGAVLLV | 530 |
| TYR | ISSDYVIPI | 829 | CLSDYVIPV | 531 |
| TYR | LLAGLVSLL | 830 | KLAGLVSSV | 532 |
| TYR | LLSPASFFS | 831 | GMSPASFFA | 533 |
| TYR | MVGAVLTAL | 832 | ALGAVLTAV | 534 |
| TYR | VLTALLAGL | 833 | YLTALLAEM | 535 |

TABLE 1A-continued

Antigenic peptides according to the invention

| Tumor antigen | Sequence human reference peptide | SEQ ID NO. human reference peptide | Sequence antigenic peptide | SEQ ID NO. antigenic peptide |
|---|---|---|---|---|
| TYR | VLTALLAGL | 833 | VLTALLAAV | 536 |
| TYR | VLTALLAGL | 833 | RLTALLAAV | 537 |
| TYR | VLTALLAGL | 833 | GLTALLAPV | 538 |
| TYR | VLTALLAGL | 833 | FLTALLATV | 539 |
| UPK2 | ALTESLLVA | 834 | TLTESLLYL | 540 |
| UPK2 | ALTESLLVA | 834 | KLTESLLTI | 541 |
| UPK2 | ALTESLLVA | 834 | ILTESLLFL | 542 |
| UPK2 | LLALLSPGA | 835 | RLALLSPYI | 543 |
| UPK2 | LVLGFIIAL | 836 | SILGFIIAA | 544 |
| UPK2 | LVLGFIIAL | 836 | LILGFIIAV | 545 |
| UPK2 | LVLGFIIAL | 836 | FVLGFIITI | 546 |
| UPK2 | LVLGFIIAL | 836 | FILGFIITI | 547 |
| UPK2 | SLSGLLSPA | 837 | SLSGLLSGV | 548 |
| UPK2 | SLSGLLSPA | 837 | FLSGLLSAL | 549 |
| UPK2 | TLPLILILL | 838 | ILPLILITV | 550 |
| UPK2 | VLGFIIALA | 839 | MLGFIIAFL | 551 |
| UPK2 | VLGFIIALA | 839 | LLGFIIAEV | 552 |
| UPK2 | VLGFIIALA | 839 | ILGFIIAAV | 553 |
| UPK2 | VLGFIIALA | 839 | FLGFIIADV | 554 |
| UPK2 | VVITVLLSV | 840 | MIITVLLLV | 555 |
| UPK2 | VVITVLLSV | 840 | FIITVLLGL | 556 |
| VCAM1 | AQIGDSVML | 841 | YQIGDSVLL | 557 |
| VCAM1 | FASSLIIPA | 842 | MLSSLIIPL | 558 |
| VCAM1 | KSIDGAYTI | 843 | ILIDGAYTV | 559 |
| VCAM1 | SILEEGSSV | 844 | YLLEEGSSV | 560 |
| WFDC2 | LLFGFTLVS | 845 | YMFGFTLTM | 561 |
| WFDC2 | LLFGFTLVS | 845 | YLFGFTLGM | 562 |
| WFDC2 | LLFGFTLVS | 845 | VLFGFTLSI | 563 |
| WFDC2 | LLFGFTLVS | 845 | RMFGFTLML | 564 |
| WFDC2 | LLFGFTLVS | 845 | LMFGFTLRT | 565 |
| WFDC2 | LLLFGFTLV | 846 | YLLFGFTRV | 566 |
| WFDC2 | RLGPLAAAL | 847 | VLGPLAALV | 567 |
| WFDC2 | RLGPLAAAL | 847 | ILGPLAAWL | 568 |
| WT1 | DLNALLPAV | 848 | SLNALLPYV | 569 |
| ZEB1 | ILIPQVAYT | 849 | MMIPQVATL | 570 |
| ZEB1 | ILIPQVAYT | 849 | MMIPQVATI | 571 |

TABLE 1A-continued

Antigenic peptides according to the invention

| Tumor antigen | Sequence human reference peptide | SEQ ID NO. human reference peptide | Sequence antigenic peptide | SEQ ID NO. antigenic peptide |
|---|---|---|---|---|
| ZEB1 | NLSDIIQNVL | 850 | YLSDIQNAI | 572 |
| ZEB1 | NLSDIQNVL | 850 | VMSDIQNRV | 573 |
| ZEB1 | VQAVVLPTV | 851 | YQAVVLPGL | 574 |
| ZNF165 | LVLEQFLTI | 852 | LLLEQFLSV | 575 |
| ZNF165 | LVLEQFLTI | 852 | LLLEQFLAI | 576 |
| ZNF165 | LVLEQFLTI | 852 | ALLEQFLTA | 577 |
| ZNF165 | RISGYISEA | 853 | GVSGYISPV | 578 |
| ZNF280A | AMTDISSLA | 854 | KLTDISSLV | 579 |
| ZNF280A | VLLSNFYYG | 855 | YLLSNFYTV | 580 |

As can be retrieved from Table 1A, the antigenic peptides according to the present invention can be categorized according to the respective "human reference peptide" and according to the respective tumor antigen.

In one embodiment, the antigenic peptide according to the present invention is a microbiota sequence variant of a fragment of the tumor antigen ACPP (human reference peptide), such as FLFLLFFWL" (SEQ ID NO: 581), "SLSLGFLFL" (SEQ ID NO: 582) or "LSLGFLFLL" (SEQ ID NO: 583). In a preferred embodiment, the antigenic peptide according to the present invention is a sequence variant of a fragment of the tumor antigen ACPP, such as antigenic peptides comprising or consisting of an amino acid sequence as set forth in any one of SEQ ID NOs 1-4. More preferably, the antigenic peptide according to the present invention is a sequence variant of the ACPP fragment (human reference peptide) "FLELLFEWL" (SEQ ID NO: 581), such as an antigenic peptide comprising or consisting of an amino acid sequence as set forth in SEQ ID NO: 1. It is also more preferred that the antigenic peptide according to the present invention is a sequence variant of the ACPP fragment (human reference peptide) "SLSLGFLFL" (SEQ ID NO: 582), such as an antigenic peptide comprising or consisting of an amino acid sequence as set forth in SEQ ID NO: 2 or 3. It is also more preferred that the antigenic peptide according to the present invention is a sequence variant of the ACPP fragment (human reference peptide) "LSLGFLFLL" (SEQ ID NO: 583), such as an antigenic peptide comprising or consisting of an amino acid sequence as set forth in SEQ ID NO: 4.

In another embodiment, the antigenic peptide according to the present invention is a microbiota sequence variant of a fragment of the tumor antigen ANKRD30A (human reference peptide), such as "YTSNDSYIV" (SEQ ID NO: 584), "ILIDSGADI" (SEQ ID NO: 585), "SLFESSAKI" (SEQ ID NO: 586) or "SLTPLLLSI" (SEQ ID NO: 587). In another preferred embodiment, the antigenic peptide according to the present invention is a sequence variant of a fragment of the tumor antigen ANKRD30A, such as antigenic peptides comprising or consisting of an amino acid sequence as set forth in any one of SEQ ID NOs 5-15. More preferably, the antigenic peptide according to the present invention is a sequence variant of the ANKRD30A fragment (human reference peptide) "YTSNDSYIV" (SEQ ID NO: 584), such as an antigenic peptide comprising or consisting of an amino acid sequence as set forth in SEQ ID NO: 5. It is also more preferred that the antigenic peptide according to the present invention is a sequence variant of the ANKRD30A fragment (human reference peptide) "ILIDSGADI" (SEQ ID NO: 585), such as an antigenic peptide comprising or consisting of an amino acid sequence as set forth in SEQ ID NO: 6, 7 or 8. It is also more preferred that the antigenic peptide according to the present invention is a sequence variant of the ANKRD30A fragment (human reference peptide) "SLFESSAKI" (SEQ ID NO: 586), such as an antigenic peptide comprising or consisting of an amino acid sequence as set forth in SEQ ID NO: 9 or 10. It is also more preferred that the antigenic peptide according to the present invention is a sequence variant of the ANKRD30A fragment (human reference peptide) "SLTPLLLSI" (SEQ ID NO: 587), such as an antigenic peptide comprising or consisting of an amino acid sequence as set forth in SEQ ID NO: 11, 12, 13, 14 or 15.

In another embodiment, the antigenic peptide according to the present invention is a microbiota sequence variant of a fragment of the tumor antigen AREG (human reference peptide), such as "MSAVILTAV" (SEQ ID NO: 588) or "ALAAIAAFM" (SEQ ID NO: 589). In another preferred embodiment, the antigenic peptide according to the present invention is a sequence variant of a fragment of the tumor antigen AREG, such as antigenic peptides comprising or consisting of an amino acid sequence as set forth in any one of SEQ ID NOs 16-24. More preferably, the antigenic peptide according to the present invention is a sequence variant of the AREG fragment (human reference peptide) "MSAVILTAV" (SEQ ID NO: 588), such as an antigenic peptide comprising or consisting of an amino acid sequence as set forth in SEQ ID NO: 16 or 17. It is also more preferred that the antigenic peptide according to the present invention is a sequence variant of the AREG fragment (human reference peptide) "ALAAIAAFM" (SEQ ID NO: 589), such as an antigenic peptide comprising or consisting of an amino acid sequence as set forth in SEQ ID NO: 18, 19, 20, 21, 22, 23 or 24.

In another embodiment, the antigenic peptide according to the present invention is a microbiota sequence variant of a fragment of the tumor antigen ASCL1 (human reference peptide), such as "VSAAFQAGV" (SEQ ID NO: 590). In another preferred embodiment, the antigenic peptide according to the present invention is a sequence variant of a fragment of the tumor antigen ASCL1, such as the antigenic peptide comprising or consisting of an amino acid sequence as set forth in SEQ ID NO: 25. Namely, the antigenic peptide according to the present invention, which comprises or consists of an amino acid sequence as set forth in SEQ ID NO: 25 is a sequence variant of the ASCL1 fragment (human reference peptide) "VSAAFQAGV" (SEQ ID NO: 590).

In another embodiment, the antigenic peptide according to the present invention is a microbiota sequence variant of a fragment of the tumor antigen ASCL2 (human reference peptide), such as "KLVNLGFQA" (SEQ ID NO: 591) or "ELLDFSSWL" (SEQ ID NO: 592). In another preferred embodiment, the antigenic peptide according to the present invention is a sequence variant of a fragment of the tumor antigen ASCL2, such as antigenic peptides comprising or consisting of an amino acid sequence as set forth in any one of SEQ ID NOs 26-29. More preferably, the antigenic peptide according to the present invention is a sequence variant of the ASCL2 fragment (human reference peptide) "KLVNLGFQA" (SEQ ID NO: 591), such as an antigenic peptide comprising or consisting of an amino acid sequence as set forth in SEQ ID NO: 26 or 27. It is also more preferred that the antigenic peptide according to the present invention is a sequence variant of the ASCL2 fragment (human reference peptide) "ELLDFSSWL" (SEQ ID NO: 592), such as an antigenic peptide comprising or consisting of an amino acid sequence as set forth in SEQ ID NO: 28 or 29.

In another embodiment, the antigenic peptide according to the present invention is a microbiota sequence variant of a fragment of the tumor antigen BIRC5 (human reference peptide), such as "LTLGEFLKL" (SEQ ID NO: 593). In another preferred embodiment, the antigenic peptide according to the present invention is a sequence variant of a fragment of the tumor antigen BIRC5, such as antigenic peptides comprising or consisting of an amino acid sequence as set forth in any one of SEQ ID NOs 30-32. More preferably, the antigenic peptide according to the present invention is a sequence variant of the BIRC5 fragment (human reference peptide) "LTLGEFLKL" (SEQ ID NO: 593), such as an antigenic peptide comprising or consisting of an amino acid sequence as set forth in SEQ ID NO: 30, 31 or 32. Even more preferably, the antigenic peptide comprises or consists of SEQ ID NO: 32.

In another embodiment, the antigenic peptide according to the present invention is a microbiota sequence variant of a fragment of the tumor antigen CA9 (human reference peptide), such as "AAGDILALV" (SEQ ID NO: 594), "ALVFGLLFA" (SEQ ID NO: 595), "FQYEGSLTT" (SEQ ID NO: 596), "HLSTAFARV" (SEQ ID NO: 597), "LSLLLLVPV" (SEQ ID NO: 598), "QLLLSLLLL" (SEQ ID NO: 599) or "VQLLLSLLL" (SEQ ID NO: 600). In another preferred embodiment, the antigenic peptide according to the present invention is a sequence variant of a fragment of the tumor antigen CA9, such as antigenic peptides comprising or consisting of an amino acid sequence as set forth in any one of SEQ ID NOs 33-50. More preferably, the antigenic peptide according to the present invention is a sequence variant of the CA9 fragment (human reference peptide) "AAGDILALV" (SEQ ID NO: 594), such as an antigenic peptide comprising or consisting of an amino acid sequence as set forth in SEQ ID NO: 33 or 34. It is also more preferred that the antigenic peptide according to the present invention is a sequence variant of the CA9 fragment (human reference peptide) "ALVFGLLFA" (SEQ ID NO: 595), such as an antigenic peptide comprising or consisting of an amino acid sequence as set forth in SEQ ID NO: 35, 36 or 37. It is also more preferred that the antigenic peptide according to the present invention is a sequence variant of the CA9 fragment (human reference peptide) "FQYEGSLTT" (SEQ ID NO: 596), such as an antigenic peptide comprising or consisting of an amino acid sequence as set forth in SEQ ID NO: 38. It is also more preferred that the antigenic peptide according to the present invention is a sequence variant of the CA9 fragment (human reference peptide) "HLSTAFARV" (SEQ ID NO: 597), such as an antigenic peptide comprising or consisting of an amino acid sequence as set forth in SEQ ID NO: 39, 40 or 41. It is also more preferred that the antigenic peptide according to the present invention is a sequence variant of the CA9 fragment (human reference peptide) "LSLLLLVPV" (SEQ ID NO: 598), such as an antigenic peptide comprising or consisting of an amino acid sequence as set forth in SEQ ID NO: 42, 43 or 44. It is also more preferred that the antigenic peptide according to the present invention is a sequence variant of the CA9 fragment (human reference peptide) "QLLLSLLLL" (SEQ ID NO: 599), such as an antigenic peptide comprising or consisting of an amino acid sequence as set forth in SEQ ID NO: 45, 46 or 47. It is also more preferred that the antigenic peptide according to the present invention is a sequence variant of the CA9 fragment (human reference peptide) "VQLLLSLLL" (SEQ ID NO: 600), such as an antigenic peptide comprising or consisting of an amino acid sequence as set forth in SEQ ID NO: 48, 49 or 50.

In another embodiment, the antigenic peptide according to the present invention is a microbiota sequence variant of a fragment of the tumor antigen CCNA1 (human reference peptide), such as "NLAKYVAEL" (SEQ ID NO: 601) or "LIAAAAFCL" (SEQ ID NO: 602). In another preferred embodiment, the antigenic peptide according to the present invention is a sequence variant of a fragment of the tumor antigen CCNA1, such as antigenic peptides comprising or consisting of an amino acid sequence as set forth in any one of SEQ ID NOs 51-55. More preferably, the antigenic peptide according to the present invention is a sequence variant of the CCNA1 fragment (human reference peptide) "NLAKYVAEL" (SEQ ID NO: 601), such as an antigenic peptide comprising or consisting of an amino acid sequence as set forth in SEQ ID NO: 51. It is also more preferred that the antigenic peptide according to the present invention is a sequence variant of the CCNA1 fragment (human reference peptide) "LIAAAAFCL" (SEQ ID NO: 602), such as an antigenic peptide comprising or consisting of an amino acid sequence as set forth in SEQ ID NO: 52, 53, 54 or 55.

In another embodiment, the antigenic peptide according to the present invention is a microbiota sequence variant of a fragment of the tumor antigen CCND1 (human reference peptide), such as "LLNDRVLRA" (SEQ ID NO: 603). In another preferred embodiment, the antigenic peptide according to the present invention is a sequence variant of a fragment of the tumor antigen CCND1, such as the antigenic peptide comprising or consisting of an amino acid sequence as set forth in SEQ ID NO: 56. Namely, the antigenic peptide according to the present invention, which comprises or consists of an amino acid sequence as set forth in SEQ ID NO: 56 is a sequence variant of the CCND1 fragment (human reference peptide) "LLNDRVLRA" (SEQ ID NO: 603).

In another embodiment, the antigenic peptide according to the present invention is a microbiota sequence variant of a fragment of the tumor antigen CDH17 (human reference peptide), such as "GILLTTLLV" (SEQ ID NO: 604), "ILAVVFIRI" (SEQ ID NO: 605), "ILLTTLLVI" (SEQ ID NO: 606) or "LVIGIILAV" (SEQ ID NO: 607). In another preferred embodiment, the antigenic peptide according to the present invention is a sequence variant of a fragment of the tumor antigen CDH17, such as antigenic peptides comprising or consisting of an amino acid sequence as set forth in any one of SEQ ID NOs 57-63. More preferably, the antigenic peptide according to the present invention is a sequence variant of the CDH17 fragment (human reference peptide) "GILLTTLLV" (SEQ ID NO: 604), such as an antigenic peptide comprising or consisting of an amino acid sequence as set forth in SEQ ID NO: 57. It is also more preferred that the antigenic peptide according to the present invention is a sequence variant of the CDH17 fragment (human reference peptide) "ILAVVFIRI" (SEQ ID NO: 605), such as an antigenic peptide comprising or consisting of an amino acid sequence as set forth in SEQ ID NO: 58 or 59. It is also more preferred that the antigenic peptide according to the present invention is a sequence variant of the CDH17 fragment (human reference peptide) "ILLTTLLVI" (SEQ ID NO: 606), such as an antigenic peptide comprising or consisting of an amino acid sequence as set forth in SEQ ID NO: 60, 61 or 62.

It is also more preferred that the antigenic peptide according to the present invention is a sequence variant of the CDH17 fragment (human reference peptide) "LVIGIILAV" (SEQ ID NO: 607), such as an antigenic peptide comprising or consisting of an amino acid sequence as set forth in SEQ ID NO: 63.

In another embodiment, the antigenic peptide according to the present invention is a microbiota sequence variant of a fragment of the tumor antigen CDH6 (human reference peptide), such as "ALVAILLCI" (SEQ ID NO: 608), "EMSDVGTFV" (SEQ ID NO: 609), "EMSTYLLPV" (SEQ ID NO: 610), "FLLEEYTGS" (SEQ ID NO: 611), "ILLCIVILL" (SEQ ID NO: 612), or "LLVTVVLFA" (SEQ ID NO: 613). In another preferred embodiment, the antigenic peptide according to the present invention is a sequence variant of a fragment of the tumor antigen CDH6, such as antigenic peptides comprising or consisting of an amino acid sequence as set forth in any one of SEQ ID NOs 64-81. More preferably, the antigenic peptide according to the present invention is a sequence variant of the CDH6 fragment (human reference peptide) "ALVAILLCI" (SEQ ID NO: 608), such as an antigenic peptide comprising or consisting of an amino acid sequence as set forth in SEQ ID NO: 64, 65, 66, 67, 68, 69 or 70. It is also more preferred that the antigenic peptide according to the present invention is a sequence variant of the CDH6 fragment (human reference peptide) "EMSDVGTFV" (SEQ ID NO: 609), such as an antigenic peptide comprising or consisting of an amino acid sequence as set forth in SEQ ID NO: 71. It is also more preferred that the antigenic peptide according to the present invention is a sequence variant of the CDH6 fragment (human reference peptide) "EMSTYLLPV" (SEQ ID NO: 610), such as an antigenic peptide comprising or consisting of an amino acid sequence as set forth in SEQ ID NO: 72. It is also more preferred that the antigenic peptide according to the present invention is a sequence variant of the CDH6 fragment (human reference peptide) "FLLEEYTGS" (SEQ ID NO: 611), such as an antigenic peptide comprising or consisting of an amino acid sequence as set forth in SEQ ID NO: 73. It is also more preferred that the antigenic peptide according to the present invention is a sequence variant of the CDH6 fragment (human reference peptide) "ILLCIVILL" (SEQ ID NO: 612), such as an antigenic peptide comprising or consisting of an amino acid sequence as set forth in SEQ ID NO: 74 or 75. It is also more preferred that the antigenic peptide according to the present invention is a sequence variant of the CDH6 fragment (human reference peptide) "LLVTVVLFA" (SEQ ID NO: 613), such as an antigenic peptide comprising or consisting of an amino acid sequence as set forth in SEQ ID NO: 76, 77, 78, 79, 80 or 81.

In another embodiment, the antigenic peptide according to the present invention is a microbiota sequence variant of a fragment of the tumor antigen CDKN2A (human reference peptide), such as "AVALVLMLL" (SEQ ID NO: 614). In another preferred embodiment, the antigenic peptide according to the present invention is a sequence variant of a fragment of the tumor antigen CDKN2A, such as the antigenic peptide comprising or consisting of an amino acid sequence as set forth in SEQ ID NO: 82. Namely, the antigenic peptide according to the present invention, which comprises or consists of an amino acid sequence as set forth in SEQ ID NO: 82 is a sequence variant of the CDKN2A fragment (human reference peptide) "AVALVLMLL" (SEQ ID NO: 614).

In another embodiment, the antigenic peptide according to the present invention is a microbiota sequence variant of a fragment of the tumor antigen CEACAM5 (human reference peptide), such as "LLTFWNPPT" (SEQ ID NO: 615). In another preferred embodiment, the antigenic peptide according to the present invention is a sequence variant of a fragment of the tumor antigen CEACAM5, such as the antigenic peptide comprising or consisting of an amino acid sequence as set forth in SEQ ID NO: 83. Namely, the antigenic peptide according to the present invention, which comprises or consists of an amino acid sequence as set forth in SEQ ID NO: 83 is a sequence variant of the CEACAM5 fragment (human reference peptide) "LLTFWNPPT" (SEQ ID NO: 615).

In another embodiment, the antigenic peptide according to the present invention is a microbiota sequence variant of a fragment of the tumor antigen CHI3L1 (human reference peptide), such as "KQLLLSAAL" (SEQ ID NO: 616), "LLLSAALSA" (SEQ ID NO: 617), "QLAGAMVWA" (SEQ ID NO: 618), "SQTGFVVLV" (SEQ ID NO: 619) or "TLASSETGV" (SEQ ID NO: 620). In another preferred embodiment, the antigenic peptide according to the present invention is a sequence variant of a fragment of the tumor antigen CHI3L1, such as antigenic peptides comprising or consisting of an amino acid sequence as set forth in any one of SEQ ID NOs 84-114. More preferably, the antigenic peptide according to the present invention is a sequence variant of the CHI3L1 fragment (human reference peptide) "KQLLLSAAL" (SEQ ID NO: 616), such as an antigenic peptide comprising or consisting of an amino acid sequence as set forth in SEQ ID NO: 84 or 85. It is also more preferred that the antigenic peptide according to the present invention is a sequence variant of the CHI3L1 fragment (human reference peptide) "LLLSAALSA" (SEQ ID NO: 617), such as an antigenic peptide comprising or consisting of an amino acid sequence as set forth in SEQ ID NO: 86, 87, 88, 89, 90, 91, 92, 93, 94, 95, 96, 97, 98, 99, 100, 101, 102, 103, 104, 105, 106, 107, 108, or 109. It is also more preferred that the antigenic peptide according to the present invention is a sequence variant of the CHI3L1 fragment (human reference peptide) "QLAGAMVWA" (SEQ ID NO: 618), such as an antigenic peptide comprising or consisting of an amino acid sequence as set forth in SEQ ID NO: 110, 111 or 112. It is also more preferred that the antigenic peptide according to the present invention is a sequence variant of the CHI3L1 fragment (human reference peptide) "SQTGFVVLV" (SEQ ID NO: 619), such as an antigenic peptide comprising or consisting of an amino acid sequence as set forth in SEQ ID NO: 113. It is also more preferred that the antigenic peptide according to the present invention is a sequence variant of the CHI3L1 fragment (human reference peptide) "TLASSETGV" (SEQ ID NO: 620), such as an antigenic peptide comprising or consisting of an amino acid sequence as set forth in SEQ ID NO: 114.

In another embodiment, the antigenic peptide according to the present invention is a microbiota sequence variant of a fragment of the tumor antigen CHI3L2 (human reference peptide), such as "ILLSIGGYL" (SEQ ID NO: 621), "HLIYSFASI" (SEQ ID NO: 622), "VLIHELAEA" (SEQ ID NO: 623), or "SLWAGVVVL" (SEQ ID NO: 624). In another preferred embodiment, the antigenic peptide according to the present invention is a sequence variant of a fragment of the tumor antigen CHI3L2, such as antigenic peptides comprising or consisting of an amino acid sequence as set forth in any one of SEQ ID NOs 115-119. More preferably, the antigenic peptide according to the present invention is a sequence variant of the CHI3L2 fragment (human reference peptide) "ILLSIGGYL" (SEQ ID NO: 621), such as an antigenic peptide comprising or consisting of an amino acid sequence as set forth in SEQ ID NO: 115. It is also more preferred that the antigenic peptide according to the present invention is a sequence variant of the CHI3L2 fragment (human reference peptide) "HLIYSFASI" (SEQ ID NO: 622), such as an antigenic peptide comprising or consisting of an amino acid sequence as set forth in SEQ ID NO: 116. It is also more preferred that the antigenic peptide according to the present invention is a sequence variant of the CHI3L2 fragment (human reference peptide) "VLIHELAEA" (SEQ ID NO: 623), such as an antigenic peptide comprising or consisting of an amino acid sequence as set forth in SEQ ID NO: 117 or 118. It is also more preferred that the antigenic peptide according to the present invention is a sequence variant of the CHI3L2 fragment (human reference peptide) "SLWAGVVVL" (SEQ ID NO: 624), such as an antigenic peptide comprising or consisting of an amino acid sequence as set forth in SEQ ID NO: 119.

In another embodiment, the antigenic peptide according to the present invention is a microbiota sequence variant of a fragment of the tumor antigen COL11A1 (human reference peptide), such as "WLWDFTVTT" (SEQ ID NO: 625). In another preferred embodiment, the antigenic peptide according to the present invention is a sequence variant of a fragment of the tumor antigen COL11A1, such as the antigenic peptide comprising or consisting of an amino acid sequence as set forth in SEQ ID NO: 120. Namely, the antigenic peptide according to the present invention, which comprises or consists of an amino acid sequence as set forth in SEQ ID NO: 120 is a sequence variant of the COL11A1 fragment (human reference peptide) "WLWDFTVTT" (SEQ ID NO: 625).

In another embodiment, the antigenic peptide according to the present invention is a microbiota sequence variant of a fragment of the tumor antigen CT83 (human reference peptide), such as "LLASSILCA" (SEQ ID NO: 626). In another preferred embodiment, the antigenic peptide according to the present invention is a sequence variant of a fragment of the tumor antigen CT83, such as antigenic peptides comprising or consisting of an amino acid sequence as set forth in any one of SEQ ID NOs 121-123. More preferably, the antigenic peptide according to the present invention is a sequence variant of the CT83 fragment (human reference peptide) "LLASSILCA" (SEQ ID NO: 626), such as an antigenic peptide comprising or consisting of an amino acid sequence as set forth in SEQ ID NO: 121, 122 or 123.

In another embodiment, the antigenic peptide according to the present invention is a microbiota sequence variant of a fragment of the tumor antigen CTCFL (human reference peptide), such as "KLAVSLAET" (SEQ ID NO: 627). In another preferred embodiment, the antigenic peptide according to the present invention is a sequence variant of a fragment of the tumor antigen CTCFL, such as the antigenic peptide comprising or consisting of an amino acid sequence as set forth in SEQ ID NO: 124. Namely, the antigenic peptide according to the present invention, which comprises or consists of an amino acid sequence as set forth in SEQ ID NO: 124 is a sequence variant of the CTCFL fragment (human reference peptide) "KLAVSLAET" (SEQ ID NO: 627).

In another embodiment, the antigenic peptide according to the present invention is a microbiota sequence variant of a fragment of the tumor antigen DCT (human reference peptide), such as "ALVGLFVLL" (SEQ ID NO: 628), "GLFVLLAFL" (SEQ ID NO: 629), "SVYDFFVWL" (SEQ ID NO: 630) or "VVMGTLVAL" (SEQ ID NO: 631). In another preferred embodiment, the antigenic peptide according to the present invention is a sequence variant of a fragment of the tumor antigen DCT, such as antigenic peptides comprising or consisting of an amino acid sequence as set forth in any one of SEQ ID NOs 125-132. More preferably, the antigenic peptide according to the present invention is a sequence variant of the DCT fragment (human reference peptide) "ALVGLFVLL" (SEQ ID NO: 628), such as an antigenic peptide comprising or consisting of an amino acid sequence as set forth in SEQ ID NO: 125 or 126. It is also more preferred that the antigenic peptide according to the present invention is a sequence variant of the DCT fragment (human reference peptide) "GLFVLLAFL" (SEQ ID NO: 629), such as an antigenic peptide comprising or consisting of an amino acid sequence as set forth in SEQ ID NO: 127, 128 or 129. It is also more preferred that the antigenic peptide according to the present invention is a sequence variant of the DCT fragment (human reference peptide) "SVYDFFVWL" (SEQ ID NO: 630), such as an antigenic peptide comprising or consisting of an amino acid sequence as set forth in SEQ ID NO: 130. It is also more preferred that the antigenic peptide according to the present invention is a sequence variant of the DCT fragment (human reference peptide) "VVMGTLVAL" (SEQ ID NO: 631), such as an antigenic peptide comprising or consisting of an amino acid sequence as set forth in SEQ ID NO: 131 or 132.

In another embodiment, the antigenic peptide according to the present invention is a microbiota sequence variant of a fragment of the tumor antigen DMRTA2 (human reference peptide), such as "GTAEGLALA" (SEQ ID NO: 632) or "GLAAGLGPA" (SEQ ID NO: 633). In another preferred embodiment, the antigenic peptide according to the present invention is a sequence variant of a fragment of the tumor antigen DMRTA2, such as antigenic peptides comprising or consisting of an amino acid sequence as set forth in any one of SEQ ID NOs 133-134. More preferably, the antigenic peptide according to the present invention is a sequence variant of the DMRTA2 fragment (human reference peptide) "GTAEGLALA" (SEQ ID NO: 632), such as an antigenic peptide comprising or consisting of an amino acid sequence as set forth in SEQ ID NO: 133. It is also more preferred that the antigenic peptide according to the present invention is a sequence variant of the DMRTA2 fragment (human reference peptide) "GLAAGLGPA" (SEQ ID NO: 633), such as an antigenic peptide comprising or consisting of an amino acid sequence as set forth in SEQ ID NO: 134.

In another embodiment, the antigenic peptide according to the present invention is a microbiota sequence variant of a fragment of the tumor antigen EGFR (human reference peptide), such as "ALESILHRI" (SEQ ID NO: 634), "ALLAALCPA" (SEQ ID NO: 635), "ALLALLAAL" (SEQ ID NO: 636), "ILDEAYVMA" (SEQ ID NO: 637), "LLLLLVVAL" (SEQ ID NO: 638), "MVGALLLLL" (SEQ ID NO: 639), "NLQEILHGA" (SEQ ID NO: 640) or "SLAVVSLNI" (SEQ ID NO: 641). In another preferred embodiment, the antigenic peptide according to the present invention is a sequence variant of a fragment of the tumor antigen EGFR, such as antigenic peptides comprising or consisting of an amino acid sequence as set forth in any one of SEQ ID NOs 135-150. More preferably, the antigenic peptide according to the present invention is a sequence variant of the EGFR fragment (human reference peptide) "ALESILHRI" (SEQ ID NO: 634), such as an antigenic peptide comprising or consisting of an amino acid sequence as set forth in SEQ ID NO: 135 or 136. It is also more preferred that the antigenic peptide according to the present invention is a sequence variant of the EGFR fragment (human reference peptide) "ALLAALCPA" (SEQ ID NO: 635), such as an antigenic peptide comprising or consisting of an amino acid sequence as set forth in SEQ ID NO: 137. It is also more preferred that the antigenic peptide according to the present invention is a sequence variant of the EGFR fragment (human reference peptide) "ALLALLAAL" (SEQ ID NO: 636), such as an antigenic peptide comprising or consisting of an amino acid sequence as set forth in SEQ ID NO: 138, 139, 140, 141, 142, 143 or 144. It is also more preferred that the antigenic peptide according to the present invention is a sequence variant of the EGFR fragment (human reference peptide) "ILDEAYVMA" (SEQ ID NO: 637), such as an antigenic peptide comprising or consisting of an amino acid sequence as set forth in SEQ ID NO: 145.

It is also more preferred that the antigenic peptide according to the present invention is a sequence variant of the EGFR fragment (human reference peptide) "LLLLLVVAL" (SEQ ID NO: 638), such as an antigenic peptide comprising or consisting of an amino acid sequence as set forth in SEQ ID NO: 146. It is also more preferred that the antigenic peptide according to the present invention is a sequence variant of the EGFR fragment (human reference peptide) "MVGALLLLL" (SEQ ID NO: 639), such as an antigenic peptide comprising or consisting of an amino acid sequence as set forth in SEQ ID NO: 147. It is also more preferred that the antigenic peptide according to the present invention is a sequence variant of the EGFR fragment (human reference peptide) "NLQEILHGA" (SEQ ID NO: 640), such as an antigenic peptide comprising or consisting of an amino acid sequence as set forth in SEQ ID NO: 148.

It is also more preferred that the antigenic peptide according to the present invention is a sequence variant of the EGFR fragment (human reference peptide) "SLAVVSLNI" (SEQ ID NO: 641), such as an antigenic peptide comprising or consisting of an amino acid sequence as set forth in SEQ ID NO: 149 or 150.

In another embodiment, the antigenic peptide according to the present invention is a microbiota sequence variant of a fragment of the tumor antigen ERBB2 (human reference peptide), such as "AVVGILLVV" (SEQ ID NO: 642), "ILDEAYVMA" (SEQ ID NO: 643), "LLALLPPGA" (SEQ ID NO: 644), "SIISAVVGI" (SEQ ID NO: 645) or "VVLGVVFGI" (SEQ ID NO: 646). In another preferred embodiment, the antigenic peptide according to the present invention is a sequence variant of a fragment of the tumor antigen ERBB2, such as antigenic peptides comprising or consisting of an amino acid sequence as set forth in any one of SEQ ID NOs 151-162. More preferably, the antigenic peptide according to the present invention is a sequence variant of the ERBB2 fragment (human reference peptide) "AVVGILLVV" (SEQ ID NO: 642), such as an antigenic peptide comprising or consisting of an amino acid sequence as set forth in SEQ ID NO: 151, 152, 153 or 154. It is also more preferred that the antigenic peptide according to the present invention is a sequence variant of the ERBB2 fragment (human reference peptide) "ILDEAYVMA" (SEQ ID NO: 643), such as an antigenic peptide comprising or consisting of an amino acid sequence as set forth in SEQ ID NO: 155. It is also more preferred that the antigenic peptide according to the present invention is a sequence variant of the ERBB2 fragment (human reference peptide) "LLALLPPGA" (SEQ ID NO: 644), such as an antigenic peptide comprising or consisting of an amino acid sequence as set forth in SEQ ID NO: 156, 157, 158 or 159. It is also more preferred that the antigenic peptide according to the present invention is a sequence variant of the ERBB2 fragment (human reference peptide) "SIISAVVGI" (SEQ ID NO: 645), such as an antigenic peptide comprising or consisting of an amino acid sequence as set forth in SEQ ID NO: 160. It is also more preferred that the antigenic peptide according to the present invention is a sequence variant of the ERBB2 fragment (human reference peptide) "VVLGVVFGI" (SEQ ID NO: 646), such as an antigenic peptide comprising or consisting of an amino acid sequence as set forth in SEQ ID NO: 161 or 162, in particular an antigenic peptide comprising or consisting of an amino acid sequence as set forth in SEQ ID NO: 162.

In another embodiment, the antigenic peptide according to the present invention is a microbiota sequence variant of a fragment of the tumor antigen ERG (human reference peptide), such as "FLLELLSDS" (SEQ ID NO: 647) or "QLWQFLLEL" (SEQ ID NO: 857). In another preferred embodiment, the antigenic peptide according to the present invention is a sequence variant of a fragment of the tumor antigen ERG, such as antigenic peptides comprising or consisting of an amino acid sequence as set forth in any one of SEQ ID NOs 163-164. More preferably, the antigenic peptide according to the present invention is a sequence variant of the ERG fragment (human reference peptide) "FLLELLSDS" (SEQ ID NO: 647), such as an antigenic peptide comprising or consisting of an amino acid sequence as set forth in SEQ ID NO: 163. It is also more preferred that the antigenic peptide according to the present invention is a sequence variant of the ERG fragment (human reference peptide) "QLWQFLLEL" (SEQ ID NO: 857), such as an antigenic peptide comprising or consisting of an amino acid sequence as set forth in SEQ ID NO: 164.

In another embodiment, the antigenic peptide according to the present invention is a microbiota sequence variant of a fragment of the tumor antigen CDH17 (human reference peptide), such as In another preferred embodiment, the antigenic peptide according to the present invention is a sequence variant of a fragment of the tumor antigen ESR1, such as antigenic peptides comprising or consisting of an amino acid sequence as set forth in any one of SEQ ID NOs 165-192. More preferably, the antigenic peptide according to the present invention is a sequence variant of the ESR1 fragment (human reference peptide) "ALLDAEPPI" (SEQ ID NO: 648), such as an antigenic peptide comprising or consisting of an amino acid sequence as set forth in SEQ ID NO: 165. It is also more preferred that the antigenic peptide according to the present invention is a sequence variant of the ESR1 fragment (human reference peptide) "KITDT-LIHL" (SEQ ID NO: 649), such as an antigenic peptide comprising or consisting of an amino acid sequence as set forth in SEQ ID NO: 166 or 167. It is also more preferred that the antigenic peptide according to the present invention is a sequence variant of the ESR1 fragment (human reference peptide) "KLLFAPNLL" (SEQ ID NO: 650), such as an antigenic peptide comprising or consisting of an amino acid sequence as set forth in SEQ ID NO: 168 or 169. It is also more preferred that the antigenic peptide according to the present invention is a sequence variant of the ESR1 fragment (human reference peptide) "LLDAEPPIL" (SEQ ID NO: 651), such as an antigenic peptide comprising or consisting of an amino acid sequence as set forth in SEQ ID NO: 170. It is also more preferred that the antigenic peptide according to the present invention is a sequence variant of the ESR1 fragment (human reference peptide) "LLNSGVYTF" (SEQ ID NO: 652), such as an antigenic peptide comprising or consisting of an amino acid sequence as set forth in SEQ ID NO: 171 or 172. It is also more preferred that the antigenic peptide according to the present invention is a sequence variant of the ESR1 fragment (human reference peptide) "LMIGLVWRS" (SEQ ID NO: 653), such as an antigenic peptide comprising or consisting of an amino acid sequence as set forth in SEQ ID NO: 173. It is also more preferred that the antigenic peptide according to the present invention is a sequence variant of the ESR1 fragment (human reference peptide) "PLYDLLLEM" (SEQ ID NO: 654), such as an antigenic peptide comprising or consisting of an amino acid sequence as set forth in SEQ ID NO: 174, 175, 176, 177, 178, 179, 180 or 181. It is also more preferred that the antigenic peptide according to the present invention is a sequence variant of the ESR1 fragment (human reference peptide) "QLLLILSHI" (SEQ ID NO: 655), such as an antigenic peptide comprising or consisting of an amino acid sequence as set forth in SEQ ID NO: 182, 183, 184, 185, 186, 187 or 188. It is also more preferred that the antigenic peptide according to the present invention is a sequence variant of the ESR1 fragment (human reference peptide) "RLAQLLLIL" (SEQ ID NO: 656), such as an antigenic peptide comprising or consisting of an amino acid sequence as set forth in SEQ ID NO: 189 or 190. It is also more preferred that the antigenic peptide according to the present invention is a sequence variant of the ESR1 fragment (human reference peptide) "TLIHLMAKA" (SEQ ID NO: 657), such as an antigenic peptide comprising or consisting of an amino acid sequence as set forth in SEQ ID NO: 191. It is also more preferred that the antigenic peptide according to the present invention is a sequence variant of the ESR1 fragment (human reference peptide) "VLD-KITDTL" (SEQ ID NO: 658), such as an antigenic peptide comprising or consisting of an amino acid sequence as set forth in SEQ ID NO: 192.

In another embodiment, the antigenic peptide according to the present invention is a microbiota sequence variant of a fragment of the tumor antigen CDH17 (human reference peptide), such as In another preferred embodiment, the antigenic peptide according to the present invention is a sequence variant of a fragment of the tumor antigen EZH2, such as antigenic peptides comprising or consisting of an amino acid sequence as set forth in any one of SEQ ID NOs 193-194. More preferably, the antigenic peptide according to the present invention is a sequence variant of the EZH2 fragment (human reference peptide) "FMVEDETVL" (SEQ ID NO: 659), such as an antigenic peptide comprising or consisting of an amino acid sequence as set forth in SEQ ID NO: 193. It is also more preferred that the antigenic peptide according to the present invention is a sequence variant of the EZH2 fragment (human reference peptide) "SMFRVLIGT" (SEQ ID NO: 660), such as an antigenic peptide comprising or consisting of an amino acid sequence as set forth in SEQ ID NO: 194.

In another embodiment, the antigenic peptide according to the present invention is a microbiota sequence variant of a fragment of the tumor antigen CDH17 (human reference peptide), such as In another preferred embodiment, the antigenic peptide according to the present invention is a sequence variant of a fragment of the tumor antigen FAP, such as antigenic peptides comprising or consisting of an amino acid sequence as set forth in any one of SEQ ID NOs 195-201. More preferably, the antigenic peptide according to the present invention is a sequence variant of the FAP fragment (human reference peptide) "ATSAVLALL" (SEQ ID NO: 661), such as an antigenic peptide comprising or consisting of an amino acid sequence as set forth in SEQ ID NO: 195, 196 or 197. It is also more preferred that the antigenic peptide according to the present invention is a sequence variant of the FAP fragment (human reference peptide) "TGWAGGFFV" (SEQ ID NO: 662), such as an antigenic peptide comprising or consisting of an amino acid sequence as set forth in SEQ ID NO: 198. It is also more preferred that the antigenic peptide according to the present invention is a sequence variant of the FAP fragment (human reference peptide) "VLALLVMCI" (SEQ ID NO: 663), such as an antigenic peptide comprising or consisting of an amino acid sequence as set forth in SEQ ID NO: 199, 200 or 201.

In another embodiment, the antigenic peptide according to the present invention is a microbiota sequence variant of a fragment of the tumor antigen CDH17 (human reference peptide), such as In another preferred embodiment the antigenic peptide according to the present invention is a sequence variant of a fragment of the tumor antigen FLT1, such as antigenic peptides comprising or consisting of an amino acid sequence as set forth in any one of SEQ ID NOs 202-216. More preferably, the antigenic peptide according to the present invention is a sequence variant of the FLT1 fragment (human reference peptide) "ALLSCLLLT" (SEQ ID NO: 664), such as an antigenic peptide comprising or consisting of an amino acid sequence as set forth in SEQ ID NO: 202, 203, 204, 205, 206, 207 or 208. It is also more preferred that the antigenic peptide according to the present invention is a sequence variant of the FLT1 fragment (human reference peptide) "CVAATLFWL" (SEQ ID NO: 665), such as an antigenic peptide comprising or consisting of an amino acid sequence as set forth in SEQ ID NO: 209. It is also more preferred that the antigenic peptide according to the present invention is a sequence variant of the FLT1 fragment (human reference peptide) "EMYSEIPEI" (SEQ ID NO: 666), such as an antigenic peptide comprising or consisting of an amino acid sequence as set forth in SEQ ID NO: 210. It is also more preferred that the antigenic peptide according to the present invention is a sequence variant of the FLT1 fragment (human reference peptide) "KMAS-TLVVA" (SEQ ID NO: 667), such as an antigenic peptide comprising or consisting of an amino acid sequence as set forth in SEQ ID NO: 211 or 212. It is also more preferred that the antigenic peptide according to the present invention is a sequence variant of the FLT1 fragment (human reference peptide) "SIFDKIYST" (SEQ ID NO: 668), such as an antigenic peptide comprising or consisting of an amino acid sequence as set forth in SEQ ID NO: 213. It is also more preferred that the antigenic peptide according to the present invention is a sequence variant of the FLT1 fragment (human reference peptide) "TLFWLLLTL" (SEQ ID NO: 669), such as an antigenic peptide comprising or consisting of an amino acid sequence as set forth in SEQ ID NO: 214. It is also more preferred that the antigenic peptide according to the present invention is a sequence variant of the FLT1 fragment (human reference peptide) "VLLWEIFSL" (SEQ ID NO: 670), such as an antigenic peptide comprising or consisting of an amino acid sequence as set forth in SEQ ID NO: 215. It is also more preferred that the antigenic peptide according to the present invention is a sequence variant of the FLT1 fragment (human reference peptide) "WLKDGLPAT" (SEQ ID NO: 671), such as an antigenic peptide comprising or consisting of an amino acid sequence as set forth in SEQ ID NO: 216.

In another embodiment, the antigenic peptide according to the present invention is a microbiota sequence variant of a fragment of the tumor antigen CDH17 (human reference peptide), such as In another preferred embodiment, the antigenic peptide according to the present invention is a sequence variant of a fragment of the tumor antigen FOXM1, such as antigenic peptides comprising or consisting of an amino acid sequence as set forth in any one of SEQ ID NOs 217-227 and 861-877, for example as set forth in any one of SEQ ID NOs 217-227. More preferably, the antigenic peptide according to the present invention is a sequence variant of the FOXM1 fragment (human reference peptide) "ILLDISFPG" (SEQ ID NO: 672), such as an antigenic peptide comprising or consisting of an amino acid sequence as set forth in SEQ ID NO: 217 or 218. Further examples of antigenic peptides according to the present invention, which are sequence variants of the FOXM1 fragment (human reference peptide) "ILLDISFPG" (SEQ ID NO: 672), include antigenic peptides comprising or consisting of an amino acid sequence as set forth in SEQ ID NO: 861, 862, 863, 864, 865 or 866. It is also more preferred that the antigenic peptide according to the present invention is a sequence variant of the FOXM1 fragment (human reference peptide) "LLDISFPGL" (SEQ ID NO: 673), such as an antigenic peptide comprising or consisting of an amino acid sequence as set forth in SEQ ID NO: 219. Another example of an antigenic peptide according to the present invention, which is a sequence variant of the FOXM1 fragment (human reference peptide) "LLDISFPGL" (SEQ ID NO: 673), includes antigenic peptides comprising or consisting of an amino acid sequence as set forth in SEQ ID NO: 867. It is also more preferred that the antigenic peptide according to the present invention is a sequence variant of the FOXM1 fragment (human reference peptide) "LMDLSTTPL" (SEQ ID NO: 674), such as an antigenic peptide comprising or consisting of an amino acid sequence as set forth in SEQ ID NO: 220. Another example of an antigenic peptide according to the present invention, which is a sequence variant of the FOXM1 fragment (human reference peptide) "LMDLSTTPL" (SEQ ID NO: 674), includes antigenic peptides comprising or consisting of an amino acid sequence as set forth in SEQ ID NO: 868. It is also more preferred that the antigenic peptide according to the present invention is a sequence variant of the FOXM1 fragment (human reference peptide) "RVSSYLVPI" (SEQ ID NO: 675), such as an antigenic peptide comprising or consisting of an amino acid sequence as set forth in SEQ ID NO: 221, 222 or 223. Further examples of antigenic peptides according to the present invention, which are sequence variants of the FOXM1 fragment (human reference peptide) "RVSSYLVPI" (SEQ ID NO: 675), include antigenic peptides comprising or consisting of an amino acid sequence as set forth in SEQ ID NO: 869, 870 or 871. It is also more preferred that the antigenic peptide according to the present invention is a sequence variant of the FOXM1 fragment (human reference peptide) "SLSKILLDI" (SEQ ID NO: 676), such as an antigenic peptide comprising or consisting of an amino acid sequence as set forth in SEQ ID NO: 224. It is also more preferred that the antigenic peptide according to the present invention is a sequence variant of the FOXM1 fragment (human reference peptide) "SQLSYSQEV" (SEQ ID NO: 677), such as an antigenic peptide comprising or consisting of an amino acid sequence as set forth in SEQ ID NO: 225 or 226. It is also more preferred that the antigenic peptide according to the present invention is a sequence variant of the FOXM1 fragment (human reference peptide) "WAAELPFPA" (SEQ ID NO: 678), such as an antigenic peptide comprising or consisting of an amino acid sequence as set forth in SEQ ID NO: 227. It is also more preferred that the antigenic peptide according to the present invention is a sequence variant of the FOXM1 fragment (human reference peptide) "NLSLHDMFV" (SEQ ID NO: 888), such as an antigenic peptide comprising or consisting of an amino acid sequence as set forth in SEQ ID NO: 872. It is also more preferred that the antigenic peptide according to the present invention is a sequence variant of the FOXM1 fragment (human reference peptide) "KMKPLLPRV" (SEQ ID NO: 889), such as an antigenic peptide comprising or consisting of an amino acid sequence as set forth in SEQ ID NO: 873 or 874. It is also more preferred that the antigenic peptide according to the present invention is a sequence variant of the FOXM1 fragment (human reference peptide) "YLVPIQFPV" (SEQ ID NO: 890), such as an antigenic peptide comprising or consisting of an amino acid sequence as set forth in SEQ ID NO: 875 or 876. It is also more preferred that the antigenic peptide according to the present invention is a sequence variant of the FOXM1 fragment (human reference peptide) "YMAMIQFAI" (SEQ ID NO: 891), such as an antigenic peptide comprising or consisting of an amino acid sequence as set forth in SEQ ID NO: 877. Even more preferably, the antigenic peptide comprises or consists of SEQ ID NO: 32.

In another embodiment, the antigenic peptide according to the present invention is a microbiota sequence variant of a fragment of the tumor antigen CDH17 (human reference peptide), such as In another preferred embodiment, the antigenic peptide according to the present invention is a sequence variant of a fragment of the tumor antigen FSIP1, such as antigenic peptides comprising or consisting of an amino acid sequence as set forth in any one of SEQ ID NOs 228-231. More preferably, the antigenic peptide according to the present invention is a sequence variant of the FSIP1 fragment (human reference peptide) "LLNESETKV" (SEQ ID NO: 679), such as an antigenic peptide comprising or consisting of an amino acid sequence as set forth in SEQ ID NO: 228. It is also more preferred that the antigenic peptide according to the present invention is a sequence variant of the FSIP1 fragment (human reference peptide) "RLVELLKDL" (SEQ ID NO: 680), such as an antigenic peptide comprising or consisting of an amino acid sequence as set forth in SEQ ID NO: 229, 230 or 231.

In another embodiment, the antigenic peptide according to the present invention is a microbiota sequence variant of a fragment of the tumor antigen GAL3ST1 (human reference peptide), such as "GLASTPEA" (SEQ ID NO: 681) or "RMAREVAAL" (SEQ ID NO: 682). In another preferred embodiment, the antigenic peptide according to the present invention is a sequence variant of a fragment of the tumor antigen GAL3ST1, such as antigenic peptides comprising or consisting of an amino acid sequence as set forth in any one of SEQ ID NOs 232-234. More preferably, the antigenic peptide according to the present invention is a sequence variant of the GAL3ST1 fragment (human reference peptide) "GLASTTPEA" (SEQ ID NO: 681), such as an antigenic peptide comprising or consisting of an amino acid sequence as set forth in SEQ ID NO: 232. It is also more preferred that the antigenic peptide according to the present invention is a sequence variant of the GAL3ST1 fragment (human reference peptide) "RMAREVAAL" (SEQ ID NO: 682), such as an antigenic peptide comprising or consisting of an amino acid sequence as set forth in SEQ ID NO: 233 or 234.

In another embodiment, the antigenic peptide according to the present invention is a microbiota sequence variant of a fragment of the tumor antigen GPR143 (human reference peptide), such as "FLLSLAFYG" (SEQ ID NO: 683), "ILNPAQGFL" (SEQ ID NO: 684), "MAWGLATLL" (SEQ ID NO: 685) or "RLALGLLQL" (SEQ ID NO: 686). In another preferred embodiment, the antigenic peptide according to the present invention is a sequence variant of a fragment of the tumor antigen GPR143, such as antigenic peptides comprising or consisting of an amino acid sequence as set forth in any one of SEQ ID NOs 235-247. More preferably, the antigenic peptide according to the present invention is a sequence variant of the GPR143 fragment (human reference peptide) "FLLSLAFYG" (SEQ ID NO: 683), such as an antigenic peptide comprising or consisting of an amino acid sequence as set forth in SEQ ID NO: 235, 236 or 237. It is also more preferred that the antigenic peptide according to the present invention is a sequence variant of the GPR143 fragment (human reference peptide) "ILNPAQGFL" (SEQ ID NO: 684), such as an antigenic peptide comprising or consisting of an amino acid sequence as set forth in SEQ ID NO: 238. It is also more preferred that the antigenic peptide according to the present invention is a sequence variant of the GPR143 fragment (human reference peptide) "MAWGLATLL" (SEQ ID NO: 685), such as an antigenic peptide comprising or consisting of an amino acid sequence as set forth in SEQ ID NO: 239. It is also more preferred that the antigenic peptide according to the present invention is a sequence variant of the GPR143 fragment (human reference peptide) "RLALGLLQL" (SEQ ID NO: 686), such as an antigenic peptide comprising or consisting of an amino acid sequence as set forth in SEQ ID NO: 240, 241, 242, 243, 245, 246 or 247.

In another embodiment, the antigenic peptide according to the present invention is a microbiota sequence variant of a fragment of the tumor antigen HES6 (human reference peptide), such as "RLLLAGAEV" (SEQ ID NO: 687). In another preferred embodiment, the antigenic peptide according to the present invention is a sequence variant of a fragment of the tumor antigen HES6, such as the antigenic peptide comprising or consisting of an amino acid sequence as set forth in SEQ ID NO: 248. Namely, the antigenic peptide according to the present invention, which comprises or consists of an amino acid sequence as set forth in SEQ ID NO: 248 is a sequence variant of the HES6 fragment (human reference peptide) "RLLLAGAEV" (SEQ ID NO: 687).

In another embodiment, the antigenic peptide according to the present invention is a microbiota sequence variant of a fragment of the tumor antigen CDH17 (human reference peptide), such as In another preferred embodiment, the antigenic peptide according to the present invention is a sequence variant of a fragment of the tumor antigen IL13RA2, such as antigenic peptides comprising or consisting of an amino acid sequence as set forth in any one of SEQ ID NOs 249-255. More preferably, the antigenic peptide according to the present invention is a sequence variant of the IL13RA2 fragment (human reference peptide) "CLYTFLIST" (SEQ ID NO: 688), such as an antigenic peptide comprising or consisting of an amino acid sequence as set forth in SEQ ID NO: 249, 250 or 251. It is also more preferred that the antigenic peptide according to the present invention is a sequence variant of the IL13RA2 fragment (human reference peptide) "FLISTTFGC" (SEQ ID NO: 689), such as an antigenic peptide comprising or consisting of an amino acid sequence as set forth in SEQ ID NO: 252. It is also more preferred that the antigenic peptide according to the present invention is a sequence variant of the IL13RA2 fragment (human reference peptide) "VLLDTNYNL" (SEQ ID NO: 690), such as an antigenic peptide comprising or consisting of an amino acid sequence as set forth in SEQ ID NO: 253. It is also more preferred that the antigenic peptide according to the present invention is a sequence variant of the IL13RA2 fragment (human reference peptide) "WLPFGFIL1" (SEQ ID NO: 691) or "WLPFGFILIL" (SEQ ID NO: 692), such as an antigenic peptide comprising or consisting of an amino acid sequence as set forth in SEQ ID NO: 254 or 255, in particular an antigenic peptide comprising or consisting of an amino acid sequence as set forth in SEQ ID NO: 255. Further examples of antigenic peptides according to the present invention, which are sequence variants of the IL13RA2 fragment (human reference peptide) "WLPFGFILIL" (SEQ ID NO: 692), include antigenic peptides comprising or consisting of an amino acid sequence as set forth in SEQ ID NO: 878 or 879. It is also more preferred that the antigenic peptide according to the present invention is a sequence variant of the IL13RA2 fragment (human reference peptide) "FLISTTFGCT" (SEQ ID NO: 892), such as an antigenic peptide comprising or consisting of an amino acid sequence as set forth in SEQ ID NO: 880, 881 or 882. It is also more preferred that the antigenic peptide according to the present invention is a sequence variant of the IL13RA2 fragment (human reference peptide) "YLYLQWQPPL" (SEQ ID NO: 893), such as an antigenic peptide comprising or consisting of an amino acid sequence as set forth in SEQ ID NO: 883. It is also more preferred that the antigenic peptide according to the present invention is a sequence variant of the IL13RA2 fragment (human reference peptide) "GVLLDTNYNL" (SEQ ID NO: 894), such as an antigenic peptide comprising or consisting of an amino acid sequence as set forth in SEQ ID NO: 884 or 885. It is also more preferred that the antigenic peptide according to the present invention is a sequence variant of the IL13RA2 fragment (human reference peptide) "FQLQNIVKPL" (SEQ ID NO: 895), such as an antigenic peptide comprising or consisting of an amino acid sequence as set forth in SEQ ID NO: 886 or 887. Even more preferably, the antigenic peptide comprises or consists of SEQ ID NO: 255.

In another embodiment, the antigenic peptide according to the present invention is a microbiota sequence variant of a fragment of the tumor antigen KISS1R (human reference peptide), such as "ALYLLPLLA" (SEQ ID NO: 693), "FALYNLLAL" (SEQ ID NO: 694), "QLFLVLQAL" (SEQ ID NO: 695), "RLVAAVVLL" (SEQ ID NO: 696), "VLAERAGAV" (SEQ ID NO: 697), "WLVPLFFAA" (SEQ ID NO: 698) or "YLLPLLATC" (SEQ ID NO: 699). In another preferred embodiment, the antigenic peptide according to the present invention is a sequence variant of a fragment of the tumor antigen KISS1R, such as antigenic peptides comprising or consisting of an amino acid sequence as set forth in any one of SEQ ID NOs 256-287. More preferably, the antigenic peptide according to the present invention is a sequence variant of the KISS1R fragment (human reference peptide) "ALYLLPLLA" (SEQ ID NO: 693), such as an antigenic peptide comprising or consisting of an amino acid sequence as set forth in SEQ ID NO: 256, 257 or 258. It is also more preferred that the antigenic peptide according to the present invention is a sequence variant of the KISS1R fragment (human reference peptide) "FALYNLLAL" (SEQ ID NO: 694), such as an antigenic peptide comprising or consisting of an amino acid sequence as set forth in SEQ ID NO: 259, 260 or 261. It is also more preferred that the antigenic peptide according to the present invention is a sequence variant of the KISS1R fragment (human reference peptide) "QLFLVLQAL" (SEQ ID NO: 695), such as an antigenic peptide comprising or consisting of an amino acid sequence as set forth in SEQ ID NO: 262. It is also more preferred that the antigenic peptide according to the present invention is a sequence variant of the KISS1R fragment (human reference peptide) "RLVAAVVLL" (SEQ ID NO: 696), such as an antigenic peptide comprising or consisting of an amino acid sequence as set forth in SEQ ID NO: 263. It is also more preferred that the antigenic peptide according to the present invention is a sequence variant of the KISS1R fragment (human reference peptide) "VLAERAGAV" (SEQ ID NO: 697), such as an antigenic peptide comprising or consisting of an amino acid sequence as set forth in SEQ ID NO: 264. It is also more preferred that the antigenic peptide according to the present invention is a sequence variant of the KISS1R fragment (human reference peptide) "WLVPLFFAA" (SEQ ID NO: 698), such as an antigenic peptide comprising or consisting of an amino acid sequence as set forth in SEQ ID NO: 266, 267, 268 or 269. It is also more preferred that the antigenic peptide according to the present invention is a sequence variant of the KISS1R fragment (human reference peptide) "YLLPLLATC" (SEQ ID NO: 699), such as an antigenic peptide comprising or consisting of an amino acid sequence as set forth in SEQ ID NO: 270, 271, 272, 273, 274, 275, 276, 277, 278, 279, 280, 281, 282, 283, 284, 285, 286 or 287.

In another embodiment, the antigenic peptide according to the present invention is a microbiota sequence variant of a fragment of the tumor antigen KLHDC8A (human reference peptide), such as "GLSDAVEAL" (SEQ ID NO: 700) or "MLREAAMGI" (SEQ ID NO: 701). In another preferred embodiment, the antigenic peptide according to the present invention is a sequence variant of a fragment of the tumor antigen KLHDC8A, such as antigenic peptides comprising or consisting of an amino acid sequence as set forth in any one of SEQ ID NOs 288-289. More preferably, the antigenic peptide according to the present invention is a sequence variant of the KLHDC8A fragment (human reference peptide) "GLSDAVEAL" (SEQ ID NO: 700), such as an antigenic peptide comprising or consisting of an amino acid sequence as set forth in SEQ ID NO: 288. It is also more preferred that the antigenic peptide according to the present invention is a sequence variant of the KLHDC8A fragment (human reference peptide) "MLREAAMGI" (SEQ ID NO: 701), such as an antigenic peptide comprising or consisting of an amino acid sequence as set forth in SEQ ID NO: 289.

In another embodiment, the antigenic peptide according to the present invention is a microbiota sequence variant of a fragment of the tumor antigen KLHL14 (human reference peptide), such as "ALIPAPELV" (SEQ ID NO: 702), "NLLHGLNLL" (SEQ ID NO: 703) or "YVSSLPQPL" (SEQ ID NO: 704). In another preferred embodiment, the antigenic peptide according to the present invention is a sequence variant of a fragment of the tumor antigen KLHL14, such as antigenic peptides comprising or consisting of an amino acid sequence as set forth in any one of SEQ ID NOs 290-292. More preferably, the antigenic peptide according to the present invention is a sequence variant of the KLHL14 fragment (human reference peptide) "ALIPAPELV" (SEQ ID NO: 702), such as an antigenic peptide comprising or consisting of an amino acid sequence as set forth in SEQ ID NO: 290. It is also more preferred that the antigenic peptide according to the present invention is a sequence variant of the KLHL14 fragment (human reference peptide) "NLLHGLNLL" (SEQ ID NO: 703), such as an antigenic peptide comprising or consisting of an amino acid sequence as set forth in SEQ ID NO: 291. It is also more preferred that the antigenic peptide according to the present invention is a sequence variant of the KLHL14 fragment (human reference peptide) "YVSSLPQPL" (SEQ ID NO: 704), such as an antigenic peptide comprising or consisting of an amino acid sequence as set forth in SEQ ID NO: 292.

In another embodiment, the antigenic peptide according to the present invention is a microbiota sequence variant of a fragment of the tumor antigen KLK4 (human reference peptide), such as "YLILGVAGS" (SEQ ID NO: 705). In another preferred embodiment, the antigenic peptide according to the present invention is a sequence variant of a fragment of the tumor antigen KLK4, such as antigenic peptides comprising or consisting of an amino acid sequence as set forth in any one of SEQ ID NOs 293-296. More preferably, the antigenic peptide according to the present invention is a sequence variant of the KLK4 fragment (human reference peptide) "YLILGVAGS" (SEQ ID NO: 705), such as an antigenic peptide comprising or consisting of an amino acid sequence as set forth in SEQ ID NO: 293, 294, 295 or 296.

In another embodiment, the antigenic peptide according to the present invention is a microbiota sequence variant of a fragment of the tumor antigen KRT81 (human reference peptide), such as "NMDCIIAEI" (SEQ ID NO: 706). In another preferred embodiment, the antigenic peptide according to the present invention is a sequence variant of a fragment of the tumor antigen KRT81, such as the antigenic peptide comprising or consisting of an amino acid sequence as set forth in SEQ ID NO: 297. Namely, the antigenic peptide according to the present invention, which comprises or consists of an amino acid sequence as set forth in SEQ ID NO: 297 is a sequence variant of the KRT81 fragment (human reference peptide) "NMDCIIAEI" (SEQ ID NO: 706).

In another embodiment, the antigenic peptide according to the present invention is a microbiota sequence variant of a fragment of the tumor antigen LEMD1 (human reference peptide), such as "AVLGIFIIV" (SEQ ID NO: 707) or "KLAVLGIFI" (SEQ ID NO: 708). In another preferred embodiment, the antigenic peptide according to the present invention is a sequence variant of a fragment of the tumor antigen LEMD1, such as antigenic peptides comprising or consisting of an amino acid sequence as set forth in any one of SEQ ID NOs 298-299. More preferably, the antigenic peptide according to the present invention is a sequence variant of the LEMD1 fragment (human reference peptide) "AVLGIFIIV" (SEQ ID NO: 707), such as an antigenic peptide comprising or consisting of an amino acid sequence as set forth in SEQ ID NO: 298. It is also more preferred that the antigenic peptide according to the present invention is a sequence variant of the LEMD1 fragment (human reference peptide) "KLAVLGIFI" (SEQ ID NO: 708), such as an antigenic peptide comprising or consisting of an amino acid sequence as set forth in SEQ ID NO: 299.

In another embodiment, the antigenic peptide according to the present invention is a microbiota sequence variant of a fragment of the tumor antigen LRRC15 (human reference peptide), such as "AIAAIVIGI" (SEQ ID NO: 709), ALACSLAAC" (SEQ ID NO: 710), "IVIGIVALA" (SEQ ID NO: 711), "RIVAVPTPL" (SEQ ID NO: 712) or "SLKELSPGI" (SEQ ID NO: 713). In another preferred embodiment, the antigenic peptide according to the present invention is a sequence variant of a fragment of the tumor antigen LRRC15, such as antigenic peptides comprising or consisting of an amino acid sequence as set forth in any one of SEQ ID NOs 300-307. More preferably, the antigenic peptide according to the present invention is a sequence variant of the LRRC15 fragment (human reference peptide) "AIAAIVIGI" (SEQ ID NO: 709), such as an antigenic peptide comprising or consisting of an amino acid sequence as set forth in SEQ ID NO: 300. It is also more preferred that the antigenic peptide according to the present invention is a sequence variant of the LRRC15 fragment (human reference peptide) "ALACSLAAC" (SEQ ID NO: 710), such as an antigenic peptide comprising or consisting of an amino acid sequence as set forth in SEQ ID NO: 301. It is also more preferred that the antigenic peptide according to the present invention is a sequence variant of the LRRC15 fragment (human reference peptide) "IVIGIVALA" (SEQ ID NO: 711), such as an antigenic peptide comprising or consisting of an amino acid sequence as set forth in SEQ ID NO: 302. It is also more preferred that the antigenic peptide according to the present invention is a sequence variant of the LRRC15 fragment (human reference peptide) "RIVAVPTPL" (SEQ ID NO: 712), such as an antigenic peptide comprising or consisting of an amino acid sequence as set forth in SEQ ID NO: 303, 304 or 305. It is also more preferred that the antigenic peptide according to the present invention is a sequence variant of the LRRC15 fragment (human reference peptide) "SLKELSPGI" (SEQ ID NO: 713), such as an antigenic peptide comprising or consisting of an amino acid sequence as set forth in SEQ ID NO: 306 or 307.

In another embodiment, the antigenic peptide according to the present invention is a microbiota sequence variant of a fragment of the tumor antigen MAGEA1 (human reference peptide), such as "KVADLVGFL" (SEQ ID NO: 714) or "LVLGTLEEV" (SEQ ID NO: 858). In another preferred embodiment, the antigenic peptide according to the present invention is a sequence variant of a fragment of the tumor antigen MAGEA1, such as antigenic peptides comprising or consisting of an amino acid sequence as set forth in any one of SEQ ID NOs 308-309. More preferably, the antigenic peptide according to the present invention is a sequence variant of the MAGEA1 fragment (human reference peptide) "KVADLVGFL" (SEQ ID NO: 714), such as an antigenic peptide comprising or consisting of an amino acid sequence as set forth in SEQ ID NO: 308. It is also more preferred that the antigenic peptide according to the present invention is a sequence variant of the MAGEA1 fragment (human reference peptide) "LVLGTLEEV" (SEQ ID NO: 858), such as an antigenic peptide comprising or consisting of an amino acid sequence as set forth in SEQ ID NO: 309.

In another embodiment, the antigenic peptide according to the present invention is a microbiota sequence variant of a fragment of the tumor antigen MAGEA4 (human reference peptide), such as "AVSSSSPLV" (SEQ ID NO: 722), "KVDELAHFL" (SEQ ID NO: 723) or "KVLEHVVRV" (SEQ ID NO: 724). In another preferred embodiment, the antigenic peptide according to the present invention is a sequence variant of a fragment of the tumor antigen MAGEA4, such as antigenic peptides comprising or consisting of an amino acid sequence as set forth in any one of SEQ ID NOs 320-322. More preferably, the antigenic peptide according to the present invention is a sequence variant of the MAGEA4 fragment (human reference peptide) "AVSSSSPLV" (SEQ ID NO: 722), such as an antigenic peptide comprising or consisting of an amino acid sequence as set forth in SEQ ID NO: 320. It is also more preferred that the antigenic peptide according to the present invention is a sequence variant of the MAGEA4 fragment (human reference peptide) "KVDELAHFL" (SEQ ID NO: 723), such as an antigenic peptide comprising or consisting of an amino acid sequence as set forth in SEQ ID NO: 321. It is also more preferred that the antigenic peptide according to the present invention is a sequence variant of the MAGEA4 fragment (human reference peptide) "KVLEHVVRV" (SEQ ID NO: 724), such as an antigenic peptide comprising or consisting of an amino acid sequence as set forth in SEQ ID NO: 322.

In another embodiment, the antigenic peptide according to the present invention is a microbiota sequence variant of a fragment of the tumor antigen MAGEA10 (human reference peptide), such as "GMLSDVQSM" (SEQ ID NO: 715) or "ILILILSIV" (SEQ ID NO: 716). In another preferred embodiment, the antigenic peptide according to the present invention is a sequence variant of a fragment of the tumor antigen MAGEA10, such as antigenic peptides comprising or consisting of an amino acid sequence as set forth in any one of SEQ ID NOs 310-313. More preferably, the antigenic peptide according to the present invention is a sequence variant of the MAGEA10 fragment (human reference peptide) "GMLSDVQSM" (SEQ ID NO: 715), such as an antigenic peptide comprising or consisting of an amino acid sequence as set forth in SEQ ID NO: 310 or 311. It is also more preferred that the antigenic peptide according to the present invention is a sequence variant of the MAGEA10 fragment (human reference peptide) "ILILILSIV" (SEQ ID NO: 716), such as an antigenic peptide comprising or consisting of an amino acid sequence as set forth in SEQ ID NO: 312 or 313.

In another embodiment, the antigenic peptide according to the present invention is a microbiota sequence variant of a fragment of the tumor antigen MAGEA11 (human reference peptide), such as "AMDAIFGSL" (SEQ ID NO: 717), "GLITKAEML" (SEQ ID NO: 718), "GTLEELPAA" (SEQ ID NO: 719) or "KVLEYIANA" (SEQ ID NO: 720). In another preferred embodiment, the antigenic peptide according to the present invention is a sequence variant of a fragment of the tumor antigen MAGEA11, such as antigenic peptides comprising or consisting of an amino acid sequence as set forth in any one of SEQ ID NOs 314-318. More preferably, the antigenic peptide according to the present invention is a sequence variant of the MAGEA11 fragment (human reference peptide) "AMDAIFGSL" (SEQ ID NO: 717), such as an antigenic peptide comprising or consisting of an amino acid sequence as set forth in SEQ ID NO: 314. It is also more preferred that the antigenic peptide according to the present invention is a sequence variant of the MAGEA11 fragment (human reference peptide) "GLITKAEML" (SEQ ID NO: 718), such as an antigenic peptide comprising or consisting of an amino acid sequence as set forth in SEQ ID NO: 315. It is also more preferred that the antigenic peptide according to the present invention is a sequence variant of the MAGEA11 fragment (human reference peptide) "GTLEELPAA" (SEQ ID NO: 719), such as an antigenic peptide comprising or consisting of an amino acid sequence as set forth in SEQ ID NO: 316 or 317. It is also more preferred that the antigenic peptide according to the present invention is a sequence variant of the MAGEA11 fragment (human reference peptide) "KVLEYIANA" (SEQ ID NO: 720), such as an antigenic peptide comprising or consisting of an amino acid sequence as set forth in SEQ ID NO: 318.

In another embodiment, the antigenic peptide according to the present invention is a microbiota sequence variant of a fragment of the tumor antigen MAGEA12 (human reference peptide), such as "QLVFGIEVV" (SEQ ID NO: 721). In another preferred embodiment, the antigenic peptide according to the present invention is a sequence variant of a fragment of the tumor antigen MAGEA12, such as the antigenic peptide comprising or consisting of an amino acid sequence as set forth in SEQ ID NO: 319. Namely, the antigenic peptide according to the present invention, which comprises or consists of an amino acid sequence as set forth in SEQ ID NO: 319 is a sequence variant of the MAGEA12 fragment (human reference peptide) "QLVFGIEVV" (SEQ ID NO: 721).

In another embodiment, the antigenic peptide according to the present invention is a microbiota sequence variant of a fragment of the tumor antigen MLANA (human reference peptide), such as "VILGVLLLI" (SEQ ID NO: 725). In another preferred embodiment, the antigenic peptide according to the present invention is a sequence variant of a fragment of the tumor antigen MLANA, such as antigenic peptides comprising or consisting of an amino acid sequence as set forth in any one of SEQ ID NOs 323-334. More preferably, the antigenic peptide according to the present invention is a sequence variant of the MLANA fragment (human reference peptide) "VILGVLLLI" (SEQ ID NO: 725), such as an antigenic peptide comprising or consisting of an amino acid sequence as set forth in SEQ ID NO: 323, 324, 325, 326, 327, 328, 329, 330, 331, 332, 333 or 334.

In another embodiment, the antigenic peptide according to the present invention is a microbiota sequence variant of a fragment of the tumor antigen NKX2-1 (human reference peptide), such as "MTAAGVPQL" (SEQ ID NO: 726) or "SVSDILSPL" (SEQ ID NO: 727). In another preferred embodiment, the antigenic peptide according to the present invention is a sequence variant of a fragment of the tumor antigen NKX2-1, such as antigenic peptides comprising or consisting of an amino acid sequence as set forth in any one of SEQ ID NOs 335-340. More preferably, the antigenic peptide according to the present invention is a sequence variant of the NKX2-1 fragment (human reference peptide) "MTAAGVPQL" (SEQ ID NO: 726), such as an antigenic peptide comprising or consisting of an amino acid sequence as set forth in SEQ ID NO: 335. It is also more preferred that the antigenic peptide according to the present invention is a sequence variant of the NKX2-1 fragment (human reference peptide) "SVSDILSPL" (SEQ ID NO: 727), such as an antigenic peptide comprising or consisting of an amino acid sequence as set forth in SEQ ID NO: 336, 337, 338, 339 or 340.

In another embodiment, the antigenic peptide according to the present invention is a microbiota sequence variant of a fragment of the tumor antigen NPTX2 (human reference peptide), such as ALLAASVAL" (SEQ ID NO: 728), "LLAASVALA" (SEQ ID NO: 729), "QLLRKVAEL" (SEQ ID NO: 730), "TLPELYAFT" (SEQ ID NO: 731) or "YLYGKIKKT" (SEQ ID NO: 732). In another preferred embodiment, the antigenic peptide according to the present invention is a sequence variant of a fragment of the tumor antigen NPTX2, such as antigenic peptides comprising or consisting of an amino acid sequence as set forth in any one of SEQ ID NOs 341-351. More preferably, the antigenic peptide according to the present invention is a sequence variant of the NPTX2 fragment (human reference peptide) "ALLAASVAL" (SEQ ID NO: 728), such as an antigenic peptide comprising or consisting of an amino acid sequence as set forth in SEQ ID NO: 341, 342, 343 or 344. It is also more preferred that the antigenic peptide according to the present invention is a sequence variant of the NPTX2 fragment (human reference peptide) "LLAASVALA" (SEQ ID NO: 729), such as an antigenic peptide comprising or consisting of an amino acid sequence as set forth in SEQ ID NO: 345, 346, 347 or 348. It is also more preferred that the antigenic peptide according to the present invention is a sequence variant of the NPTX2 fragment (human reference peptide) "QLLRKVAEL" (SEQ ID NO: 730), such as an antigenic peptide comprising or consisting of an amino acid sequence as set forth in SEQ ID NO: 349. It is also more preferred that the antigenic peptide according to the present invention is a sequence variant of the NPTX2 fragment (human reference peptide) "TLPELYAFT" (SEQ ID NO: 731), such as an antigenic peptide comprising or consisting of an amino acid sequence as set forth in SEQ ID NO: 350. It is also more preferred that the antigenic peptide according to the present invention is a sequence variant of the NPTX2 fragment (human reference peptide) "YLYGKIKKT" (SEQ ID NO: 732), such as an antigenic peptide comprising or consisting of an amino acid sequence as set forth in SEQ ID NO: 351.

In another embodiment, the antigenic peptide according to the present invention is a microbiota sequence variant of a fragment of the tumor antigen CDH17 (human reference peptide), such as In another preferred embodiment, the antigenic peptide according to the present invention is a sequence variant of a fragment of the tumor antigen PAGE3, such as antigenic peptides comprising or consisting of an amino acid sequence as set forth in any one of SEQ ID NOs 352-354. More preferably, the antigenic peptide according to the present invention is a sequence variant of the PAGE3 fragment (human reference peptide) "QVLGLAAYL" (SEQ ID NO: 733), such as an antigenic peptide comprising or consisting of an amino acid sequence as set forth in SEQ ID NO: 352, 353 or 354.

In another embodiment, the antigenic peptide according to the present invention is a microbiota sequence variant of a fragment of the tumor antigen CDH17 (human reference peptide), such as In another preferred embodiment, the antigenic peptide according to the present invention is a sequence variant of a fragment of the tumor antigen PAX2, such as antigenic peptides comprising or consisting of an amino acid sequence as set forth in any one of SEQ ID NOs 355-358. More preferably, the antigenic peptide according to the present invention is a sequence variant of the PAX2 fragment (human reference peptide) "GLDEVKSSL" (SEQ ID NO: 734), such as an antigenic peptide comprising or consisting of an amino acid sequence as set forth in SEQ ID NO: 355, 356, 357 or 358.

In another embodiment, the antigenic peptide according to the present invention is a microbiota sequence variant of a fragment of the tumor antigen CDH17 (human reference peptide), such as In another preferred embodiment, the antigenic peptide according to the present invention is a sequence variant of a fragment of the tumor antigen PCDHB16, such as antigenic peptides comprising or consisting of an amino acid sequence as set forth in any one of SEQ ID NOs 359-365. More preferably, the antigenic peptide according to the present invention is a sequence variant of the PCDHB16 fragment (human reference peptide) "FVLLSLSGA" (SEQ ID NO: 735), such as an antigenic peptide comprising or consisting of an amino acid sequence as set forth in SEQ ID NO: 359. It is also more preferred that the antigenic peptide according to the present invention is a sequence variant of the PCDHB16 fragment (human reference peptide) "SLFLFSVLL" (SEQ ID NO: 736), such as an antigenic peptide comprising or consisting of an amino acid sequence as set forth in SEQ ID NO: 360. It is also more preferred that the antigenic peptide according to the present invention is a sequence variant of the PCDHB16 fragment (human reference peptide) "SLTVYLVVA" (SEQ ID NO: 737), such as an antigenic peptide comprising or consisting of an amino acid sequence as set forth in SEQ ID NO: 361. It is also more preferred that the antigenic peptide according to the present invention is a sequence variant of the PCDHB16 fragment (human reference peptide) "VLLFVA-VRL" (SEQ ID NO: 738), such as an antigenic peptide comprising or consisting of an amino acid sequence as set forth in SEQ ID NO: 362, 363 or 364. It is also more preferred that the antigenic peptide according to the present invention is a sequence variant of the PCDHB16 fragment (human reference peptide) "VSSLFLFSV" (SEQ ID NO: 739), such as an antigenic peptide comprising or consisting of an amino acid sequence as set forth in SEQ ID NO: 365.

In another embodiment, the antigenic peptide according to the present invention is a microbiota sequence variant of a fragment of the tumor antigen PIWIL1 (human reference peptide), such as "SIAGFVASI" (SEQ ID NO: 740). In another preferred embodiment, the antigenic peptide according to the present invention is a sequence variant of a fragment of the tumor antigen PIWIL1, such as the antigenic peptide comprising or consisting of an amino acid sequence as set forth in SEQ ID NO: 366. Namely, the antigenic peptide according to the present invention, which comprises or consists of an amino acid sequence as set forth in SEQ ID NO: 366 is a sequence variant of the PIWIL1 fragment (human reference peptide) "SIAGFVASI" (SEQ ID NO: 740).

In another embodiment, the antigenic peptide according to the present invention is a microbiota sequence variant of a fragment of the tumor antigen PMEL (human reference peptide), such as "ILLVLMAVV" (SEQ ID NO: 741), "LIVGILLVL" (SEQ ID NO: 742), "LMAVVLASL" (SEQ ID NO: 743), "PLLDGTATL" (SEQ ID NO: 744), "SLADTNSLA" (SEQ ID NO: 745) or "VLQAAIPLT" (SEQ ID NO: 746). In another preferred embodiment, the antigenic peptide according to the present invention is a sequence variant of a fragment of the tumor antigen PMEL, such as antigenic peptides comprising or consisting of an amino acid sequence as set forth in any one of SEQ ID NOs 367-379. More preferably, the antigenic peptide according to the present invention is a sequence variant of the PMEL fragment (human reference peptide) "ILLVLMAVV" (SEQ ID NO: 741), such as an antigenic peptide comprising or consisting of an amino acid sequence as set forth in SEQ ID NO: 367. It is also more preferred that the antigenic peptide according to the present invention is a sequence variant of the PMEL fragment (human reference peptide) "LIVGILLVL" (SEQ ID NO: 742), such as an antigenic peptide comprising or consisting of an amino acid sequence as set forth in SEQ ID NO: 368, 369, 370, 371, 372 or 373. It is also more preferred that the antigenic peptide according to the present invention is a sequence variant of the PMEL fragment (human reference peptide) "LMAVVLASL" (SEQ ID NO: 743), such as an antigenic peptide comprising or consisting of an amino acid sequence as set forth in SEQ ID NO: 374 or 375. It is also more preferred that the antigenic peptide according to the present invention is a sequence variant of the PMEL fragment (human reference peptide) "PLLDGTATL" (SEQ ID NO: 744), such as an antigenic peptide comprising or consisting of an amino acid sequence as set forth in SEQ ID NO: 376. It is also more preferred that the antigenic peptide according to the present invention is a sequence variant of the PMEL fragment (human reference peptide) "SLADTNSLA" (SEQ ID NO: 745), such as an antigenic peptide comprising or consisting of an amino acid sequence as set forth in SEQ ID NO: 377 or 378. It is also more preferred that the antigenic peptide according to the present invention is a sequence variant of the PMEL fragment (human reference peptide) "VLQAAIPLT" (SEQ ID NO: 746), such as an antigenic peptide comprising or consisting of an amino acid sequence as set forth in SEQ ID NO: 379.

In another embodiment, the antigenic peptide according to the present invention is a microbiota sequence variant of a fragment of the tumor antigen PRAME (human reference peptide), such as "AVLDGLDVL" (SEQ ID NO: 747), "QLLALLPSL" (SEQ ID NO: 748), "RLRELLCEL" (SEQ ID NO: 749) or "VLYPVPLES" (SEQ ID NO: 750). In another preferred embodiment, the antigenic peptide according to the present invention is a sequence variant of a fragment of the tumor antigen PRAME, such as antigenic peptides comprising or consisting of an amino acid sequence as set forth in any one of SEQ ID NOs 380-387. More preferably, the antigenic peptide according to the present invention is a sequence variant of the PRAME fragment (human reference peptide) "AVLDGLDVL" (SEQ ID NO: 747), such as an antigenic peptide comprising or consisting of an amino acid sequence as set forth in SEQ ID NO: 380 or 381. It is also more preferred that the antigenic peptide according to the present invention is a sequence variant of the PRAME fragment (human reference peptide) "QLLALLPSL" (SEQ ID NO: 748), such as an antigenic peptide comprising or consisting of an amino acid sequence as set forth in SEQ ID NO: 382, 383, 384 or 385. It is also more preferred that the antigenic peptide according to the present invention is a sequence variant of the PRAME fragment (human reference peptide) "RLRELLCEL" (SEQ ID NO: 749), such as an antigenic peptide comprising or consisting of an amino acid sequence as set forth in SEQ ID NO: 386. It is also more preferred that the antigenic peptide according to the present invention is a sequence variant of the PRAME fragment (human reference peptide) "VLYPVPLES" (SEQ ID NO: 750), such as an antigenic peptide comprising or consisting of an amino acid sequence as set forth in SEQ ID NO: 387.

In another embodiment, the antigenic peptide according to the present invention is a microbiota sequence variant of a fragment of the tumor antigen PTHLH (human reference peptide), such as AVFLLSYAV" (SEQ ID NO: 751). In another preferred embodiment, the antigenic peptide according to the present invention is a sequence variant of a fragment of the tumor antigen PTHLH, such as the antigenic peptide comprising or consisting of an amino acid sequence as set forth in SEQ ID NO: 388. Namely, the antigenic peptide according to the present invention, which comprises or consists of an amino acid sequence as set forth in SEQ ID NO: 388 is a sequence variant of the PTHLH fragment (human reference peptide) "AVFLLSYAV" (SEQ ID NO: 751).

In another embodiment, the antigenic peptide according to the present invention is a microbiota sequence variant of a fragment of the tumor antigen SEMG1 (human reference peptide), such as "FVLSLLLIL" (SEQ ID NO: 752), "IIFVLSLLL" (SEQ ID NO: 753) or "LILEKQAAV" (SEQ ID NO: 754). In another preferred embodiment, the antigenic peptide according to the present invention is a sequence variant of a fragment of the tumor antigen SEMG1, such as antigenic peptides comprising or consisting of an amino acid sequence as set forth in any one of SEQ ID NOs 389-400. More preferably, the antigenic peptide according to the present invention is a sequence variant of the SEMG1 fragment (human reference peptide) "FVLSLL-LIL" (SEQ ID NO: 752), such as an antigenic peptide comprising or consisting of an amino acid sequence as set forth in SEQ ID NO: 389, 390, 391, 392, 393, 394, 395, 396 or 397. It is also more preferred that the antigenic peptide according to the present invention is a sequence variant of the SEMG1 fragment (human reference peptide) "IIFVLSLLL" (SEQ ID NO: 753), such as an antigenic peptide comprising or consisting of an amino acid sequence as set forth in SEQ ID NO: 398 or 399. It is also more preferred that the antigenic peptide according to the present invention is a sequence variant of the SEMG1 fragment (human reference peptide) "LILEKQAAV" (SEQ ID NO: 754), such as an antigenic peptide comprising or consisting of an amino acid sequence as set forth in SEQ ID NO: 400.

In another embodiment, the antigenic peptide according to the present invention is a microbiota sequence variant of a fragment of the tumor antigen SERHL2 (human reference peptide), such as "LISELKLAV" (SEQ ID NO: 755), "RAIEHVLQV" (SEQ ID NO: 756), "SSFDRLIPL" (SEQ ID NO: 757) or "TLKEQFQFV" (SEQ ID NO: 758). In another preferred embodiment, the antigenic peptide according to the present invention is a sequence variant of a fragment of the tumor antigen SERHL2, such as antigenic peptides comprising or consisting of an amino acid sequence as set forth in any one of SEQ ID NOs 401-405. More preferably, the antigenic peptide according to the present invention is a sequence variant of the SERHL2 fragment (human reference peptide) "LISELKLAV" (SEQ ID NO: 755), such as an antigenic peptide comprising or consisting of an amino acid sequence as set forth in SEQ ID NO: 401. It is also more preferred that the antigenic peptide according to the present invention is a sequence variant of the SERHL2 fragment (human reference peptide) "RAIEHVLQV" (SEQ ID NO: 756), such as an antigenic peptide comprising or consisting of an amino acid sequence as set forth in SEQ ID NO: 402. It is also more preferred that the antigenic peptide according to the present invention is a sequence variant of the SERHL2 fragment (human reference peptide) "SSFDRLIPL" (SEQ ID NO: 757), such as an antigenic peptide comprising or consisting of an amino acid sequence as set forth in SEQ ID NO: 403 or 404. It is also more preferred that the antigenic peptide according to the present invention is a sequence variant of the SERHL2 fragment (human reference peptide) "TLKEQFQFV" (SEQ ID NO: 758), such as an antigenic peptide comprising or consisting of an amino acid sequence as set forth in SEQ ID NO: 405.

In another embodiment, the antigenic peptide according to the present invention is a microbiota sequence variant of a fragment of the tumor antigen SLC45A3 (human reference peptide), such as "AILDSAFLL" (SEQ ID NO: 759), "AIS-LVFSLV" (SEQ ID NO: 760), "ALQILPYTL" (SEQ ID NO: 761), "ALTGFTFSA" (SEQ ID NO: 762), "AQLLL-VNLL" (SEQ ID NO: 763), "CLFGLLTLI" (SEQ ID NO: 764), "GILLSLFLI" (SEQ ID NO: 765), "GLLPPPPAL" (SEQ ID NO: 766), "GLLTLIFLT" (SEQ ID NO: 767), "GLVAIYFAT" (SEQ ID NO: 768), "NLGALLPRL" (SEQ ID NO: 769) or "SVAAFPVAA" (SEQ ID NO: 770). In another preferred embodiment, the antigenic peptide according to the present invention is a sequence variant of a fragment of the tumor antigen SLC45A3, such as antigenic peptides comprising or consisting of an amino acid sequence as set forth in any one of SEQ ID NOs 406-427. More preferably, the antigenic peptide according to the present invention is a sequence variant of the SLC45A3 fragment (human reference peptide) "AILDSAFLL" (SEQ ID NO: 759), such as an antigenic peptide comprising or consisting of an amino acid sequence as set forth in SEQ ID NO: 406. It is also more preferred that the antigenic peptide according to the present invention is a sequence variant of the SLC45A3 fragment (human reference peptide) "AIS-LVFSLV" (SEQ ID NO: 760), such as an antigenic peptide comprising or consisting of an amino acid sequence as set forth in SEQ ID NO: 407 or 408. It is also more preferred that the antigenic peptide according to the present invention is a sequence variant of the SLC45A3 fragment (human reference peptide) "ALQILPYTL" (SEQ ID NO: 761), such as an antigenic peptide comprising or consisting of an amino acid sequence as set forth in SEQ ID NO: 409. It is also more preferred that the antigenic peptide according to the present invention is a sequence variant of the SLC45A3 fragment (human reference peptide) "ALTGFTFSA" (SEQ ID NO: 762), such as an antigenic peptide comprising or consisting of an amino acid sequence as set forth in SEQ ID NO: 410. It is also more preferred that the antigenic peptide according to the present invention is a sequence variant of the SLC45A3 fragment (human reference peptide) "AQLLL-VNLL" (SEQ ID NO: 763), such as an antigenic peptide comprising or consisting of an amino acid sequence as set forth in SEQ ID NO: 411. It is also more preferred that the antigenic peptide according to the present invention is a sequence variant of the SLC45A3 fragment (human reference peptide) "CLFGLLTLI" (SEQ ID NO: 764), such as an antigenic peptide comprising or consisting of an amino acid sequence as set forth in SEQ ID NO: 412, 413, 414 or 415. It is also more preferred that the antigenic peptide according to the present invention is a sequence variant of the SLC45A3 fragment (human reference peptide) "GILLSLFLI" (SEQ ID NO: 765), such as an antigenic peptide comprising or consisting of an amino acid sequence as set forth in SEQ ID NO: 416 or 417. It is also more preferred that the antigenic peptide according to the present invention is a sequence variant of the SLC45A3 fragment (human reference peptide) "GLLPPPPAL" (SEQ ID NO: 766), such as an antigenic peptide comprising or consisting of an amino acid sequence as set forth in SEQ ID NO: 418. It is also more preferred that the antigenic peptide according to the present invention is a sequence variant of the SLC45A3 fragment (human reference peptide) "GLLTLIFLT" (SEQ ID NO: 767), such as an antigenic peptide comprising or consisting of an amino acid sequence as set forth in SEQ ID NO: 419, 420, 421, 422 or 423. It is also more preferred that the antigenic peptide according to the present invention is a sequence variant of the SLC45A3 fragment (human reference peptide) "GLVAIYFAT" (SEQ ID NO: 768), such as an antigenic peptide comprising or consisting of an amino acid sequence as set forth in SEQ ID NO: 424. It is also more preferred that the antigenic peptide according to the present invention is a sequence variant of the SLC45A3 fragment (human reference peptide) "NLGALLPRL" (SEQ ID NO: 769), such as an antigenic peptide comprising or consisting of an amino acid sequence as set forth in SEQ ID NO: 425 or 426. It is also more preferred that the antigenic peptide according to the present invention is a sequence variant of the SLC45A3 fragment (human reference peptide) "SVAAFPVAA" (SEQ ID NO: 770), such as an antigenic peptide comprising or consisting of an amino acid sequence as set forth in SEQ ID NO: 427.

In another embodiment, the antigenic peptide according to the present invention is a microbiota sequence variant of a fragment of the tumor antigen SLC6A3 (human reference peptide), such as "FLLSLFCVT" (SEQ ID NO: 771), "FSLGVGFGV" (SEQ ID NO: 772), "GLIDEFQLL" (SEQ ID NO: 773), "GMESVITGL" (SEQ ID NO: 774), "ILFGVLIEA" (SEQ ID NO: 775), "KIDFLLSVI" (SEQ ID NO: 776), "LLFMVIAGM" (SEQ ID NO: 777), "LVPYLLFMV" (SEQ ID NO: 778) or "QLTACLVLV" (SEQ ID NO: 779). In another preferred embodiment, the antigenic peptide according to the present invention is a sequence variant of a fragment of the tumor antigen SLC6A3, such as antigenic peptides comprising or consisting of an amino acid sequence as set forth in any one of SEQ ID NOs 428-441. More preferably, the antigenic peptide according to the present invention is a sequence variant of the SLC6A3 fragment (human reference peptide) "FLLSLFCVT" (SEQ ID NO: 771), such as an antigenic peptide comprising or consisting of an amino acid sequence as set forth in SEQ ID NO: 428, 429 or 430. It is also more preferred that the antigenic peptide according to the present invention is a sequence variant of the SLC6A3 fragment (human reference peptide) "FSLGVGFGV" (SEQ ID NO: 772), such as an antigenic peptide comprising or consisting of an amino acid sequence as set forth in SEQ ID NO: 431 or 432. It is also more preferred that the antigenic peptide according to the present invention is a sequence variant of the SLC6A3 fragment (human reference peptide) "GLIDEFQLL" (SEQ ID NO: 773), such as an antigenic peptide comprising or consisting of an amino acid sequence as set forth in SEQ ID NO: 433. It is also more preferred that the antigenic peptide according to the present invention is a sequence variant of the SLC6A3 fragment (human reference peptide) "GMESVITGL" (SEQ ID NO: 774), such as an antigenic peptide comprising or consisting of an amino acid sequence as set forth in SEQ ID NO: 434. It is also more preferred that the antigenic peptide according to the present invention is a sequence variant of the SLC6A3 fragment (human reference peptide) "ILFGVLIEA" (SEQ ID NO: 775), such as an antigenic peptide comprising or consisting of an amino acid sequence as set forth in SEQ ID NO: 435 or 436. It is also more preferred that the antigenic peptide according to the present invention is a sequence variant of the SLC6A3 fragment (human reference peptide) "KIDFLLSVI" (SEQ ID NO: 776), such as an antigenic peptide comprising or consisting of an amino acid sequence as set forth in SEQ ID NO: 437. It is also more preferred that the antigenic peptide according to the present invention is a sequence variant of the SLC6A3 fragment (human reference peptide) "LLFMVIAGM" (SEQ ID NO: 777), such as an antigenic peptide comprising or consisting of an amino acid sequence as set forth in SEQ ID NO: 438 or 439. It is also more preferred that the antigenic peptide according to the present invention is a sequence variant of the SLC6A3 fragment (human reference peptide) "LVPYLLFMV" (SEQ ID NO: 778), such as an antigenic peptide comprising or consisting of an amino acid sequence as set forth in SEQ ID NO: 440. It is also more preferred that the antigenic peptide according to the present invention is a sequence variant of the SLC6A3 fragment (human reference peptide) "QLTACLVLV" (SEQ ID NO: 779), such as an antigenic peptide comprising or consisting of an amino acid sequence as set forth in SEQ ID NO: 441.

In another embodiment, the antigenic peptide according to the present invention is a microbiota sequence variant of a fragment of the tumor antigen SNX31 (human reference peptide), such as "MISEKMVKL" (SEQ ID NO: 780). In another preferred embodiment, the antigenic peptide according to the present invention is a sequence variant of a fragment of the tumor antigen SNX31, such as the antigenic peptide comprising or consisting of an amino acid sequence as set forth in SEQ ID NO: 442. Namely, the antigenic peptide according to the present invention, which comprises or consists of an amino acid sequence as set forth in SEQ ID NO: 442 is a sequence variant of the SNX31 fragment (human reference peptide) "MISEKMVKL" (SEQ ID NO: 780).

In another embodiment, the antigenic peptide according to the present invention is a microbiota sequence variant of a fragment of the tumor antigen SOX11 (human reference peptide), such as "LMFDLSLNF" (SEQ ID NO: 781). In another preferred embodiment, the antigenic peptide according to the present invention is a sequence variant of a fragment of the tumor antigen SOX11, such as antigenic peptides comprising or consisting of an amino acid sequence as set forth in any one of SEQ ID NOs 443-445. More preferably, the antigenic peptide according to the present invention is a sequence variant of the SOX11 fragment (human reference peptide) "LMFDLSLNF" (SEQ ID NO: 781), such as an antigenic peptide comprising or consisting of an amino acid sequence as set forth in SEQ ID NO: 443, 444 or 445.

In another embodiment, the antigenic peptide according to the present invention is a microbiota sequence variant of a fragment of the tumor antigen SOX17 (human reference peptide), such as "ALPAVMAGL" (SEQ ID NO: 782) or "GLAEPQAAA" (SEQ ID NO: 783). In another preferred embodiment, the antigenic peptide according to the present invention is a sequence variant of a fragment of the tumor antigen SOX17, such as antigenic peptides comprising or consisting of an amino acid sequence as set forth in any one of SEQ ID NOs 446-449. More preferably, the antigenic peptide according to the present invention is a sequence variant of the SOX17 fragment (human reference peptide) "ALPAVMAGL" (SEQ ID NO: 782), such as an antigenic peptide comprising or consisting of an amino acid sequence as set forth in SEQ ID NO: 446. It is also more preferred that the antigenic peptide according to the present invention is a sequence variant of the SOX17 fragment (human reference peptide) "GLAEPQAAA" (SEQ ID NO: 783), such as an antigenic peptide comprising or consisting of an amino acid sequence as set forth in SEQ ID NO: 447, 448 or 449.

In another embodiment, the antigenic peptide according to the present invention is a microbiota sequence variant of a fragment of the tumor antigen SPINK1 (human reference peptide), such as "GIFLLSALA" (SEQ ID NO: 784). In another preferred embodiment the antigenic peptide according to the present invention is a sequence variant of a fragment of the tumor antigen SPINK1, such as the antigenic peptide comprising or consisting of an amino acid sequence as set forth in SEQ ID NO: 450. Namely, the antigenic peptide according to the present invention, which comprises or consists of an amino acid sequence as set forth in SEQ ID NO: 450 is a sequence variant of the SPINK1 fragment (human reference peptide) "GIFLLSALA" (SEQ ID NO: 784).

In another embodiment, the antigenic peptide according to the present invention is a microbiota sequence variant of a fragment of the tumor antigen STEAP1 (human reference peptide), such as "ASLTFLYTL" (SEQ ID NO: 785), "AVLHAIYSL" (SEQ ID NO: 786), "FFFAVLHAI" (SEQ ID NO: 787), "GVIAAIVQL" (SEQ ID NO: 788), "KIAAIIASL" (SEQ ID NO: 789), "LIFKSILFL" (SEQ ID NO: 790), "LLLGTIHAL" (SEQ ID NO: 791), "LLSFFFAVL" (SEQ ID NO: 792), "MIAVFLPIV" (SEQ ID NO: 793) or "SLLLGTIHA" (SEQ ID NO: 794). In another preferred embodiment, the antigenic peptide according to the present invention is a sequence variant of a fragment of the tumor antigen STEAP1, such as antigenic peptides comprising or consisting of an amino acid sequence as set forth in any one of SEQ ID NOs 451-468. More preferably, the antigenic peptide according to the present invention is a sequence variant of the STEAP1 fragment (human reference peptide) "ASLTFLYTL" (SEQ ID NO: 785), such as an antigenic peptide comprising or consisting of an amino acid sequence as set forth in SEQ ID NO: 451. It is also more preferred that the antigenic peptide according to the present invention is a sequence variant of the STEAP1 fragment (human reference peptide) "AVLHAIYSL" (SEQ ID NO: 786), such as an antigenic peptide comprising or consisting of an amino acid sequence as set forth in SEQ ID NO: 452. It is also more preferred that the antigenic peptide according to the present invention is a sequence variant of the STEAP1 fragment (human reference peptide) "FFFAVLHAI" (SEQ ID NO: 787), such as an antigenic peptide comprising or consisting of an amino acid sequence as set forth in SEQ ID NO: 453. It is also more preferred that the antigenic peptide according to the present invention is a sequence variant of the STEAP1 fragment (human reference peptide) "GVIAAIVQL" (SEQ ID NO: 788), such as an antigenic peptide comprising or consisting of an amino acid sequence as set forth in SEQ ID NO: 454, 455, 456 or 457. It is also more preferred that the antigenic peptide according to the present invention is a sequence variant of the STEAP1 fragment (human reference peptide) "KIAAIIASL" (SEQ ID NO: 789), such as an antigenic peptide comprising or consisting of an amino acid sequence as set forth in SEQ ID NO: 458, 459 or 460. It is also more preferred that the antigenic peptide according to the present invention is a sequence variant of the STEAP1 fragment (human reference peptide) "LIFKSILFL" (SEQ ID NO: 790), such as an antigenic peptide comprising or consisting of an amino acid sequence as set forth in SEQ ID NO: 461. It is also more preferred that the antigenic peptide according to the present invention is a sequence variant of the STEAP1 fragment (human reference peptide) "LLLGTIHAL" (SEQ ID NO: 791), such as an antigenic peptide comprising or consisting of an amino acid sequence as set forth in SEQ ID NO: 462. It is also more preferred that the antigenic peptide according to the present invention is a sequence variant of the STEAM fragment (human reference peptide) "LLSFFFAVL" (SEQ ID NO: 792), such as an antigenic peptide comprising or consisting of an amino acid sequence as set forth in SEQ ID NO: 463, 464 or 465. It is also more preferred that the antigenic peptide according to the present invention is a sequence variant of the STEAP1 fragment (human reference peptide) "MIAVFLPIV" (SEQ ID NO: 793), such as an antigenic peptide comprising or consisting of an amino acid sequence as set forth in SEQ ID NO: 466. It is also more preferred that the antigenic peptide according to the present invention is a sequence variant of the STEAP1 fragment (human reference peptide) "SLLLGTIHA" (SEQ ID NO: 794), such as an antigenic peptide comprising or consisting of an amino acid sequence as set forth in SEQ ID NO: 467 or 468.

In another embodiment, the antigenic peptide according to the present invention is a microbiota sequence variant of a fragment of the tumor antigen TBL1Y (human reference peptide), such as "SLSLIVAVI" (SEQ ID NO: 795). In another preferred embodiment, the antigenic peptide according to the present invention is a sequence variant of a fragment of the tumor antigen TBL1Y, such as antigenic peptides comprising or consisting of an amino acid sequence as set forth in any one of SEQ ID NOs 469-470. More preferably, the antigenic peptide according to the present invention is a sequence variant of the TBL1Y fragment (human reference peptide) "SLSLIVAVI" (SEQ ID NO: 795), such as an antigenic peptide comprising or consisting of an amino acid sequence as set forth in SEQ ID NO: 469 or 470.

In another embodiment, the antigenic peptide according to the present invention is a microbiota sequence variant of a fragment of the tumor antigen TDRD1 (human reference peptide), such as "IISPNLFYA" (SEQ ID NO: 796), "LLDHVLIEM" (SEQ ID NO: 797), "VLIDEHLVL" (SEQ ID NO: 798), "YSSEVLEYM" (SEQ ID NO: 799). In another preferred embodiment, the antigenic peptide according to the present invention is a sequence variant of a fragment of the tumor antigen TDRD1, such as antigenic peptides comprising or consisting of an amino acid sequence as set forth in any one of SEQ ID NOs 471-474. More preferably, the antigenic peptide according to the present invention is a sequence variant of the TDRD1 fragment (human reference peptide) "IISPNLFYA" (SEQ ID NO: 796), such as an antigenic peptide comprising or consisting of an amino acid sequence as set forth in SEQ ID NO: 471. It is also more preferred that the antigenic peptide according to the present invention is a sequence variant of the TDRD1 fragment (human reference peptide) "LLDHVLIEM" (SEQ ID NO: 797), such as an antigenic peptide comprising or consisting of an amino acid sequence as set forth in SEQ ID NO: 472. It is also more preferred that the antigenic peptide according to the present invention is a sequence variant of the TDRD1 fragment (human reference peptide) "VLIDEHLVL" (SEQ ID NO: 798), such as an antigenic peptide comprising or consisting of an amino acid sequence as set forth in SEQ ID NO: 473. It is also more preferred that the antigenic peptide according to the present invention is a sequence variant of the TDRD1 fragment (human reference peptide) "YSSEVLEYM" (SEQ ID NO: 799), such as an antigenic peptide comprising or consisting of an amino acid sequence as set forth in SEQ ID NO: 474.

In another embodiment, the antigenic peptide according to the present invention is a microbiota sequence variant of a fragment of the tumor antigen TOP2A (human reference peptide), such as "ILLRPDTYI" (SEQ ID NO: 800), "LMMTIINLA" (SEQ ID NO: 801), "QLAGSVAEM" (SEQ ID NO: 802), "SLMMTIINL" (SEQ ID NO: 803), "TMLSSLARL" (SEQ ID NO: 804) or "YIFTMLSSL" (SEQ ID NO: 805). In another preferred embodiment, the antigenic peptide according to the present invention is a sequence variant of a fragment of the tumor antigen TOP2A, such as antigenic peptides comprising or consisting of an amino acid sequence as set forth in any one of SEQ ID NOs 475-483. More preferably, the antigenic peptide according to the present invention is a sequence variant of the TOP2A fragment (human reference peptide) "ILLRPDTYI" (SEQ ID NO: 800), such as an antigenic peptide comprising or consisting of an amino acid sequence as set forth in SEQ ID NO: 475.

It is also more preferred that the antigenic peptide according to the present invention is a sequence variant of the TOP2A fragment (human reference peptide) "LMMTIINLA" (SEQ ID NO: 801), such as an antigenic peptide comprising or consisting of an amino acid sequence as set forth in SEQ ID NO: 476, 477 or 478. It is also more preferred that the antigenic peptide according to the present invention is a sequence variant of the TOP2A fragment (human reference peptide) "QLAGSVAEM" (SEQ ID NO:

802), such as an antigenic peptide comprising or consisting of an amino acid sequence as set forth in SEQ ID NO: 479 or 480.

It is also more preferred that the antigenic peptide according to the present invention is a sequence variant of the TOP2A fragment (human reference peptide) "SLMMTIINL" (SEQ ID NO: 803), such as an antigenic peptide comprising or consisting of an amino acid sequence as set forth in SEQ ID NO: 481. It is also more preferred that the antigenic peptide according to the present invention is a sequence variant of the TOP2A fragment (human reference peptide) "TMLSSLARL" (SEQ ID NO: 804), such as an antigenic peptide comprising or consisting of an amino acid sequence as set forth in SEQ ID NO: 482. It is also more preferred that the antigenic peptide according to the present invention is a sequence variant of the TOP2A fragment (human reference peptide) "YIFTMLSSL" (SEQ ID NO: 805), such as an antigenic peptide comprising or consisting of an amino acid sequence as set forth in SEQ ID NO: 483.

In another embodiment, the antigenic peptide according to the present invention is a microbiota sequence variant of a fragment of the tumor antigen TPTE (human reference peptide), such as DLAGVIIEL" (SEQ ID NO: 806), "FGLFGVFLV" (SEQ ID NO: 807), "GLFGVFLVL" (SEQ ID NO: 808), "ILDTAIIVI" (SEQ ID NO: 809), "IVSSFAFGL" (SEQ ID NO: 810), "RLLRLIILL" (SEQ ID NO: 811), "SLAIALFFL" (SEQ ID NO: 812) or "YFWLHTSFI" (SEQ ID NO: 813). In another preferred embodiment, the antigenic peptide according to the present invention is a sequence variant of a fragment of the tumor antigen TPTE, such as antigenic peptides comprising or consisting of an amino acid sequence as set forth in any one of SEQ ID NOs 484-504. More preferably, the antigenic peptide according to the present invention is a sequence variant of the TPTE fragment (human reference peptide) "DLAGVIIEL" (SEQ ID NO: 806), such as an antigenic peptide comprising or consisting of an amino acid sequence as set forth in SEQ ID NO: 484, 485, 486, 487, 488, 489 or 490. It is also more preferred that the antigenic peptide according to the present invention is a sequence variant of the TPTE fragment (human reference peptide) "FGLFGVFLV" (SEQ ID NO: 807), such as an antigenic peptide comprising or consisting of an amino acid sequence as set forth in SEQ ID NO: 491, 492, 493 or 494. It is also more preferred that the antigenic peptide according to the present invention is a sequence variant of the TPTE fragment (human reference peptide) "GLFGVFLVL" (SEQ ID NO: 808), such as an antigenic peptide comprising or consisting of an amino acid sequence as set forth in SEQ ID NO: 495, 496 or 497. It is also more preferred that the antigenic peptide according to the present invention is a sequence variant of the TPTE fragment (human reference peptide) "ILDTAIIVI" (SEQ ID NO: 809), such as an antigenic peptide comprising or consisting of an amino acid sequence as set forth in SEQ ID NO: 498 or 499. It is also more preferred that the antigenic peptide according to the present invention is a sequence variant of the TPTE fragment (human reference peptide) "IVSSFAFGL" (SEQ ID NO: 810), such as an antigenic peptide comprising or consisting of an amino acid sequence as set forth in SEQ ID NO: 500 or 501. It is also more preferred that the antigenic peptide according to the present invention is a sequence variant of the TPTE fragment (human reference peptide) "RLLRLIILL" (SEQ ID NO: 811), such as an antigenic peptide comprising or consisting of an amino acid sequence as set forth in SEQ ID NO: 502. It is also more preferred that the antigenic peptide according to the present invention is a sequence variant of the TPTE fragment (human reference peptide) "SLAIALFFL" (SEQ ID NO: 812), such as an antigenic peptide comprising or consisting of an amino acid sequence as set forth in SEQ ID NO: 503. It is also more preferred that the antigenic peptide according to the present invention is a sequence variant of the TPTE fragment (human reference peptide) "YFWLHTSFI" (SEQ ID NO: 813), such as an antigenic peptide comprising or consisting of an amino acid sequence as set forth in SEQ ID NO: 504.

In another embodiment, the antigenic peptide according to the present invention is a microbiota sequence variant of a fragment of the tumor antigen TRPM8 (human reference peptide), such as "AMFGYTVGT" (SEQ ID NO: 814), "FIAGIVFRL" (SEQ ID NO: 815), "FLLLFAYVL" (SEQ ID NO: 816), "LLFAYVLLM" (SEQ ID NO: 817), "LLLFAYVLL" (SEQ ID NO: 818), "LVLYSLVFV" (SEQ ID NO: 819), "NILLVNLLV" (SEQ ID NO: 820), "QIADVIASL" (SEQ ID NO: 821), "VLYSLVFVL" (SEQ ID NO: 822) or "YLVKINTKA" (SEQ ID NO: 823). In another preferred embodiment, the antigenic peptide according to the present invention is a sequence variant of a fragment of the tumor antigen TRPM8, such as antigenic peptides comprising or consisting of an amino acid sequence as set forth in any one of SEQ ID NOs 505-518. More preferably, the antigenic peptide according to the present invention is a sequence variant of the TRPM8 fragment (human reference peptide) "AMFGYTVGT" (SEQ ID NO: 814), such as an antigenic peptide comprising or consisting of an amino acid sequence as set forth in SEQ ID NO: 505. It is also more preferred that the antigenic peptide according to the present invention is a sequence variant of the TRPM8 fragment (human reference peptide) "FIAGIVFRL" (SEQ ID NO: 815), such as an antigenic peptide comprising or consisting of an amino acid sequence as set forth in SEQ ID NO: 506. It is also more preferred that the antigenic peptide according to the present invention is a sequence variant of the TRPM8 fragment (human reference peptide) "FLLLFAYVL" (SEQ ID NO: 816), such as an antigenic peptide comprising or consisting of an amino acid sequence as set forth in SEQ ID NO: 507. It is also more preferred that the antigenic peptide according to the present invention is a sequence variant of the TRPM8 fragment (human reference peptide) "LLFAYVLLM" (SEQ ID NO: 817), such as an antigenic peptide comprising or consisting of an amino acid sequence as set forth in SEQ ID NO: 508 or 509. It is also more preferred that the antigenic peptide according to the present invention is a sequence variant of the TRPM8 fragment (human reference peptide) "LLLFAYVLL" (SEQ ID NO: 818), such as an antigenic peptide comprising or consisting of an amino acid sequence as set forth in SEQ ID NO: 510. It is also more preferred that the antigenic peptide according to the present invention is a sequence variant of the TRPM8 fragment (human reference peptide) "LVLYSLVFV" (SEQ ID NO: 819), such as an antigenic peptide comprising or consisting of an amino acid sequence as set forth in SEQ ID NO: 511. It is also more preferred that the antigenic peptide according to the present invention is a sequence variant of the TRPM8 fragment (human reference peptide) "NILLVNLLV" (SEQ ID NO: 820), such as an antigenic peptide comprising or consisting of an amino acid sequence as set forth in SEQ ID NO: 512. It is also more preferred that the antigenic peptide according to the present invention is a sequence variant of the TRPM8 fragment (human reference peptide) "QIADVIASL" (SEQ ID NO: 821), such as an antigenic peptide comprising or consisting of an amino acid sequence as set forth in SEQ ID NO: 513, 514, 515 or 516. It is also more preferred that the antigenic peptide according to the present invention is a sequence variant of the TRPM8 fragment (human reference peptide) "VLYSLVFVL" (SEQ ID NO: 822), such as an antigenic peptide comprising or consisting of an amino acid sequence as set forth in SEQ ID NO: 517. It is also more preferred that the antigenic peptide according to the present invention is a sequence variant of the TRPM8 fragment (human reference peptide) "YLVKINTKA" (SEQ ID NO: 823), such as an antigenic peptide comprising or consisting of an amino acid sequence as set forth in SEQ ID NO: 518.

In another embodiment, the antigenic peptide according to the present invention is a microbiota sequence variant of a fragment of the tumor antigen TYMS (human reference peptide), such as "FLDSLGFST" (SEQ ID NO: 824), "SLRDEFPLL" (SEQ ID NO: 825) or "VLEELLWFI" (SEQ ID NO: 826). In another preferred embodiment, the antigenic peptide according to the present invention is a sequence variant of a fragment of the tumor antigen TYMS, such as antigenic peptides comprising or consisting of an amino acid sequence as set forth in any one of SEQ ID NOs 519-524. More preferably, the antigenic peptide according to the present invention is a sequence variant of the TYMS fragment (human reference peptide) "FLDSLGFST" (SEQ ID NO: 824), such as an antigenic peptide comprising or consisting of an amino acid sequence as set forth in SEQ ID NO: 519, 520 or 521. It is also more preferred that the antigenic peptide according to the present invention is a sequence variant of the TYMS fragment (human reference peptide) "SLRDEFPLL" (SEQ ID NO: 825), such as an antigenic peptide comprising or consisting of an amino acid sequence as set forth in SEQ ID NO: 522 or 523. It is also more preferred that the antigenic peptide according to the present invention is a sequence variant of the TYMS fragment (human reference peptide) "VLEELLWFI" (SEQ ID NO: 826), such as an antigenic peptide comprising or consisting of an amino acid sequence as set forth in SEQ ID NO: 524.

In another embodiment, the antigenic peptide according to the present invention is a microbiota sequence variant of a fragment of the tumor antigen TYR (human reference peptide), such as "ALLAGLVSL" (SEQ ID NO: 827), "AMVGAVLTA" (SEQ ID NO: 828), "ISSDYVIPI" (SEQ ID NO: 829), "LLAGLVSLL" (SEQ ID NO: 830), "LLSPASFFS" (SEQ ID NO: 831), "MVGAVLTAL" (SEQ ID NO: 832) or "VLTALLAGL" (SEQ ID NO: 833). In another preferred embodiment, the antigenic peptide according to the present invention is a sequence variant of a fragment of the tumor antigen TYR, such as antigenic peptides comprising or consisting of an amino acid sequence as set forth in any one of SEQ ID NOs 525-539. More preferably, the antigenic peptide according to the present invention is a sequence variant of the TYR fragment (human reference peptide) "ALLAGLVSL" (SEQ ID NO: 827), such as an antigenic peptide comprising or consisting of an amino acid sequence as set forth in SEQ ID NO: 525 or 526. It is also more preferred that the antigenic peptide according to the present invention is a sequence variant of the TYR fragment (human reference peptide) "AMVGAVLTA" (SEQ ID NO: 828), such as an antigenic peptide comprising or consisting of an amino acid sequence as set forth in SEQ ID NO: 527, 528, 529 or 530. It is also more preferred that the antigenic peptide according to the present invention is a sequence variant of the TYR fragment (human reference peptide) "ISSDYVIPI" (SEQ ID NO: 829), such as an antigenic peptide comprising or consisting of an amino acid sequence as set forth in SEQ ID NO: 531. It is also more preferred that the antigenic peptide according to the present invention is a sequence variant of the TYR fragment (human reference peptide) "LLAGLVSLL" (SEQ ID NO: 830), such as an antigenic peptide comprising or consisting of an amino acid sequence as set forth in SEQ ID NO: 532. It is also more preferred that the antigenic peptide according to the present invention is a sequence variant of the TYR fragment (human reference peptide) "LLSPASFFS" (SEQ ID NO: 831), such as an antigenic peptide comprising or consisting of an amino acid sequence as set forth in SEQ ID NO: 533. It is also more preferred that the antigenic peptide according to the present invention is a sequence variant of the TYR fragment (human reference peptide) "MVGAVLTAL" (SEQ ID NO: 832), such as an antigenic peptide comprising or consisting of an amino acid sequence as set forth in SEQ ID NO: 534. It is also more preferred that the antigenic peptide according to the present invention is a sequence variant of the TYR fragment (human reference peptide) "VLTALLAGL" (SEQ ID NO: 833), such as an antigenic peptide comprising or consisting of an amino acid sequence as set forth in SEQ ID NO: 535, 536, 537, 538 or 539.

In another embodiment, the antigenic peptide according to the present invention is a microbiota sequence variant of a fragment of the tumor antigen UPK2 (human reference peptide), such as "ALTESLLVA" (SEQ ID NO: 834), "LLALLSPGA" (SEQ ID NO: 835), "LVLGFIIAL" (SEQ ID NO: 836), "SLSGLLSPA" (SEQ ID NO: 837), "TLPLILILL" (SEQ ID NO: 838), "VLGFIIALA" (SEQ ID NO: 839) or "VVITVLLSV" (SEQ ID NO: 840). In another preferred embodiment, the antigenic peptide according to the present invention is a sequence variant of a fragment of the tumor antigen UPK2, such as antigenic peptides comprising or consisting of an amino acid sequence as set forth in any one of SEQ ID NOs 540-556. More preferably, the antigenic peptide according to the present invention is a sequence variant of the UPK2 fragment (human reference peptide) "ALTESLLVA" (SEQ ID NO: 834), such as an antigenic peptide comprising or consisting of an amino acid sequence as set forth in SEQ ID NO: 540, 541 or 542. It is also more preferred that the antigenic peptide according to the present invention is a sequence variant of the UPK2 fragment (human reference peptide) "LLALLSPGA" (SEQ ID NO: 835), such as an antigenic peptide comprising or consisting of an amino acid sequence as set forth in SEQ ID NO: 543. It is also more preferred that the antigenic peptide according to the present invention is a sequence variant of the UPK2 fragment (human reference peptide) "LVLGFI-IAL" (SEQ ID NO: 836), such as an antigenic peptide comprising or consisting of an amino acid sequence as set forth in SEQ ID NO: 544, 545, 546 or 547. It is also more preferred that the antigenic peptide according to the present invention is a sequence variant of the UPK2 fragment (human reference peptide) "SLSGLLSPA" (SEQ ID NO: 837), such as an antigenic peptide comprising or consisting of an amino acid sequence as set forth in SEQ ID NO: 548 or 549. It is also more preferred that the antigenic peptide according to the present invention is a sequence variant of the UPK2 fragment (human reference peptide) "TLPLILILL" (SEQ ID NO: 838), such as an antigenic peptide comprising or consisting of an amino acid sequence as set forth in SEQ ID NO: 550. It is also more preferred that the antigenic peptide according to the present invention is a sequence variant of the UPK2 fragment (human reference peptide) "VLGFIIALA" (SEQ ID NO: 839), such as an antigenic peptide comprising or consisting of an amino acid sequence as set forth in SEQ ID NO: 551, 552, 553 or 554. It is also more preferred that the antigenic peptide according to the present invention is a sequence variant of the UPK2 fragment (human reference peptide) "VVITVLLSV" (SEQ ID NO: 840), such as an antigenic peptide comprising or consisting of an amino acid sequence as set forth in SEQ ID NO: 555 or 556.

In another embodiment, the antigenic peptide according to the present invention is a microbiota sequence variant of a fragment of the tumor antigen VCAM1 (human reference peptide), such as "AQIGDSVML" (SEQ ID NO: 841), "FASSLIIPA" (SEQ ID NO: 842), "KSIDGAYTI" (SEQ ID NO: 843) or "SILEEGSSV" (SEQ ID NO: 844). In another preferred embodiment, the antigenic peptide according to the present invention is a sequence variant of a fragment of the tumor antigen VCAM1, such as antigenic peptides comprising or consisting of an amino acid sequence as set forth in any one of SEQ ID NOs 557-560. More preferably, the antigenic peptide according to the present invention is a sequence variant of the VCAM1 fragment (human reference peptide) "AQIGDSVML" (SEQ ID NO: 841), such as an antigenic peptide comprising or consisting of an amino acid sequence as set forth in SEQ ID NO: 557. It is also more preferred that the antigenic peptide according to the present invention is a sequence variant of the VCAM1 fragment (human reference peptide) "FASSLIIPA" (SEQ ID NO: 842), such as an antigenic peptide comprising or consisting of an amino acid sequence as set forth in SEQ ID NO: 558. It is also more preferred that the antigenic peptide according to the present invention is a sequence variant of the VCAM1 fragment (human reference peptide) "KSIDGAYTI" (SEQ ID NO: 843), such as an antigenic peptide comprising or consisting of an amino acid sequence as set forth in SEQ ID NO: 559. It is also more preferred that the antigenic peptide according to the present invention is a sequence variant of the VCAM1 fragment (human reference peptide) "SILEEGSSV" (SEQ ID NO: 844), such as an antigenic peptide comprising or consisting of an amino acid sequence as set forth in SEQ ID NO: 560.

In another embodiment, the antigenic peptide according to the present invention is a microbiota sequence variant of a fragment of the tumor antigen WFDC2 (human reference peptide), such as "LLFGFTLVS" (SEQ ID NO: 845), "LLLFGFTLV" (SEQ ID NO: 846) or "RLGPLAAAL" (SEQ ID NO: 847). In another preferred embodiment, the antigenic peptide according to the present invention is a sequence variant of a fragment of the tumor antigen WFDC2, such as antigenic peptides comprising or consisting of an amino acid sequence as set forth in any one of SEQ ID NOs 561-568. More preferably, the antigenic peptide according to the present invention is a sequence variant of the WFDC2 fragment (human reference peptide) "LLFGFTLVS" (SEQ ID NO: 845), such as an antigenic peptide comprising or consisting of an amino acid sequence as set forth in SEQ ID NO: 561, 562, 563, 564 or 565. It is also more preferred that the antigenic peptide according to the present invention is a sequence variant of the WFDC2 fragment (human reference peptide) "LLLFGFTLV" (SEQ ID NO: 846), such as an antigenic peptide comprising or consisting of an amino acid sequence as set forth in SEQ ID NO: 566. It is also more preferred that the antigenic peptide according to the present invention is a sequence variant of the WFDC2 fragment (human reference peptide) "RLGPLAAAL" (SEQ ID NO: 847), such as an antigenic peptide comprising or consisting of an amino acid sequence as set forth in SEQ ID NO: 567 or 568.

In another embodiment, the antigenic peptide according to the present invention is a microbiota sequence variant of a fragment of the tumor antigen WT1 (human reference peptide), such as "DLNALLPAV" (SEQ ID NO: 848). In another preferred embodiment, the antigenic peptide according to the present invention is a sequence variant of a fragment of the tumor antigen WT1, such as the antigenic peptide comprising or consisting of an amino acid sequence as set forth in SEQ ID NO: 569. Namely, the antigenic peptide according to the present invention, which comprises or consists of an amino acid sequence as set forth in SEQ ID NO: 569 is a sequence variant of the WT1 fragment (human reference peptide) "DLNALLPAV" (SEQ ID NO: 848).

In another embodiment, the antigenic peptide according to the present invention is a microbiota sequence variant of a fragment of the tumor antigen ZEB1 (human reference peptide), such as "ILIPQVAYT" (SEQ ID NO: 849), "NLSDIQNVL" (SEQ ID NO: 850) or "VQAVVLPTV" (SEQ ID NO: 851). In another preferred embodiment, the antigenic peptide according to the present invention is a sequence variant of a fragment of the tumor antigen ZEB1, such as antigenic peptides comprising or consisting of an amino acid sequence as set forth in any one of SEQ ID NOs 570-574. More preferably, the antigenic peptide according to the present invention is a sequence variant of the ZEB1 fragment (human reference peptide) "ILIPQVAYT" (SEQ ID NO: 849), such as an antigenic peptide comprising or consisting of an amino acid sequence as set forth in SEQ ID NO: 570 or 571. It is also more preferred that the antigenic peptide according to the present invention is a sequence variant of the ZEB1 fragment (human reference peptide) "NLSDIQNVL" (SEQ ID NO: 850), such as an antigenic peptide comprising or consisting of an amino acid sequence as set forth in SEQ ID NO: 572 or 573. It is also more preferred that the antigenic peptide according to the present invention is a sequence variant of the ZEB1 fragment (human reference peptide) "VQAVVLPTV" (SEQ ID NO: 851), such as an antigenic peptide comprising or consisting of an amino acid sequence as set forth in SEQ ID NO: 574.

In another embodiment, the antigenic peptide according to the present invention is a microbiota sequence variant of a fragment of the tumor antigen ZNF165 (human reference peptide), such as "LVLEQFLTI" (SEQ ID NO: 852) or "RISGYISEA" (SEQ ID NO: 853). In another preferred embodiment, the antigenic peptide according to the present invention is a sequence variant of a fragment of the tumor antigen ZNF165, such as antigenic peptides comprising or consisting of an amino acid sequence as set forth in any one of SEQ ID NOs 575-578. More preferably, the antigenic peptide according to the present invention is a sequence variant of the ZNF165 fragment (human reference peptide) "LVLEQFLTI" (SEQ ID NO: 852), such as an antigenic peptide comprising or consisting of an amino acid sequence as set forth in SEQ ID NO: 575, 576 or 577. It is also more preferred that the antigenic peptide according to the present invention is a sequence variant of the ZNF165 fragment (human reference peptide) "RISGYISEA" (SEQ ID NO: 853), such as an antigenic peptide comprising or consisting of an amino acid sequence as set forth in SEQ ID NO: 578.

In another embodiment, the antigenic peptide according to the present invention is a microbiota sequence variant of a fragment of the tumor antigen ZNF280A (human reference peptide), such as "AMTDISSLA" (SEQ ID NO: 854) or "VLLSNFYYG" (SEQ ID NO: 855). In another preferred embodiment, the antigenic peptide according to the present invention is a sequence variant of a fragment of the tumor antigen ZNF280A, such as antigenic peptides comprising or consisting of an amino acid sequence as set forth in any one of SEQ ID NOs 579-580. More preferably, the antigenic peptide according to the present invention is a sequence variant of the ZNF280A fragment (human reference peptide)

"AMTDISSLA" (SEQ ID NO: 854), such as an antigenic peptide comprising or consisting of an amino acid sequence as set forth in SEQ ID NO: 579. It is also more preferred that the antigenic peptide according to the present invention is a sequence variant of the ZNF280A fragment (human reference peptide) "VLLSNFYYG" (SEQ ID NO: 855), such as an antigenic peptide comprising or consisting of an amino acid sequence as set forth in SEQ ID NO: 580.

Preferably, the antigenic peptide according to the present invention comprises or consists of an amino acid sequence as set forth in any one of SEQ ID NOs 1-160, 162-253 and 255-580. More preferably, the antigenic peptide according to the present invention comprises or consists of an amino acid sequence as set forth in any one of SEQ ID NOs 30, 31, 32, 87, 97, 145, 193, 194, 220, 221, 255, 521 and 524. Even more preferably, the antigenic peptide according to the present invention comprises or consists of an amino acid sequence as set forth in any one of SEQ ID NOs 30, 31, 32, 87, 97, 193, 194, 220, 255, 521 and 524. Still more preferably, the antigenic peptide according to the present invention comprises or consists of an amino acid sequence as set forth in any one of SEQ ID NOs 30, 31, 32, 87, 97, 194, 220, 255, 521 and 524. Most preferably, the antigenic peptide according to the present invention comprises or consists of an amino acid sequence as set forth in any one of SEQ ID NOs 30, 32, 87, 97, and 194.

Moreover, the antigenic peptide according to the present invention comprises or consists of an amino acid sequence as set forth in any one of SEQ ID NOs 30, 32, 194, 220, 254 or 255 is particularly preferred. Most preferably, the antigenic peptide according to the present invention comprises or consists of an amino acid sequence as set forth in SEQ ID NO: 30 or 32. Most preferably, the antigenic peptide according to the present invention comprises or consists of an amino acid sequence as set forth in SEQ ID NO: 194 or 220. Most preferably, the antigenic peptide according to the present invention comprises or consists of an amino acid sequence as set forth in SEQ ID NO: 254 or 255.

As shown in the examples herein, the specific antigenic peptides according to the present invention allow the raise of a strong immune response against themselves, and most importantly, allow the raise of a strong immune response against peptides having amino acid similarity therewith which are comprised in the tumor antigen, even if the human reference peptides comprised in the tumor antigen may be tolerogenic.

Advantageously, the antigenic peptides according to the present invention may be in the form of immunogenic compounds, in particular for use in the prevention or in the treatment of a cancer.

Immunogenic Compounds Comprising the Antigenic Peptide According to the Invention In a further aspect, the present invention also provides an immunogenic compound comprising an antigenic peptide according to the present invention as described above. In particular, preferred embodiments of the antigenic peptide as described above also apply for the immunogenic compound according to the present invention. For example, the antigenic peptide comprised in the immunogenic compound preferably comprises or consists of an amino acid sequence as set forth in any one of SEQ ID NOs 1 to 580 and 861 to 887, such as an antigenic peptide comprising or consisting of an amino acid sequence as set forth in any one of SEQ ID NOs 1 to 580. For example, antigenic peptides according to the present invention comprising or consisting of an amino acid sequence as set forth in any one of SEQ ID NOs 1-160, 162-253 and 255-580 are more preferred. For example, antigenic peptides according to the present invention comprising or consisting of an amino acid sequence as set forth in any one of SEQ ID NOs 30, 31, 32, 87, 97, 145, 193, 194, 220, 221, 255, 521 and 524 are even more preferred. For example, antigenic peptides according to the present invention comprising or consisting of an amino acid sequence as set forth in any one of SEQ ID NOs 30, 31, 32, 87, 97, 193, 194, 220, 255, 521 and 524 are still more preferred. For example, antigenic peptides according to the present invention comprising or consisting of an amino acid sequence as set forth in any one of SEQ ID NOs 30, 31, 32, 87, 97, 194, 220, 255, 521 and 524 are still more preferred. For example, antigenic peptides according to the present invention comprising or consisting of an amino acid sequence as set forth in any one of SEQ ID NOs 30, 32, 87, 97, and 194 are most preferred. For example, antigenic peptides according to the present invention comprising or consisting of an amino acid sequence as set forth in any one of SEQ ID NOs 30, 32, 194, 220, 254 or 255 are particularly preferred. Also combinations thereof are preferred, namely, immunogenic compound comprising distinct antigenic peptides according to the present invention.

As used herein, the term "immunogenic compound" refers to a compound that is able to induce, increase, prolong or maintain an immune response, in particular which induces, increases, prolongs or maintains an immune response, when it is administered to a mammal, and especially when it is administered to a human individual.

In general, the term "immunogenic compound" includes all kinds of compounds comprising the antigenic peptide according to the present invention. For example, the antigenic peptide according to the present invention may be linked to a carrier molecule or the antigenic peptide according to the present invention may be comprised in a polypeptide or protein (which polypeptide or protein may occur "separately", i.e. not linked to any other compound, or the polypeptide or protein comprising the antigenic peptide may be linked to a carrier molecule).

Preferably, the immunogenic compound according to present invention comprises the antigenic peptide and a carrier molecule, in particular wherein the antigenic peptide (or a polypeptide or protein comprising the antigenic peptide) is linked to a carrier molecule. A preferred carrier molecule is a carrier protein or a carrier peptide. According to a preferred embodiment, the antigenic peptide as above defined, or a polypeptide/protein comprising said antigenic peptide, is linked to a carrier protein or a carrier peptide, for example by a covalent or non-covalent bond. Alternatively, such a carrier protein or carrier peptide as described herein) may be (separately) co-administered in the form of immune adjuvant (i.e., not as an "immunogenic compound", but as co-administration/combination therapy as described herein below).

The carrier molecule may also be a lipid or a lipid-like moiety. In this case, the immunogenic compound may be a lipopeptide. As used herein, the term "lipopeptide" refers to a molecule that comprises a lipid or a lipid-like moiety covalently linked to a peptide moiety. In general, a "lipid" is soluble in nonpolar solvents, but usually a "lipid" does not (or does not easily) dissolve in water. Examples of a lipid or a lipid-like moiety include, but are not limited to, fatty acids, waxes, sterols, monoglycerides, diglycerides, triglycerides and phospolipids. The lipid may be a fatty acid, a glycerolipid, a gylcerophospholipid, a sphingolipid, a sterol lipid, a prenol lipid, a saccharolipid, or a polyketide. Preferably, the lipid is a fatty acid or a derivative thereof (including monoglycerides, diglycerides, triglycerides and phospolipids). Fatty acids typically contain a hydrocarbon chain that terminates with a carboxylic group. Fatty acids may be saturated or unsaturated. Fatty acids may be attached to functional groups, e.g., containing oxygens, halogens, nitrogen or sulfur. Preferred fatty acids are saturated or unsaturated long-chain fatty acids, such as myristic acid with 14 carbon atoms ($CH_3(CH_2)_{12}COOH$) or palmitic acid with 16 carbon atoms ($CH_3(CH_2)_{14}COOH$), as well as phospholipids, such as phosphatidylglycerol (PG).

Preferably, the antigenic peptide as described herein, or a polypeptide/protein comprising the antigenic peptide, may be co-administered or linked, for example by covalent or non-covalent bond, to a protein/peptide having immunoadjuvant properties, such as providing stimulation of CD4+ Th1 cells. While the antigenic peptide as described herein preferably binds to MHC class I, CD4+ helper epitopes may be additionally used to provide an efficient immune response. Th1 helper cells are able to sustain efficient dendritic cell (DC) activation and specific CTL activation by secreting interferon-gamma (IFN-γ), tumor necrosis factor-alpha (TNF-α) and interleukin-2 (IL-2) and enhancing expression of costimulatory signal on DCs and T cells (Galaine et al., Interest of Tumor-Specific CD4 T Helper 1 Cells for Therapeutic Anticancer Vaccine. Vaccines (Basel). 2015 Jun. 30; 3(3):490-502).

For example, the adjuvant peptide/protein may preferably be a non-tumor antigen that recalls immune memory or provides a non-specific help or could be a specific tumor-derived helper peptide. Several helper peptides have been described in the literature for providing a nonspecific T cell help, such as tetanus helper peptide, keyhole limpet hemocyanin peptide or PADRE peptide (Adotévi et al., Targeting antitumor CD4 helper T cells with universal tumor-reactive helper peptides derived from telomerase for cancer vaccine. Hum Vaccin Immunother. 2013 May; 9(5):1073-7, Slingluff C L, The present and future of peptide vaccines for cancer: single or multiple, long or short, alone or in combination? Cancer J. 2011 September-October; 17(5):343-50). Accordingly, tetanus helper peptide, keyhole limpet hemocyanin peptide and PADRE peptide are preferred examples of such adjuvant peptide/proteins. Moreover, specific tumor derived helper peptides are preferred. Specific tumor derived helper peptides are typically presented by MHC class II, in particular by HLA-DR, HLA-DP or HLA-DQ. Specific tumor derived helper peptides may be fragments of sequences of shared overexpressed tumor antigens, such as HER2, NY-ESO-1, hTERT or IL13RA2. Such fragments have preferably a length of at least 10 amino acids, more preferably of at least 11 amino acids, even more preferably of at least 12 amino acids and most preferably of at least 13 amino acids. In particular, fragments of shared overexpressed tumor antigens, such as HER2, NY-ESO-1, hTERT or IL13RA2, having a length of 13 to 24 amino acids are preferred. Preferred fragments bind to MHC class II and may, thus, be identified using, for example, the MHC class II binding prediction tools of IEDB (Immune epitope database and analysis resource; Supported by a contract from the National Institute of Allergy and Infectious Diseases, a component of the National Institutes of Health in the Department of Health and Human Services; URL: http://www.iedb.org/; http://tools.iedb.org/mhcii/). Preferably, the adjuvant peptide/protein may be the HHD-DR3 peptide of sequence MAKTIAYDEEARRGLERGLN (SEQ ID NO: 856). Another preferred example is h-pAg T13L (sequence: TPPAYRPPNAPIL; SEQ ID NO: 860; Bhasin M, Singh H, Raghava GP (2003) MHCBN: a comprehensive database of MHC binding and non-binding peptides. Bioinformatics 19: 665-666). Further examples of preferred adjuvant peptides/proteins, in particular of helper peptides, include the UCP2 peptide (for example as described in WO 2013/135553 A1 or in Dosset et al. Clin Cancer Res. 2012 Nov. 15; 18(22): 6284-95) and the BIRC5 peptide (for example as described in EP2119726 A1 or in Widenmeyer et al. Int J Cancer. 2012 Jul. 1; 131(1):140-9). The most preferred helper peptide is the UCP2 peptide (amino acid sequence: KSVWSKLQSIGIRQH; SEQ ID NO: 859, for example as described in WO 2013/135553 A1 or in Dosset et al., Clin Cancer Res. 2012 Nov. 15; 18(22):6284-95).

It is also preferred that the immunogenic compound according to the present invention is a polypeptide or a protein comprising the antigenic peptide according to the present invention. Preferably, such a protein or polypeptide is a recombinant protein or polypeptide, for example a fusion protein. The term "recombinant" means that it does not occur in nature.

In a preferred embodiment, the immunogenic compound according to the present invention comprises or consists of a polypeptide of formula (I)

PepNt-CORE-PepCt    (I)

wherein:
"PepNt" consists of a polypeptide having a length varying from 0 to 500 amino acid residues and is located at the N-terminal end of the polypeptide of formula (I);
"CORE" consists of an antigenic peptide according to the present invention as defined above; and
"PepCt" consists of a polypeptide having a length varying from 0 to 500 amino acid residues and is located at the C-terminal end of the polypeptide of formula (I).

For example, the immunogenic compound may comprise or consist of a polypeptide of formula (Ia) or (Ib):

PepNt-CORE    (Ia); or

CORE-PepCt    (Ib)

wherein "PepNt" and "PepCt" and "CORE" are as defined above.

Preferably, the polypeptide of formula (I), (Ia) or (Ib) is a fusion peptide or fusion protein, in particular a recombinant fusion peptide or protein.

It is also preferred that the polypeptide or the immunogenic compound as defined above, comprises from 9 to 1000 amino acids; which includes 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67? 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 250, 300, 350, 400, 450, 500, 600, 700, 800, 900 and 1000 amino acids. Accordingly, the length of "PepNt" and "PepCt", if applicable, may be defined accordingly.

Thus, "PepNt" and "PepCt", as defined above, may comprise from 0 to 500 amino acid residues; which includes 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 250, 300, 350, 400, 450, and 500 amino acid residues.

The types of carrier molecules used for generating an immunogenic compound of the invention, such as an immunogenic compound comprising or consisting of a polypeptide of formula (I) linked to a carrier molecule, are well in the general knowledge of the one skilled in the art. In particular, the function of the carrier molecule is to provide cytokine help (or T-cell help) in order to enhance the immune response against tumor antigen.

Preferably, the antigenic peptide is linked to a carrier molecule, in particular to a carrier protein, preferably by covalent or non-covalent bond. The carrier molecule to which the peptide is optionally bound can be selected from a wide variety of known carriers. Examples of carrier molecules for vaccine purposes encompass proteins such as human or bovine serum albumin and keyhole limpet haemocyanin (KLH) and fatty acids. Other embodiments of carrier molecules to which an antigenic peptide of formula (I) may be covalently linked include bacterial toxins or toxoids, such as diphtheria, cholera, E. coli heat labile or tetanus toxoids, the N. meningitidis outer membrane protein (European patent application no EP0372501), synthetic peptides (European patent applications no EP0378881 and no EP0427347), heat shock proteins (PCT application no WO93/17712), Pertussis proteins (PCT application no WO98/58668), protein D from H. influenzae (PCT application no WO00/56360) and toxin A or B from C. difficile (International patent application WO00/61761).

More preferably, the carrier protein or carrier peptide is a protein/peptide having immuno-adjuvant properties, such as providing stimulation of CD4+ Th1 cells as described herein. A preferred example thereof is a non-tumor antigen that recalls immune memory or provides a non-specific help or could be a specific tumor-derived helper peptide, such as tetanus helper peptide, keyhole limpet hemocyanin peptide or PADRE peptide. Another preferred example is a specific tumor derived helper peptide, which may be presented by MHC II, in particular by HLA-DR, HLA-DP or HLA-DQ, such as fragments of shared overexpressed tumor antigens, e.g. HER2, NY-ESO-1, hTERT or IL13RA2, as described above. In a preferred embodiment, the carrier protein or carrier peptide is a protein/peptide having immuno-adjuvant properties may be a HHD-DR3 carrier peptide MAK-TIAYDEEARRGLERGLN (SEQ ID NO: 856). In particular, "PepNt" and/or "PepCt" may correspond to a carrier protein or carrier peptide, such as the HHD-DR3 carrier peptide MAKTIAYDEEARRGLERGLN (SEQ ID NO: 856).

Another preferred example is h-pAg T13L (sequence: TPPAYRPPNAPIL; SEQ ID NO: 860; Bhasin M, Singh H, Raghava GP (2003) MHCBN: a comprehensive database of MHC binding and non-binding peptides. Bioinformatics 19: 665-666). Further examples of preferred carrier proteins/ peptides, in particular of helper peptides, include the UCP2 peptide (for example as described in WO 2013/135553 A1 or in Dosset et al., Clin Cancer Res. 2012 Nov. 15; 18(22): 6284-95) and the BIRC5 peptide (for example as described in EP2119726 A1 or in Widenmeyer et al., Int) Cancer. 2012 Jul. 1; 131(1):140-9). The most preferred helper peptide is the UCP2 peptide (amino acid sequence: KSVWSKLQSI-GIRQH; SEQ ID NO: 859).

Moreover, in the polypeptide according to formula (I), (Ia) or (Ib), "PepNt" and/or "PepCt" may preferably correspond to such a protein/peptide having immuno-adjuvant properties, such as providing stimulation of CD4+ Th1 cells as described herein.

Moreover, the immunogenic compound may comprise or consist of such a protein/peptide having immuno-adjuvant properties, such as providing stimulation of CD4₊ Th1 cells as described herein, linked covalently to the N-terminus of the antigenic peptide according to the present invention or to the N-Terminus of a polypeptide/protein comprising said antigenic peptide.

Preferably, the antigenic peptide according to the present invention (or the polypeptide/protein comprising said antigenic peptide) is covalently bound to the carrier molecule through a linker moiety.

Preferred linker agents encompass the linker agents named GMBS, sulfo-GMBS, SMPB and sulfo-SMPB.

In some embodiments of an immunogenic compound as defined above, the linker agent is selected from the group consisting of GMBS (N-[γ-maleimidobutyryl-oxy]succinimide ester), Sulfo-GMBS (N-[γ-maleimidobutyryl-oxy] sulfosuccinimide ester), SMPB (succinimidyl 4-[p-maleimidophenyl]butyrate) and Sulfo-SMPB (sulfosuccinimidyl 4-[p-maleimidophenyl]butyrate).

Methods for conjugating two proteins with a linker agent in general, and more particularly with a linker agent selected from the group consisting of GMBS, Sulfo-GMBS, SMPB and Sulfo-SMPB, are well known by the one skilled in the art. Illustratively, such protocols are disclosed in the leaflets that are made publicly available by the Pierce Company (Illinois, USA). GMBS, Sulfo-GMBS, SMPB and Sulfo-SMPB consist of heterobifunctional linker agents that contain both a N-hydroxysuccinimide (NHS) ester group and a maleimide group. Conjugation using GMBS, Sulfo-GMBS, SMPB or Sulfo-SMPB is usually performed by a two-step procedure. In a first step, the amine-containing protein is reacted with a several-fold molar excess of the linker agent at pH 7-9 to form amide bonds, followed by removal of excess non-reacted linker agent, usually by desalting or dialysis. In a second step, the sulfhydryl-containing molecule (e.g. peptide of formula (I)) is added to react with the maleimide groups already attached to the first protein at pH 6.5-7.5 to form stable thioether bonds.

Using SMPB or Sulfo-SMPB as linker agents for covalently linking the antigenic peptide according to the present invention (or the polypeptide/protein comprising said antigenic peptide, such as the polypeptide of formula (I)) to the amine-containing carrier protein, leads to a conjugate of formula (II) below:

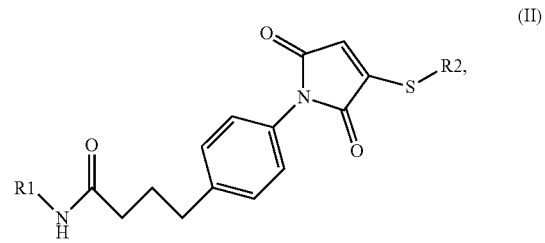

wherein:
R1 consists of one reactive group of the amine-containing carrier protein, and wherein the NH group attached thereto derives from (i) the alpha amino group located at the N-terminal end of the amine-containing carrier protein or (ii) a lateral chain amino group from a Lysine (K) amino acid residue of the amine-containing carrier protein; and
R2 consists of the antigenic peptide according to the present invention (or the polypeptide/protein comprising said antigenic peptide, such as a polypeptide of formula (I)), and wherein the sulphur (S) atom attached thereto derives from a sulfhydryl (SH) group of a cysteine residue located at the N-terminal end or at the C-terminal end of a peptide of formula (I). In some embodiments, the sulfhydryl moiety could be part of an unnatural amino acid, or any other molecule present at the end of the peptide of formula (I).

Using GMBS or Sulfo-GMBS as linker agents for covalently linking the antigenic peptide according to the present invention (or the polypeptide/protein comprising said antigenic peptide, such as a polypeptide of formula (I)) to the amine-containing carrier protein, in particular the CRM197 carrier, protein leads to a conjugate of formula (III) below:

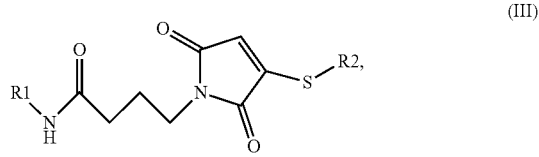

wherein:
- R1 consists of one reactive group of the amine-containing carrier protein, and wherein the NH group attached thereto derives from (i) the alpha amino group located at the N-terminal end of the amine-containing carrier protein or (ii) a lateral chain amino group from a Lysine (K) amino acid residue of the amine-containing carrier protein; and
- R2 consists of the antigenic peptide according to the present invention (or the polypeptide/protein comprising said antigenic peptide, such as a polypeptide of formula (I)), and wherein the sulphur (S) atom attached thereto derives from a sulfhydryl (SH) group of a cysteine residue located at the N-terminal end or at the C-terminal end of a peptide of formula (I). In some embodiments, the sulfhydryl moiety could be part of an unnatural amino acid, or any other molecule present at the end of the peptide of formula (I).

Peptide-MHC (pMHC) Multimers Comprising the Antigenic Peptide

In a further aspect, the present invention also provides a Peptide-MHC (pMHC) multimer comprising an antigenic peptide according to the present invention.

As used herein, the term "peptide-MHC multimer" (pMHC) refers to a stable multimeric complex composed of major histocompatibility complex (MHC) protein subunits loaded with an antigenic peptide of the invention. In general, "MHC multimers" are oligomeric forms of MHC molecules. The main function of an MHC molecule is to bind to an antigen. According to the invention, said antigen is the antigenic peptide according to the invention. Accordingly, a complex of MHC proteins "loaded" with the antigenic peptide of the invention typically means that the antigenic peptide of the invention is bound to one or more of the MHC proteins. The "peptide-MHC multimers" (pMHC) of the invention include, but are not limited to, a peptide-MHC dimer, trimer, tetramer, pentamer, hexamer, heptamer or octamer. MHC tetramers and pentamers are preferred. The term "Major Histocompatibility Complex" (MHC) is a generic designation meant to encompass the histo-compatibility antigen systems described in different species including the human leucocyte antigens (HLA). In humans there are three major different genetic loci that encode MHC class I molecules: HLA-A, HLA-B, and HLA-C. HLA-A*01, HLA-A*02, and HLA-A*11 are examples of different MHC class I alleles that can be expressed from these loci.

In one embodiment of the invention, the pMHC multimer is a peptide/MHC class I multimer. In another particular embodiment, the pMHC multimer is a HLA corresponding to MHC class I/peptide multimer. Accordingly, the pMHC multimer may be a HLA-peptide multimer selected from the group consisting of HLA-A-peptide multimer, HLA-B-peptide multimer, HLA-C-peptide multimer, HLA-E-peptide multimer, MICA-peptide multimer and MICB-peptide multimer.

Methods for obtaining pHMC multimers are known in the art and described, for example, in WO96/26962 and WO01/18053, which are incorporated herein by reference.

In addition to the MHC molecule and the antigenic peptide of the invention, the pMHC may contain further components, such as a multimerization agent and/or a label (e.g., for visualization). Examples of labels include, but are not limited to, fluorescent labels, e.g. fluorescently labelled proteins, such as streptavidin. Fluorescent labels include allophycocyanin (APC), phycoerythrin (PE), R-phycoerythrin (R-PE) and fluorescein isothiocyanate (FITC). A preferred label is biotin.

In one embodiment of the invention, said pMHC multimer can be used to visualize T cell populations that are specific for the MHC class I peptide complex or a HLAs corresponding to MHC class I/peptide complex as described here above. For example, the pMHC multimer may be a multimer where the heavy chain of the MHC is biotinylated, which allows combination as a tetramer with streptavidine. Such pMHC tetramer has an increased avidity for the appropriate TCR-carrier T lymphocytes and can therefore be used to visualize reactive populations by immunofluorescence. In another embodiment of the invention, said pMHC multimer can be used for the detection and/or isolation by screening (in flow cytometry or by immunomagnetic screening) of T cell populations that are specific for a pMHC complex as described here above.

Cells Loaded with the Antigenic Peptide or the Immunogenic Compound

In a further aspect, the present invention also provides a cell loaded with an antigenic peptide according to the present invention or with the immunogenic compound comprising an antigenic peptide according to the present invention as described above. In particular, preferred embodiments of the antigenic peptide as described above also apply for such a cell according to the present invention. For example, the antigenic peptide loaded to the cell or comprised in the immunogenic compound loaded to the cell preferably comprises or consists of an amino acid sequence as set forth in any one of SEQ ID NOs 1 to 580 and 861 to 887, such as an antigenic peptide comprising or consisting of an amino acid sequence as set forth in any one of SEQ ID NOs 1 to 580. For example, antigenic peptides according to the present invention comprising or consisting of an amino acid sequence as set forth in any one of SEQ ID NOs 1-160, 162-253 and 255-580 are more preferred. For example, antigenic peptides according to the present invention comprising or consisting of an amino acid sequence as set forth in any one of SEQ ID NOs 30, 31, 32, 87, 97, 145, 193, 194, 220, 221, 255, 521 and 524 are even more preferred. For example, antigenic peptides according to the present invention comprising or consisting of an amino acid sequence as set forth in any one of SEQ ID NOs 30, 31, 32, 87, 97, 193, 194, 220, 255, 521 and 524 are still more preferred. For example, antigenic peptides according to the present invention comprising or consisting of an amino acid sequence as set forth in any one of SEQ ID NOs 30, 31, 32, 87, 97, 194, 220, 255, 521 and 524 are still more preferred. For example, antigenic peptides according to the present invention comprising or consisting of an amino acid sequence as set forth in any one of SEQ ID NOs 30, 32, 87, 97, and 194 are most preferred. For example, antigenic peptides according to the present invention comprising or consisting of an amino acid sequence as set forth in any one of SEQ ID NOs 30, 32, 194, 220, 254 or 255 are particularly preferred. Also combinations thereof are preferred, namely, cells loaded with distinct antigenic peptides according to the present invention (or with the respective immunogenic compound(s)).

A preferred cell loaded with the antigenic peptide according to the present invention or with the immunogenic compound according to the present invention is an antigen presenting cell (APC), more preferably a dendritic cell (DC).

APCs are of particular interest, as their main function is to process antigens and present it on the cell surface to the T cells of the immune system, so as to initiate and modulate T-cell responses in vivo. In the context of the present invention, it is preferred that the APCs are loaded with the antigenic peptide(s) and/or immunogenic compound(s) according to the invention. This may be done by exposing APCs in vitro with said antigenic peptide(s) and/or immunogenic compound(s) (as described in Rizzo M M, Alaniz L, Mazzolini G. Ex vivo loading of autologous dendritic cells with tumor antigens. Methods Mol Biol. 2014; 1139:41-4; Rolinski J, Hus I. Breaking immunotolerance of tumors: a new perspective for dendritic cell therapy. J Immunotoxicol. 2014 October; 11(4):311-8).

Preferred APCs according to the invention are dendritic cells (DCs). It can indeed be advantageous to combine at least one antigenic peptide or immunogenic compound according to the invention with DCs, as those are the most potent APCs and have been reported to be frequently functionally defective in cancer patients. DCs can be easily obtained by the skilled person in the art from either healthy compatible donors (i.e. the DCs are HLA-related) or from the patient himself provided that they are functional (i.e. the DCs are autologous), for example by direct isolation from the peripheral blood, or by derivation from peripheral blood cells such as CD14+ monocytes or CD34+ hematopoietic precursors (Figdor C G, de Vries I J, Lesterhuis W J, Melief C J. Dendritic cell immunotherapy: mapping the way. Nat Med. 2004 May; 10(5):475-80). DCs can indeed be distinguished from other cells of peripheral blood by their surface markers, such as S100, p55, CD83, and/or OX62, and may thus be isolated and purified based on said markers using cell cultures techniques well-known in the art.

Nucleic Acids Encoding the Antigenic Peptides and Host Cells Comprising Nucleic Acids In a further aspect, the present invention also provides nucleic acid encoding the antigenic peptide according to the present invention, the polypeptide of formula (I) as defined above, or the immunogenic compound according to the present invention, wherein the immunogenic compound is a peptide or a protein. In particular, preferred embodiments of the antigenic peptide as described above also apply for such a nucleic acid according to the present invention. For example, the antigenic peptide encoded by the nucleic acid preferably comprises or consists of an amino acid sequence as set forth in any one of SEQ ID NOs 1 to 580 and 861 to 887, such as an antigenic peptide comprising or consisting of an amino acid sequence as set forth in any one of SEQ ID NOs 1 to 580. For example, antigenic peptides according to the present invention comprising or consisting of an amino acid sequence as set forth in any one of SEQ ID NOs 1-160, 162-253 and 255-580 are more preferred. For example, antigenic peptides according to the present invention comprising or consisting of an amino acid sequence as set forth in any one of SEQ ID NOs 30, 31, 32, 87, 97, 145, 193, 194, 220, 221, 255, 521 and 524 are even more preferred. For example, antigenic peptides according to the present invention comprising or consisting of an amino acid sequence as set forth in any one of SEQ ID NOs 30, 31, 32, 87, 97, 193, 194, 220, 255, 521 and 524 are still more preferred. For example, antigenic peptides according to the present invention comprising or consisting of an amino acid sequence as set forth in any one of SEQ ID NOs 30, 31, 32, 87, 97, 194, 220, 255, 521 and 524 are still more preferred. For example, antigenic peptides according to the present invention comprising or consisting of an amino acid sequence as set forth in any one of SEQ ID NOs 30, 32, 87, 97, and 194 are most preferred. For example, antigenic peptides according to the present invention comprising or consisting of an amino acid sequence as set forth in any one of SEQ ID NOs 30, 32, 194, 220, 254 or 255 are particularly preferred. Also combinations thereof are preferred, namely, nucleic acids encoding distinct antigenic peptides according to the present invention.

Nucleic acids preferably comprise single stranded, double stranded or partially double stranded nucleic acids, preferably selected from gDNA, cDNA, RNA, antisense DNA, antisense RNA, complementary RNA/DNA sequences with or without expression elements, a mini-gene, gene fragments, regulatory elements, promoters, and combinations thereof.

Further preferred examples of nucleic acid (molecules) and/or polynucleotides include, e.g., a recombinant polynucleotide, a vector, an oligonucleotide, an RNA molecule such as an rRNA, an mRNA, or a tRNA, or a DNA molecule as described above. It is thus preferred that the nucleic acid (molecule) is a DNA molecule or an RNA molecule; preferably selected from gDNA; cDNA; rRNA; mRNA; antisense DNA; antisense RNA; complementary RNA and/or DNA sequences; RNA and/or DNA sequences with or without expression elements, regulatory elements, and/or promoters; a vector; and combinations thereof.

It is of great interest in the fields of therapeutics, diagnostics, reagents and for biological assays to be able to deliver a nucleic acid, e.g., a ribonucleic acid (RNA) inside a cell, whether in vitro, in vivo, in situ or ex vivo, such as to cause intracellular translation of the nucleic acid and production of an encoded peptide of interest. Of particular importance is the delivery and function of a non-integrative polynucleotide. Accordingly, nucleic acids, which do not integrate into the chromosomes of the host, are preferred, such as mRNA. In general, nucleic acids, such as mRNA, may be optimized for expression of the antigenic peptide of the invention, e.g. by methods known in the art, such as codon optimization. In addition, the nucleic acid may be modified, for example, in order to enhance its stability, prolong its lifetime and/or to increase the expression of the antigenic peptide of the invention. Accordingly, optimized or modified mRNA (mmRNA), which encodes an antigenic peptide according to the present invention, is preferred. The mmRNA are distinguished from wild type mRNA in their functional and/or structural design features for optimal delivery of the mRNA and/or for optimal expression of the antigenic peptide of the invention (for example as described in WO 2013/151672 A2, WO 2013/101690 A1, WO2013/052523 A, which are incorporated herein by reference). In general, nucleic acids may be delivered "naked" or associated with a carrier, e.g., a cationic carrier. Cationic carriers (positively charged) typically associate easily with nucleic acids, which are negatively charged. The carrier may be any of any kind including, for example, polymers, proteins, lipids and nanoparticles. Cationic lipids and nanoparticles (in particular lipid nanoparticles, LNPs) are preferred for nucleic acid delivery. Accordingly, the present invention also provides a nucleic acid as described herein associated with a carrier (e.g., a lipid, in particular a cationic lipid or an LNP).

In some embodiments, the nucleic acid molecule may be a vector. The term "vector", as used in the context of the present invention, refers to a nucleic acid molecule, preferably to an artificial nucleic acid molecule, i.e. a nucleic acid molecule which does not occur in nature. A vector in the context of the present invention is suitable for incorporating or harboring a desired nucleic acid sequence. Such vectors may be storage vectors, expression vectors, cloning vectors, transfer vectors etc. A storage vector is a vector which allows the convenient storage of a nucleic acid molecule. Thus, the vector may comprise a sequence corresponding, e.g., to a desired antigenic peptide according to the present invention. An expression vector may be used for production of expression products such as RNA, e.g. mRNA, or peptides, polypeptides or proteins. For example, an expression vector may comprise sequences needed for transcription of a sequence stretch of the vector, such as a promoter sequence. A cloning vector is typically a vector that contains a cloning site, which may be used to incorporate nucleic acid sequences into the vector. A cloning vector may be, e.g., a plasmid vector or a bacteriophage vector. A transfer vector may be a vector which is suitable for transferring nucleic acid molecules into cells or organisms, for example, viral vectors. A vector in the context of the present invention may be, e.g., an RNA vector or a DNA vector. Preferably, a vector is a DNA molecule. For example, a vector in the sense of the present application comprises a cloning site, a selection marker, such as an antibiotic resistance factor, and a sequence suitable for multiplication of the vector, such as an origin of replication. Preferably, a vector in the context of the present application is a plasmid vector. Preferably, a vector in the context of the present application is an expression vector. A preferred vector is a vector for expression in bacterial cells. More preferably, the vector is useful for expression in so-called "live bacterial vaccine vectors", wherein live bacterial cells (such as bacteria or bacterial spores, e.g., endospores, exospores or microbial cysts) can serve as vaccines. Preferred examples thereof are described in da Silva et al., Live bacterial vaccine vectors: an overview; Braz J Microbiol. 2015 Mar. 4; 45(4):1117-29.

Nucleic acids encoding antigenic peptides according to the invention may be in the form of naked nucleic acids, or nucleic acids cloned into plasmids or viral vectors (Tregoning and Kinnear, Using Plasmids as DNA Vaccines for Infectious Diseases. Microbiol Spectr. 2014 December; 2(6). doi: 10.1128/microbiolspec.PLAS-0028-2014), the latter being particularly preferred. Examples of suitable viral vectors according to the invention include, without limitation, retrovirus, adenovirus, adeno-associated virus (AAV), herpes virus and poxvirus vectors. It is within the skill of the person in the art to clone a nucleic acid into a plasmid or viral vector, using standard recombinant techniques in the art.

In a further aspect, the present invention also provides a host cell comprising the nucleic acid according to the present invention. Also combinations thereof are preferred, namely, host cells comprising distinct nucleic acids according to the present invention, for example encoding distinct antigenic peptides according to the present invention.

Preferably, the nucleic acid comprised in the host cell is preferably a vector. Preferably, the host cell is a bacterial cell. Such a host cell may be preferably used for production of the antigenic peptide according to the present invention or the immunogenic compound according to the present invention. Moreover, such a host cell may also be an active component in a vaccine.

Preferably, the host cell is a bacterial cell, more preferably a gut bacterial cell. The term "gut bacterial cell" refers to bacteria residing in the (human) gut.

Such a bacterial host cell may serve as "live bacterial vaccine vector", wherein live bacterial cells (such as bacteria or bacterial spores, e.g., endospores, exospores or microbial cysts) can serve as vaccines. Preferred examples thereof are described in da Silva et al., Live bacterial vaccine vectors: an overview; Braz J Microbiol. 2015 Mar. 4; 45(4):1117-29.

Bacterial cells (such as bacteria or bacterial spores, e.g., endospores, exospores or microbial cysts), in particular (entire) gut bacterial species, can be advantageous, as they have the potential to trigger a greater immune response than the (poly)peptides or nucleic acids they contain.

Alternatively, bacterial cells, in particular gut bacteria, according to the invention may be in the form of probiotics, i.e. of live gut bacterium, which can thus be used as food additive due to the health benefits it can provide. Those can be for example lyophilized in granules, pills or capsules, or directly mixed with dairy products for consumption.

Nanoparticles Comprising the Antigenic Peptide or the Immunogenic Compound

In a further aspect, the present invention also provides a nanoparticle comprising, in particular a nanoparticle loaded with,
  at least one of the antigenic peptides according to the present invention, or
  at least one of the immunogenic compounds according to the present invention;
and, optionally, with an adjuvant.

In particular, preferred embodiments of the antigenic peptide as described above also apply for such a nanoparticle according to the present invention. For example, the antigenic peptide loaded to the nanoparticle or comprised in the immunogenic compound loaded to the nanoparticle preferably comprises or consists of an amino acid sequence as set forth in any one of SEQ ID NOs 1 to 580 and 861 to 887, such as an antigenic peptide comprising or consisting of an amino acid sequence as set forth in any one of SEQ ID NOs 1 to 580. For example, antigenic peptides according to the present invention comprising or consisting of an amino acid sequence as set forth in any one of SEQ ID NOs 1-160, 162-253 and 255-580 are more preferred. For example, antigenic peptides according to the present invention comprising or consisting of an amino acid sequence as set forth in any one of SEQ ID NOs 30, 31, 32, 87, 97, 145, 193, 194, 220, 221, 255, 521 and 524 are even more preferred. For example, antigenic peptides according to the present invention comprising or consisting of an amino acid sequence as set forth in any one of SEQ ID NOs 30, 31, 32, 87, 97, 193, 194, 220, 255, 521 and 524 are still more preferred. For example, antigenic peptides according to the present invention comprising or consisting of an amino acid sequence as set forth in any one of SEQ ID NOs 30, 31, 32, 87, 97, 194, 220, 255, 521 and 524 are still more preferred. For example, antigenic peptides according to the present invention comprising or consisting of an amino acid sequence as set forth in any one of SEQ ID NOs 30, 32, 87, 97, and 194 are most preferred. For example, antigenic peptides according to the present invention comprising or consisting of an amino acid sequence as set forth in any one of SEQ ID NOs 30, 32, 194, 220, 254 or 255 are particularly preferred. Also combinations thereof are preferred, namely, nanoparticles loaded with distinct antigenic peptides according to the present invention (or with the respective immunogenic compound (s)).

Nanoparticles, in particular for use as vaccines, are known in the art and described, for example, in Shao et al., Nanoparticle-based immunotherapy for cancer, ACS Nano 2015, 9(1):16-30; Zhao et al., Nanoparticle vaccines, Vaccine 2014, 32(3):327-37; and Gregory et al., Vaccine delivery using nanoparticles, Front Cell Infect Microbial. 2013, 3:13, doi: 10.3389/fcimb.2013.00013. eCollection 2013, Review. In particular, the nanoparticle is used for delivery of the antigenic peptide (or the immunogenic compound/polypeptide/protein/nucleic acid comprising the antigenic peptide) and may optionally also act as an adjuvant. The antigenic peptide (the immunogenic compound/polypeptide/protein/nucleic acid comprising the antigenic peptide) is typically either encapsulated within the nanoparticle or linked/bound to (decorated onto) the surface of the nanoparticle ("coating"). Compared to conventional approaches, nanoparticles can protect the payload (antigen/adjuvant) from the surrounding biological milieu, increase the half-life, minimize the systemic toxicity, promote the delivery to APCs, or even directly trigger the activation of TAA-specific T-cells. Preferably, the nanoparticle has a size (diameter) of no more than 300 nm, more preferably of no more than 200 nm and most preferably of no more than 100 nm. Such nanoparticles are adequately sheltered from phagocyte uptake, with high structural integrity in the circulation and long circulation times, capable of accumulating at sites of tumor growth, and able to penetrate deep into the tumor mass.

Examples of nanoparticles include polymeric nanoparticles such as poly(ethylene glycol) (PEG) and poly (D,L-lactic-coglycolic acid) (PLGA); inorganic nanoparticles such as gold nanoparticles, iron oxide beads, iron-oxide zinc-oxide nanoparticles, carbon nanotubes and mesoporous silica nanoparticles; liposomes, such as cationic liposomes; immunostimulating complexes (ISCOM); virus-like particles (VLP); and self-assembled proteins.

Polymeric nanoparticles are nanoparticles based on/comprising polymers, such as poly(D,L-lactide-co-glycolide) (PLG), poly(D,L-lactic-coglycolic acid)(PLGA), poly(γ-glutamic acid) (γ-PGA), poly(ethylene glycol) (PEG), and polystyrene. Polymeric nanoparticles may entrap an antigen (e.g., the antigenic peptide or a (poly)peptide comprising the same) or bind to/conjugate to an antigen (e.g., the antigenic peptide or a (poly)peptide comprising the same). Polymeric nanoparticles may be used for delivery, e.g. to certain cells, or sustain antigen release by virtue of their slow biodegradation rate. For example, g-PGA nanoparticles may be used to encapsulate hydrophobic antigens. Polystyrene nanoparticles can conjugate to a variety of antigens as they can be surface-modified with various functional groups. Polymers, such as Poly(L-lactic acid) (PLA), PLGA, PEG, and natural polymers such as polysaccharides may also be used to synthesize hydrogel nanoparticles, which are a type of nano-sized hydrophilic three-dimensional polymer network. Nanogels have favorable properties including flexible mesh size, large surface area for multivalent conjugation, high water content, and high loading capacity for antigens. Accordingly, a preferred nanoparticle is a nanogel, such as a chitosan nanogel. Preferred polymeric nanoparticles are nanoparticles based on/comprising PEG and PLGA.

Inorganic nanoparticles are nanoparticles based on/comprising inorganic substances, and examples of such nanoparticles include gold nanoparticles, iron oxide beads, iron-oxide zinc-oxide nanoparticles, carbon nanoparticles (e.g., carbon nanotubes) and mesoporous silica nanoparticles. Inorganic nanoparticles provide a rigid structure and controllable synthesis. For example, gold nanoparticles can be easily produced in different shapes, such as spheres, rods, cubes. Inorganic nanoparticles may be surface-modified, e.g. with carbohydrates. Carbon nanoparticles provide good biocompatibility and may be produced, for example, as nanotubes or (mesoporous) spheres. For example, multiple copies of the antigenic peptide according to the present invention (or a (poly)peptide comprising the same) may be conjugated onto carbon nanoparticles, e.g. carbon nanotubes. Mesoporous carbon nanoparticles are preferred for oral administration. Silica-based nanoparticles (SiNPs) are also preferred. SiNPs are biocompatible and show excellent properties in selective tumor targeting and vaccine delivery. The abundant silanol groups on the surface of Si NPs may be used for further modification to introduce additional functionality, such as cell recognition, absorption of specific biomolecules, improvement of interaction with cells, and enhancement of cellular uptake. Mesoporous silica nanoparticles are particularly preferred.

Liposomes are typically formed by phospholipids, such as 1,2-dioleoyl-3-trimethylammonium propane (DOTAP). In general, cationic liposomes are preferred. Liposomes are self-assembling with a phospholipid bilayer shell and an aqueous core. Liposomes can be generated as unilameller vesicles (having a single phospholipid bilayer) or as multi-lameller vesicles (having several concentric phospholipid shells separated by layers of water). Accordingly, antigens can be encapsulated in the core or between different layers/shells. Preferred liposome systems are those approved for human use, such as Inflexal® V and Epaxal®.

Immunostimulating complexes (ISCOM) are cage like particles of about 40 nm (diameter), which are colloidal saponin containing micelles, for example made of the saponin adjuvant Quil-A, cholesterol, phospholipids, and the (poly)peptide antigen (such as the antigenic peptide or a polypeptide comprising the same). These spherical particles can trap the antigen by apolar interactions. Two types of ISCOMs have been described, both of which consist of cholesterol, phospholipid (typically either phosphatidylethanolamine or phosphatidylcholine) and saponin (such as Quil-A).

Virus-like particles (VLP) are self-assembling nanoparticles formed by self-assembly of biocompatible capsid proteins. Due to the naturally-optimized nanoparticle size and repetitive structural order VLPs can induce potent immune responses. VLPs can be derived from a variety of viruses with sizes ranging from 20 nm to 800 nm, typically in the range of 20-150 nm. VLPs can be engineered to express additional peptides or proteins either by fusing these peptides/proteins to the particle or by expressing multiple antigens. Moreover, antigens can be chemically coupled onto the viral surface to produce bioconjugate VLPs.

Examples of self-assembled proteins include ferritin and major vault protein (MVP). Ferritin is a protein that can self-assemble into nearly-spherical 10 nm structure. Ninety-six units of MVP can self-assemble into a barrel-shaped vault nanoparticle, with a size of approximately 40 nm wide and 70 nm long. Antigens that are genetically fused with a minimal interaction domain can be packaged inside vault nanoparticles by self-assembling process when mixed with MVPs. Accordingly, the antigen (such as the antigenic peptide according to the present invention of a polypeptide comprising the same) may be fused to a self-assembling protein or to a fragment/domain thereof, such as the minimal interaction domain of MVP. Accordingly, the present invention also provides a fusion protein comprising a self-assembling protein (or a fragment/domain thereof) and the antigenic peptide according to the present invention.

In general, preferred examples of nanoparticles (NPs) include iron oxide beads, polystyrene microspheres, poly(γ-glutamic acid) (γ-PGA) NPs, iron oxide-zinc oxide NPs, cationized gelatin NPs, pluronic-stabilized poly(propylene sulfide) (PPS) NPs, PLGA NPs, (cationic) liposomes, (pH-responsive) polymeric micelles, PLGA, cancer cell membrane coated PLGA, lipid-calcium-phosphate (LCP) NPs, liposome-protamine-hyaluronic acid (LPH) NPs, polystyrene latex beads, magnetic beads, iron-dextran particles and quantum dot nanocrystals.

Preferably, the nanoparticle further comprises an adjuvant, for example a toll-like receptor (TLR) agonist. Thereby, the antigenic peptide (the immunogenic compound/polypeptide/protein/nucleic acid comprising the antigenic peptide) can be delivered together with an adjuvant, for example to antigen-presenting cells (APCs), such as dendritic cells (DCs). The adjuvant may be encapsulated by the nanoparticle or bound to/conjugated to the surface of the nanoparticle, preferably similarly to the antigenic peptide.

Particularly preferred adjuvants are polyinosinic:polycytidylic acid (also referred to as "poly I:C") and/or its derivative poly-ICLC. Poly I:C is a mismatched double-stranded RNA with one strand being a polymer of inosinic acid, the other a polymer of cytidylic acid. Poly I:C is an immunostimulant known to interact with toll-like receptor 3 (TLR3). Poly I:C is structurally similar to double-stranded RNA, which is the "natural" stimulant of TLR3. Accordingly, poly I:C may be considered a synthetic analog of double-stranded RNA. Poly-ICLC is a synthetic complex of carboxymethylcellulose, polyinosinic-polycytidylic acid, and poly-L-lysine double-stranded RNA. Similar to poly I:C, also poly-ICLC is a ligand for TLR3. Poly I:C and poly-ICLC typically stimulate the release of cytotoxic cytokines. A preferred example of poly-ICLC is Hiltonol®.

Pharmaceutical Compositions

In a further aspect, the present invention also provides a pharmaceutical composition comprising at least one of the following:
- the antigenic peptide according to the present invention as described herein,
- the immunogenic compound according to the present invention as described herein,
- the nanoparticle according to the present invention as described herein,
- the cell according to the present invention as described herein,
- the nucleic acid according to the present invention as described herein, and/or
- the host cell according to the present invention as described herein, and, optionally, one or more pharmaceutically acceptable excipients or carriers.

In particular, preferred embodiments of the antigenic peptide as described above also apply for such a pharmaceutical composition according to the present invention. For example, the antigenic peptide comprised in the pharmaceutical composition or the antigenic peptide comprised in any of the immunogenic compound, the nanoparticle, the cell, the nucleic acid or the host cell comprised by the pharmaceutical composition preferably comprises or consists of an amino acid sequence as set forth in any one of SEQ ID NOs 1 to 580 and 861 to 887, such as an antigenic peptide comprising or consisting of an amino acid sequence as set forth in any one of SEQ ID NOs 1 to 580. For example, antigenic peptides according to the present invention comprising or consisting of an amino acid sequence as set forth in any one of SEQ ID NOs 1-160, 162-253 and 255-580 are more preferred. For example, antigenic peptides according to the present invention comprising or consisting of an amino acid sequence as set forth in any one of SEQ ID NOs 30, 31, 32, 87, 97, 145, 193, 194, 220, 221, 255, 521 and 524 are even more preferred. For example, antigenic peptides according to the present invention comprising or consisting of an amino acid sequence as set forth in any one of SEQ ID NOs 30, 31, 32, 87, 97, 193, 194, 220, 255, 521 and 524 are still more preferred. For example, antigenic peptides according to the present invention comprising or consisting of an amino acid sequence as set forth in any one of SEQ ID NOs 30, 31, 32, 87, 97, 194, 220, 255, 521 and 524 are still more preferred. For example, antigenic peptides according to the present invention comprising or consisting of an amino acid sequence as set forth in any one of SEQ ID NOs 30, 32, 87, 97, and 194 are most preferred. For example, antigenic peptides according to the present invention comprising or consisting of an amino acid sequence as set forth in any one of SEQ ID NOs 30, 32, 194, 220, 254 or 255 are particularly preferred.

Also combinations thereof are preferred, namely, pharmaceutical compositions comprising distinct antigenic peptides according to the present invention. For example, the pharmaceutical composition may comprise
 (i) at least two distinct antigenic peptides according to the present invention;
 (ii) at least two distinct immunogenic compounds according to the present invention;
 (iii) at least two distinct nanoparticles according to the present invention; and/or
 (iv) at least two distinct nucleic acids according to the present invention.

Accordingly, the present invention provides a pharmaceutical composition comprising (at least) one antigenic peptide according to the present invention as described herein. Moreover, the present invention also provides a pharmaceutical composition comprising (at least) one immunogenic compound according to the present invention as described herein. Moreover, the present invention also provides a pharmaceutical composition comprising (at least) one nanoparticle according to the present invention as described herein. Moreover, the present invention also provides a pharmaceutical composition comprising (at least) one cell according to the present invention as described herein. Moreover, the present invention also provides a pharmaceutical composition comprising (at least) one nucleic acid according to the present invention as described herein. Moreover, the present invention also provides a pharmaceutical composition comprising (at least) one host cell according to the present invention as described herein.

Preferably, the pharmaceutical composition comprises at least two distinct antigenic peptides according to the present invention.

In particular, the present invention provides a pharmaceutical composition comprising a first antigenic peptide according to the present invention, which comprises or consists of a microbiota sequence variant of a fragment of the human tumor antigen BIRC5, and a second antigenic peptide according to the present invention, which comprises or consists of a microbiota sequence variant of a fragment of the human tumor antigen FOXM1. Preferably, the first antigenic peptide comprises or consists of a microbiota sequence variant of the BIRC5 fragment (human reference peptide) "LTLGEFLKL" (SEQ ID NO: 593), such as an antigenic peptide comprising or consisting of an amino acid sequence as set forth in SEQ ID NO: 30, 31 or 32, and the second antigenic peptide comprises or consists of a microbiota sequence variant of the FOXM1 fragment (human reference peptide) "LMDLSTTPL" (SEQ ID NO: 674), such as an antigenic peptide comprising or consisting of an amino acid sequence as set forth in SEQ ID NO: 220 or 868. Even more preferably, the pharmaceutical composition comprises an antigenic peptide comprising or consisting of SEQ ID NO: 32 and an antigenic peptide comprising or consisting of SEQ ID NO: 220.

In particular, the present invention also provides a pharmaceutical composition comprising a first antigenic peptide according to the present invention, which comprises or consists of a microbiota sequence variant of a fragment of the human tumor antigen BIRC5, and a second antigenic peptide according to the present invention, which comprises or consists of a microbiota sequence variant of a fragment of the tumor antigen IL13RA2. Preferably, the first antigenic peptide comprises or consists of a microbiota sequence variant of the BIRC5 fragment (human reference peptide) "LTLGEFLKL" (SEQ ID NO: 593), such as an antigenic peptide comprising or consisting of an amino acid sequence as set forth in SEQ ID NO: 30, 31 or 32, and the second antigenic peptide comprises or consists of a microbiota sequence variant of the IL13RA2 fragment (human reference peptide) "WLPFGFILI" (SEQ ID NO: 691) or "WLPFGFILIL" (SEQ ID NO: 692), such as an antigenic peptide comprising or consisting of an amino acid sequence as set forth in SEQ ID NO: 254, 255, 878 or 879. Even more preferably, the pharmaceutical composition comprises an antigenic peptide comprising or consisting of SEQ ID NO: 32 and an antigenic peptide comprising or consisting of SEQ ID NO: 255.

In particular, the present invention also provides a pharmaceutical composition comprising a first antigenic peptide according to the present invention, which comprises or consists of a microbiota sequence variant of a fragment of the human tumor antigen FOXM1, and a second antigenic peptide according to the present invention, which comprises or consists of a microbiota sequence variant of a fragment of the human tumor antigen IL13RA2. Preferably, the first antigenic peptide comprises or consists of a microbiota sequence variant of the FOXM1 fragment (human reference peptide) "LMDLSTTPL" (SEQ ID NO: 674), such as an antigenic peptide comprising or consisting of an amino acid sequence as set forth in SEQ ID NO: 220 or 868, and the second antigenic peptide comprises or consists of a microbiota sequence variant of the IL13RA2 fragment (human reference peptide) "WLPFGFILI" (SEQ ID NO: 691) or "WLPFGFILIL" (SEQ ID NO: 692), such as an antigenic peptide comprising or consisting of an amino acid sequence as set forth in SEQ ID NO: 254, 255, 878 or 879. Even more preferably, the pharmaceutical composition comprises an antigenic peptide comprising or consisting of SEQ ID NO: 220 and an antigenic peptide comprising or consisting of SEQ ID NO: 255.

More preferably, the pharmaceutical composition comprises at least three distinct antigenic peptides according to the present invention.

In particular, the present invention also provides a pharmaceutical composition comprising a first antigenic peptide according to the present invention, which comprises or consists of a microbiota sequence variant of a fragment of the human tumor antigen BIRC5, a second antigenic peptide according to the present invention, which comprises or consists of a microbiota sequence variant of a fragment of the human tumor antigen FOXM1, and a third antigenic peptide according to the present invention, which comprises or consists of a microbiota sequence variant of a fragment of the human tumor antigen IL13RA2. Preferably, the first antigenic peptide comprises or consists of a microbiota sequence variant of the BIRC5 fragment (human reference peptide) "LTLGEFLKL" (SEQ ID NO: 593), such as an antigenic peptide comprising or consisting of an amino acid sequence as set forth in SEQ ID NO: 30, 31 or 32; the second antigenic peptide comprises or consists of a microbiota sequence variant of the FOXM1 fragment (human reference peptide) "LMDLS I IPL" (SEQ ID NO: 674), such as an antigenic peptide comprising or consisting of an amino acid sequence as set forth in SEQ ID NO: 220 or 868; and the third antigenic peptide comprises or consists of a microbiota sequence variant of the IL13RA2 fragment (human reference peptide) "WLPFGFILI" (SEQ ID NO: 691) or "WLPFGFILIL" (SEQ ID NO: 692), such as an antigenic peptide comprising or consisting of an amino acid sequence as set forth in SEQ ID NO: 254, 255, 878 or 879. Even more preferably, the pharmaceutical composition comprises an antigenic peptide comprising or consisting of an amino acid sequence as set forth in SEQ ID NO: 30, an antigenic peptide comprising or consisting of an amino acid sequence as set forth in SEQ ID NO: 220, and an antigenic peptide comprising or consisting of an amino acid sequence as set forth in SEQ ID NO: 255.

It is understood that the pharmaceutical composition may also contain—instead of the above-described preferred combinations of antigenic peptides—a respective combination of immunogenic compounds of the invention, a respective combination of nanoparticles of the invention or a respective combination of nucleic acids of the invention.

Preferably, the pharmaceutical composition further comprises one or more pharmaceutically acceptable excipients or carriers.

The pharmaceutical composition of the invention may be in any form suitable for the purposes of the invention. For example, said composition may be in a form suitable for parenteral, enteral or topical administration, such as a liquid suspension, a solid dosage form (granules, pills, capsules or tablets), or a paste or gel. It is within the skill of the person in the art to select the appropriate form of the composition for the intended purpose.

The composition according to the invention can further comprise other active agents, for example such, which can enhance the effects of the antigenic peptide or immunogenic compound. Alternatively, the composition may not comprise any other active agents (i.e., other than the antigenic peptide according to the present invention, the immunogenic compound according to the present invention, the nanoparticle according to the present invention, the cell according to the present invention, the nucleic acid according to the present invention, and/or the host cell according to the present invention).

The pharmaceutical composition as defined herein is preferably an immunogenic composition, i.e. a composition that is able to induce, increase, prolong or maintain an immune response. This may be achieved by an antigenic peptide according to the present invention or by an immunogenic compound according to the present invention comprised in said composition. Preferably, the pharmaceutical composition further comprises one or more immuno-adjuvant substances. A pharmaceutical composition, in particular an immunogenic composition, may also be termed "vaccine composition" in the present specification.

Preferably, the pharmaceutical composition further comprises at least one immunostimulatory agent, in particular so as to increase, potentiate, prolong or maintain the immune response mediated by the antigenic peptide. Preferred immunostimulatory agents according to the invention include, without limitation, immune adjuvants, antigen-presenting cells, and combinations thereof. Preferably, the immunostimulatory agent is an immune adjuvant or an antigen-presenting cell (APC).

Preferably, the immunostimulatory agent is an immune adjuvant. Some immune adjuvants are capable of favoring and prolonging the duration of interaction between an antigen and the immune system, while others are capable of recruiting and activating cells of the natural immunity so as to induce an adaptive response. The adjuvants belonging to the former category include, without limitation, mineral compounds such as alum, aluminum hydroxide, aluminum phosphate, calcium phosphate hydroxide; and oil-based emulsions such as paraffin oil, starch oil, Freund's complete/incomplete adjuvant (FCA/FIA), saponins (e.g. from the plants Quillaja, Soybean, Polygala senega). The adjuvants of belonging to the latter category include, without limitation, immunostimulatory complexes (ISCOMs) such as cytokines (e.g. GM-CSF; Interleukins such as IL-1, IL-2, IL6, IL8, or IL12; Tumor necrosis factors (TNFs) such as TNFα or TNFβ; Interferons IFNS such as IFNα, IFNβ, IFNγ or IFNδ, etc); ligands of toll-like receptors (TLRs) such as imiquimod, resiquimod or MPL; exosomes such as exosomes derived from dendritic cells (DCs) or from tumor cells; bacterial products such as heat-shock proteins (HSPs such as gp96, hsp90, hsp70, calreticulin, hsp110, hsp170), pathogen-associated molecular patterns (PAMPs), trehalose dimicolate (TDM), muramyldipeptide (MDP), polysaccharide (PLS) such as polysaccharide-K.

More preferably, the immune adjuvant is a protein/peptide having immuno-adjuvant properties, such as providing stimulation of CD4+ Th1 cells, as described herein. A preferred example thereof is a non-tumor antigen that recalls immune memory or provides a non-specific help or could be a specific tumor-derived helper peptide, such as tetanus helper peptide, keyhole limpet hemocyanin peptide or PADRE peptide, as described herein. Another preferred example is a specific tumor derived helper peptide, which may be presented by MHC II, in particular by HLA-DR, HLA-DP or HLA-DQ, such as fragments of shared overexpressed tumor antigens, e.g. HER2, NY-ESO-1, hTERT or IL13RA2, as described above. In particular, the immune adjuvant may be the HHD-DR3 peptide of sequence MAKTIAYDEEARRGLERGLN (SEQ ID NO: 856). This peptide represents another example of a helper peptide (having immuno-adjuvant properties), which is preferred in the context of the present invention. Another preferred example is h-pAg T13L (sequence: TPPAYRPPNAPIL; SEQ ID NO: 860; Bhasin M, Singh H, Raghava GP (2003) MHCBN: a comprehensive database of MHC binding and non-binding peptides. Bioinformatics 19: 665-666). Further examples of preferred immune adjuvants, in particular of helper peptides, include the UCP2 peptide (for example as described in WO 2013/135553 A1 or in Dosset et al., Clin Cancer Res. 2012 Nov. 15; 18(22):6284-95) and the BIRC5 peptide (for example as described in EP2119726 A1 or in Widenmeyer et al., Int J Cancer. 2012 Jul. 1; 131(1):140-9). The most preferred helper peptide is the UCP2 peptide (amino acid sequence: KSVWSKLQSIGIRQH; SEQ ID NO: 859).

Preferably, the pharmaceutical composition comprises at least two distinct antigenic peptides according to the present invention and a helper peptide, preferably the UCP2 peptide (SEQ ID NO: 859).

Preferably, the pharmaceutical composition comprises a first antigenic peptide according to the present invention comprising or consisting of a microbiota sequence variant of a fragment of the human tumor antigen BIRC5, a second antigenic peptide according to the present invention comprising or consisting of a microbiota sequence variant of a fragment of the human tumor antigen FOXM1 and a helper peptide, preferably the UCP2 peptide (SEQ ID NO: 859). More preferably, the pharmaceutical composition comprises a first antigenic peptide according to the present invention comprising or consisting of a microbiota sequence variant of the BIRC5 fragment (human reference peptide) "LTLGEFLKL" (SEQ ID NO: 593), such as an antigenic peptide comprising or consisting of an amino acid sequence as set forth in SEQ ID NO: 30, 31 or 32; a second antigenic peptide according to the present invention comprising or consisting of a microbiota sequence variant of the FOXM1 fragment (human reference peptide) "LMDLSTTPL" (SEQ ID NO: 674), such as an antigenic peptide comprising or consisting of an amino acid sequence as set forth in SEQ ID NO: 220 or 868; and a helper peptide, preferably the UCP2 peptide (SEQ ID NO: 859). Even more preferably, the pharmaceutical composition comprises an antigenic peptide comprising or consisting of SEQ ID NO: 32; an antigenic peptide comprising or consisting of SEQ ID NO: 220; and the UCP2 helper peptide (SEQ ID NO: 859).

It is also preferred, that the pharmaceutical composition comprises a first antigenic peptide according to the present invention comprising or consisting of a microbiota sequence variant of a fragment of the human tumor antigen BIRC5, a second antigenic peptide according to the present invention comprising or consisting of a microbiota sequence variant of a fragment of the human tumor antigen IL13RA2, and a helper peptide, preferably the UCP2 peptide (SEQ ID NO: 859). More preferably, the pharmaceutical composition comprises a first antigenic peptide according to the present invention comprising or consisting of a microbiota sequence variant of the BIRC5 fragment (human reference peptide) "LTLGEFLKL" (SEQ ID NO: 593), such as an antigenic peptide comprising or consisting of an amino acid sequence as set forth in SEQ ID NO: 30, 31 or 32; a second antigenic peptide according to the present invention comprising or consisting of a microbiota sequence variant of a fragment of the tumor antigen IL13RA2 (human reference peptide) "WLPFGFILI" (SEQ ID NO: 691) or "WLPFGFILIL" (SEQ ID NO: 692), such as an antigenic peptide comprising or consisting of an amino acid sequence as set forth in SEQ ID NO: 254, 255, 878 or 879; and a helper peptide, preferably the UCP2 peptide (SEQ ID NO: 859). Even more preferably, the pharmaceutical composition comprises an antigenic peptide comprising or consisting of SEQ ID NO: 32; an antigenic peptide comprising or consisting of SEQ ID NO: 255; and the UCP2 helper peptide (SEQ ID NO: 859).

It is also preferred, that the pharmaceutical composition comprises a first antigenic peptide according to the present invention comprising or consisting of a microbiota sequence variant of a fragment of the human tumor antigen FOXM1; a second antigenic peptide according to the present invention comprising or consisting of a microbiota sequence variant of a fragment of the tumor antigen IL13RA2; and a helper peptide, preferably the UCP2 peptide (SEQ ID NO: 859). More preferably, the pharmaceutical composition comprises a first antigenic peptide according to the present invention comprising or consisting of a microbiota sequence variant of the FOXM1 fragment (human reference peptide) "LMDLSTTPL" (SEQ ID NO: 674), such as an antigenic peptide comprising or consisting of an amino acid sequence as set forth in SEQ ID NO: 220 or 868; a second antigenic peptide according to the present invention comprising or consisting of a microbiota sequence variant of the IL13RA2 fragment (human reference peptide) "WLPFGFILI" (SEQ ID NO: 691) or "WLPFGFILIL" (SEQ ID NO: 692), such as an antigenic peptide comprising or consisting of an amino acid sequence as set forth in SEQ ID NO: 254, 255, 878 or 879; and a helper peptide, preferably the UCP2 peptide (SEQ ID NO: 859). Even more preferably, the pharmaceutical composition comprises an antigenic peptide comprising or consisting of SEQ ID NO: 220; an antigenic peptide comprising or consisting of SEQ ID NO: 255; and the UCP2 helper peptide (SEQ ID NO: 859).

More preferably, the pharmaceutical composition comprises at least three distinct antigenic peptides according to the present invention and a helper peptide, preferably the UCP2 peptide (SEQ ID NO: 859).

In particular, the pharmaceutical composition may comprise a first antigenic peptide according to the present invention comprising or consisting of a microbiota sequence variant of a fragment of the human tumor antigen BIRC5, a second antigenic peptide according to the present invention comprising or consisting of a microbiota sequence variant of a fragment of the human tumor antigen FOXM1, a third antigenic peptide according to the present invention comprising or consisting of a microbiota sequence variant of a fragment of the human tumor antigen IL13RA2 and a helper peptide, preferably the UCP2 peptide (SEQ ID NO: 859). Even more preferably, the pharmaceutical composition comprises a first antigenic peptide according to the present invention comprising or consisting of a microbiota sequence variant of the BIRC5 fragment (human reference peptide) "LTLGEFLKL" (SEQ ID NO: 593), such as an antigenic peptide comprising or consisting of an amino acid sequence as set forth in SEQ ID NO: 30, 31 or 32; a second antigenic peptide according to the present invention comprising or consisting of a microbiota sequence variant of the FOXM1 fragment (human reference peptide) "LMDLSTTPL" (SEQ ID NO: 674), such as an antigenic peptide comprising or consisting of an amino acid sequence as set forth in SEQ ID NO: 220 or 868; a third antigenic peptide according to the present invention comprising or consisting of a microbiota sequence variant of the IL13RA2 fragment (human reference peptide) "WLPFGFILI" (SEQ ID NO: 691) or "WLPFGFILIL" (SEQ ID NO: 692), such as an antigenic peptide comprising or consisting of an amino acid sequence as set forth in SEQ ID NO: 254, 255, 878 or 879; and a helper peptide, preferably the UCP2 peptide (SEQ ID NO: 859). Still more preferably, the pharmaceutical composition comprises the antigenic peptide comprising or consisting of an amino acid sequence as set forth in SEQ ID NO: 30, the antigenic peptide comprising or consisting of an amino acid sequence as set forth in SEQ ID NO: 220, the antigenic peptide comprising or consisting of an amino acid sequence as set forth in SEQ ID NO: 255, and a helper peptide, preferably the UCP2 peptide (SEQ ID NO: 859).

Particularly preferred immune adjuvants are polyinosinic: polycytidylic acid (also referred to as "poly I:C") and/or its derivative poly-ICLC. Poly I:C is a mismatched double-stranded RNA with one strand being a polymer of inosinic acid, the other a polymer of cytidylic acid. Poly I:C is an immunostimulant known to interact with toll-like receptor 3 (TLR3). Poly I:C is structurally similar to double-stranded RNA, which is the "natural" stimulant of TLR3. Accordingly, poly I:C may be considered a synthetic analog of double-stranded RNA. Poly-ICLC is a synthetic complex of carboxymethylcellulose, polyinosinic-polycytidylic acid, and poly-L-lysine double-stranded RNA. Similar to poly I:C, also poly-ICLC is a ligand for TLR3. Poly I:C and poly-ICLC typically stimulate the release of cytotoxic cytokines. A preferred example of poly-ICLC is Hiltonol®.

Most preferably, the adjuvant is Montanide, such as Montanide ISA 51 VG and/or Montanide ISA 720 VG. Those adjuvants are rendering stable water-in-oil emulsions when mixed with water based antigenic media. Montanide ISA 51 VG is based on a blend of mannide monooleate surfactant and mineral oil, whereas Montanide ISA 720 VG uses a non-mineral oil (Aucouturier J, Dupuis L, Deville S, Ascarateil S, Ganne V. Montanide ISA 720 and 51: a new generation of water in oil emulsions as adjuvants for human vaccines. Expert Rev Vaccines. 2002 June; 1(1):111-8; Ascarateil S, Puget A, Koziol M-E. Safety data of Montanide ISA 51 VG and Montanide ISA 720 VG, two adjuvants dedicated to human therapeutic vaccines. Journal for Immunotherapy of Cancer. 2015; 3(Suppl 2):P428. doi:10.1186/2051-1426-3-S2-P428).

It is also preferred that the immunostimulatory agent is an antigen-presenting cell (APC). APCs are also of particular interest, as their main function is to process antigens and present it on the cell surface to the T cells of the immune system, so as to initiate and modulate T-cell responses in vivo. In the present composition, it is preferred that the APCs are loaded with the antigenic peptide(s) and/or immunogenic compound(s) according to the invention, which can be done by exposing APCs in vitro with said antigenic peptide(s) and/or immunogenic compound(s) (Rizzo et al., Methods Mol Biol. 2014; 1139:41-4; Rolinski and Hus, J Immunotoxicol. 2014 October; 11(4):311-8).

Preferaby, the APC is a dendritic cell (DC). DCs are the most potent APCs and have been reported to be frequently functionally defective in cancer patients. DCs can be easily obtained by the skilled person in the art from either healthy compatible donors (i.e. the dendritic cells are HLA-related) or from the patient himself provided that they are functional (i.e. the DCs are autologous), for example by direct isolation from the peripheral blood, or by derivation from peripheral blood cells such as CD14+ monocytes or CD34+ hematopoietic precursors (Emens et al., 2008). DCs can indeed be distinguished from other cells of peripheral blood by their surface markers, such as S100, p55, CD83, and/or OX62, and may thus be isolated and purified based on said markers using cell cultures techniques well-known in the art.

According to a preferred embodiment, the pharmaceutical composition may further comprise at least one anti-cancer therapeutic agent. Said therapeutic agent is thus preferably capable of preventing and/or treating the same type of cancer than the one for which the antigenic peptide according to the invention is used. Preferably, the anti-cancer therapeutic agent is selected from antibodies, tumor cell lysates, chemotherapeutic agents, radiotherapeutic agents, immune checkpoint modulators and combinations thereof.

Antibodies are particularly advantageous in cancer therapy as they can either bind to specific antigens on cancer cell surfaces, thereby directing the therapy to the tumor (i.e. these are referred as tumor-targeting antibodies), or block immune checkpoints that are dysregulated in cancer (i.e. these are referred herein as immunomodulatory antibodies). The purpose of the later type of antibodies is to inhibit cancer immune resistance, which can notably be observed against T cells that are specific for tumor antigens. Indeed, as well-known in the art, under normal physiological conditions, immune checkpoints are crucial for the maintenance of self-tolerance (i.e. prevention of autoimmunity) and protect tissues from damage when the immune system is responding to pathogenic infection. However, in cancer, immune-checkpoints expression can be dysregulated as an important mechanism of immune resistance. Said resistance has notably been observed in melanoma, ovarian, lung, glioblastoma, breast, and pancreatic cancers with regard to the PD-L1 checkpoint (Konishi et al., B7-H1 expression on non-small cell lung cancer cells and its relationship with tumor-infiltrating lymphocytes and their PD-1 expression. Clin Cancer Res. 2004 Aug. 1; 10(15):5094-100; Ghebeh et al., The B7-H1 (PD-L1) T lymphocyte-inhibitory molecule is expressed in breast cancer patients with infiltrating ductal carcinoma: correlation with important high-risk prognostic factors. Neoplasia. 2006 March; 8(3):190-8; Hino et al., Tumor cell expression of programmed cell death-1 ligand 1 is a prognostic factor for malignant melanoma. Cancer. 2010 Apr. 1; 116(7):1757-66). Other examples of immune checkpoints include, without limitation, PD-L2, PD-1, CD80, CD86, CTLA-4, B7H3, B7H4, PVR, TIGIT, GAL9, LAG-3, GITR, CD137, T1M3, VISTA, VISTA-R (Pico de Coaña et al., Checkpoint blockade for cancer therapy: revitalizing a suppressed immune system. Trends Mol Med. 2015 August; 21(8):482-91; Pardoll D M. The blockade of immune checkpoints in cancer immunotherapy. Nat Rev Cancer. 2012 Mar. 22; 12(4):252-64).

Antibodies are usually employed for the above purposes either in the form of naked monoclonal antibodies (i.e. non-conjugated), or conjugated to another molecule which can be toxic to cells or radioactive.

Examples of well-known monoclonal tumor-targeting antibodies used in cancer immunotherapy include, without limitation, alemtuzumab (chronic lymphocytic leukemia), bevacizumab (colorectal cancer, glioblastoma multiforme, cervical cancer, lung cancer, renal cancer), brentuximab/vedotin (lymphomas), blinatumumab (acute lymphoblastic leukemia), catumaxomab (malignant ascites in EPCAM+ cancers), cetuximab (head and neck cancer, colorectal cancer), denosurnab (breast, prostate and bone cancers), Gemtuzumab/ozogamicin (acute myeloid keulemia), ibritumomab/tiuxetan (non-Hodgkin lymphoma), panitumumab (colorectal cancer), pertuzumab (breast cancer), obinutuzumab (chronic lymphocytic leukemia), ofatumumab (chronic lymphocytic leukemia), opilimumab (melanoma), ramucirumab (gastric and gastro-oeasophageal cancers), rituximab (chronic lymphocytic leukemia and non-Hodgkin lymphoma), siltuximab (multicentric's Catsleman's disease), tositumomab (non-Hodgkin lymphoma), and trastuzumab (breast, gastric and gastro-oeasophageal cancers); while examples of immunomodulatory antibodies include, without limitation, ipilimumab (melanoma) which blocks the CTLA4-dependent immune checkpoint, nivolumab (melanoma, lung cancer) and prembrolizubmab (melanoma) which both block the PDCD1-dependent immune checkpoint, as well as MPDL3280A, MED14736, MEDI0680, and MSB0010718C which all block the PD-L1-dependent immune checkpoint (Sharma and Allison, The future of immune checkpoint therapy. Science. 2015 Apr. 3; 348(6230):56-61).

Other antibodies for cancer immunotherapy have been described in Buqué et al., Trial Watch: Immunomodulatory monoclonal antibodies for oncological indications. Oncoimmunology. 2015 Mar. 2; 4(4):e1008814. eCollection 2015 April; Redman et al., Mechanisms of action of therapeutic antibodies for cancer. Mol Immunol. 2015 October; 67(2 Pt A):28-45; Simpson and Caballero, Monoclonal antibodies for the therapy of cancer MC Proc. 2014; 8(Suppl 4): O6 as well as on the antibody society website (list of therapeutic monoclonal antibodies approved or in review in the European Union or United States available on the weblink http://www.antibodysociety.org/news/approved_mabs.php).

Tumor cell lysates may also be combined with the antigenic peptide(s) according to the invention. Tumor cells are indeed capable of priming the immune response, by presenting endogenous peptides-MHC complexes, as well as via dendritic cells (DCs) of the host which can process and present the antigen delivered by said lysates. The range of antigens against which an immune response can be induced is thereby increased. Tumor cell lysates can be easily obtained by treating tumor cells with a heat shock and/or a chemical treatment, and can be autologous (i.e. isolated from the patient), or allogeneic (i.e. isolated from another subject).

Standard chemotherapeutic drugs and radiotherapeutic agents need not be further described herein as they have been extensively described in the literature, notably by Baskar et al. (Baskar et al., Cancer and radiation therapy: current advances and future directions. Int J Med Sci. 2012; 9(3):193-9), Paci et al., (Paci et al., Review of therapeutic drug monitoring of anticancer drugs part 1-cytotoxics. Eur J Cancer. 2014 August; 50(12):2010-9) and Widmer et al. (Widmer et al., Review of therapeutic drug monitoring of anticancer drugs part two—targeted therapies. Eur) Cancer. 2014 August; 50(12):2020-36). A list of such drugs and agents is also available on the cancer.gov website (http://www.cancer.gov/about-cancer/treatment/drugs).

Preferably, the immune checkpoint modulator for combination with the antigenic peptide as defined herein is an activator or an inhibitor of one or more immune checkpoint molecule(s) selected from CD27, CD28, CD40, CD122, CD137, OX40, GITR, ICOS, A2AR, B7-H3, B7-H4, BTLA, CD40, CTLA-4, IDO, KIR, LAG3, PD-1, TIM-3, VISTA, CEACAM1, GARP, PS, CSF1R, CD94/NKG2A, TDO, GITR, TNFR and/or FasR/DcR3; or an activator or an inhibitor of one or more ligands thereof.

More preferably, the immune checkpoint modulator is an activator of a (co-)stimulatory checkpoint molecule or an inhibitor of an inhibitory checkpoint molecule or a combination thereof. Accordingly, the immune checkpoint modulator is more preferably (i) an activator of CD27, CD28, CD40, CD122, CD137, OX40, GITR and/or ICOS or (ii) an inhibitor of A2AR, B7-H3, B7-H4, BTLA, CD40, CTLA-4, IDO, KIR, LAG3, PD-1, PDL-1, PD-L2, TIM-3, VISTA, CEACAM1, GARP, PS, CSF1R, CD94/NKG2A, TDO, TNFR and/or FasR/DcR3.

Even more preferably, the immune checkpoint modulator is an inhibitor of an inhibitory checkpoint molecule (but preferably no inhibitor of a stimulatory checkpoint molecule). Accordingly, the immune checkpoint modulator is even more preferably an inhibitor of A2AR, B7-H3, B7-H4, BTLA, CTLA-4, IDO, KIR, LAG3, PD-1, PDL-1, PD-L2, TIM-3, VISTA, CEACAM1, GARP, PS, CSF1R, CD94/NKG2A, TDO, TNFR and/or DcR3 or of a ligand thereof.

It is also preferred that the immune checkpoint modulator is an activator of a stimulatory or costimulatory checkpoint molecule (but preferably no activator of an inhibitory checkpoint molecule). Accordingly, the immune checkpoint modulator is more preferably an activator of CD27, CD28, CD40, CD122, CD137, OX40, GITR and/or ICOS or of a ligand thereof.

It is even more preferred that the immune checkpoint modulator is a modulator of the CD40 pathway, of the IDO pathway, of the LAG3 pathway, of the CTLA-4 pathway and/or of the PD-1 pathway. In particular, the immune checkpoint modulator is preferably a modulator of CD40, LAG3, CTLA-4, PD-L1, PD-L2, PD-1 and/or IDO, more preferably the immune checkpoint modulator is an inhibitor of CTLA-4, PD-L1, PD-L2, PD-1, LAG3, and/or IDO or an activator of CD40, even more preferably the immune checkpoint modulator is an inhibitor of CTLA-4, PD-L1, PD-1, LAG3 and/or IDO, even more preferably the immune checkpoint modulator is an inhibitor of LAG3, CTLA-4 and/or PD-1, and most preferably the immune checkpoint modulator is an inhibitor of CTLA-4 and/or PD-1.

Accordingly, the checkpoint modulator for combination with the antigenic peptide may be selected from known modulators of the CTLA-4 pathway or the PD-1 pathway. Preferably, the checkpoint modulator for combination with the antigenic peptide as defined herein may be selected from known modulators of the CTLA-4 pathway or the PD-1 pathway. Particularly preferably, the immune checkpoint modulator is a PD-1 inhibitor. Preferred inhibitors of the CTLA-4 pathway and of the PD-1 pathway include the monoclonal antibodies Yervoy® (Ipilimumab; Bristol Myers Squibb) and Tremelimumab (Pfizer/MedImmune) as well as Opdivo® (Nivolumab; Bristol Myers Squibb), Keytrude (Pembrolizumab, also known as Lambrolizumab or MK-3475; Merck), Imfinzi® (Durvalumab, also known as MED14736; MedImmune/AstraZeneca), Tecentriq® (Atezolizumab, also known as MPDL3280A; Roche/Genentech), Pidilizumab (CT-011; CureTech), MEDI0680 (AMP-514; AstraZeneca), Bavencio® (Avelumab; Merck KGaA/Pfizer, also known as MSB-0010718C), MIH1 (Affymetrix), LY3300054 (Eli Lilly) and Spartalizumab (also known as PDR001; Novartis). More preferred checkpoint inhibitors include the CTLA-4 inhibitors Yervoy® (Ipilimumab; Bristol Myers Squibb) and Tremelimumab (Pfizer/MedImmune) as well as the PD-1 inhibitors Opdivo® (Nivolumab; Bristol Myers Squibb), Keytruda® (Pembrolizumab; Merck), Pidilizumab (CT-011; CureTech), MEDI0680 (AMP-514; AstraZeneca), AMP-224 (a PD-L2 Fc fusion protein; MedImmune).

It is also preferred that the immune checkpoint modulator for combination with the antigenic peptide as defined herein is selected from the group consisting of Pembrolizumab, Ipilimumab, Nivolumab, Atezolizumab, Durvalumab, Tremelimumab, Avelumab, Spartalizumab, LAG525 (an anti-LAG-3 monoclonal antibody), Epacadostat (also known as INCB24360; an IDO inhibitor), Varlilumab (an anti-CD27 monoclonal antibody), Urelumab (an anti-CD137 monoclonal antibody), AMP-224 and CM-24 (an anti-CEACAM1 monoclonal antibody).

It is within the skill of ordinary person in the art to select the appropriate immune anti-cancer therapeutic agent for the purposes of the invention. For example, should one wish to prevent or treat melanoma, a lysate from melanoma cells and/or the antibody Ipilimumab can preferably be used, along with an appropriate antigenic peptide. Appropriate antigenic peptides may be selected by (i) selecting an appropriate tumor antigen for a certain type of cancer as known in the art and/or as described herein in Table 1B and (ii) selecting an appropriate antigenic peptide according to the invention for the selected tumor antigen, as described above, e.g. in Table 1A.

The anti-cancer therapeutic agent can also be administered in combination with the composition of the invention, either simultaneously, separately, or sequentially. Should the composition and the therapeutic agent be administered in a separate or sequential manner, those may be administered in distinct pharmaceutical forms.

Thus, in another aspect, the invention relates to a composition of the invention and at least one anti-cancer therapeutic agent as described above, as a combined preparation for a simultaneous, separate, or sequential administration. In other terms, the invention proposes a combined use of the composition the invention and least one anti-cancer therapeutic agent as described above, for a simultaneous, separate, or sequential administration.

Kits-of-Parts

In a further aspect, the present invention also provides a kit-of-parts (also referred to herein as "kit") comprising at least one of the following:

the antigenic peptide according to the present invention as described herein, the immunogenic compound according to the present invention as described herein, the nanoparticle according to the present invention as described herein, the cell according to the present invention as described herein, the nucleic acid according to the present invention as described herein, the host cell according to the present invention as described herein, and/or the pharmaceutical composition according to the present invention as described herein.

In particular, preferred embodiments of the antigenic peptide as described above also apply for such a kit according to the present invention. For example, the antigenic peptide comprised in the kit or the antigenic peptide comprised in any of the immunogenic compound, the nanoparticle, the cell, the nucleic acid, the host cell or the pharmaceutical composition comprised in the kit preferably comprises or consists of an amino acid sequence as set forth in any one of SEQ ID NOs 1 to 580 and 861 to 887, such as an antigenic peptide comprising or consisting of an amino acid sequence as set forth in any one of SEQ ID NOs 1 to 580. For example, antigenic peptides according to the present invention comprising or consisting of an amino acid sequence as set forth in any one of SEQ ID NOs 1-160, 162-253 and 255-580 are more preferred. For example, antigenic peptides according to the present invention comprising or consisting of an amino acid sequence as set forth in any one of SEQ ID NOs 30, 31, 32, 87, 97, 145, 193, 194, 220, 221, 255, 521 and 524 are even more preferred. For example, antigenic peptides according to the present invention comprising or consisting of an amino acid sequence as set forth in any one of SEQ ID NOs 30, 31, 32, 87, 97, 193, 194, 220, 255, 521 and 524 are still more preferred. For example, antigenic peptides according to the present invention comprising or consisting of an amino acid sequence as set forth in any one of SEQ ID NOs 30, 31, 32, 87, 97, 194, 220, 255, 521 and 524 are still more preferred. For example, antigenic peptides according to the present invention comprising or consisting of an amino acid sequence as set forth in any one of SEQ ID NOs 30, 32, 87, 97, and 194 are most preferred. For example, antigenic peptides according to the present invention comprising or consisting of an amino acid sequence as set forth in any one of SEQ ID NOs 30, 32, 194, 220, 254 or 255 are particularly preferred.

Also combinations thereof are preferred, namely, kits comprising distinct antigenic peptides according to the present invention. In particular, the kit-of-parts of the invention may comprise more than one of the above described components, e.g. 2, 3, 4, 5, 6, 7, 8, 9, or 10 distinct components.

For example, the kit-of-parts according to the present invention may comprise at least two (e.g. 2, 3, 4, 5, 6, 7, 8, 9, or 10) different immunogenic compounds, at least two (e.g. 2, 3, 4, 5, 6, 7, 8, 9, or 10) different antigenic peptides, at least two (e.g. 2, 3, 4, 5, 6, 7, 8, 9, or 10) different nanoparticles, at least two (e.g. 2, 3, 4, 5, 6, 7, 8, 9, or 10) different cells, at least two (e.g. 2, 3, 4, 5, 6, 7, 8, 9, or 10) different nucleic acids, at least two (e.g. 2, 3, 4, 5, 6, 7, 8, 9, or 10) different host cells, and/or at least two (e.g. 2, 3, 4, 5, 6, 7, 8, 9, or 10) different pharmaceutical compositions. Preferably, such different components comprised by the kit-of-parts as described above differ in the antigenic peptides according to the present invention, for example one component relating to a first antigenic peptide, and one component relating to a second antigenic peptide (distinct from the first antigenic peptide). For example, the kit may comprise at least two distinct immunogenic compounds according to the present invention. For example, the kit may comprise at least two distinct antigenic peptides according to the present invention. For example, the kit may comprise at least two distinct nanoparticles according to the present invention. For example, the kit may comprise at least two distinct nucleic acids according to the present invention.

Preferred combinations of antigenic peptides according to the present invention included in the kit correspond to the preferred combinations of antigenic peptides according to the present invention included in the pharmaceutical composition as described above.

Accordingly, the present invention provides a kit comprising (at least one) antigenic peptide according to the present invention as described herein. Moreover, the present invention also provides a kit comprising (at least one) immunogenic compound according to the present invention as described herein. Moreover, the present invention also provides a kit comprising (at least one) nanoparticle according to the present invention as described herein. Moreover, the present invention also provides a kit comprising (at least one) cell according to the present invention as described herein. Moreover, the present invention also provides a kit comprising (at least one) nucleic acid according to the present invention as described herein. Moreover, the present invention also provides a kit comprising (at least one) host cell according to the present invention as described herein.

The various components of the kit-of-parts may be packaged in one or more containers. The above components may be provided in a lyophilized or dry form or dissolved in a suitable buffer. The kit may also comprise additional reagents including, for instance, preservatives, growth media, and/or buffers for storage and/or reconstitution of the above-referenced components, washing solutions, and the like.

Accordingly, the present invention provides a kit comprising at least two, preferably three distinct antigenic peptides according to the present invention as described herein (or immunogenic compounds, nanoparticles, nucleic acids, cells, etc. as described above, which differ regarding the antigenic peptide), and, optionally, a helper peptide, such as the UCP2 peptide, and/or an adjuvant, such as MONTANIDE ISA 51. Distinct antigenic peptides (or immunogenic compounds, nanoparticles, nucleic acids, cells, etc. as described above, which differ regarding the antigenic peptide) may be contained in the same or in distinct containers. For example, the kit may comprise a (single) container containing a first antigenic peptide as described herein and a second antigenic peptide as described herein. Said (single) container may additionally also comprise a helper peptide, such as UCP2. Optionally, the first and second antigenic peptide (and optionally the helper peptide) contained in the (single) container may be formulated together, e.g. in water for injection and/or Dimethyl sulfoxide (DMSO). Additionally, the kit may comprise a further container (distinct from the container containing the antigenic peptides), which contains the adjuvant, e.g. MONTANIDE ISA 51.

It is thus preferred that the kit comprises
(i) a first vial comprising one or more antigenic peptides of the invention (e.g., at least 200 or 300 µg of each antigenic peptide), and, optionally, a helper peptide, such as UCP2 (e.g., at least 200 or 300 µg of the helper peptide), optionally formulated in water for injection and dimethyl sulfoxide (DMSO); and
(ii) a second vial comprising MONTANIDE ISA 51 (e.g., at least 0.4 or 0.5 ml).

In addition, the kit may comprise one or more (e.g., 2 or 3) syringes, for example silicon- and rubber-free syringes. The kit may also comprise a connector, such as an I-connector.

Non-limiting examples of such connectors are:
the I-connector developed by Green Peptide (Japan),
the connector of reference DIDRACDLLFT from Didanorm (France),
the I-connector (ref: ODG0015ST) from Promepla (Monaco), and
the I-connector (ref: MX494) from Smiths medical (US).

The syringes are preferably suitable for MONTANIDE, i.e., silicon-free and rubber free (i.e., without any rubber tip free on the plunger), and preferably also latex-free. Non-limiting examples of such syringes are:
2 ml INKJET (Ref: 4606701V from B-Braun, Germany),
5 ml INKJET (Ref: 4606710V from B-Braun, Germany),
2 ml Norm-Ject (Ref: 4020.000V0 from Henke Sass Wolf GMBH, Germany), and
5 ml Norm-Ject (Ref: 4050.000V0 from Henke Sass Wolf GMBH, Germany).

For example, the kit may comprise (i) a first vial comprising at least 300 µg of an antigenic peptide of the invention (or two or three antigenic peptides, at least 300 µg of each), and optionally at least 300 µg of UCP2, formulated in water for Injection and Dimethyl sulfoxide (DMSO), (ii) a second vial comprising at least 0.5 ml of MONTANIDE ISA 51, (iii) two silicon- and rubber-free syringes, and (iv) an I-connector.

Optionally, the kit can also comprise a vial of water for injection and/or a vial adapter. A sterile needle can also be comprised, e.g. for vaccinating the patient after obtaining the emulsion. The syringes in the kit can be, for example, 2 ml syringes.

In one particular embodiment, the kit comprises three distinct antigenic peptides according to the present invention, the UCP2 peptide, and MONTANIDE ISA 51, wherein said kit comprises (i) a first vial comprising at least 300 µg of each of the three antigenic peptides of the invention, at least 300 µg of UCP2 (SEQ ID NO: 859), formulated in water for injection and DMSO, (ii) a second vial comprising at least 0.5 ml of MONTANIDE ISA 51, (iii) two silicon- and rubber-free syringes, and (iv) an I-connector. The three antigenic peptides of the invention included in the kit are preferably an antigenic peptide comprising or consisting of an amino acid sequence as set forth in SEQ ID NO: 32, an antigenic peptide comprising or consisting of an amino acid sequence as set forth in SEQ ID NO: 220 and an antigenic peptide comprising or consisting of an amino acid sequence as set forth in SEQ ID NO: 255.

In addition, the kit-of-parts according to the present invention may optionally contain instructions of use.

Accordingly, it is preferred that the kit comprises a package insert or instruction leaflet with directions to prevent or to treat a cancer by using the immunogenic compound according to the present invention, the antigenic peptide according to the present invention, the nanoparticle according to the present invention, the cell according to the present invention, the nucleic acid according to the present invention, the host cell according to the present invention, or the pharmaceutical composition according to the present invention.

It is also preferred that, in addition to any of components as described above, the kit comprises an anti-cancer therapeutic agent as described herein.

Moreover, the present invention also provides a vaccination kit for treating, preventing and/or stabilizing a cancer, comprising the pharmaceutical composition as described herein or a vaccine as described herein and instructions for use of said pharmaceutical composition or of said vaccine in the prevention and/or treatment of a cancer.

Medical Treatment and Uses

As stated above, the composition of the invention can be particularly useful for therapeutic purposes, notably for triggering a specific immune response towards a particular tumor antigen/protein, for example to prevent or treat cancer in a patient in need thereof.

In view thereof, the present invention provides
- the antigenic peptide according to the present invention as described herein,
- the immunogenic compound according to the present invention as described herein,
- the nanoparticle according to the present invention as described herein,
- the cell according to the present invention as described herein,
- the nucleic acid according to the present invention as described herein,
- the host cell according to the present invention as described herein,
- the pharmaceutical composition according to the present invention as described herein, or
- the kit according to the present invention as described herein for use in the prevention and/or in the treatment of a cancer.

In particular, preferred embodiments of the antigenic peptide as described above also apply for the use according to the present invention in the prevention and/or in the treatment of a cancer. For example, the antigenic peptide used in the prevention and/or in the treatment of a cancer or the antigenic peptide comprised in any of the immunogenic compound, the nanoparticle, the cell, the nucleic acid, the host cell or the pharmaceutical composition used in the prevention and/or in the treatment of a cancer preferably comprises or consists of an amino acid sequence as set forth in any one of SEQ ID NOs 1 to 580 and 861 to 887, such as an antigenic peptide comprising or consisting of an amino acid sequence as set forth in any one of SEQ ID NOs 1 to 580. For example, antigenic peptides according to the present invention comprising or consisting of an amino acid sequence as set forth in any one of SEQ ID NOs 1-160, 162-253 and 255-580 are more preferred. For example, antigenic peptides according to the present invention comprising or consisting of an amino acid sequence as set forth in any one of SEQ ID NOs 30, 31, 32, 87, 97, 145, 193, 194, 220, 221, 255, 521 and 524 are even more preferred. For example, antigenic peptides according to the present invention comprising or consisting of an amino acid sequence as set forth in any one of SEQ ID NOs 30, 31, 32, 87, 97, 193, 194, 220, 255, 521 and 524 are still more preferred. For example, antigenic peptides according to the present invention comprising or consisting of an amino acid sequence as set forth in any one of SEQ ID NOs 30, 31, 32, 87, 97, 194, 220, 255, 521 and 524 are still more preferred. For example, antigenic peptides according to the present invention comprising or consisting of an amino acid sequence as set forth in any one of SEQ ID NOs 30, 32, 87, 97, and 194 are most preferred. For example, antigenic peptides according to the present invention comprising or consisting of an amino acid sequence as set forth in any one of SEQ ID NOs 30, 32, 194, 220, 254 or 255 are particularly preferred.

Also combinations thereof are preferred, namely, distinct antigenic peptides according to the present invention for use in the prevention and/or in the treatment of a cancer. In particular, more than one of the above described components may be used in the prevention and/or in the treatment of a cancer. For example, at least two different antigenic peptides, at least two different immunogenic compounds, at least two different nanoparticles, at least two different cells, at least two different nucleic acids, at least two different host cells, and/or at least two different pharmaceutical compositions may be used in the prevention and/or in the treatment of a cancer. Preferably, such different components used in the prevention and/or in the treatment of a cancer as described above differ in the antigenic peptides according to the present invention, for example one component relating to a first antigenic peptide, and one component relating to a second antigenic peptide (distinct from the first antigenic peptide). For example, at least two distinct immunogenic compounds according to the present invention may be used in the prevention and/or in the treatment of a cancer. For example, at least two distinct antigenic peptides according to the present invention may be used in the prevention and/or in the treatment of a cancer. For example, at least two distinct nanoparticles according to the present invention may be used in the prevention and/or in the treatment of a cancer. For example, at least two distinct nucleic acids according to the present invention may be used in the prevention and/or in the treatment of a cancer.

Accordingly, the present invention provides (at least one) antigenic peptide according to the present invention as described herein for use in the prevention and/or in the treatment of a cancer. Moreover, the present invention also provides (at least one) immunogenic compound according to the present invention as described herein for use in the prevention and/or in the treatment of a cancer. Moreover, the present invention also provides (at least one) nanoparticle according to the present invention as described herein for use in the prevention and/or in the treatment of a cancer. Moreover, the present invention also provides (at least one) cell according to the present invention as described herein for use in the prevention and/or in the treatment of a cancer. Moreover, the present invention also provides (at least one) nucleic acid according to the present invention as described herein for use in the prevention and/or in the treatment of a cancer. Moreover, the present invention also provides (at least one) host cell according to the present invention as described herein for use in the prevention and/or in the treatment of a cancer. Moreover, the present invention also provides (at least one) pharmaceutical composition according to the present invention as described herein for use in the prevention and/or in the treatment of a cancer. Moreover, the present invention also provides a kit according to the present invention as described herein for use in the prevention and/or in the treatment of a cancer.

Accordingly, the present invention also provides a method for preventing and/or treating a cancer or initiating, enhancing or prolonging an anti-tumor-response in a subject in need thereof comprising administering to the subject the antigenic peptide according to the present invention,
the immunogenic compound according to the present invention,
the nanoparticle according to the present invention,
the cell according to the present invention,
the nucleic acid according to the present invention,
the host cell according to the present invention,
the pharmaceutical composition according to the present invention,
the kit according to the present invention, or
the combination according to the present invention as described herein.

Preferably, the cancer to be prevented and/or treated is selected from glioma, kidney cancer, skin cancer, in particular melanoma, lung cancer, ovarian cancer, breast cancer, colorectal cancer, liver cancer, pancreatic cancer, head and neck cancer, urothelial cancer and prostate cancer.

Moreover, the present invention provides a method for eliciting or improving, in a subject, an immune response against one or multiple epitopes that is dependent on CM+ cytotoxic T cells, wherein said method comprises administering to said subject any one of:

the antigenic peptide according to the present invention,
the immunogenic compound according to the present invention,
the nanoparticle according to the present invention,
the cell according to the present invention,
the nucleic acid according to the present invention,
the host cell according to the present invention,
the pharmaceutical composition according to the present invention,
the kit according to the present invention, or
the combination according to the present invention as described herein.

An immune response that is dependent on CD8$^+$ response can be determined by evaluating an inflammatory response, a pro-inflammatory cytokine response, including an increase in the expression of one or more of IFN-γ, TNF-α and IL-2 mRNA or protein relative to the level before administration of the compounds of the invention. It can also be measured by an increase in the frequency or absolute number of antigen-specific T cells after administration of the compounds of the invention, measured by HLA-peptide multimer staining, ELISPOT assays, and delayed type hypersensitivity tests. It can also be indirectly measured by an increase in antigen-specific serum antibodies that are dependent on antigen-specific T helper cells.

The present invention also provides a method for eliciting or improving, in a subject, an immune response against one or multiple antigens or antigenic epitopes that is restricted by multiple MHC class I molecules, wherein said method comprises administering to said subject any one of:

the antigenic peptide according to the present invention,
the immunogenic compound according to the present invention,
the nanoparticle according to the present invention,
the cell according to the present invention,
the nucleic acid according to the present invention,
the host cell according to the present invention,
the pharmaceutical composition according to the present invention,
the kit according to the present invention, or
the combination according to the present invention as described herein.

A method for eliciting or improving, in a subject, an immune response against multiple epitopes as described herein, that is restricted by multiple MHC class I molecules can be determined by evaluating a cytokine response, including an increase in the expression of one or more of IFN-γ, TNF-α and IL-2 mRNA or protein relative to the level before administration of the compounds of the invention, after in vitro stimulation of T cells with individual peptides binding to discrete MHC class I molecules on antigen presenting cells. Restriction to MHC class I molecules can also be validated by using antigen presenting cells expressing MHC class I molecules, or by using MHC class I blocking antibodies. It can also be measured by an increase in the frequency or absolute number of antigen-specific T cells after administration of the compounds of the invention, measured by HLA-peptide multimer staining, using multimers assembled with MHC class I molecules.

Thus, in another aspect, the present invention also provides the antigenic peptide according to the present invention,
the immunogenic compound according to the present invention,
the nanoparticle according to the present invention,
the cell according to the present invention,
the nucleic acid according to the present invention,
the host cell according to the present invention,
the pharmaceutical composition according to the present invention,
the kit according to the present invention, or
the combination according to the present invention as described herein.

for use as a medicament.

The invention relates more particularly to a composition as defined above, for use as a vaccine for immunotherapy. Moreover, the antigenic peptide according to the present invention,
the immunogenic compound according to the present invention,
the nanoparticle according to the present invention,
the cell according to the present invention,
the nucleic acid according to the present invention,
the host cell according to the present invention,
the pharmaceutical composition according to the present invention,
the kit according to the present invention, or
the combination according to the present invention as described herein may be used as vaccine, in particular for (cancer) immunotherapy.

As used in the context of the present invention, the term "vaccine" refers to a (biological) preparation that provides innate and/or adaptive immunity, typically to a particular disease, preferably cancer. Thus, a vaccine supports in particular an innate and/or an adaptive immune response of the immune system of a subject to be treated. For example, the antigenic peptide according to the present invention typically leads to or supports an adaptive immune response in the patient to be treated.

In the context of the present invention, the vaccine (composition) can induce a specific immune response against a tumor antigen, and is thus preferably used to prevent or treat cancer. A vaccine for preventing or treating cancer may also be referred to as "cancer vaccine".

Accordingly, in a preferred embodiment, the invention relates to a composition as defined above, for use in the prevention and/or treatment of cancer in a subject in need thereof. More preferably, the invention relates to the use of the composition of the invention for manufacturing a medicament to prevent or treat cancer in a subject in need thereof. In other words, the invention relates to a method for preventing or treating cancer in a subject in need thereof, comprising administering an effective amount of the composition of the invention, to said subject.

Preferably the cancer to be prevented and/or treated by
the antigenic peptide according to the present invention,
the immunogenic compound according to the present invention,
the nanoparticle according to the present invention,
the cell according to the present invention,
the nucleic acid according to the present invention,
the host cell according to the present invention,
the pharmaceutical composition according to the present invention,
the kit according to the present invention, or
the combination according to the present invention as described herein relates to the (reference) tumor antigen of the antigenic peptide as described herein. Namely, appropriate antigenic peptides may be selected by (i) selecting an appropriate tumor antigen for a certain type of cancer as known in the art and/or as described herein in Table 1B (below) and (ii) selecting an appropriate antigenic peptide according to the invention for the selected tumor antigen, as described above, e.g. in Table 1A. One skilled in the art will readily understand that an antigenic peptide of the invention can be selected based upon the nature of the cancer to be prevented or treated, and/or on the human gene/human tumor antigen involved in said cancer.

Accordingly, preferred examples of cancer are shown in Table 1B below. In particular, the antigenic peptides according to the present invention are sequence variants of fragments of the tumor antigens shown in Table 1B and may be used in particular in the disease outlined for the respective tumor antigen in Table 1B.

TABLE 1B list of tumor antigens and associated therapeutic indications

| Tumor antigen | Full name tumor antigen | Cancers associated with tumor antigen |
| --- | --- | --- |
| ACPP | acid phosphatase, prostate | Diseases associated with ACPP include prostate cancer, ovarian cancer and prostatic adenoma |
| ANKRD30A | ankyrin repeat domain 30A | Diseases associated with ANKRD30A include breast cancer |
| AREG | amphiregulin | Diseases associated with AREG include colorectal cancer |
| ASCL1 | achaete-scute family bHLH transcription factor 1 | Diseases associated with ASCL1 include glioma and lung cancer |
| ASCL2 | achaete-scute family bHLH transcription factor 2 | Diseases associated with ASCL2 include colorectal cancer and stomach cancer |
| BIRC5 | baculoviral IAP repeat containing 5 | Diseases associated with BIRC5 include glioma, kidney cancer, lung cancer, ovarian cancer, breast cancer, colorectal cancer and head and neck cancer |
| CA9 | carbonic anhydrase 9 | Diseases associated with CA9 include kidney cancer |
| CCNA1 | cyclin A1 | Diseases associated with CCNA1 include ovarian cancer and head and neck cancer |
| CCND1 | cyclin D1 | Diseases associated with CCND1 include kidney cancer, skin cancer and breast cancer |
| CDH17 | cadherin 17 | Diseases associated with CDH17 include colorectal cancer, pancreatic cancer and stomach cancer |
| CDH6 | cadherin 6 | Diseases associated with CDH6 include kidney cancer and ovarian cancer |
| CDKN2A | cyclin dependent kinase inhibitor 2A | Diseases associated with CDKN2A include glioma, skin cancer, lung cancer, ovarian cancer, breast cancer, head and neck cancer and stomach cancer |
| CEACAM5 | carcinoembryonic antigen related cell adhesion molecule 5 | Diseases associated with CEACAM5 include gut carcinoma, colorectal cancer, urachal cancer, gastrointestinal cancer and pancreatic cancer |
| CHI3L1 | chitinase 3 like 1 | Diseases associated with CHI3L1 include glioma and kidney cancer |
| CHI3L2 | chitinase 3 like 2 | Diseases associated with CHI3L2 include glioma |
| COL11A1 | collagen type XI alpha 1 chain | Diseases associated with COL11A1 include breast cancer and pancreatic cancer |
| CT83 | cancer/testis antigen 83 | Diseases associated with CT83 include lung cancer and stomach cancer |
| CTCFL | CCCTC-binding factor like | Diseases associated with CTCFL include skin cancer and ovarian cancer |
| DCT | dopachrome tautomerase | Diseases associated with DCT include skin cancer |
| DMRTA2 | DMRT like family A2 | Diseases associated with DMRTA2 include glioma |
| EGFR | epidermal growth factor receptor | Diseases associated with EGFR include numerous cancers, including glioma, kidney cancer, lung cancer, head and neck cancer and urothelial cancer |
| ERBB2 | erb-b2 receptor tyrosine kinase 2 | Diseases associated with ERBB2 include numerous cancers, including breast cancer, glioma, urothelial cancer and ovarian cancer |
| ERG | ERG, ETS transcription factor | Diseases associated with ERG include prostate cancer |

TABLE 1B-continued list of tumor antigens and associated therapeutic indications

| Tumor antigen | Full name tumor antigen | Cancers associated with tumor antigen |
| --- | --- | --- |
| ESR1 | estrogen receptor 1 | Diseases associated with ESR1 include breast cancer |
| EZH2 | enhancer of zeste 2 polycomb repressive complex 2 subunit | Diseases associated with EZH2 include many forms of cancers, including lung cancer, lymphoblastoma, glioma, kidney cancer, skin cancer, ovarian cancer, breast cancer, colorectal cancer, head and neck cancer, stomach cancer, urothelial cancer and prostate cancer |
| FAP | fibroblast activation protein alpha | Diseases associated with FAP include lung cancer, colorectal cancer, pancreatic cancer and head and neck cancer |
| FLT1 | fms related tyrosine kinase 1 | Diseases associated with FLT1 include kidney cancer |
| FOXM1 | forkhead box M1 | Diseases associated with FOXM1 include numerous types of cancer including glioma, kidney cancer, skin cancer, lung cancer, ovarian cancer, breast cancer, colorectal cancer and head and neck cancer |
| FSIP1 | fibrous sheath interacting protein 1 | Diseases associated with FSIP1 include breast cancer |
| GAL3ST1 | galactose-3-O-sulfotransferase 1 | Diseases associated with GAL3ST1 include kidney cancer |
| GPR143 | G protein-coupled receptor 143 | Diseases associated with GPR143 include skin cancer |
| HES6 | hes family bHLH transcription factor 6 | Diseases associated with HES6 include various cancers including glioma, kidney cancer, skin cancer, lung cancer, breast cancer, colorectal cancer and pancreatic cancer |
| IL13RA2 | interleukin 13 receptor subunit alpha 2 | Diseases associated with IL13RA2 include colorectal cancer, ovarian cancer, testis cancer, renal cell carcinoma, prostate cancer, glioma, skin cancer, head and neck cancer, astrocytoma, melanoma, pancreatic cancer and breast cancer metastasis |
| KISS1R | KISS1 receptor | Diseases associated with KISS1R include kidney cancer |
| KLHDC8A | kelch domain containing 8A | Diseases associated with KLHDC8A include glioma |
| KLHL14 | kelch like family member 14 | Diseases associated with KLHL14 include ovarian cancer |
| KLK4 | kallikrein related peptidase 4 | Diseases associated with KLK4 include prostate cancer |
| KRT81 | keratin 81 | Diseases associated with KRT81 include breast cancer |
| LEMD1 | LEM domain containing 1 | Diseases associated with LEMD1 include lung cancer, ovarian cancer, colorectal cancer and pancreatic cancer |
| LRRC15 | leucine rich repeat containing 15 | Diseases associated with LRRC15 include breast cancer |
| MAGEA1 | MAGE family member A1 | Diseases associated with MAGEA1 include melanoma and hemangioma of liver, non-small cell lung cancer, gastric cancer, head and neck cancer and melanoma |
| MAGEA4 | MAGE family member A4 | Diseases associated with MAGEA4 include melanoma and testicular leukemia, thyroid cancer, breast cancer including estrogen receptor negative breast cancer and non-small cell lung cancer |
| MAGEA10 | MAGE family member A10 | Diseases associated with MAGEA10 include glioma and lung cancer |
| MAGEA11 | MAGE family member A11 | Diseases associated with MAGEA11 include skin cancer, lung cancer and colorectal cancer |
| MAGEA12 | MAGE family member A12 | Diseases associated with MAGEA12 include skin cancer |
| MLANA | melan-A | Diseases associated with MLANA include melanoma |
| NKX2-1 | NK2 homeobox 1 | Diseases associated with NKX2-1 include lung cancer |
| NPTX2 | neuronal pentraxin 2 | Diseases associated with NPTX2 include kidney cancer |
| PAGE3 | PAGE family member 3 | Diseases associated with PAGE3 include numerous types of cancer including glioma, kidney cancer, skin cancer, lung cancer, ovarian cancer, breast cancer, colorectal cancer, liver cancer, pancreatic cancer, stomach cancer, urothelial cancer, prostate cancer and head and neck cancer |
| PAX2 | paired box 2 | Diseases associated with PAX2 include kidney cancer |
| PCDHB16 | protocadherin beta 16 | Diseases associated with PCDHB16 include glioma, kidney cancer and breast cancer |

TABLE 1B-continued list of tumor antigens and associated therapeutic indications

| Tumor antigen | Full name tumor antigen | Cancers associated with tumor antigen |
|---|---|---|
| PIWIL1 | piwi like RNA-mediated gene silencing 1 | Diseases associated with PIWIL1 include colorectal cancer and stomach cancer |
| PMEL | premelanosome protein | Diseases associated with PMEL include melanoma |
| PRAME | preferentially expressed antigen in melanoma | Diseases associated with PRAME include skin cancer |
| PTHLH | parathyroid hormone like hormone | Diseases associated with PTHLH include breast cancer |
| SEMG1 | semenogelin 1 | Diseases associated with SEMG1 include prostate cancer |
| SERHL2 | serine hydrolase like 2 | Diseases associated with SERHL2 include breast cancer |
| SLC45A3 | solute carrier family 45 member 3 | Diseases associated with SLC45A3 include prostate cancer |
| SLC6A3 | solute carrier family 6 member 3 | Diseases associated with SLC6A3 include kidney cancer |
| SNX31 | sorting nexin 31 | Diseases associated with SNX31 include urothelial cancer |
| SOX11 | SRY-box 11 | Diseases associated with SOX11 include glioma |
| SOX17 | SRY-box 17 | Diseases associated with SOX17 include ovarian cancer |
| SPINK1 | serine peptidase inhibitor, Kazal type 1 | Diseases associated with SPINK1 include pancreatic cancer |
| STEAP1 | STEAP family member 1 | Diseases associated with STEAP1 include prostate cancer |
| TBL1Y | transducin beta like 1 Y-linked | Diseases associated with TBL1Y include prostate cancer |
| TDRD1 | tudor domain containing 1 | Diseases associated with TDRD1 include prostate cancer |
| TOP2A | DNA topoisomerase II alpha | Diseases associated with TOP2A include lung cancer and breast cancer |
| TPTE | transmembrane phosphatase with tensin homology | Diseases associated with TPTE include skin cancer, lung cancer and breast cancer |
| TRPM8 | transient receptor potential cation channel subfamily M member 8 | Diseases associated with TRPM8 include prostate cancer |
| TYMS | thymidylate synthetase | Diseases associated with TYMS include glioma, kidney cancer and skin cancer |
| TYR | tyrosinase | Diseases associated with TYR include skin cancer and melanoma |
| UPK2 | uroplakin 2 | Diseases associated with UPK2 include kidney cancer |
| VCAM1 | vascular cell adhesion molecule 1 | Diseases associated with VCAM1 include kidney cancer |
| WFDC2 | WAP four-disulfide core domain 2 | Diseases associated with WFDC2 include ovarian cancer |
| WT1 | Wilms tumor 1 | Diseases associated with WT1 include glioma, kidney cancer and ovarian cancer |
| ZEB1 | zinc finger E-box binding homeobox 1 | Diseases associated with ZEB1 include glioma |
| ZNF165 | zinc finger protein 165 | Diseases associated with ZNF165 include pancreatic cancer |
| ZNF280A | zinc finger protein 280A | Diseases associated with ZNF280A include include glioma, skin cancer, lung cancer and ovarian cancer |

In general, antigenic peptides of the invention may be administered "naked" or in the form of immunogenic compounds according to the present invention, cells loaded therewith according to the present invention, nanoparticles according to the present invention, nucleic acids according to the present invention, host cells according to the present invention and/or pharmaceutical compositions according to the present invention.

In a preferred embodiment, they may be administered in the form of a micro-organism such as a gut bacterial species. Entire gut bacterial species can also be advantageous as they have the potential to trigger a greater immune response than the (poly)peptides or nucleic acids they contain. Alternatively, gut bacteria according to the invention may be in the form of probiotics, i.e. of live gut bacterium, which can thus be used as food additive thanks to the health benefits it can provide. Those can be for example lyophilized in granules, pills or capsules, or directly mixed with dairy products for consumption.

Methods of administration are well-known to the skilled person in the art. With regard to the composition of the invention, it can be directly administered into the subject, into the affected organ (i.e. local administration) or systemically (i.e. enteral or parenteral administration), or even applied ex vivo to cells derived from the subject or a human cell line which are subsequently administered to the subject, or even used in vitro to select a subpopulation of immune cells derived from the subject, which are then re-administered to the said subject. Enteral administrations include oral and rectal administrations, as well as administrations via gastric feeding tubes, duodenal feeding tubes or gastrostomy, while parenteral administrations includes, among others, subcutaneous, intravenous, intramuscular, intra-arterial, intradermal, intraosseous, intracerebral, and intrathecal injections. The administration method will often depend upon the antigenic peptide(s) and/or immunogenic compound(s) present in the composition, and the type of cancer to be treated and other active agents that may be contained in said composition. For example, the administration is preferably an intramuscular or an intradermal injection if the immunogenic compound is a nucleic acid as defined above, the oral/nasal administration being particularly preferred if said nucleic acid is cloned into a viral vector. Alternatively, the administration is preferably an intramuscular, an intradermal or an oral administration if the antigenic peptide and/or immunogenic compound is a (poly)peptide as defined above or if it is loaded in/on a nanoparticle as described herein. Yet, still alternatively, the administration is preferably an oral administration if the antigenic peptide and/or immunogenic compound is delivered in the form of a gut bacterium as defined above, notably if the gut bacterium is in the form of probiotics.

The antigenic peptides, the immunogenic compounds and the nucleic acids according to the invention can further be encapsulated so as to facilitate their administration to the subject in need thereof. For example, those may be encapsulated into peptide nanocarriers (preferable if the immunogenic compound is a nucleic acid or a (poly)peptide), into virosomes (preferable if the immunogenic compound is a nucleic acid or a (poly)peptide), or into lipid-based carrier systems such as liposome-polycation-DNA complex (preferable if the immunogen is a nucleic acid or a (poly)peptide) (Trovato M, De Berardinis P. Novel antigen delivery systems. World J Virol. 2015 Aug. 12; 4(3):156-68; Saade F, Petrovsky N. Technologies for enhanced efficacy of DNA vaccines. Expert Rev Vaccines. 2012 February; 11(2):189-209; Li et al., Peptide Vaccine: Progress and Challenges. Vaccines (Basel). 2014 Jul. 2; 2(3):515-36).

The composition may also be administered more than once so as to achieve the desired effect. In a preferred embodiment, said composition is administered repeatedly, at least twice, and preferably more than twice. This can be done over an extended period of time, such as weekly, every other week, monthly, yearly, or even several years after the first administration to ensure that the subject is properly immunized.

Combination Therapy

The administration of the antigenic peptide according to the present invention, the immunogenic compound according to the present invention, the nanoparticle according to the present invention, the cell according to the present invention, the nucleic acid according to the present invention, the host cell according to the present invention, and the pharmaceutical composition according to the present invention, in particular in the methods and uses according to the invention, can be carried out alone or in combination with a co-agent useful for treating and/or preventing cancer, such as an anti-cancer therapeutic agent.

Said therapeutic agent is thus preferably capable of preventing and/or treating the same type of cancer as the one for which the antigenic peptide according to the invention is used. Particularly preferred anti-cancer therapeutic agents according to the invention include, without limitation, antibodies, tumor cell lysates, chemotherapeutic agents, radiotherapeutic agents, immune checkpoint modulators and combinations thereof.

Antibodies are particularly advantageous in cancer therapy as they can either bind to specific antigens on cancer cell surfaces, thereby directing the therapy to the tumor (i.e. these are referred as tumor-targeting antibodies), or block immune checkpoints that are dysregulated in cancer (i.e. these are referred herein as immunomodulatory antibodies). The purpose of the later type of antibodies is to inhibit cancer immune resistance, which can notably be observed against T cells that are specific for tumour antigens. Indeed, as well-known in the art, under normal physiological conditions, immune checkpoints are crucial for the maintenance of self-tolerance (i.e. prevention of autoimmunity) and protect tissues from damage when the immune system is responding to pathogenic infection. However, in cancer, immune-checkpoints expression can be dysregulated as an important mechanism of immune resistance. Said resistance has notably been observed in melanoma, ovarian, lung, glioblastoma, breast, and pancreatic cancers with regard to the PD-L1 checkpoint (Konishi et al., B7-H1 expression on non-small cell lung cancer cells and its relationship with tumor-infiltrating lymphocytes and their PD-1 expression. Clin Cancer Res. 2004 Aug. 1; 10(15):5094-100; Ghebeh et al., The B7-H1 (PD-L1) T lymphocyte-inhibitory molecule is expressed in breast cancer patients with infiltrating ductal carcinoma: correlation with important high-risk prognostic factors. Neoplasia. 2006 March; 8(3):190-8; Hino et al., Tumor cell expression of programmed cell death-1 ligand 1 is a prognostic factor for malignant melanoma. Cancer. 2010 Apr. 1; 116(7):1757-66). Other examples of immune checkpoints include, without limitation, PD-L2, PD-1, CD80, CD86, CTLA4, B7H3, B7H4, PVR, TIGIT, GAL9, LAG-3, GITR, CD137, TIM3, VISTA, VISTA-R (Pico de Coaña et al., Checkpoint blockade for cancer therapy: revitalizing a suppressed immune system. Trends Mol Med. 2015 August; 21(8):482-91; Pardoll DM1. The blockade of immune checkpoints in cancer immunotherapy. Nat Rev Cancer. 2012 Mar. 22; 12(4):252-64).

Antibodies are usually employed for the above purposes either in the form of naked monoclonal antibodies (i.e. non-conjugated), or conjugated to another molecule which can be toxic to cells or radioactive.

Examples of well-known monoclonal tumor-targeting antibodies used in cancer immunotherapy include, without limitation, alemtuzumab (chronic lymphocytic leukemia), bevacizumab (colorectal cancer, glioblastoma multiforme, cervical cancer, lung cancer, renal cancer), brentuximab/vedotin (lymphomas), blinatumumab (acute lymphoblastic leukemia), catumaxomab (malignant ascites in EPCAM+ cancers), cetuximab (head and neck cancer, colorectal cancer), denosumab (breast, prostate and bone cancers), Gemtuzumab/ozogamicin (acute myeloid keulemia), ibritumomab/tiuxetan (non-Hodgkin lymphoma), panitumumab (colorectal cancer), pertuzumab (breast cancer), obinutuzumab (chronic lymphocytic leukemia), ofatumumab (chronic lymphocytic leukemia), opilimumab (melanoma), ramucirumab (gastric and gastro-oeasophageal cancers), rituximab (chronic lymphocytic leukemia and non-Hodgkin lymphoma), siltuximab (multicentric's Catsleman's disease), tositumomab (non-Hodgkin lymphoma), and trastuzumab (breast, gastric and gastro-oeasophageal cancers); while examples of immunomodulatory antibodies include, without limitation, ipilimumab (melanoma) which blocks the CTLA4-dependent immune checkpoint, nivolumab (melanoma, lung cancer) and prembrolizubmab (melanoma) which both block the PDCD1-dependent immune checkpoint, as well as MPDL3280A, MEDI4736, MEDI0680, and MSB0010718C which all block the PD-L1-dependent immune checkpoint (Sharma and Allison, The future of immune checkpoint therapy. Science. 2015 Apr. 3; 348(6230):56-61).

Other antibodies for cancer immunotherapy have been described in Buqué et al. (Buqué et al., Trial Watch: Immunomodulatory monoclonal antibodies for oncological indications. Oncoimmunology. 2015 Mar. 2; 4(4):e1008814. eCollection 2015 April), Redman et al. (Redman et al., Mechanisms of action of therapeutic antibodies for cancer. Mol Immunol. 2015 October; 67(2 Pt A):28-45), and in Simpson and Caballero, Monoclonal antibodies for the therapy of cancer MC Proc. 2014; 8(Suppl 4): 06 as well as on the antibody society website (list of therapeutic monoclonal antibodies approved or in review in the European Union or United States available on the weblink http://www.antibodysociety.org/news/approved_mabs.php).

Tumor cell lysates may also be combined with the antigenic peptide(s) according to the invention. Tumor cells are indeed capable of priming the immune response, by presenting endogenous peptides-MHC complexes, as well as via dendritic cells (DCs) of the host which can process and present the antigen delivered by said lysates. The range of antigens against which an immune response can be induced is thereby increased. Tumor cell lysates can be easily obtained by treating tumor cells with a heat shock and/or a chemical treatment, and can be autologous (i.e. isolated from the patient), or allogeneic (i.e. isolated from another subject).

Standard chemotherapeutic drugs and radiotherapeutic agents need not be further described herein as they have been extensively described in the literature, notably by Baskar et al. (Baskar et al., Cancer and radiation therapy: current advances and future directions. Int J Med Sci. 2012; 9(3):193-9), Paci et al. (Paci et al., Review of therapeutic drug monitoring of anticancer drugs part 1—cytotoxics. Eur J Cancer. 2014 August; 50(12):2010-9) and Widmer et al. (Widmer et al., Review of therapeutic drug monitoring of anticancer drugs part two—targeted therapies. Eur J Cancer. 2014 August; 50(12):2020-36). A list of such drugs and agents is also available on the cancer.gov website (http://www.cancer.gov/about-cancer/treatment/drugs).

Preferably, the immune checkpoint modulator for combination with the antigenic peptide as defined herein is an activator or an inhibitor of one or more immune checkpoint molecule(s) selected from CD27, CD28, CD40, CD122, CD137, OX40, GITR, ICOS, A2AR, B7-H3, B7-H4, BTLA, CD40, CTLA-4, IDO, KIR, LAG3, PD-1, TIM-3, VISTA, CEACAM1, GARP, PS, CSF1R, CD94/NKG2A, TDO, GITR, TNFR and/or FasR/DcR3; or an activator or an inhibitor of one or more ligands thereof.

More preferably, the immune checkpoint modulator is an activator of a (co-)stimulatory checkpoint molecule or an inhibitor of an inhibitory checkpoint molecule or a combination thereof. Accordingly, the immune checkpoint modulator is more preferably (i) an activator of CD27, CD28, CD40, CD122, CD137, OX40, GITR and/or ICOS or (ii) an inhibitor of A2AR, B7-H3, B7-H4, BTLA, CD40, CTLA-4, IDO, KIR, LAG3, PD-1, PDL-1, PD-L2, TIM-3, VISTA, CEACAM1, GARP, PS, CSF1R, CD94/NKG2A, TDO, TNFR and/or FasR/DcR3.

Even more preferably, the immune checkpoint modulator is an inhibitor of an inhibitory checkpoint molecule (but preferably no inhibitor of a stimulatory checkpoint molecule). Accordingly, the immune checkpoint modulator is even more preferably an inhibitor of A2AR, B7-H3, B7-H4, BTLA, CTLA-4, IDO, KIR, LAG3, PD-1, PDL-1, PD-L2, TIM-3, VISTA, CEACAM1, GARP, PS, CSF1R, CD94/NKG2A, TDO, TNFR and/or DcR3 or of a ligand thereof.

It is also preferred that the immune checkpoint modulator is an activator of a stimulatory or costimulatory checkpoint molecule (but preferably no activator of an inhibitory checkpoint molecule). Accordingly, the immune checkpoint modulator is more preferably an activator of CD27, CD28, CD40, CD122, CD137, OX40, GITR and/or ICOS or of a ligand thereof.

It is even more preferred that the immune checkpoint modulator is a modulator of the CD40 pathway, of the IDO pathway, of the LAG3 pathway, of the CTLA-4 pathway and/or of the PD-1 pathway. In particular, the immune checkpoint modulator is preferably a modulator of CD40, LAG3, CTLA-4, PD-L1, PD-L2, PD-1 and/or IDO, more preferably the immune checkpoint modulator is an inhibitor of CTLA-4, PD-L1, PD-L2, PD-1, LAG3, and/or IDO or an activator of CD40, even more preferably the immune checkpoint modulator is an inhibitor of CTLA-4, PD-L1, PD-1, LAG3 and/or IDO, even more preferably the immune checkpoint modulator is an inhibitor of LAG3, CTLA-4 and/or PD-1, and most preferably the immune checkpoint modulator is an inhibitor of CTLA-4 and/or PD-1.

Accordingly, the checkpoint modulator for combination with the antigenic peptide may be selected from known modulators of the CTLA-4 pathway or the PD-1 pathway. Preferably, the checkpoint modulator for combination with the antigenic peptide as defined herein may be selected from known modulators of the CTLA-4 pathway or the PD-1 pathway. Particularly preferably, the immune checkpoint modulator is a PD-1 inhibitor. Preferred inhibitors of the CTLA-4 pathway and of the PD-1 pathway include the monoclonal antibodies Yervoy® (Ipilimumab; Bristol Myers Squibb) and Tremelimumab (Pfizer/MedImmune) as well as Opdivo® (Nivolumab; Bristol Myers Squibb), Keytruda® (Pembrolizumab; also known as Lambrolizumab or MK-3475; Merck), Imfinzi® (Durvalumab also known as MEDI4736; MedImmune/AstraZeneca), Tecentriq® (Atezolizumab also known as MPDL3280A; Roche/Genentech), Pidilizumab (CT-011; CureTech), MEDI0680 (AMP-514; AstraZeneca), Bavencio® (Avelumab; Merck KGaA/Pfizer also known as MSB-0010718C), MIH1 (Affymetrix), LY3300054 (Eli Lilly) and and Spartalizumab (also known as PDR001; Novartis). More preferred checkpoint inhibitors include the CTLA-4 inhibitors Yervoy® (Ipilirnumab; Bristol Myers Squibb) and Tremelimumab (Pfizer/MedImmune) as well as the PD-1 inhibitors Opdivo® (Nivolumab; Bristol Myers Squibb), Keytruda® (Pembrolizumab; Merck), Pidilizumab (CT-011; CureTech), MEDI0680 (AMP-514; AstraZeneca), AMP-224 (a PD-L2 Fc fusion protein; MedImmune).

It is also preferred that the immune checkpoint modulator for combination with the antigenic peptide as defined herein is selected from the group consisting of Pembrolizumab, Ipilimumab, Nivolumab, Atezolizumab, MEDI4736, Tremelimumab, Avelumab, Spartalizumab, LAG525 (an anti-LAG3 monoclonal antibody), Epacadostat (formely INCB24360; an IDO inhibitor), Varlilumab (an anti-CD27 monoclonal antibody), Urelumab (an anti-CD137 monoclonal antibody), AMP-224 and CM-24 (an anti-CEACAM1 monoclonal antibody).

It is within the skill of ordinary person in the art to select the appropriate immune anti-cancer therapeutic agent for the purposes of the invention. For example, should one wish to prevent or treat melanoma, a lysate from melanoma cells and/or the antibody Ipilimumab can preferably be used, along with the corresponding antigenic peptide according to the present invention as described herein.

The anti-cancer therapeutic agent can also be administered in association with the antigenic peptide according to the present invention, the immunogenic compound according to the present invention, the nanoparticle according to the present invention, the cell according to the present invention, the nucleic acid according to the present invention, the host cell according to the present invention, or the pharmaceutical composition according to the present invention, either at about the same time or consecutively as described herein and in the same or distinct pharmaceutical forms. Thus, the invention proposes a combined use of the composition the invention and least one anti-cancer therapeutic agent as described above, for a simultaneous, separate, or sequential administration as described herein.

Furthermore, the present invention also relates to a combination of at least two distinct antigenic peptides according to the present invention, e.g. for use in the prevention and/or treatment of a cancer. Furthermore, the present invention also relates to a combination of at least two distinct immunogenic compounds according to the present invention, e.g. for use in the prevention and/or treatment of a cancer. Furthermore, the present invention also relates to a combination of at least two distinct nanoparticles according to the present invention, e.g. for use in the prevention and/or treatment of a cancer. Furthermore, the present invention also relates to a combination of at least two distinct nucleic acids according to the present invention, e.g. for use in the prevention and/or treatment of a cancer.

Thus, according to a preferred embodiment, at least two antigenic peptides according to the present invention may be administered in combination, for example in the same pharmaceutical composition. For example, at least 3 antigenic peptides, at least 4 antigenic peptides, at least 5 antigenic peptides, at least 6 antigenic peptides, at least 7 antigenic peptides, at least 8 antigenic peptides, at least 9 antigenic peptides, at least 10 antigenic peptides, at least 11 antigenic peptides, at least 12 antigenic peptides, at least 13 antigenic peptides, at least 14 antigenic peptides, at least 15 antigenic peptides, at least 20 antigenic peptides, at least 25 antigenic peptides, at least 50 antigenic peptides, at least 100 antigenic peptides, at least 500 antigenic peptides, at least 1000 antigenic peptides, or at least 1500 antigenic peptides are administered in combination, for example in the same pharmaceutical composition. It is within the skill of the person in the art to select the combination of antigenic peptides and/or immunogenic compounds that is suitable for the intended purpose. For example, should one wish to prevent or treat melanoma which involves a tumor antigen encoded by a gene according to Table 1B, one can select any combination of the corresponding antigenic peptides as described in Table 1A.

In a particularly preferred embodiment two distinct antigenic peptides according to the present invention (e.g., relating to the same type of cancer and/or to the same reference antigen) are combined. For example,
 (i) at least two distinct immunogenic compounds according to the present invention;
 (ii) at least two distinct antigenic peptides according to the present invention;
 (iii) at least two distinct nanoparticles according to the present invention; or
 (iv) at least two distinct nucleic acids according to the present invention
may be combined.

For example, the present invention provides a combination of
 (i) a first antigenic peptide according to the present invention, and
 (ii) a second antigenic peptide according to the present invention (distinct from the first) preferably for use in the prevention and/or treatment of a cancer.

For example, the present invention provides a combination of
 (i) an immunogenic compound according to the present invention comprising a first antigenic peptide according to the present invention, and
 (ii) an immunogenic compound according to the present invention comprising a second antigenic peptide according to the present invention (distinct from the first)
preferably for use in the prevention and/or treatment of a cancer.

For example, the present invention provides a combination of
 (i) a nanoparticle according to the present invention comprising a first antigenic peptide according to the present invention, and
 (ii) a nanoparticle according to the present invention comprising a second antigenic peptide according to the present invention (distinct from the first)
preferably for use in the prevention and/or treatment of a cancer.

For example, the present invention provides a combination of
 (i) a nucleic acid according to the present invention comprising a polynucleotide encoding a first antigenic peptide according to the present invention and
 (ii) a nucleic acid according to the present invention comprising a polynucleotide encoding a second antigenic peptide according to the present invention (distinct from the first)
preferably for use in the prevention and/or treatment of a cancer.

Moreover, the antigenic peptide according to the present invention may also be combined with the corresponding (human) tumor antigen epitope (as described above regarding the peptide "families"). Thereby, selection of T-cell clones, which are very efficient against the tumor, is obtained/supported. In particular, the antigenic peptide according to the present invention and the corresponding (human) tumor antigen epitope may be co-administered. Such co-administration may be at about the same time (simultaneously) or consecutively, whereby in consecutive administration it is preferred that the antigenic peptide according to the present invention is administered first and the corresponding (human) tumor antigen epitope is administered thereafter. In particular, the antigenic peptide according to the present invention may be administered first, and the corresponding (human) tumor antigen epitope may be used as (re)boost. For example, the antigenic peptide according to SEQ ID NO: 30, 31 or 32 may be combined with the reference peptide according to SEQ ID NO: 593. In another example, the antigenic peptide according to SEQ ID NO: 87 or 97 may be combined with the reference peptide according to SEQ ID NO: 617. In another example, the antigenic peptide according to SEQ ID NO: 145 may be combined with the reference peptide according to SEQ ID NO: 637. In another example, the antigenic peptide according to SEQ ID NO: 193 may be combined with the reference peptide according to SEQ ID NO: 659. In another example, the antigenic peptide according to SEQ ID NO: 194 may be combined with the reference peptide according to SEQ ID NO: 660. In another example, the antigenic peptide according to SEQ ID NO: 221 may be combined with the reference peptide according to SEQ ID NO: 675. In another example, the antigenic peptide according to SEQ ID NO: 220 may be combined with the reference peptide according to SEQ ID NO: 674. In another example, the antigenic peptide according to SEQ ID NO: 255 may be combined with the reference peptide according to SEQ ID NO: 691. In another example, the antigenic peptide according to SEQ ID NO: 524 may be combined with the reference peptide according to SEQ ID NO: 826. In another example, the antigenic peptide according to SEQ ID NO: 521 may be combined with the reference peptide according to SEQ ID NO: 824.

The peptides, which are to be combined, such as (a) the antigenic peptide according to the present invention and the corresponding (human) tumor antigen epitope or (b) two distinct antigenic peptides according to the present invention, may be administered

- in the same immunogenic compound according to the present invention or in distinct immunogenic compounds according to the present invention,
- (loaded) in the same nanoparticle according to the present invention or in distinct nanoparticles according to the present invention,
- (loaded) in the same cell according to the present invention or in distinct cells according to the present invention,
- (encoded by) the same nucleic acid according to the present invention or by distinct nucleic acids according to the present invention,
- (expressed by) the same host cell according to the present invention or by distinct host cells according to the present invention, or
- (comprised) in the same pharmaceutical composition according to the present invention or in distinct pharmaceutical composition according to the present invention.

In the following it may be referred to "two distinct components" (of a combination for use according to the present invention). In general, the expression "two distinct components" in the context of a combination, e.g. for use according to the present invention (a combination therapy), refers to (1) a first component, such as the antigenic peptide according to the present invention as described herein, the immunogenic compound according to the present invention as described herein, the nanoparticle according to the present invention as described herein, the cell according to the present invention as described herein, the nucleic acid according to the present invention as described herein, the host cell according to the present invention as described herein, or the pharmaceutical composition according to the present invention as described herein; and (2) a second component (which is distinct from the first component), such as the anti-cancer therapeutic agent as described above, a distinct antigenic peptide according to the present invention as described herein, a distinct immunogenic compound according to the present invention as described herein, a distinct nanoparticle according to the present invention as described herein, a distinct cell according to the present invention as described herein, a distinct nucleic acid according to the present invention as described herein, a distinct host cell according to the present invention as described herein, a distinct pharmaceutical composition according to the present invention as described herein, or one or more (fragments of) human tumor antigens in any form ("naked", as immunogenic compound as described herein, as nanoparticle as described herein, as (host) cell as described herein, as nucleic acid as described herein or as pharmaceutical composition as described herein).

Accordingly, the "two distinct components", as referred to herein in the context of a combination for use according to the present invention (a combination therapy), are preferably active components in the context of the disease (cancer) to be prevented and/or treated. In other words, each of the at least two distinct components may also be useful for preventing and/or treating said cancer, if administered separately (not in combination as described herein)—although the combination (i.e. combined administration) typically potentiates their preventive and/or therapeutic effect (such as the immune response), in particular in a synergistic manner.

Accordingly, the present invention also provides the combination of (at least) two distinct antigenic peptides according to the present invention as described herein. In this context, the (at least) two distinct antigenic peptides may be in any form, e.g., "naked", comprised in immunogenic compounds, nanoparticles, (pharmaceutical) compositions or cells loaded therewith, or encoded by nucleic acids (e.g., vectors). Accordingly, the (at least) two distinct antigenic peptides may be comprised in (at least) two distinct components (to be combined).

In a preferred embodiment, the at least two distinct components of the combination according to the present invention are at least distinct antigenic peptides according to the present invention (in any form, e.g. comprised in immunogenic compounds, nanoparticles, cells, pharmaceutical compositions, encoded by the nucleic acids, etc.).

Preferably, the at least two distinct components of the combination for use according to the present invention relate to the same type of cancer, for example to the same or distinct antigens associated with this cancer and/or to the same or distinct (reference) epitopes within an antigen associated with this cancer. More preferably, the at least two distinct components relate to the same tumor antigen.

In certain embodiments, the at least two distinct components of the combination for use according to the present invention are comprised in the same or distinct compositions. In certain embodiments, the at least two distinct components of the combination for use according to the present invention are administered via the same or distinct routes of administration. In certain embodiments, the at least two distinct components of the combination for use according to the present invention are administered at about the same time (simultaneously) or consecutively.

Preferably, the at least two distinct components of the combination for use according to the present invention are administered at about the same time. In more general, it is preferred that the first component is administered at about the same time as the second component, wherein the at least two distinct components of the combination for use according to the present invention are preferably administered in the same form (i.e., in the same type of formulation, e.g., as nanoparticles, as pharmaceutical compositions, etc.).

"At about the same time", as used herein, means in particular simultaneous administration or that directly after administration of the first component, the second component is administered or directly after administration of the second component, the first component is administered. The skilled person understands that "directly after" includes the time necessary to prepare the second administration—in particular the time necessary for exposing and disinfecting the location for the second administration as well as appropriate preparation of the "administration device" (e.g., syringe, pump, etc.). Simultaneous administration also includes if the periods of administration of the first component and of the second component overlap or if, for example, one component is administered over a longer period of time, such as 30 min, 1 h, 2 h or even more, e.g. by infusion, and the other component is administered at some time during such a long period. Administration of the first component and of the second component at about the same time is in particular preferred if different routes of administration and/or different administration sites are used.

It is also preferred that the at least two distinct components of the combination for use according to the present invention are administered consecutively. In more general, it is preferred that the first component and the second component are administered consecutively, wherein the at least two distinct components of the combination for use according to the present invention are preferably administered in the same form (i.e., in the same type of formulation, e.g., as nanoparticles, as pharmaceutical compositions, etc.).

This means that the first component is administered before or after the second component. In consecutive administration, the time between administration of the first component and administration of the second component is preferably no more than one week, more preferably no more than 3 days, even more preferably no more than 2 days and most preferably no more than 24 h. It is particularly preferred that the first component and the second component are administered at the same day with the time between administration of the first component and administration of the second component being preferably no more than 6 hours, more preferably no more than 3 hours, even more preferably no more than 2 hours and most preferably no more than 1 h.

Preferably, the first component and the second component are administered via the same route of administration. In more general, it is preferred that the first component and the second component are administered via the same route of administration, wherein the at least two distinct components of the combination for use according to the present invention are preferably administered in the same form (i.e., in the same type of formulation, e.g., as nanoparticles, as pharmaceutical compositions, etc.).

It is also preferred that the at least two distinct components of the combination for use according to the present invention are administered via distinct routes of administration. In more general, it is preferred that the first component and the second component are administered via distinct routes of administration, wherein the at least two distinct components of the combination for use according to the present invention are preferably administered in the same form (i.e., in the same type of formulation, e.g., as nanoparticles, as pharmaceutical compositions, etc.).

Preferably, the at least two distinct components of the combination for use according to the present invention are comprised in the same composition. In more general, it is preferred that the first component and the second component are comprised in the same composition, wherein the at least two distinct components of the combination for use according to the present invention are preferably administered in the same form (i.e., in the same type of formulation, e.g., as nanoparticles, etc.).

It is also preferred that the at least two distinct components of the combination for use according to the present invention are comprised in distinct compositions. In more general, it is preferred that the first component and the second component are comprised in distinct compositions, wherein the at least two distinct components of the combination for use according to the present invention are preferably administered in the same form (i.e., in the same type of formulation, e.g., as nanoparticles, etc.).

In particular, the present invention provides a combination, e.g. for use in the prevention and/or treatment of a cancer, comprising a first antigenic peptide according to the present invention, which comprises or consists of a microbiota sequence variant of a fragment of the human tumor antigen BIRC5, and a second antigenic peptide according to the present invention, which comprises or consists of a microbiota sequence variant of a fragment of the human tumor antigen FOXM1. Preferably, the first antigenic peptide comprises or consists of a microbiota sequence variant of the BIRC5 fragment (human reference peptide) "LTLGEFLKL" (SEQ ID NO: 593), such as an antigenic peptide comprising or consisting of an amino acid sequence as set forth in SEQ ID NO: 30, 31 or 32, and the second antigenic peptide comprises or consists of a microbiota sequence variant of the FOXM1 fragment (human reference peptide) "LMDLSTTPL" (SEQ ID NO: 674), such as an antigenic peptide comprising or consisting of an amino acid sequence as set forth in SEQ ID NO: 220 or 868. Even more preferably, the combination, e.g. for use in the prevention and/or treatment of a cancer, comprises an antigenic peptide comprising or consisting of SEQ ID NO: 32 and an antigenic peptide comprising or consisting of SEQ ID NO: 220.

In particular, the present invention also provides a combination, e.g. for use in the prevention and/or treatment of a cancer, comprising a first antigenic peptide according to the present invention, which comprises or consists of a microbiota sequence variant of a fragment of the human tumor antigen BIRC5, and a second antigenic peptide according to the present invention, which comprises or consists of a microbiota sequence variant of a fragment of the tumor antigen IL13RA2. Preferably, the first antigenic peptide comprises or consists of a microbiota sequence variant of the BIRC5 fragment (human reference peptide) "LTLGEFLKL" (SEQ ID NO: 593), such as an antigenic peptide comprising or consisting of an amino acid sequence as set forth in SEQ ID NO: 30, 31 or 32, and the second antigenic peptide comprises or consists of a microbiota sequence variant of the IL13RA2 fragment (human reference peptide) "WLPFGFILI" (SEQ ID NO: 691) or "WLPFGFILIL" (SEQ ID NO: 692), such as an antigenic peptide comprising or consisting of an amino acid sequence as set forth in SEQ ID NO: 254, 255, 878 or 879. Even more preferably, the combination, e.g. for use in the prevention and/or treatment of a cancer, comprises an antigenic peptide comprising or consisting of SEQ ID NO: 32 and an antigenic peptide comprising or consisting of SEQ ID NO: 255.

In particular, the present invention also provides a combination, e.g. for use in the prevention and/or treatment of a cancer, comprising a first antigenic peptide according to the present invention, which comprises or consists of a microbiota sequence variant of a fragment of the human tumor antigen FOXM1, and a second antigenic peptide according to the present invention, which comprises or consists of a microbiota sequence variant of a fragment of the human tumor antigen IL13RA2. Preferably, the first antigenic peptide comprises or consists of a microbiota sequence variant of the FOXM1 fragment (human reference peptide)

"LMDLSTTPL" (SEQ ID NO: 674), such as an antigenic peptide comprising or consisting of an amino acid sequence as set forth in SEQ ID NO: 220 or 868, and the second antigenic peptide comprises or consists of a microbiota sequence variant of the IL13RA2 fragment (human reference peptide) "WLPFGFILI" (SEQ ID NO: 691) or "WLPFGFILIL" (SEQ ID NO: 692), such as an antigenic peptide comprising or consisting of an amino acid sequence as set forth in SEQ ID NO: 254, 255, 878 or 879. Even more preferably, the combination, e.g. for use in the prevention and/or treatment of a cancer, comprises an antigenic peptide comprising or consisting of SEQ ID NO: 220 and an antigenic peptide comprising or consisting of SEQ ID NO: 255.

More preferably, the combination according to the present invention (e.g. for use in the prevention and/or treatment of a cancer) comprises at least three distinct components as described above, in particular at least three distinct antigenic peptides according to the present invention. The above description regarding the combination of two distinct components applies accordingly for three distinct components.

Accordingly, the present invention also provides a combination, e.g. for use in the prevention and/or treatment of a cancer, comprising a first antigenic peptide according to the present invention, which comprises or consists of a microbiota sequence variant of a fragment of the human tumor antigen BIRC5, a second antigenic peptide according to the present invention, which comprises or consists of a microbiota sequence variant of a fragment of the human tumor antigen FOXM1, and a third antigenic peptide according to the present invention, which comprises or consists of a microbiota sequence variant of a fragment of the human tumor antigen IL13RA2. Preferably, the first antigenic peptide comprises or consists of a microbiota sequence variant of the BIRC5 fragment (human reference peptide) "LTLGEFLKL" (SEQ ID NO: 593), such as an antigenic peptide comprising or consisting of an amino acid sequence as set forth in SEQ ID NO: 30, 31 or 32; the second antigenic peptide comprises or consists of a microbiota sequence variant of the FOXM1 fragment (human reference peptide) "LMDLSTTPL" (SEQ ID NO: 674), such as an antigenic peptide comprising or consisting of an amino acid sequence as set forth in SEQ ID NO: 220 or 868; and the third antigenic peptide comprises or consists of a microbiota sequence variant of the IL13RA2 fragment (human reference peptide) "WLPFGFILI" (SEQ ID NO: 691) or "WLPFGFILIL" (SEQ ID NO: 692), such as an antigenic peptide comprising or consisting of an amino acid sequence as set forth in SEQ ID NO: 254, 255, 878 or 879. Even more preferably, the combination, e.g. for use in the prevention and/or treatment of a cancer, comprises an antigenic peptide comprising or consisting of an amino acid sequence as set forth in SEQ ID NO: 30, an antigenic peptide comprising or consisting of an amino acid sequence as set forth in SEQ ID NO: 220, and an antigenic peptide comprising or consisting of an amino acid sequence as set forth in SEQ ID NO: 255.

It is understood that the combination, e.g. for use in the prevention and/or treatment of a cancer, may also contain—instead of the above-described preferred combinations of antigenic peptides—a respective combination of immunogenic compounds of the invention, a respective combination of nanoparticles of the invention or a respective combination of nucleic acids of the invention.

BRIEF DESCRIPTION OF THE FIGURES

In the following a brief description of the appended figures will be given. The figures are intended to illustrate the present invention in more detail. However, they are not intended to limit the subject matter of the invention in any way.

EXAMPLES

Figure 1:
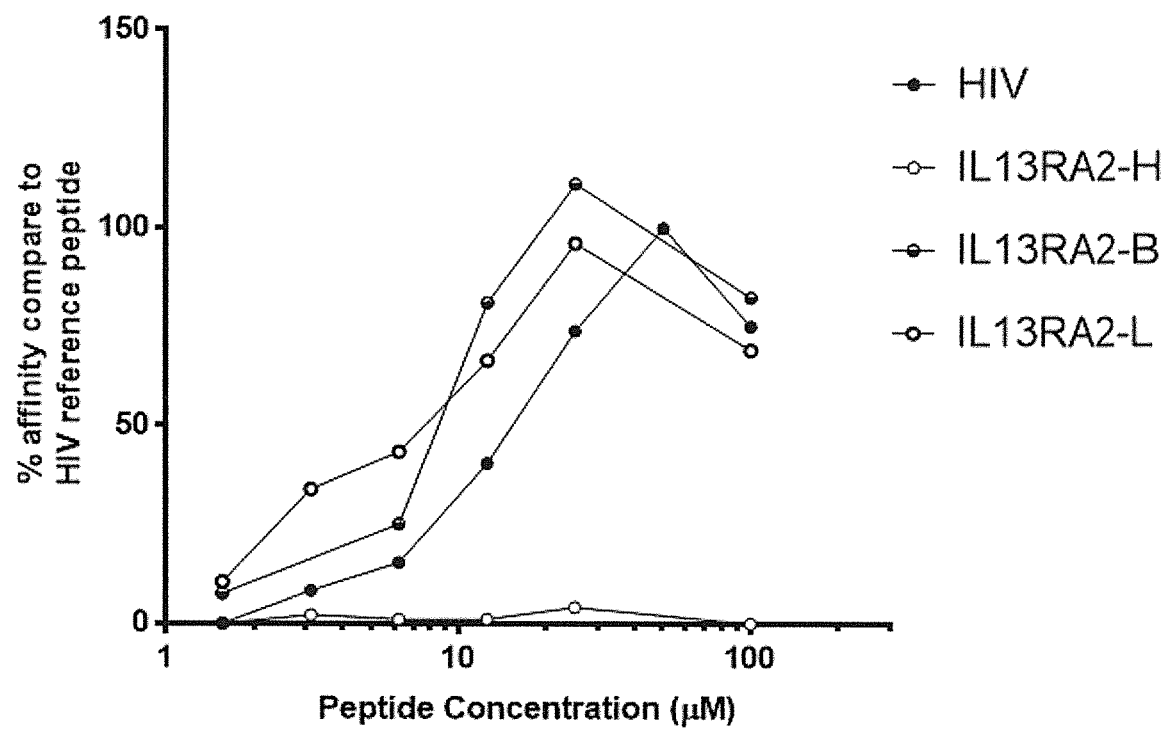
FIG. 1: shows for Example 2 in vitro affinity for antigenic peptides IL13RA2-B and IL13RA2-L in comparison to the corresponding human IL13RA2 epitope IL13RA2-H.
Figure 2:
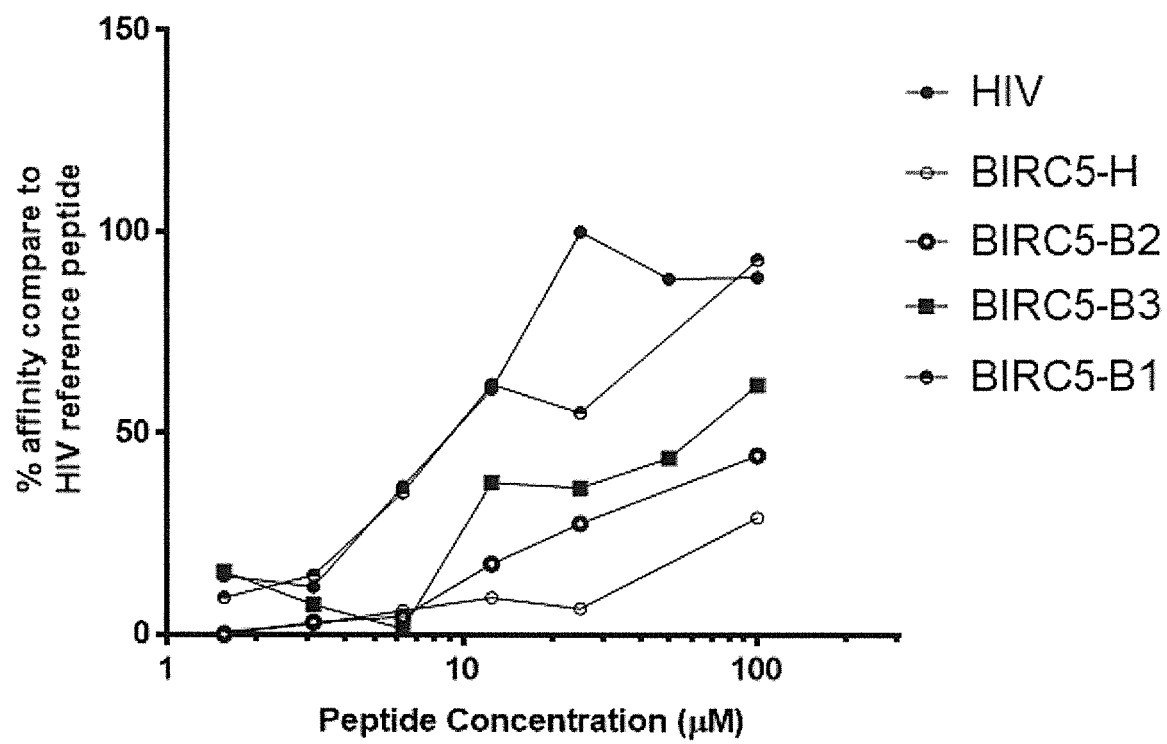
FIG. 2: shows for Example 2 in vitro affinity for antigenic peptides BIRC5-B1, BIRC5-B2 and BIRC5-B3 in comparison to the corresponding human BIRC5 epitope BIRC5-H.
Figure 3:
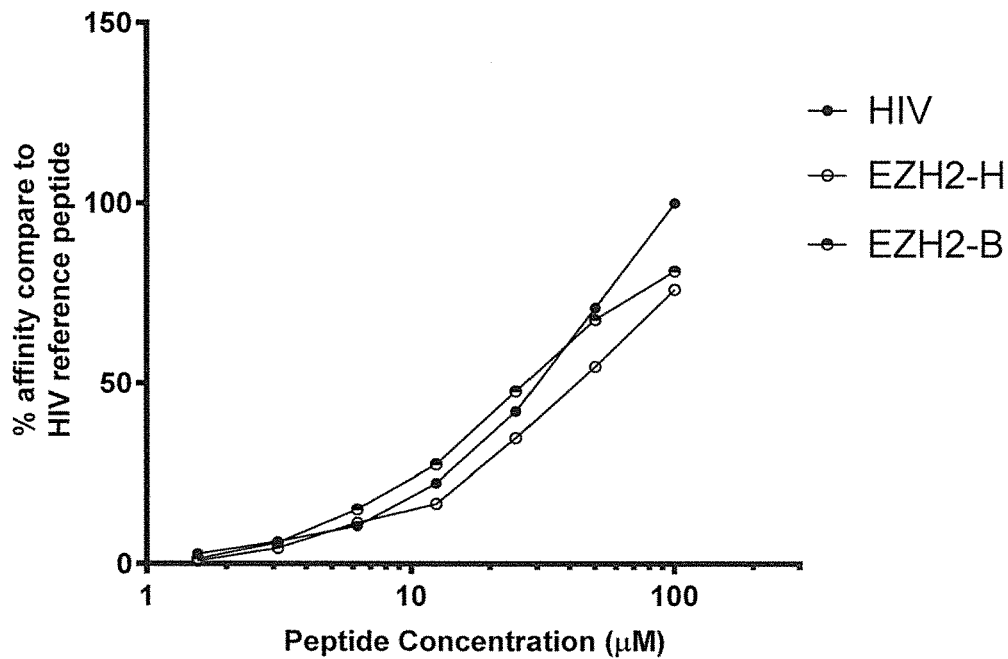
FIG. 3: shows for Example 2 in vitro affinity for (A) antigenic peptide EZH2-B in comparison to the corresponding human EZH2 epitope EZH2-H and (B) antigenic peptide EZH2-B2 in comparison to the corresponding human EZH2 epitope EZH2-H2.
Figure 3:
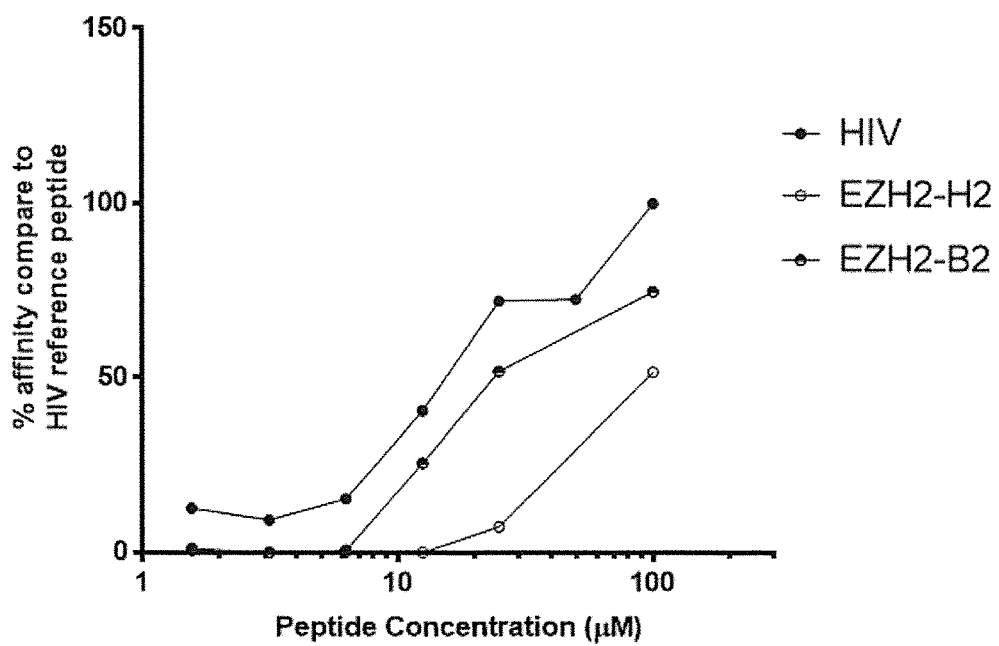
Figure 4:
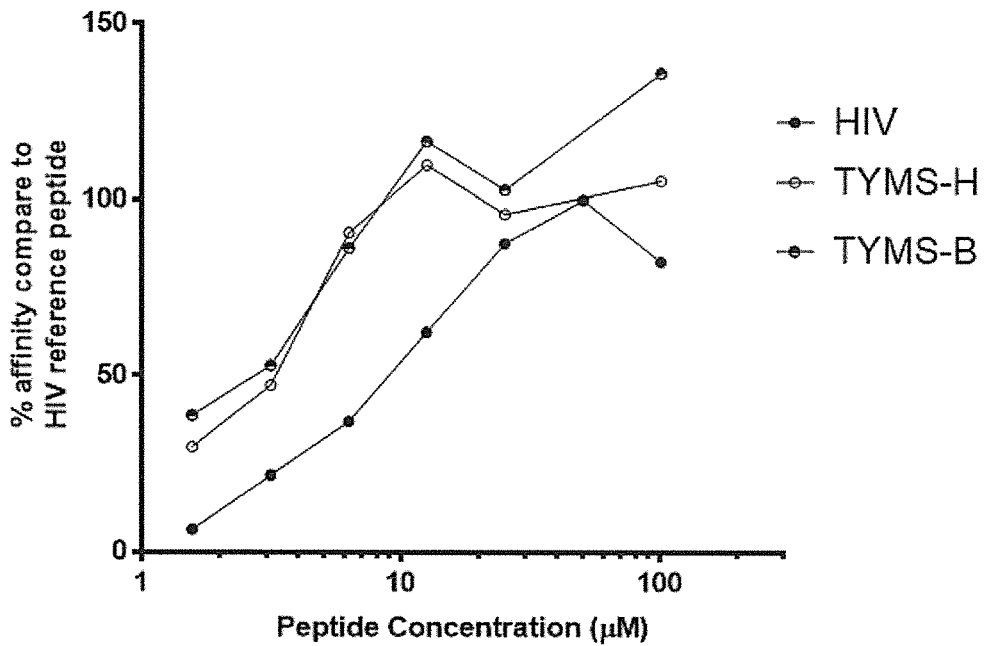
FIG. 4: shows for Example 2 in vitro affinity for (A) antigenic peptide TYMS-B in comparison to the corresponding human TYMS epitope TYMS-H and (B) antigenic peptide TYMS-B2 in comparison to the corresponding human TYMS epitope TYMS-H2.
Figure 4:
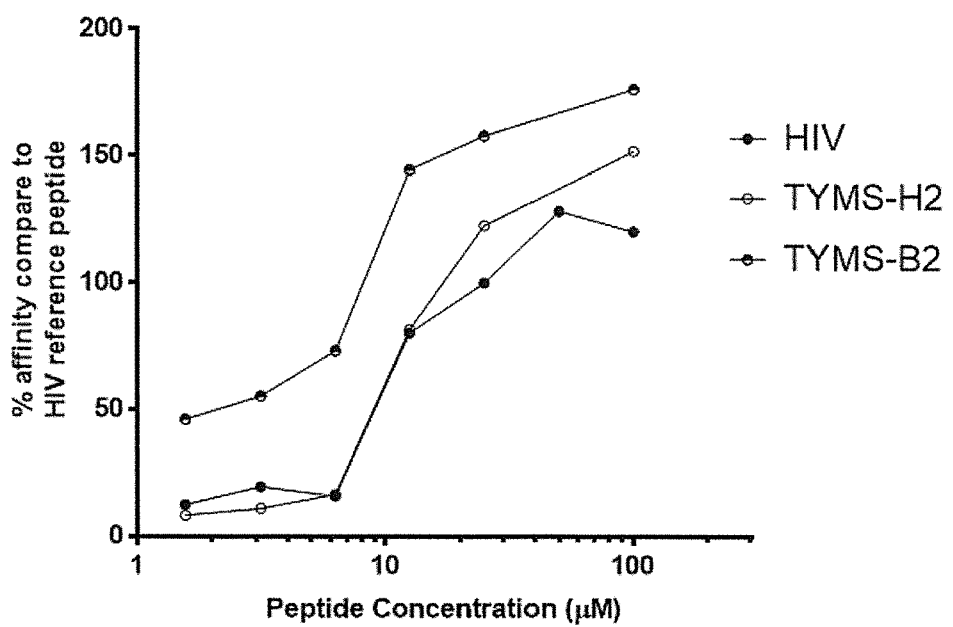
Figure 5:
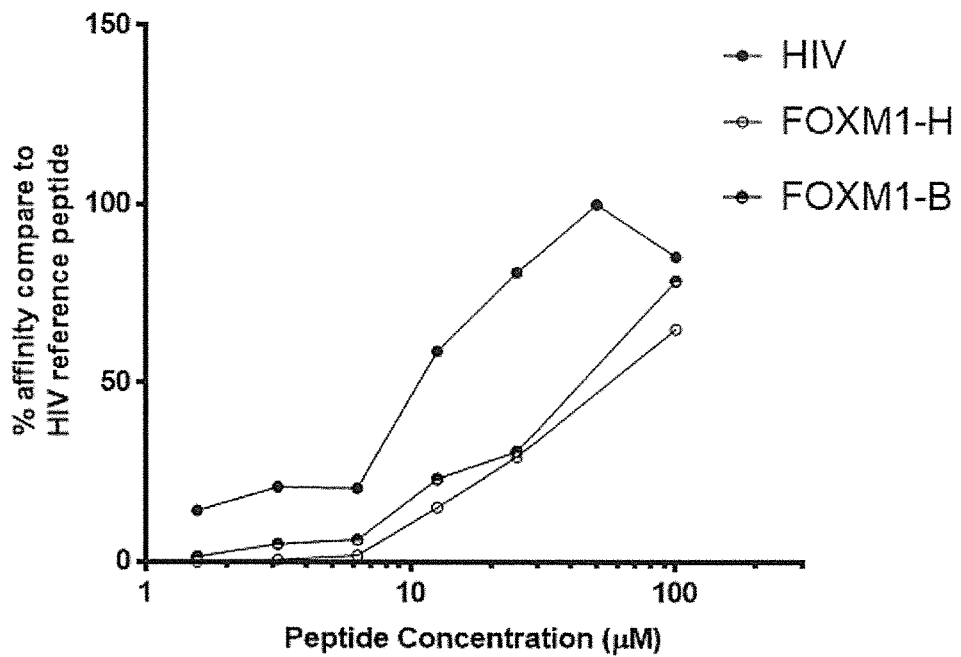
FIG. 5: shows for Example 2 in vitro affinity for (A) antigenic peptide FOXM1-B in comparison to the corresponding human FOXM1 epitope FOXM1-H and (B) antigenic peptide FOXM1-B2 in comparison to the corresponding human FOXM1 epitope FOXM1-H2.
Figure 5:
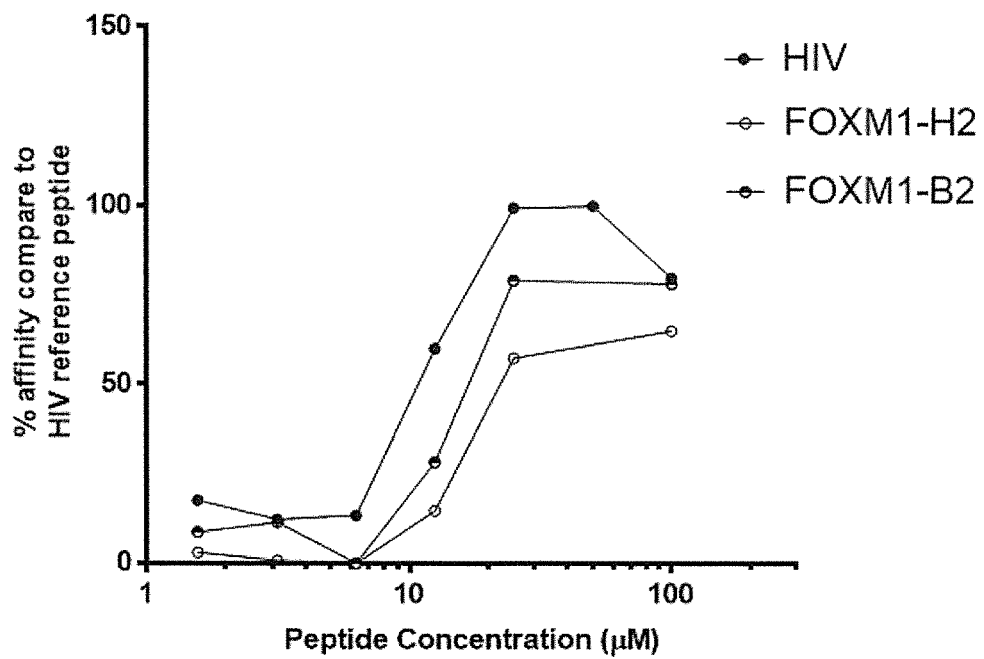

In the following, particular examples illustrating various embodiments and aspects of the invention are presented.

However, the present invention shall not to be limited in scope by the specific embodiments described herein. The following preparations and examples are given to enable those skilled in the art to more clearly understand and to practice the present invention. The present invention, however, is not limited in scope by the exemplified embodiments, which are intended as illustrations of single aspects of the invention only, and methods which are functionally equivalent are within the scope of the invention. Indeed, various modifications of the invention in addition to those described herein will become readily apparent to those skilled in the art from the foregoing description, accompanying figures and the examples below. All such modifications fall within the scope of the appended claims.

Example 1: Antigenic Peptides have Superior Binding Affinity Compared to Human Peptides Binding affinity of the exemplified antigenic peptides of the present invention and of the corresponding fragments of human tumor antigens (human reference peptides) to MHC class I was predicted in silica.

Such prediction has been obtained by using NetMHC 4.0 Server (http://www.cbs.dtu.dk/services/NetMHC/) and as described in Andreatta M, Nielsen M Gapped sequence alignment using artificial neural networks: application to the MHC class I system. Bioinformatics (2016) Feb. 15; 32(4): 511-7. This method generates high-accuracy predictions of major histocompatibility complex (MHC): peptide binding, in particular for peptides having a length of 8-11 amino acids.

Table 2 below shows the results, i.e. information about prediction of peptide-MHC class I binding.

TABLE 2

In silico prediction of peptide-MHC class I binding.

| Tumor antigen | SEQ ID NO. human reference peptide | Binding affinity prediction human reference peptide (nM) | SEQ ID NO. antigenic peptide | Binding affinity prediction antigenic peptide (nM) |
|---|---|---|---|---|
| ACPP | 581 | 7.84 | 1 | 6.81 |
| ACPP | 582 | 70.75 | 2 | 19.02 |
| ACPP | 582 | 70.75 | 3 | 8.76 |
| ACPP | 583 | 186.03 | 4 | 5.16 |
| ANKRD30A | 584 | 94.32 | 5 | 6.03 |
| ANKRD30A | 585 | 210.49 | 6 | 17.64 |
| ANKRD30A | 585 | 210.49 | 7 | 11.20 |
| ANKRD30A | 585 | 210.49 | 8 | 22.76 |
| ANKRD30A | 586 | 19.65 | 9 | 7.27 |
| ANKRD30A | 586 | 19.65 | 10 | 12.28 |
| ANKRD30A | 587 | 27.61 | 11 | 13.89 |
| ANKRD30A | 587 | 27.61 | 12 | 17.81 |
| ANKRD30A | 587 | 27.61 | 13 | 4.93 |
| ANKRD30A | 587 | 27.61 | 14 | 7.60 |
| ANKRD30A | 587 | 27.61 | 15 | 6.72 |
| AREG | 588 | 638.46 | 16 | 34.31 |
| AREG | 588 | 638.46 | 17 | 19.29 |
| AREG | 589 | 55.99 | 18 | 12.69 |
| AREG | 589 | 55.99 | 19 | 16.12 |
| AREG | 589 | 55.99 | 20 | 8.29 |
| AREG | 589 | 55.99 | 21 | 11.08 |
| AREG | 589 | 55.99 | 22 | 15.31 |
| AREG | 589 | 55.99 | 23 | 12.64 |
| AREG | 589 | 55.99 | 24 | 12.77 |
| ASCL1 | 590 | 1467.39 | 25 | 18.36 |
| ASCL2 | 591 | 102.76 | 26 | 29.90 |
| ASCL2 | 591 | 102.76 | 27 | 51.07 |
| ASCL2 | 592 | 80.88 | 28 | 11.95 |
| ASCL2 | 592 | 80.88 | 29 | 5.31 |
| BIRC5 | 593 | 1413.34 | 30 | 17.18 |
| BIRC5 | 593 | 1413.34 | 31 | 48.50 |
| BIRC5 | 593 | 1413.34 | 32 | 5.40 |
| CA9 | 594 | 261.09 | 33 | 17.82 |
| CA9 | 594 | 261.09 | 34 | 28.33 |
| CA9 | 595 | 105.51 | 35 | 22.38 |
| CA9 | 595 | 105.51 | 36 | 9.88 |
| CA9 | 595 | 105.51 | 37 | 40.34 |
| CA9 | 596 | 44.01 | 38 | 21.18 |
| CA9 | 597 | 83.40 | 39 | 20.04 |
| CA9 | 597 | 83.40 | 40 | 22.39 |
| CA9 | 597 | 83.40 | 41 | 37.70 |
| CA9 | 598 | 639.25 | 42 | 6.03 |
| CA9 | 598 | 639.25 | 43 | 11.77 |
| CA9 | 598 | 639.25 | 44 | 44.14 |
| CA9 | 599 | 250.07 | 45 | 17.99 |
| CA9 | 599 | 250.07 | 46 | 13.94 |
| CA9 | 599 | 250.07 | 47 | 28.39 |
| CA9 | 600 | 926.80 | 48 | 38.72 |
| CA9 | 600 | 926.80 | 49 | 50.95 |
| CA9 | 600 | 926.80 | 50 | 19.91 |
| CCNA1 | 601 | 23.44 | 51 | 7.14 |
| CCNA1 | 602 | 125.47 | 52 | 19.85 |
| CCNA1 | 602 | 125.47 | 53 | 19.59 |
| CCNA1 | 602 | 125.47 | 54 | 29.54 |
| CCNA1 | 602 | 125.47 | 55 | 4.69 |
| CCND1 | 603 | 146.91 | 56 | 39.32 |
| CDH17 | 604 | 256.56 | 57 | 19.45 |
| CDH17 | 605 | 176.80 | 58 | 25.52 |
| CDH17 | 605 | 176.80 | 59 | 13.81 |
| CDH17 | 606 | 55.58 | 60 | 8.96 |
| CDH17 | 606 | 55.58 | 61 | 10.34 |
| CDH17 | 606 | 55.58 | 62 | 18.19 |
| CDH17 | 607 | 31.40 | 63 | 10.43 |
| CDH6 | 608 | 70.52 | 64 | 5.24 |
| CDH6 | 608 | 70.52 | 65 | 18.50 |
| CDH6 | 608 | 70.52 | 66 | 7.58 |
| CDH6 | 608 | 70.52 | 67 | 10.94 |
| CDH6 | 608 | 70.52 | 68 | 8.93 |
| CDH6 | 608 | 70.52 | 69 | 27.51 |
| CDH6 | 608 | 70.52 | 70 | 45.84 |
| CDH6 | 609 | 149.17 | 71 | 31.98 |
| CDH6 | 610 | 20.01 | 72 | 4.27 |
| CDH6 | 611 | 106.71 | 73 | 16.73 |
| CDH6 | 612 | 19.90 | 74 | 11.85 |
| CDH6 | 612 | 19.90 | 75 | 12.92 |
| CDH6 | 613 | 85.54 | 76 | 12.49 |
| CDH6 | 613 | 85.54 | 77 | 14.18 |
| CDH6 | 613 | 85.54 | 78 | 11.69 |
| CDH6 | 613 | 85.54 | 79 | 26.76 |
| CDH6 | 613 | 85.54 | 80 | 13.91 |
| CDH6 | 613 | 85.54 | 81 | 64.63 |
| CDKN2A | 614 | 609.17 | 82 | 13.54 |
| CEACAM5 | 615 | 126.68 | 83 | 17.05 |
| CHI3L1 | 616 | 374.26 | 84 | 14.77 |
| CHI3L1 | 616 | 374.26 | 85 | 13.27 |
| CHI3L1 | 617 | 49.46 | 86 | 6.69 |
| CHI3L1 | 617 | 49.46 | 87 | 7.55 |
| CHI3L1 | 617 | 49.46 | 88 | 43.85 |
| CHI3L1 | 617 | 49.46 | 89 | 20.12 |
| CHI3L1 | 617 | 49.46 | 90 | 11.41 |
| CHI3L1 | 617 | 49.46 | 91 | 38.08 |
| CHI3L1 | 617 | 49.46 | 92 | 21.15 |
| CHI3L1 | 617 | 49.46 | 93 | 12.59 |
| CHI3L1 | 617 | 49.46 | 94 | 8.44 |
| CHI3L1 | 617 | 49.46 | 95 | 10.00 |
| CHI3L1 | 617 | 49.46 | 96 | 11.72 |
| CHI3L1 | 617 | 49.46 | 97 | 8.56 |

TABLE 2-continued

In silico prediction of peptide-MHC class I binding.

| Tumor antigen | SEQ ID NO. human reference peptide | Binding affinity prediction human reference peptide (nM) | SEQ ID NO. antigenic peptide | Binding affinity prediction antigenic peptide (nM) |
| --- | --- | --- | --- | --- |
| CHI3L1 | 617 | 49.46 | 98 | 53.90 |
| CHI3L1 | 617 | 49.46 | 99 | 33.87 |
| CHI3L1 | 617 | 49.46 | 100 | 17.70 |
| CHI3L1 | 617 | 49.46 | 101 | 29.51 |
| CHI3L1 | 617 | 49.46 | 102 | 6.12 |
| CHI3L1 | 617 | 49.46 | 103 | 31.73 |
| CHI3L1 | 617 | 49.46 | 104 | 27.90 |
| CHI3L1 | 617 | 49.46 | 105 | 6.00 |
| CHI3L1 | 617 | 49.46 | 106 | 15.57 |
| CHI3L1 | 617 | 49.46 | 107 | 47.62 |
| CHI3L1 | 617 | 49.46 | 108 | 13.60 |
| CHI3L1 | 617 | 49.46 | 109 | 35.37 |
| CHI3L1 | 618 | 184.90 | 110 | 5.98 |
| CHI3L1 | 618 | 184.90 | 111 | 5.46 |
| CHI3L1 | 618 | 184.90 | 112 | 46.78 |
| CHI3L1 | 619 | 89.58 | 113 | 30.62 |
| CHI3L1 | 620 | 116.85 | 114 | 11.40 |
| CHI3L2 | 621 | 71.53 | 115 | 18.40 |
| CHI3L2 | 622 | 62.20 | 116 | 16.60 |
| CHI3L2 | 623 | 33.99 | 117 | 5.25 |
| CHI3L2 | 623 | 33.99 | 118 | 24.67 |
| CHI3L2 | 624 | 14.03 | 119 | 7.34 |
| COL11A1 | 625 | 8.14 | 120 | 2.73 |
| CT83 | 626 | 39.72 | 121 | 6.47 |
| CT83 | 626 | 39.72 | 122 | 18.16 |
| CT83 | 626 | 39.72 | 123 | 19.51 |
| CTCFL | 627 | 202.12 | 124 | 5.50 |
| DCT | 628 | 67.88 | 125 | 9.23 |
| DCT | 628 | 67.88 | 126 | 19.60 |
| DCT | 629 | 33.01 | 127 | 8.70 |
| DCT | 629 | 33.01 | 128 | 14.83 |
| DCT | 629 | 33.01 | 129 | 11.42 |
| DCT | 630 | 24.75 | 130 | 10.84 |
| DCT | 631 | 53.11 | 131 | 10.04 |
| DCT | 631 | 53.11 | 132 | 75.39 |
| DMRTA2 | 632 | 560.82 | 133 | 15.32 |
| DMRTA2 | 633 | 121.55 | 134 | 6.77 |
| EGFR | 634 | 262.29 | 135 | 12.94 |
| EGFR | 634 | 262.29 | 136 | 18.28 |
| EGFR | 635 | 13.68 | 137 | 4.03 |
| EGFR | 636 | 12.26 | 138 | 3.81 |
| EGFR | 636 | 12.26 | 139 | 4.70 |
| EGFR | 636 | 12.26 | 140 | 4.18 |
| EGFR | 636 | 12.26 | 141 | 5.65 |
| EGFR | 636 | 12.26 | 142 | 6.77 |
| EGFR | 636 | 12.26 | 143 | 3.75 |
| EGFR | 636 | 12.26 | 144 | 4.99 |
| EGFR | 637 | 61.00 | 145 | 11.98 |
| EGFR | 638 | 93.43 | 146 | 23.35 |
| EGFR | 639 | 226.82 | 147 | 25.04 |
| EGFR | 640 | 78.07 | 148 | 4.72 |
| EGFR | 641 | 116.72 | 149 | 45.62 |
| EGFR | 641 | 116.72 | 150 | 20.54 |
| ERBB2 | 642 | 271.92 | 151 | 17.06 |
| ERBB2 | 642 | 271.92 | 152 | 73.58 |
| ERBB2 | 642 | 271.92 | 153 | 31.31 |
| ERBB2 | 642 | 271.92 | 154 | 23.78 |
| ERBB2 | 643 | 61.00 | 155 | 11.98 |
| ERBB2 | 644 | 78.48 | 156 | 7.26 |
| ERBB2 | 644 | 78.48 | 157 | 17.51 |
| ERBB2 | 644 | 78.48 | 158 | 8.66 |
| ERBB2 | 644 | 78.48 | 159 | 5.60 |
| ERBB2 | 645 | 112.27 | 160 | 14.20 |
| ERBB2 | 646 | 43.79 | 161 | 10.47 |
| ERBB2 | 646 | 43.79 | 162 | 17.29 |
| ERG | 647 | 131.75 | 163 | 3.21 |
| ERG | 857 | 19.28 | 164 | 6.61 |
| ESR1 | 648 | 8.71 | 165 | 5.96 |
| ESR1 | 649 | 74.42 | 166 | 4.99 |
| ESR1 | 649 | 74.42 | 167 | 7.11 |
| ESR1 | 650 | 44.48 | 168 | 5.98 |
| ESR1 | 650 | 44.48 | 169 | 17.96 |
| ESR1 | 651 | 87.59 | 170 | 5.52 |
| ESR1 | 652 | 1197.89 | 171 | 15.76 |
| ESR1 | 652 | 1197.89 | 172 | 16.48 |
| ESR1 | 653 | 150.15 | 173 | 4.45 |
| ESR1 | 654 | 353.62 | 174 | 2.20 |
| ESR1 | 654 | 353.62 | 175 | 2.89 |
| ESR1 | 654 | 353.62 | 176 | 5.67 |
| ESR1 | 654 | 353.62 | 177 | 31.36 |
| ESR1 | 654 | 353.62 | 178 | 8.16 |
| ESR1 | 654 | 353.62 | 179 | 8.17 |
| ESR1 | 654 | 353.62 | 180 | 7.28 |
| ESR1 | 654 | 353.62 | 181 | 2.81 |
| ESR1 | 655 | 255.96 | 182 | 23.09 |
| ESR1 | 655 | 255.96 | 183 | 15.10 |
| ESR1 | 655 | 255.96 | 184 | 13.13 |
| ESR1 | 655 | 255.96 | 185 | 11.02 |
| ESR1 | 655 | 255.96 | 186 | 59.71 |
| ESR1 | 655 | 255.96 | 187 | 17.37 |
| ESR1 | 655 | 255.96 | 188 | 9.52 |
| ESR1 | 656 | 131.20 | 189 | 32.95 |
| ESR1 | 656 | 131.20 | 190 | 6.68 |
| ESR1 | 657 | 126.34 | 191 | 5.67 |
| ESR1 | 658 | 159.50 | 192 | 5.57 |
| EZH2 | 659 | 20.00 | 193 | 25.28 |
| EZH2 | 660 | 63.82 | 194 | 22.39 |
| FAP | 661 | 512.58 | 195 | 10.02 |
| FAP | 661 | 512.58 | 196 | 42.73 |
| FAP | 661 | 512.58 | 197 | 47.13 |
| FAP | 662 | 1616.20 | 198 | 7.97 |
| FAP | 663 | 106.57 | 199 | 11.88 |
| FAP | 663 | 106.57 | 200 | 17.55 |
| FAP | 663 | 106.57 | 201 | 17.08 |
| FLT1 | 664 | 63.37 | 202 | 10.87 |
| FLT1 | 664 | 63.37 | 203 | 9.10 |
| FLT1 | 664 | 63.37 | 204 | 5.89 |
| FLT1 | 664 | 63.37 | 205 | 12.69 |
| FLT1 | 664 | 63.37 | 206 | 12.60 |
| FLT1 | 664 | 63.37 | 207 | 5.18 |
| FLT1 | 664 | 63.37 | 208 | 15.58 |
| FLT1 | 665 | 227.40 | 209 | 7.81 |
| FLT1 | 666 | 112.02 | 210 | 6.16 |
| FLT1 | 667 | 42.43 | 211 | 4.48 |
| FLT1 | 667 | 42.43 | 212 | 13.08 |
| FLT1 | 668 | 44.22 | 213 | 3.66 |
| FLT1 | 669 | 24.87 | 214 | 5.44 |
| FLT1 | 670 | 5.89 | 215 | 3.18 |
| FLT1 | 671 | 558.96 | 216 | 20.59 |
| FOXM1 | 672 | 36.15 | 217 | 5.22 |
| FOXM1 | 672 | 36.15 | 218 | 2.79 |
| FOXM1 | 672 | 36.15 | 861 | 2.42 |
| FOXM1 | 672 | 36.15 | 862 | 4.16 |
| FOXM1 | 672 | 36.15 | 863 | 15.79 |
| FOXM1 | 672 | 36.15 | 864 | 2.99 |
| FOXM1 | 672 | 36.15 | 865 | 2.98 |
| FOXM1 | 672 | 36.15 | 866 | 2.92 |
| FOXM1 | 673 | 46.25 | 219 | 13.40 |
| FOXM1 | 673 | 46.25 | 867 | 34.24 |
| FOXM1 | 674 | 26.60 | 220 | 15.68 |
| FOXM1 | 674 | 26.60 | 868 | 29.42 |
| FOXM1 | 675 | 53.72 | 221 | 7.72 |
| FOXM1 | 675 | 53.72 | 222 | 7.03 |
| FOXM1 | 675 | 53.72 | 223 | 11.75 |
| FOXM1 | 675 | 53.72 | 869 | 3.16 |
| FOXM1 | 675 | 53.72 | 870 | 4.76 |
| FOXM1 | 675 | 53.72 | 871 | 34.60 |
| FOXM1 | 676 | 203.88 | 224 | 43.00 |
| FOXM1 | 677 | 31.23 | 225 | 7.56 |
| FOXM1 | 677 | 31.23 | 226 | 6.92 |

TABLE 2-continued

In silico prediction of peptide-MHC class I binding.

| Tumor antigen | SEQ ID NO. human reference peptide | Binding affinity prediction human reference peptide (nM) | SEQ ID NO. antigenic peptide | Binding affinity prediction antigenic peptide (nM) |
|---|---|---|---|---|
| FOXM1 | 678 | 144.91 | 227 | 5.90 |
| FOXM1 | 888 | 48.87 | 872 | 48.49 |
| FOXM1 | 889 | 35.91 | 873 | 64.21 |
| FOXM1 | 889 | 35.91 | 874 | 25.70 |
| FOXM1 | 890 | 2.22 | 875 | 9.69 |
| FOXM1 | 890 | 2.22 | 876 | 15.82 |
| FOXM1 | 891 | 3.73 | 877 | 17.91 |
| FSIP1 | 679 | 70.88 | 228 | 21.67 |
| FSIP1 | 680 | 602.51 | 229 | 19.24 |
| FSIP1 | 680 | 602.51 | 230 | 51.70 |
| FSIP1 | 680 | 602.51 | 231 | 36.16 |
| GAL3ST1 | 681 | 71.36 | 232 | 8.07 |
| GAL3ST1 | 682 | 133.28 | 233 | 25.02 |
| GAL3ST1 | 682 | 133.28 | 234 | 35.65 |
| GPR143 | 683 | 27.67 | 235 | 8.90 |
| GPR143 | 683 | 27.67 | 236 | 9.55 |
| GPR143 | 683 | 27.67 | 237 | 21.93 |
| GPR143 | 684 | 345.70 | 238 | 74.50 |
| GPR143 | 685 | 274.36 | 239 | 12.76 |
| GPR143 | 686 | 108.41 | 240 | 21.48 |
| GPR143 | 686 | 108.41 | 241 | 26.02 |
| GPR143 | 686 | 108.41 | 242 | 20.01 |
| GPR143 | 686 | 108.41 | 243 | 5.57 |
| GPR143 | 686 | 108.41 | 244 | 15.06 |
| GPR143 | 686 | 108.41 | 245 | 24.30 |
| GPR143 | 686 | 108.41 | 246 | 6.35 |
| GPR143 | 686 | 108.41 | 247 | 30.08 |
| HES6 | 687 | 66.43 | 248 | 39.04 |
| IL13RA2 | 688 | 132.87 | 249 | 5.99 |
| IL13RA2 | 688 | 132.87 | 250 | 10.47 |
| IL13RA2 | 688 | 132.87 | 251 | 15.64 |
| IL13RA2 | 689 | 45.46 | 252 | 3.78 |
| IL13RA2 | 690 | 7.76 | 253 | 5.35 |
| IL13RA2 | 691 | 171.06 | 254 | 8.49 |
| IL13RA2 | 692 | 78.00 | 255 | 3.77 |
| IL13RA2 | 692 | 78.00 | 878 | 4.82 |
| IL13RA2 | 692 | 78.00 | 879 | 3.97 |
| IL13RA2 | 892 | 44.03 | 880 | 28.67 |
| IL13RA2 | 892 | 44.03 | 881 | 10.01 |
| IL13RA2 | 892 | 44.03 | 882 | 31.65 |
| IL13RA2 | 893 | 8.37 | 883 | 17.68 |
| IL13RA2 | 894 | 117.95 | 884 | 13.66 |
| IL13RA2 | 894 | 117.95 | 885 | 13.66 |
| IL13RA2 | 895 | 137.80 | 886 | 23.34 |
| IL13RA2 | 895 | 137.80 | 887 | 31.28 |
| KISS1R | 693 | 143.54 | 256 | 20.53 |
| KISS1R | 693 | 143.54 | 257 | 28.11 |
| KISS1R | 693 | 143.54 | 258 | 44.06 |
| KISS1R | 694 | 141.98 | 259 | 12.78 |
| KISS1R | 694 | 141.98 | 260 | 14.02 |
| KISS1R | 694 | 141.98 | 261 | 21.16 |
| KISS1R | 695 | 237.51 | 262 | 41.96 |
| KISS1R | 696 | 80.71 | 263 | 12.37 |
| KISS1R | 697 | 148.34 | 264 | 20.84 |
| KISS1R | 698 | 23.99 | 265 | 14.74 |
| KISS1R | 698 | 23.99 | 266 | 16.42 |
| KISS1R | 698 | 23.99 | 267 | 4.30 |
| KISS1R | 698 | 23.99 | 268 | 5.23 |
| KISS1R | 698 | 23.99 | 269 | 14.10 |
| KISS1R | 699 | 76.87 | 270 | 4.08 |
| KISS1R | 699 | 76.87 | 271 | 4.99 |
| KISS1R | 699 | 76.87 | 272 | 8.08 |
| KISS1R | 699 | 76.87 | 273 | 13.54 |
| KISS1R | 699 | 76.87 | 274 | 9.53 |
| KISS1R | 699 | 76.87 | 275 | 5.96 |
| KISS1R | 699 | 76.87 | 276 | 23.28 |
| KISS1R | 699 | 76.87 | 277 | 4.61 |
| KISS1R | 699 | 76.87 | 278 | 25.31 |
| KISS1R | 699 | 76.87 | 279 | 13.98 |
| KISS1R | 699 | 76.87 | 280 | 4.72 |
| KISS1R | 699 | 76.87 | 281 | 9.40 |
| KISS1R | 699 | 76.87 | 282 | 32.74 |
| KISS1R | 699 | 76.87 | 283 | 16.73 |
| KISS1R | 699 | 76.87 | 284 | 72.01 |
| KISS1R | 699 | 76.87 | 285 | 6.18 |
| KISS1R | 699 | 76.87 | 286 | 20.88 |
| KISS1R | 699 | 76.87 | 287 | 18.73 |
| KLHDC8A | 700 | 35.26 | 288 | 3.46 |
| KLHDC8A | 701 | 172.00 | 289 | 35.47 |
| KLHL14 | 702 | 17.84 | 290 | 7.70 |
| KLHL14 | 703 | 34.68 | 291 | 8.63 |
| KLHL14 | 704 | 77.24 | 292 | 16.82 |
| KLK4 | 705 | 270.66 | 293 | 10.04 |
| KLK4 | 705 | 270.66 | 294 | 19.56 |
| KLK4 | 705 | 270.66 | 295 | 15.44 |
| KLK4 | 705 | 270.66 | 296 | 38.82 |
| KRT81 | 706 | 21.85 | 297 | 10.20 |
| LEMD1 | 707 | 136.71 | 298 | 15.87 |
| LEMD1 | 708 | 88.07 | 299 | 25.93 |
| LRRC15 | 709 | 82.50 | 300 | 6.46 |
| LRRC15 | 710 | 1001.18 | 301 | 21.72 |
| LRRC15 | 711 | 259.30 | 302 | 9.78 |
| LRRC15 | 712 | 258.37 | 303 | 11.59 |
| LRRC15 | 712 | 258.37 | 304 | 7.37 |
| LRRC15 | 712 | 258.37 | 305 | 18.92 |
| LRRC15 | 713 | 145.27 | 306 | 22.64 |
| LRRC15 | 713 | 145.27 | 307 | 13.47 |
| MAGEA1 | 714 | 165.35 | 308 | 20.56 |
| MAGEA1 | 858 | 59.75 | 309 | 17.40 |
| MAGEA10 | 715 | 94.39 | 310 | 7.76 |
| MAGEA10 | 715 | 94.39 | 311 | 32.14 |
| MAGEA10 | 716 | 98.71 | 312 | 17.05 |
| MAGEA10 | 716 | 98.71 | 313 | 15.58 |
| MAGEA11 | 717 | 102.07 | 314 | 43.72 |
| MAGEA11 | 718 | 455.06 | 315 | 13.01 |
| MAGEA11 | 719 | 324.53 | 316 | 4.07 |
| MAGEA11 | 719 | 324.53 | 317 | 7.58 |
| MAGEA11 | 720 | 27.38 | 318 | 9.42 |
| MAGEA12 | 721 | 243.84 | 319 | 9.58 |
| MAGEA4 | 722 | 257.20 | 320 | 12.43 |
| MAGEA4 | 723 | 60.75 | 321 | 5.71 |
| MAGEA4 | 724 | 16.67 | 322 | 4.57 |
| MLANA | 725 | 114.10 | 323 | 5.47 |
| MLANA | 725 | 114.10 | 324 | 20.46 |
| MLANA | 725 | 114.10 | 325 | 9.29 |
| MLANA | 725 | 114.10 | 326 | 15.44 |
| MLANA | 725 | 114.10 | 327 | 20.04 |
| MLANA | 725 | 114.10 | 328 | 19.83 |
| MLANA | 725 | 114.10 | 329 | 5.48 |
| MLANA | 725 | 114.10 | 330 | 21.30 |
| MLANA | 725 | 114.10 | 331 | 9.05 |
| MLANA | 725 | 114.10 | 332 | 19.05 |
| MLANA | 725 | 114.10 | 333 | 32.71 |
| MLANA | 725 | 114.10 | 334 | 26.26 |
| NKX2-1 | 726 | 138.71 | 335 | 5.30 |
| NKX2-1 | 727 | 54.26 | 336 | 3.57 |
| NKX2-1 | 727 | 54.26 | 337 | 2.92 |
| NKX2-1 | 727 | 54.26 | 338 | 31.31 |
| NKX2-1 | 727 | 54.26 | 339 | 16.53 |
| NKX2-1 | 727 | 54.26 | 340 | 32.65 |
| NPTX2 | 728 | 23.10 | 341 | 9.27 |
| NPTX2 | 728 | 23.10 | 342 | 10.16 |
| NPTX2 | 728 | 23.10 | 343 | 17.81 |
| NPTX2 | 728 | 23.10 | 344 | 11.59 |
| NPTX2 | 729 | 39.51 | 345 | 18.64 |
| NPTX2 | 729 | 39.51 | 346 | 8.01 |
| NPTX2 | 729 | 39.51 | 347 | 7.87 |
| NPTX2 | 729 | 39.51 | 348 | 5.76 |
| NPTX2 | 730 | 106.32 | 349 | 12.85 |
| NPTX2 | 731 | 268.65 | 350 | 34.09 |

TABLE 2-continued

In silico prediction of peptide-MHC class I binding.

| Tumor antigen | SEQ ID NO. human reference peptide | Binding affinity prediction human reference peptide (nM) | SEQ ID NO. antigenic peptide | Binding affinity prediction antigenic peptide (nM) |
|---|---|---|---|---|
| NPTX2 | 732 | 408.67 | 351 | 25.81 |
| PAGE3 | 733 | 379.62 | 352 | 8.32 |
| PAGE3 | 733 | 379.62 | 353 | 19.22 |
| PAGE3 | 733 | 379.62 | 354 | 16.27 |
| PAX2 | 734 | 99.81 | 355 | 5.65 |
| PAX2 | 734 | 99.81 | 356 | 11.74 |
| PAX2 | 734 | 99.81 | 357 | 26.27 |
| PAX2 | 734 | 99.81 | 358 | 19.79 |
| PCDHB16 | 735 | 205.70 | 359 | 7.64 |
| PCDHB16 | 736 | 53.23 | 360 | 23.60 |
| PCDHB16 | 737 | 413.71 | 361 | 25.77 |
| PCDHB16 | 738 | 234.89 | 362 | 50.41 |
| PCDHB16 | 738 | 234.89 | 363 | 97.85 |
| PCDHB16 | 738 | 234.89 | 364 | 6.18 |
| PCDHB16 | 739 | 452.03 | 365 | 5.49 |
| PIWIL1 | 740 | 51.24 | 366 | 16.50 |
| PMEL | 741 | 40.34 | 367 | 9.19 |
| PMEL | 742 | 483.91 | 368 | 17.06 |
| PMEL | 742 | 483.91 | 369 | 101.71 |
| PMEL | 742 | 483.91 | 370 | 29.33 |
| PMEL | 742 | 483.91 | 371 | 31.31 |
| PMEL | 742 | 483.91 | 372 | 79.31 |
| PMEL | 742 | 483.91 | 373 | 73.91 |
| PMEL | 743 | 27.82 | 374 | 13.22 |
| PMEL | 743 | 27.82 | 375 | 20.06 |
| PMEL | 744 | 322.67 | 376 | 35.49 |
| PMEL | 745 | 146.77 | 377 | 10.60 |
| PMEL | 745 | 146.77 | 378 | 17.17 |
| PMEL | 746 | 226.06 | 379 | 21.42 |
| PRAME | 747 | 282.46 | 380 | 14.96 |
| PRAME | 747 | 282.46 | 381 | 11.11 |
| PRAME | 748 | 8.33 | 382 | 2.65 |
| PRAME | 748 | 8.33 | 383 | 3.77 |
| PRAME | 748 | 8.33 | 384 | 4.71 |
| PRAME | 748 | 8.33 | 385 | 3.34 |
| PRAME | 749 | 175.38 | 386 | 46.71 |
| PRAME | 750 | 626.66 | 387 | 7.06 |
| PTHLH | 751 | 47.35 | 388 | 9.23 |
| SEMG1 | 752 | 43.54 | 389 | 15.12 |
| SEMG1 | 752 | 43.54 | 390 | 15.08 |
| SEMG1 | 752 | 43.54 | 391 | 30.58 |
| SEMG1 | 752 | 43.54 | 392 | 28.77 |
| SEMG1 | 752 | 43.54 | 393 | 29.87 |
| SEMG1 | 752 | 43.54 | 394 | 13.74 |
| SEMG1 | 752 | 43.54 | 395 | 24.69 |
| SEMG1 | 752 | 43.54 | 396 | 23.53 |
| SEMG1 | 752 | 43.54 | 397 | 34.57 |
| SEMG1 | 753 | 306.98 | 398 | 44.52 |
| SEMG1 | 753 | 306.98 | 399 | 83.94 |
| SEMG1 | 754 | 58.73 | 400 | 9.85 |
| SERHL2 | 755 | 125.11 | 401 | 21.05 |
| SERHL2 | 756 | 238.87 | 402 | 3.98 |
| SERHL2 | 757 | 133.08 | 403 | 20.14 |
| SERHL2 | 757 | 133.08 | 404 | 17.25 |
| SERHL2 | 758 | 125.30 | 405 | 69.45 |
| SLC45A3 | 759 | 13.80 | 406 | 4.22 |
| SLC45A3 | 760 | 528.37 | 407 | 111.79 |
| SLC45A3 | 760 | 528.37 | 408 | 51.45 |
| SLC45A3 | 761 | 119.20 | 409 | 38.29 |
| SLC45A3 | 762 | 11.94 | 410 | 2.83 |
| SLC45A3 | 763 | 963.46 | 411 | 17.62 |
| SLC45A3 | 764 | 37.99 | 412 | 7.52 |
| SLC45A3 | 764 | 37.99 | 413 | 26.14 |
| SLC45A3 | 764 | 37.99 | 414 | 4.86 |
| SLC45A3 | 764 | 37.99 | 415 | 10.47 |
| SLC45A3 | 765 | 147.42 | 416 | 29.12 |
| SLC45A3 | 765 | 147.42 | 417 | 21.68 |
| SLC45A3 | 766 | 53.08 | 418 | 20.75 |
| SLC45A3 | 767 | 29.75 | 419 | 7.15 |
| SLC45A3 | 767 | 29.75 | 420 | 7.33 |
| SLC45A3 | 767 | 29.75 | 421 | 5.53 |
| SLC45A3 | 767 | 29.75 | 422 | 3.97 |
| SLC45A3 | 767 | 29.75 | 423 | 2.84 |
| SLC45A3 | 768 | 166.51 | 424 | 14.86 |
| SLC45A3 | 769 | 127.11 | 425 | 7.72 |
| SLC45A3 | 769 | 127.11 | 426 | 15.75 |
| SLC45A3 | 770 | 655.74 | 427 | 46.76 |
| SLC6A3 | 771 | 38.06 | 428 | 22.35 |
| SLC6A3 | 771 | 38.06 | 429 | 11.72 |
| SLC6A3 | 771 | 38.06 | 430 | 17.36 |
| SLC6A3 | 772 | 54.47 | 431 | 15.80 |
| SLC6A3 | 772 | 54.47 | 432 | 16.20 |
| SLC6A3 | 773 | 13.67 | 433 | 6.53 |
| SLC6A3 | 774 | 197.36 | 434 | 8.04 |
| SLC6A3 | 775 | 10.25 | 435 | 5.46 |
| SLC6A3 | 775 | 10.25 | 436 | 3.85 |
| SLC6A3 | 776 | 674.92 | 437 | 7.48 |
| SLC6A3 | 777 | 77.72 | 438 | 11.66 |
| SLC6A3 | 777 | 77.72 | 439 | 9.25 |
| SLC6A3 | 778 | 64.33 | 440 | 39.26 |
| SLC6A3 | 779 | 39.85 | 441 | 15.82 |
| SNX31 | 780 | 107.98 | 442 | 11.01 |
| SOX11 | 781 | 250.95 | 443 | 34.11 |
| SOX11 | 781 | 250.95 | 444 | 4.54 |
| SOX11 | 781 | 250.95 | 445 | 3.62 |
| SOX17 | 782 | 45.00 | 446 | 13.91 |
| SOX17 | 783 | 628.41 | 447 | 64.48 |
| SOX17 | 783 | 628.41 | 448 | 20.94 |
| SOX17 | 783 | 628.41 | 449 | 80.99 |
| SPINK1 | 784 | 683.89 | 450 | 62.86 |
| STEAP1 | 785 | 294.89 | 451 | 4.18 |
| STEAP1 | 786 | 46.06 | 452 | 15.04 |
| STEAP1 | 787 | 220.39 | 453 | 7.44 |
| STEAP1 | 788 | 549.08 | 454 | 49.18 |
| STEAP1 | 788 | 549.08 | 455 | 11.72 |
| STEAP1 | 788 | 549.08 | 456 | 5.65 |
| STEAP1 | 788 | 549.08 | 457 | 43.68 |
| STEAP1 | 789 | 27.88 | 458 | 10.31 |
| STEAP1 | 789 | 27.88 | 459 | 13.27 |
| STEAP1 | 789 | 27.88 | 460 | 5.52 |
| STEAP1 | 790 | 43.73 | 461 | 12.06 |
| STEAP1 | 791 | 11.48 | 462 | 3.54 |
| STEAP1 | 792 | 114.85 | 463 | 71.35 |
| STEAP1 | 792 | 114.85 | 464 | 45.04 |
| STEAP1 | 792 | 114.85 | 465 | 24.30 |
| STEAP1 | 793 | 17.41 | 466 | 5.58 |
| STEAP1 | 794 | 108.68 | 467 | 14.56 |
| STEAP1 | 794 | 108.68 | 468 | 38.72 |
| TBL1Y | 795 | 266.17 | 469 | 47.46 |
| TBL1Y | 795 | 266.17 | 470 | 24.18 |
| TDRD1 | 796 | 25.66 | 471 | 9.56 |
| TDRD1 | 797 | 39.35 | 472 | 8.52 |
| TDRD1 | 798 | 49.63 | 473 | 23.68 |
| TDRD1 | 799 | 518.24 | 474 | 9.97 |
| TOP2A | 800 | 111.32 | 475 | 14.85 |
| TOP2A | 801 | 8.69 | 476 | 3.98 |
| TOP2A | 801 | 8.69 | 477 | 4.60 |
| TOP2A | 801 | 8.69 | 478 | 2.56 |
| TOP2A | 802 | 209.11 | 479 | 16.24 |
| TOP2A | 802 | 209.11 | 480 | 8.73 |
| TOP2A | 803 | 13.42 | 481 | 7.20 |
| TOP2A | 804 | 22.95 | 482 | 4.92 |
| TOP2A | 805 | 9.84 | 483 | 7.56 |
| TPTE | 806 | 463.88 | 484 | 4.68 |
| TPTE | 806 | 463.88 | 485 | 3.96 |
| TPTE | 806 | 463.88 | 486 | 6.26 |
| TPTE | 806 | 463.88 | 487 | 13.78 |
| TPTE | 806 | 463.88 | 488 | 11.78 |
| TPTE | 806 | 463.88 | 489 | 15.72 |
| TPTE | 806 | 463.88 | 490 | 6.82 |

TABLE 2-continued

In silico prediction of peptide-MHC class I binding.

| Tumor antigen | SEQ ID NO. human reference peptide | Binding affinity prediction human reference peptide (nM) | SEQ ID NO. antigenic peptide | Binding affinity prediction antigenic peptide (nM) |
|---|---|---|---|---|
| TPTE | 807 | 288.31 | 491 | 4.57 |
| TPTE | 807 | 288.31 | 492 | 5.24 |
| TPTE | 807 | 288.31 | 493 | 5.23 |
| TPTE | 807 | 288.31 | 494 | 8.96 |
| TPTE | 808 | 48.59 | 495 | 8.16 |
| TPTE | 808 | 48.59 | 496 | 14.63 |
| TPTE | 808 | 48.59 | 497 | 12.62 |
| TPTE | 809 | 51.09 | 498 | 10.30 |
| TPTE | 809 | 51.09 | 499 | 7.49 |
| TPTE | 810 | 98.14 | 500 | 13.70 |
| TPTE | 810 | 98.14 | 501 | 44.96 |
| TPTE | 811 | 26.77 | 502 | 5.21 |
| TPTE | 812 | 14.61 | 503 | 5.25 |
| TPTE | 813 | 655.75 | 504 | 29.36 |
| TRPM8 | 814 | 22.11 | 505 | 3.85 |
| TRPM8 | 815 | 6.88 | 506 | 2.87 |
| TRPM8 | 816 | 17.00 | 507 | 8.54 |
| TRPM8 | 817 | 20.72 | 508 | 3.08 |
| TRPM8 | 817 | 20.72 | 509 | 6.82 |
| TRPM8 | 818 | 97.59 | 510 | 16.59 |
| TRPM8 | 819 | 27.88 | 511 | 9.89 |
| TRPM8 | 820 | 396.02 | 512 | 8.37 |
| TRPM8 | 821 | 64.07 | 513 | 24.24 |
| TRPM8 | 821 | 64.07 | 514 | 27.93 |
| TRPM8 | 821 | 64.07 | 515 | 11.79 |
| TRPM8 | 821 | 64.07 | 516 | 18.44 |
| TRPM8 | 822 | 13.38 | 517 | 4.54 |
| TRPM8 | 823 | 80.70 | 518 | 19.78 |
| TYMS | 824 | 17.03 | 519 | 14.15 |
| TYMS | 824 | 17.03 | 520 | 11.59 |
| TYMS | 824 | 17.03 | 521 | 4.57 |
| TYMS | 825 | 104.14 | 522 | 21.32 |
| TYMS | 825 | 104.14 | 523 | 25.31 |
| TYMS | 826 | 10.01 | 524 | 3.45 |
| TYR | 827 | 7.58 | 525 | 3.75 |
| TYR | 827 | 7.58 | 526 | 3.96 |
| TYR | 828 | 89.30 | 527 | 57.36 |
| TYR | 828 | 89.30 | 528 | 20.14 |
| TYR | 828 | 89.30 | 529 | 19.81 |
| TYR | 828 | 89.30 | 530 | 23.50 |
| TYR | 829 | 172.53 | 531 | 3.17 |
| TYR | 830 | 22.89 | 532 | 6.48 |
| TYR | 831 | 454.20 | 533 | 20.88 |
| TYR | 832 | 239.36 | 534 | 18.48 |
| TYR | 833 | 42.36 | 535 | 11.41 |
| TYR | 833 | 42.36 | 536 | 14.65 |
| TYR | 833 | 42.36 | 537 | 16.03 |
| TYR | 833 | 42.36 | 538 | 7.40 |
| TYR | 833 | 42.36 | 539 | 4.75 |
| UPK2 | 834 | 107.50 | 540 | 9.06 |
| UPK2 | 834 | 107.50 | 541 | 12.77 |
| UPK2 | 834 | 107.50 | 542 | 9.19 |
| UPK2 | 835 | 62.49 | 543 | 12.45 |
| UPK2 | 836 | 46.89 | 544 | 42.83 |
| UPK2 | 836 | 46.89 | 545 | 10.01 |
| UPK2 | 836 | 46.89 | 546 | 10.53 |
| UPK2 | 836 | 46.89 | 547 | 7.26 |
| UPK2 | 837 | 27.00 | 548 | 12.89 |
| UPK2 | 837 | 27.00 | 549 | 6.74 |
| UPK2 | 838 | 366.36 | 550 | 54.32 |
| UPK2 | 839 | 210.79 | 551 | 22.97 |
| UPK2 | 839 | 210.79 | 552 | 16.83 |
| UPK2 | 839 | 210.79 | 553 | 26.98 |
| UPK2 | 839 | 210.79 | 554 | 17.24 |
| UPK2 | 840 | 50.83 | 555 | 16.79 |
| UPK2 | 840 | 50.83 | 556 | 14.52 |
| VCAM1 | 841 | 612.18 | 557 | 32.28 |
| VCAM1 | 842 | 97.02 | 558 | 4.32 |
| VCAM1 | 843 | 593.47 | 559 | 3.12 |
| VCAM1 | 844 | 207.18 | 560 | 5.51 |
| WFDC2 | 845 | 397.49 | 561 | 4.56 |
| WFDC2 | 845 | 397.49 | 562 | 5.04 |
| WFDC2 | 845 | 397.49 | 563 | 7.54 |
| WFDC2 | 845 | 397.49 | 564 | 8.54 |
| WFDC2 | 845 | 397.49 | 565 | 39.96 |
| WFDC2 | 846 | 10.86 | 566 | 4.19 |
| WFDC2 | 847 | 265.28 | 567 | 50.35 |
| WFDC2 | 847 | 265.28 | 568 | 114.90 |
| WT1 | 848 | 450.86 | 569 | 3.26 |
| ZEB1 | 849 | 44.34 | 570 | 9.16 |
| ZEB1 | 849 | 44.34 | 571 | 10.63 |
| ZEB1 | 850 | 246.22 | 572 | 7.49 |
| ZEB1 | 850 | 246.22 | 573 | 30.71 |
| ZEB1 | 851 | 58.11 | 574 | 20.17 |
| ZNF165 | 852 | 107.27 | 575 | 4.35 |
| ZNF165 | 852 | 107.27 | 576 | 11.00 |
| ZNF165 | 852 | 107.27 | 577 | 18.48 |
| ZNF165 | 853 | 375.88 | 578 | 29.16 |
| ZNF280A | 854 | 88.70 | 579 | 7.54 |
| ZNF280A | 855 | 340.56 | 580 | 2.32 |

A comparison between the binding affinity predicted for each antigenic peptide according to the invention and for the human reference peptide reveals a superior binding affinity of the antigenic peptide according to the present invention.

Example 2: Antigenic Peptides have Superior Affinity to the HLA-A*0201 Allele Next, binding affinity of various selected antigenic peptides and of the corresponding fragments of human tumor antigens (human reference peptides) to the HLA-A*0201 allele was confirmed in vitro. Namely, the antigenic peptides of sequence SEQ ID NO: 32 («FMLGEFLKL», also referred herein as BIRC5-B1); SEQ ID NO: 30 («YTLGEFLYI» also referred herein as BIRC5-B2); and SEQ ID NO: 31 («GLLGEFLQI» also referred herein as BIRC5-B3) were compared to the corresponding reference human peptides derived from BIRC5 («LTLGEFLK», SEQ ID NO: 593, also referred herein as BIRC5-H). Moreover, antigenic peptides of sequence SEQ ID NO: 97 («LLLSAALSV» also referred herein as CHI3L1B); and SEQ ID NO: 87 («YLLSAALTI» also referred herein as CHI3L1B3) were compared to the corresponding reference human peptide derived from CHI3L1 («LLLSAALSA», SEQ ID NO: 617, also referred herein as CHI3L1H). Moreover, the antigenic peptide of sequence SEQ ID NO: 145 («ILDEAYVRV») also referred herein as EGFR-B) was compared to the corresponding reference human peptide derived from EGFR («ILDEAYVMA», SEQ ID NO: 637, also referred herein as EGFR-H). Moreover, the antigenic peptides of sequence SEQ ID NO: 193 («FLVEDETVI» also referred herein as EZH2-B) and sequence SEQ ID NO: 194 («AVFRVLIPV» also referred herein as EZH2-B2) were compared to the corresponding reference human peptides derived from EZH2 («FMVEDETVL», SEQ ID NO: 659, also referred herein as EZH2-H and «SMFRVLIGT», SEQ ID NO: 660, also referred herein as EZH2-H2, respectively). Moreover, the antigenic peptides of sequence SEQ ID NO: 221 («RLSSYLVEI» also referred herein as FOXM1-B) and sequence SEQ ID NO:

220 («LMDLSTTEV» also referred herein as FOXM1-B2) were compared to the corresponding reference human peptides derived from FOXM1 («RVSSYLVPI», SEQ ID NO: 675, also referred herein as FOXM1-H and «LMDLSTTPL», SEQ ID NO: 674, also referred herein as FOXM1-H2, respectively). Moreover, the antigenic peptides of sequence SEQ ID NO: 254 («FLPFGFILV» also referred herein as IL13RA2-B) and sequence SEQ ID NO: 255 («FLPFGFILPV» also referred herein as IL13RA2-L) were compared to the corresponding reference human peptide derived from IL13RA2 («WLPFGFILP», SEQ ID NO: 691, also referred herein as IL13RA2-H). Moreover, the antigenic peptides of sequence SEQ ID NO: 524 («SMEELLWFV» also referred herein as TYMS-B) and sequence SEQ ID NO: 521 («FLDSLGFSL» also referred herein as TYMS-B2) were compared to the corresponding reference human peptides derived from TYMS («VLEELLWFI», SEQ ID NO: 826, also referred herein as TYMS-H, and «FLDSLGEST», SEQ ID NO: 824, also referred herein as TYMS-H2, respectively).

A. Materials and Methods

A1. Measuring the Affinity of the Peptide to T2 Cell Line.

The experimental protocol is similar to the one that was validated for peptides presented by the HLA-A*0201 (Tourdot et al., A general strategy to enhance immunogenicity of low-affinity HLA-A2.1-associated peptides: implication in the identification of cryptic tumor epitopes. Eur J Immunol. 2000 December; 30(12):3411-21). Affinity measurement of the peptides is achieved with the human tumoral cell T2 which expresses the HLA-A*0201 molecule, but which is TAP1/2 negative and incapable of presenting endogenous peptides.

T2 cells ($2.10^5$ cells per well) are incubated with decreasing concentrations of peptides from 100 µM to 1.5625 µM in a AIMV medium supplemented with 100 ng/µl of human β2m at 37° C. for 16 hours. Cells are then washed two times and marked with the anti-HLA-A2 antibody coupled to PE (clone BB7.2, BD Pharmagen).

The analysis is achieved by FACS (Guava Easy Cyte).

For each peptide concentration, the geometric mean of the labelling associated with the peptide of interest is substracted from background noise and reported as a percentage of the geometric mean of the HLA-A*0202 labelling obtained for the reference peptide HIV pol 589-597 at a concentration of 100 µM. The relative affinity is then determined as follows:

relative affinity=concentration of each peptide inducing 20% of expression of HLA-A*0201/concentration of the reference peptide inducing 20% of expression of HLA-A*0201.

A2. Solubilisation of Peptides

Each peptide is solubilized by taking into account the amino acid composition. For peptides which do not include any Cystein, Methionin, or Tryptophane, the addition of DMSO is possible to up to 10% of the total volume. Other peptides are resuspended in water or PBS pH7.4.

B. Results

The mean relative fluorescence intensity values (data are normalized to the mean fluorescence of HIV peptide, i.e. a value of 100 is equal to the best binding observed with HIV peptide) of T2 cells obtained for the various concentrations of each peptide are shown in Table 3 below:

TABLE 3

| Peptide Name | SEQ ID NO. | Peptide concentration (µM) | | | | | |
|---|---|---|---|---|---|---|---|
| | | 100 | 50 | 25 | 6.25 | 3.125 | 1.5625 |
| BIRC5-H | 593 | 35.6 | 18.9 | 9.8 | 10.8 | 1.4 | 1.7 |
| BIRC5-B1 | 32 | 117.0 | 77.1 | 61.7 | 36.1 | 22.3 | 1.9 |
| BIRC5-B2 | 30 | 58.0 | 54.4 | 29.6 | 9.0 | 6.6 | nd |
| BIRC5-B3 | 31 | 35.0 | 29.8 | 20.9 | nd | 8.9 | 9.4 |
| CHI3L1 H | 617 | 11.2 | 14.5 | 4.9 | 4.4 | 1.0 | -1.9 |
| CHI3L1 B | 97 | 58.9 | 85.0 | 45.3 | 44.0 | 23.9 | 13.5 |
| CHI3L1 B3 | 87 | 76.9 | 108.0 | 36.7 | 30.2 | 14.3 | 2.5 |
| EGFR-H | 637 | 87.4 | 107.4 | 91.5 | 33.7 | 28.6 | 12.0 |
| EGFR-B | 145 | 70.3 | 66.7 | 53.2 | 29.2 | 22.7 | 12.7 |
| EZH2-H | 659 | 95.4 | 66.0 | 40.7 | 10.6 | 0.7 | 0.0 |
| EZH2-B | 193 | 94.9 | 82.6 | 53.9 | 28.9 | 14.4 | 5.5 |
| EZH2-H2 | 660 | 78.2 | nd | 13.3 | 0.0 | 0.0 | 0.0 |
| EZH2-B2 | 194 | 112.4 | nd | 74.8 | 0.5 | 0.0 | 0.0 |
| FOXM1-H | 675 | 83.8 | 30.7 | 10.5 | 0.0 | 0.0 | 0.0 |
| FOXM1-B | 221 | 47.5 | 21.3 | 7.6 | 0.0 | 0.0 | 0.0 |
| FOXM1-H2 | 674 | 77.6 | 62.5 | 65.4 | 19.7 | 0.9 | 5.3 |
| FOXM1-B2 | 220 | 105.0 | 91.5 | 98.2 | 33.5 | 12.7 | 7.2 |
| IL13RA2-H | 691 | 26.5 | 14.2 | 11.2 | 9.6 | 3.7 | 3.0 |
| IL13RA2-B | 254 | 128.4 | 112.7 | 86.5 | 40.8 | 15.7 | 14.8 |
| IL13RA2-L | 255 | 107.7 | 85.5 | 77.3 | 30.4 | 19.8 | 13.3 |
| TYMS H | 826 | 50.2 | 40.4 | 38.1 | 26.6 | 15.3 | 8.6 |
| TYMS B | 524 | 80.9 | 65.7 | 49.3 | 36.0 | 30.4 | 15.9 |
| TYMS H2 | 824 | 50.6 | 37.2 | 32.5 | 6.1 | 4.5 | 1.6 |
| TYMS B2 | 521 | 71.3 | 62.0 | 61.1 | 27.5 | 21.5 | 10.7 |

Table 4 below summarizes for each tested peptide the concentration required to induce 20% of HLA-A2 expression and the in vitro binding affinity.

TABLE 4

| Peptide | SEQ ID NO | Concentration of peptide that induces 20% of HLA-A2 expression (µM) | In vitro binding affinity |
|---|---|---|---|
| BIRC5-H | 593 | 53.0 | 16.1 |
| BIRC5-B1 | 32 | 2.7 | 0.8 |
| BIRC5-B2 | 30 | 14.7 | 4.5 |
| B1RC5-B3 | 31 | 22.9 | 7.0 |
| CHI3L1 H | 617 | ND | ND |
| CHI3L1 B | 97 | 3.6 | 0.9 |
| CHI3L1 B3 | 87 | 8.6 | 2.2 |
| EGFR-H | 637 | 2.8 | 0.2 |
| EGFR-B | 145 | 3.1 | 0.2 |
| EZH2-H | 659 | 13.3 | 1.1 |
| EZH2-B | 193 | 8.8 | 0.7 |
| EZH2-H2 | 660 | 39.2 | 7.8 |
| EZH2-B2 | 194 | 8.3 | 1.7 |
| FOXM1-H | 675 | 37.6 | 3.7 |
| FOXM1-B | 221 | 46.7 | 4.6 |
| FOXM1-H2 | 674 | 12.6 | 2.5 |
| FOXM1-B2 | 220 | 6.7 | 1.3 |
| IL13RA2-H | 691 | ND | ND |
| IL13RA2-B | 254 | 2.9 | 0.3 |
| IL13RA2-L | 255 | 3.2 | 0.3 |
| TYMS H | 826 | 4.1 | 0.3 |
| TYMS B | 524 | 1.1 | 0.1 |
| TYMS H2 | 824 | 9.5 | 0.8 |
| TYMS B2 | 521 | 2.7 | 0.2 |

ND—not determined

Figure 6:
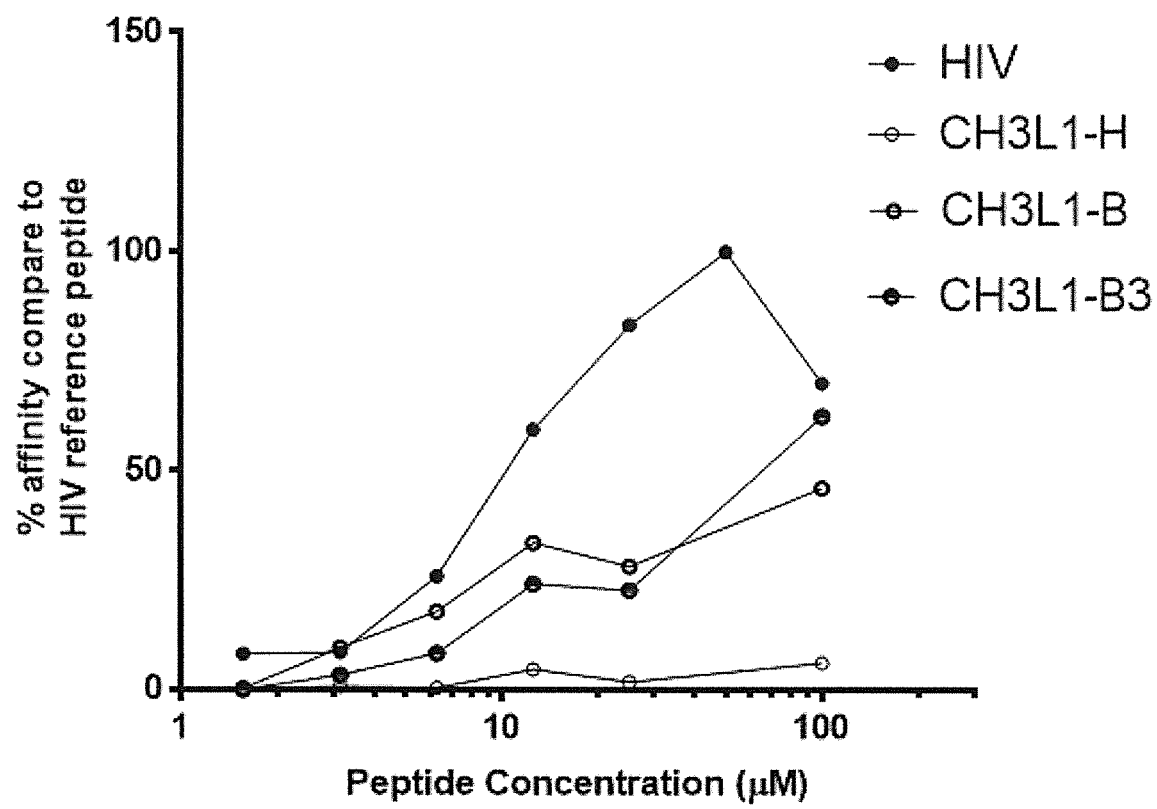
FIG. 6: shows for Example 2 in vitro affinity for antigenic peptides CHI3L1-B and CHI3L1-B3 in comparison to the corresponding human CHI3L1 epitope CHI3L1-H.

In addition, FIGS. 1-6 illustrate the results for selected examples, namely for antigenic peptides IL13RA2-B and IL13RA2-L in comparison to the corresponding human IL13RA2 fragment IL13RA2-H (FIG. 1), for antigenic peptides BIRC5-B1, BIRC5-B2 and BIRC5-B3 in comparison to the corresponding human BIRC5 fragment B1RC5-H (FIG. 2), for antigenic peptide EZH2-B in comparison to the corresponding human EZH2 fragment EZH2-H (FIG. 3A) and antigenic peptide EZH2-B2 in comparison to the corresponding human EZH2 fragment EZH2-H2 (FIG. 3B), for antigenic peptide TYMS-B in comparison to the corresponding human TYMS fragment TYMS-H (FIG. 4A) and antigenic peptide TYMS-B2 in comparison to the corresponding human TYMS fragment TYMS-H2 (FIG. 4B), for antigenic peptide FOXM1-B in comparison to the corresponding human FOXM1 fragment FOXM1-H (FIG. 5A) and antigenic peptide FOXM1-B2 in comparison to the corresponding human FOXM1 fragment FOXM1-H2 (FIG. 5B), and for antigenic peptides CHI3L1-B and CHI3L1-B3 in comparison to the corresponding human CHI3L1 fragment CHI3L1-H (FIG. 6).

In summary, the results show that the antigenic peptides according to the present invention show at least similar binding affinity to HLA-A*0201 as the corresponding human tumor antigen fragments. In most cases, the binding affinity observed for the antigenic peptides according to the present invention was stronger than that of the corresponding human epitopes. Without being bound to any theory it is assumed that such a strong binding affinity of the antigenic peptides according to the present invention reflects their ability to raise an immune response (i.e., their immunogenicity).

Figure 7:
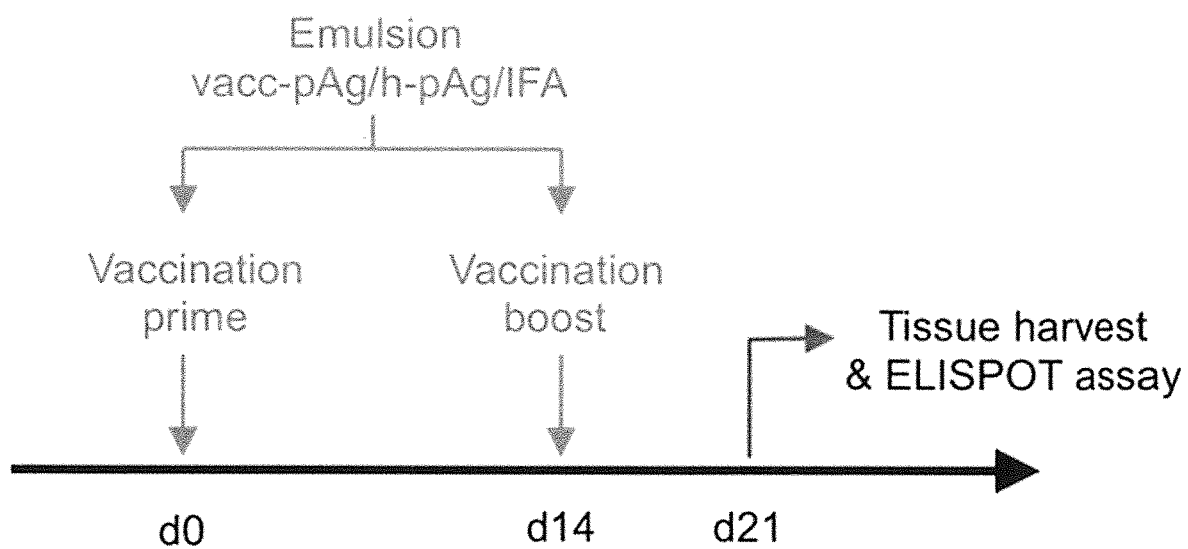
FIG. 7: shows for Example 3 a schematic view of the immunization scheme. d: day.

Example 3: Vaccination of Mice with Antigenic Peptides According to the Present Invention Induces Improved T Cell Responses in ELISPOT-IFNγ Assay A. Materials and Methods
A.1 Mouse Model The immunization scheme is shown in FIG. 7. Briefly, HLA-A2 humanized mice (HLA-A2 (CB6F1-Tg(HLA-A*0201/H2-Kb)A*0201) were assigned randomly (based on mouse sex and age) to experimental groups, wherein each group was immunized with a specific vaccination peptide (vacc-pAg) combined to a common helper peptide (h-pAg T13L; sequence: TPPAYRPPNAPIL; SEQ ID NO: 860; Bhasin M, Singh H, Raghava GP (2003) MHCBN: a comprehensive database of MHC binding and non-binding peptides. Bioinformatics 19: 665-666) (as outlined in Table 5 below). The vacc-pAg were compared in couples (group 1 vs. group 2, group 1 vs. group 3; group 1 vs. group 4; group 5 vs. group 6; group 7 vs. group 8; group 9 vs. group 10). Thereby, both native and optimized versions of a single peptide were compared in each wave.

TABLE 5

Experimental group composition. h-pAg: 'helper' peptide; vacc-pAg: vaccination peptide. The number of boost injections is indicated into brackets.

| Group | Peptide (vacc-pAg) | Helper (h-Ag) | Prime | Boost | Animal Number |
|---|---|---|---|---|---|
| 1 | BIRC5-H (100 μg) | T13L (150 μg) | + | +(1X) | 5 |
| 2 | BIRC5-B1 (100 μg) | T13L (150 μg) | + | +(1X) | 5 |
| 3 | BIRC5-B2 (100 μg) | T13L (150 μg) | + | +(1X) | 5 |
| 4 | BIRC5-B3 (100 μg) | T13L (150 μg) | + | +(1X) | 5 |
| 5 | FOXM1-H2 (100 μg) | T13L (150 μg) | + | +(1X) | 5 |
| 6 | FOXM1-B2 (100 μg) | T13L (150 μg) | + | +(1X) | 5 |
| 7 | EZH2-H2 (100 μg) | T13L (150 μg) | + | +(1X) | 5 |
| 8 | EZH2-B2 (100 μg) | T13L (150 μg) | + | +(1X) | 5 |
| 9 | IL13RA2-H (100 μg) | T13L (150 μg) | + | +(1X) | 5 |
| 10 | IL13RA2-B (100 μg) | T13L (150 μg) | + | +(1X) | 5 |

The peptides were provided as follows:
vacc-pAg: BIRC5-H, BIRC5-B1, BIRC5-B2, BIRC5-B3, FOXM1-H2, FOXM1-B2, EZH2-H2, EZH2-B2, 1L13RA2-H and IL13RA2-B; all produced and provided at a 4 mg/ml (4 mM) concentration;
h-pAg: T13L; Eurogentec batch 1713334 re-suspended in pure distilled water at a 10 mg/mL concentration The animals were immunized on day 0 (d0) with a prime injection, and on d14 with a boost injection. Each mouse was injected s.c. at tail base with 100 μL of an oil-based emulsion that contained:
100 μg of vacc-pAg (25 μL of 4 mg/mL stock per mouse);
150 μg of h-pAg (15 μL of 10 mg/mL stock per mouse);
10 μL of PBS to reach a total volume of 50 μL (per mouse);
Incomplete Freund's Adjuvant (IFA) added at 1:1 (v:v) ratio (50 μL per mouse).

A separate emulsion was prepared for each vacc-pAg, as follows: IFA reagent was added to the vacc-pAg/h-pAg/PBS mixture in a 15 mL tube and mixed on vortex for repeated cycles of 1 min until forming a thick emulsion.

A.2 Analysis

Seven days after the boost injection (i.e. on d21), the animals were euthanized and the spleen was harvested. Splenocytes were prepared by mechanical disruption of the organ followed by 70 μm-filtering and Ficoll density gradient purification.

The splenocytes were immediately used in an ELISPOT-IFNγ assay (Table 6). Experimental conditions were repeated in triplicates, using $2*10^5$ total splenocytes per well, and were cultured in presence of vacc-pAg (10 μM), Ionomycin (0.1 μM) plus PMA (1 μM) or medium-only to assess for their capacity to secrete IFNγ. The commercial ELISPOT-IFNγ kit (Diaclone Kit Mujrine IFNγ ELISpot) was used following the manufacturer's instructions, and the assay was performed after about 19 h of incubation.

TABLE 6

Setup of the ELISPOT-IFNγ assay.

| Group | Stimulus | Wells | Animal | Total |
|---|---|---|---|---|
| 1 | BIRC5-H (10 μM) | 3 | 5 | 15 |
| | Ionomycin (0.1 μM) PMA 1 μM) | 3 | 5 | 15 |
| | Medium | 3 | 5 | 15 |
| 2 | BIRC5-B1 (10 μM) | 3 | 5 | 15 |
| | Ionomycin (0.1 μM) PMA 1 μM) | 3 | 5 | 15 |
| | Medium | 3 | 5 | 15 |
| 3 | BIRC5-B2 (10 μM) | 3 | 5 | 15 |
| | Ionomycin (0.1 μM) PMA 1 μM) | 3 | 5 | 15 |
| | Medium | 3 | 5 | 15 |
| 4 | BIRC5-B3 (10 μM) | 3 | 5 | 15 |
| | Ionomycin (0.1 μM) PMA 1 μM) | 3 | 5 | 15 |
| | Medium | 3 | 5 | 15 |
| 5 | FOXM1-H2 (10 μM) | 3 | 5 | 15 |
| | Ionomycin (0.1 μM) PMA 1 μM) | 3 | 5 | 15 |
| | Medium | 3 | 5 | 15 |

TABLE 6-continued

Setup of the ELISPOT-IFNγ assay.

| Group | Stimulus | Wells | Animal | Total |
|---|---|---|---|---|
| 6 | FOXM1-B2 (10 μM) | 3 | 5 | 15 |
|  | Ionomycin (0.1 μM) PMA 1 μM) | 3 | 5 | 15 |
|  | Medium | 3 | 5 | 15 |
| 7 | EZH2-H2 (10 μM) | 3 | 5 | 15 |
|  | Ionomycin (0.1 μM) PMA 1 μM) | 3 | 5 | 15 |
|  | Medium | 3 | 5 | 15 |
| 8 | EZH2-B2 (10 μM) | 3 | 5 | 15 |
|  | Ionomycin (0.1 μM) PMA 1 μM) | 3 | 5 | 15 |
|  | Medium | 3 | 5 | 15 |
| 9 | IL13RA2-H (10 μM) | 3 | 5 | 15 |
|  | Ionomycin (0.1 μM) PMA 1μM) | 3 | 5 | 15 |
|  | Medium | 3 | 5 | 15 |
| 10 | IL13RA2-B (10 μM) | 3 | 5 | 15 |
|  | Ionomycin (0.1 μM) PMA 1 μM) | 3 | 5 | 15 |
|  | Medium | 3 | 5 | 15 |

Spots were counted on a CTL ELISpot reader. Data plotting and statistical analysis were performed with the Prism-5 software (GraphPad Software Inc.).

B. Results

A total of 50 HLA-A2 (CB6F1-Tg(HLA-A*0201/H2-Kb) A*0201) mice were used for these experiment. All mice were aged of 6 to 9 weeks at the experiment starting date. Both males and females were used in the study. Animals have been housed in groups of 5 per cage at maximum. At time of sacrifice, the spleen T cell population was analysed by flow cytometry, showing that the large majority belonged to the $CD4_+$ T cell subset.

After plating and incubation with the appropriate stimuli, the IFNγ-producing cells were revealed and counted. The data were then normalized as a number of specific spots (the average counts obtained in the 'medium only' condition being subtracted) per $50*10^3$ total T cells.

Figure 8:
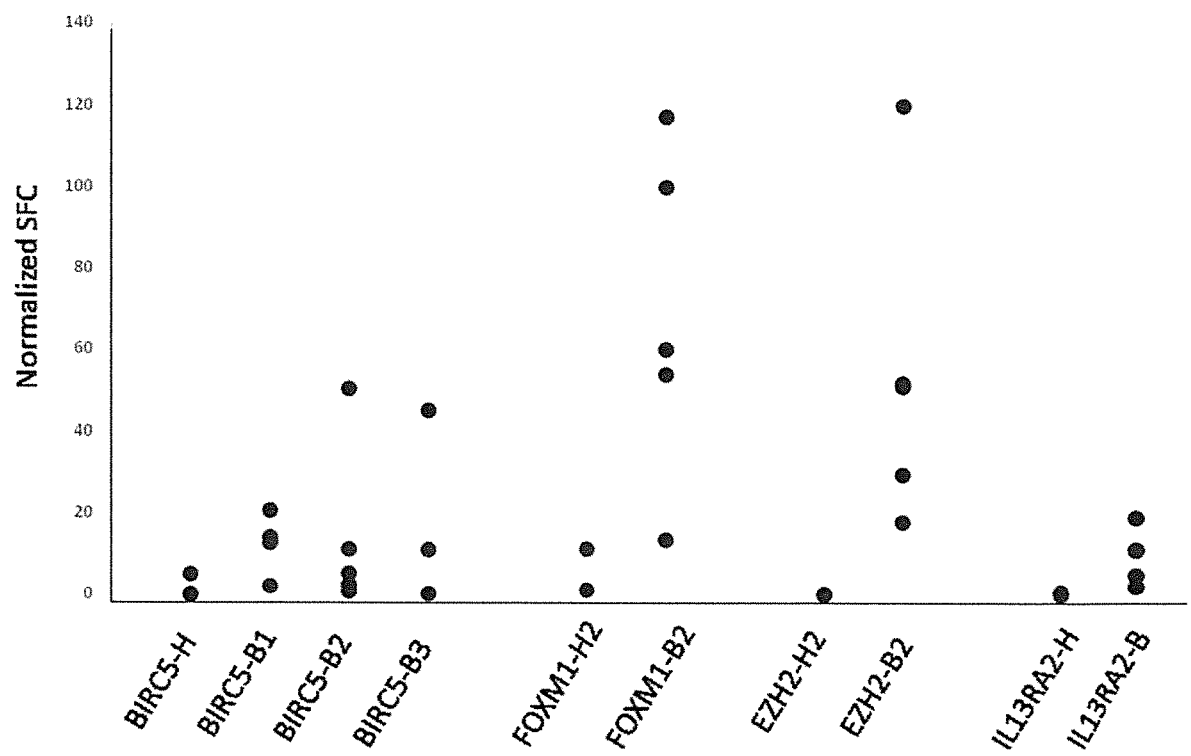
FIG. 8: shows for Example 3 ELISPOT results for mice vaccinated with the antigenic peptides as indicated in the figure (BIRC5-H, BIRC5-B1, B1RC5-B2, BIRC5-B3, FOXM1-H2, FOXM1-B2, EZH2-H2, EZH2-B2, IL13RA2-H, IL13RA2-B. For each group the normalized number of spot-forming cells (SFC) is shown. Each dot represents the average value for one individual/mouse.

The individual average values (obtained from the triplicates) were next used to plot the group average values. As the functional capacity of T cells might vary from individual to individual, the data were also expressed as the percentage of the ionomycin plus PMA response per individual (see FIG. 8).

Overall, vaccination with the antigenic peptides according to the present invention (BIRC5-B1, BIRC5-B2, BIRC5-B3, FOXM1-B2, EZH2-B2 and IL13RA2-B) induced improved T cell responses in the ELISPOT-IFNγ assay, as compared to the respective human reference epitopes (BIRC5-H, FOXM1-H2, EZH2-H2 and IL13RA2-H).

Example 4: Immunogenicity of IL13R2A-L in HLA-A2 Transgenic Mice and Cross-Reactivity with the Corresponding Human Peptide A. Materials and Methods The antigenic peptide of the present invention IL13RA2-L (SEQ ID NO: 255) and the corresponding human reference peptide IL13RA2-H (SEQ ID NO: 691) were tested in distinct groups of male and female HHD DR3 mice expressing human HLA-A2 and HLA-DR3 MHC and lacking the murine H-2 class I and class II MHCs. Groups of 5 mice (male and female) were subcutaneously injected on days 0 and 14 with 100 μg of IL13RA2-L (SEQ ID NO: 255) or IL13RA2-H (SEQ ID NO: 691), 150 μg of helper peptide (DR3) and IFA. On day 21, the mice were euthanized and splenocytes were prepared and stimulated in vitro with IL13RA2-L or the human corresponding peptide IL13RA2-H to assess their capacity to secrete IFN—as assessed by ELISpot. Concanavalin A (ConA) was used as a positive control.

B. Results

Figure 9:
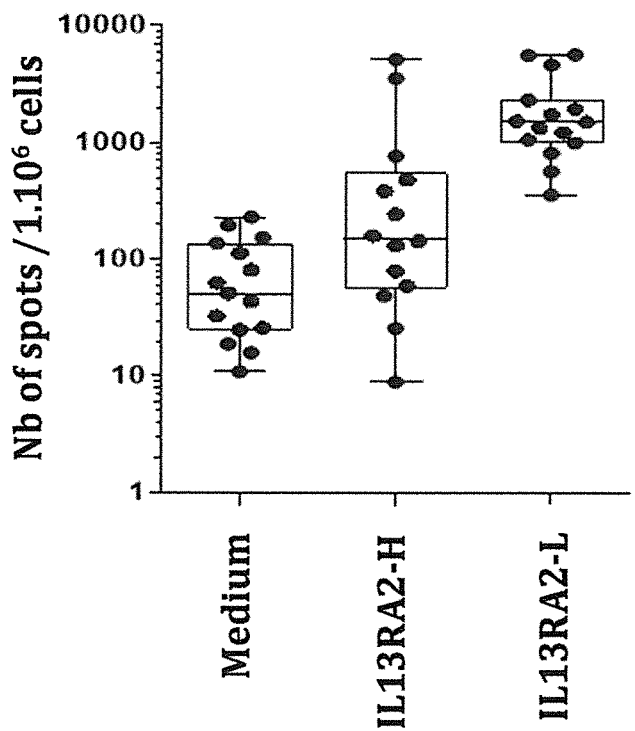
FIG. 9: shows for Example 4 ELISPOT results for HLA-A2 transgenic mice vaccinated with the antigenic peptide IL13R2A-L as indicated in the figure and cross-reactivity with the human corresponding peptide IL13RA2-H. For each group the normalized number of spot-forming cells (SFC) is shown.

The number of spot forming cells (SFC) (normalized to the number of CD8 cells) are depicted in FIG. 9. Results are shown for mice immunized with IL13RA2-L. The results show that immunisation of mice with IL13RA2-L allows to induce T-cells that are able to react strongly after challenge with either IL13RA2-L or the human corresponding peptide. Thus, IL13RA2-L is strongly immunogenic and is able to drive an effective immune response against the corresponding human peptide. As expected, the immunisation of mice with the human corresponding peptide IL13RA2-H does not induce an immune response after challenge with either IL13RA2-L or the human corresponding peptide IL13RA2-H (data not shown).

These results were confirmed in HHD DR1 mice expressing human HLA-A2 and HLA-DR1 MHC and lacking the murine H-2 class I and class II MHCs (groups of 5 mice).

Example 5: Immunogenicity of BIRC5-B1 in HLA-A2 Transgenic Mice and Cross-Reactivity with the Corresponding Human Peptide A. Materials and Methods The antigenic peptide of the invention BIRC5-B1 (SEQ ID NO: 32) and the corresponding human peptide BIRC5-H (SEQ ID NO: 593) were tested in distinct groups of male and female HHD DR3 mice expressing human HLA-A2 and HLA-DR3 MHC and lacking the murine H-2 class I and class II MHCs. Groups of 5 mice (male and female) were subcutaneously injected on days 0 and 14 with 100 μg of BIRC5-B1 or BIRC5-H, 150 μg of helper peptide (DR3) and IFA. On day 21, the mice were euthanized and splenocytes were prepared and stimulated in vitro with BIRC5-B1 or the human peptide BIRC5-H to assess their capacity to secrete IFN—as assessed by ELISpot. ConA was used as a positive control.

B. Results

Figure 10:
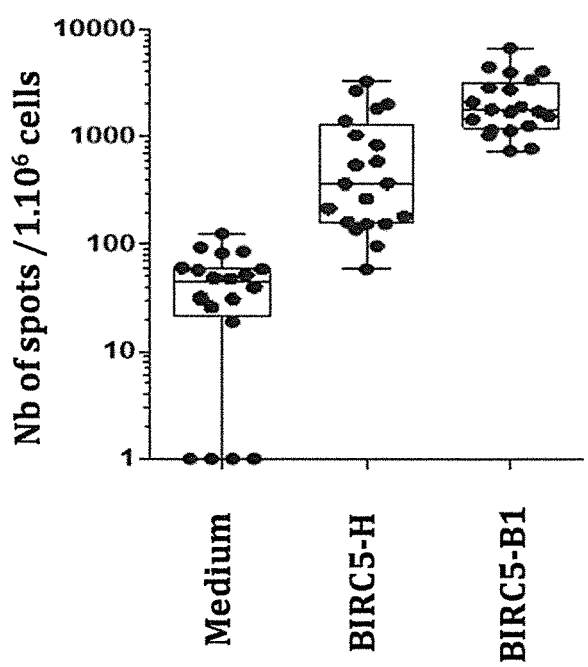
FIG. 10: shows for Example 5 ELISPOT results for HLA-A2 transgenic mice vaccinated with the antigenic peptide BIRC5-B1 as indicated in the figure and cross-reactivity with the human corresponding peptide BIRC5-H. For each group the normalized number of spot-forming cells (SFC) is shown.

The number of SFC (normalized to the number of CD8 cells) are depicted in FIG. 10. Results are shown for mice immunized with BIRC5-B1. The results show that immunisation of mice with BIRC5-B1 allows to induce T-cells that are able to react strongly after challenge with either BIRC5-B1 or the human corresponding peptide BIRC5-H. Thus, BIRC5-B1 is strongly immunogenic and is able to drive an effective immune response against human corresponding peptide. Immunisation of mice with the human corresponding peptide BIRC5-H does not induce any immune response against BIRC5-B1 or the human corresponding peptide (data not shown).

These results were confirmed in HHD DR1 mice expressing human HLA-A2 and HLA-DR1 MHC and lacking the murine H-2 class 1 and class II MHCs (groups of 5 mice).

Figure 11:
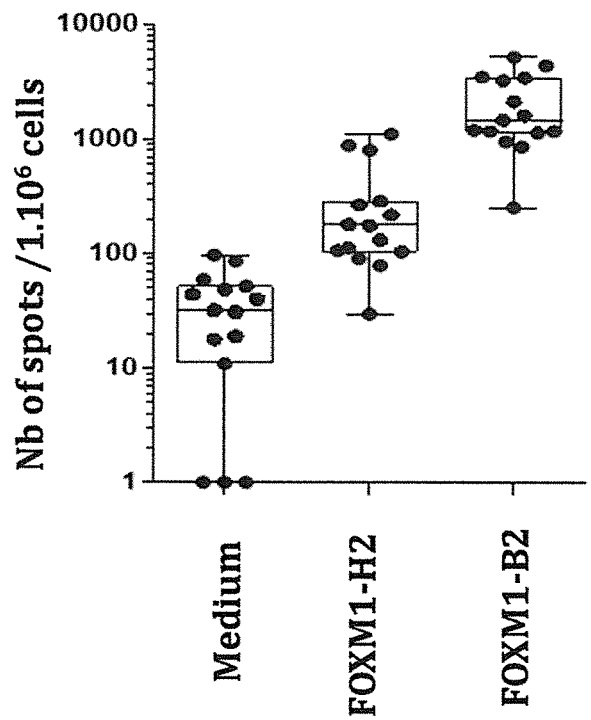
FIG. 11: shows for Example 6 ELISPOT results for HLA-A2 transgenic mice vaccinated with the antigenic peptide FOXM1-B2 as indicated in the figure and cross-reactivity with the human corresponding peptide FOXM1-H2. For each group the normalized number of spot-forming cells (SFC) is shown.

Example 6: Immunogenicity of FOXM1-B2 in HLA-A2 Transgenic Mice and Cross-Reactivity with the Corresponding Human Peptide A. Materials and Methods The antigenic peptide of the invention FOXM1-B2 (SEQ ID NO: 220) and the corresponding human peptide FOXM1-H2 (SEQ ID NO: 674) were tested in distinct groups of male and female HHD DR3 mice expressing human HLA-A2 and HLA-DR3 MHC and lacking the murine H-2 class I and class II MHCs. Groups of 5 mice (male and female) were subcutaneously injected on days 0 and 14 with 100 µg of FOXM1-B2 or FOXM1-H2, 150 µg of helper peptide (DR3) and IFA. On day 21, the mice were euthanized and splenocytes were prepared and stimulated in vitro with FOXM1-B2 or the human corresponding peptide FOXM1-H2 to assess their capacity to secrete IFN—as assessed by ELISpot. ConA was used as a positive control
B. Results The number of SFC (normalized to the number of CD8 cells) are depicted in FIG. 11. Results are shown for mice immunized with FOXM1-B2. The results show that immunisation of mice with FOXM1-B2 allows to induce T-cells that are able to react strongly after challenge with either FOXM1-B2 or human corresponding peptide. Thus, FOXM1-B2 is strongly immunogenic and is able to drive an effective immune response against human corresponding peptide FOXM1-H2. Immunisation of mice with the human corresponding peptide FOXM1-H2 does not induce immune response against FOXM1-B2 or the human corresponding peptide (data not shown).

These results were confirmed in HHD DR1 mice expressing human HLA-A2 and HLA-DR1 MHC and lacking the murine H-2 class I and class II MHCs (groups of 5 mice).

Altogether, these immunogenicity studies described in Examples 4 to 6 performed in HHD DR3 and HHD DR1 mice showed that the three antigenic peptides of the invention, IL13RA2-L, BIRC5-B1 and FOXM1-B2, induced strong immune responses. Cross-reactivity of the T cells generated against IL13RA2-L, BIRC5-B1 and FOXM1-B2 for the corresponding human peptides was shown in HHD DR3 and HHD DR1 mice.

Accordingly, those results provide experimental evidence that antigen-based immunotherapy is able to improve T cell response in vivo and that the antigenic peptides according to the present invention are particularly efficient for that purpose.

Example 7: IL13RA2-B has Superior Affinity to the HLA-A*0201 Allele

This Example provides evidence that the antigenic peptide of the invention as set forth in SEQ ID NO: 254 (FLPFGFILV, also referred to herein as IL13RA2-B) has higher affinity to the HLA-A*0201 allele than other sequence variants of the corresponding reference human peptide derived from IL13RA2 (IL13RA2-H, WLPFGFILI, SEQ ID NO: 691). In this experiment, the antigenic peptide of sequence SEQ ID NO: 254 (IL13RA2-B) was compared to
- the comparative peptide "1A9V" (SEQ ID NO: 896), as described by Eguchi Junichi et al., 2006, Identification of interleukin-13 receptor alpha 2 peptide analogues capable of inducing improved antiglioma CTL responses. Cancer Research 66(11): 5883-5891, in which the tryptophan at position 1 of SEQ ID NO: 691 was substituted by alanine (1A) and the isoleucine at position 9 of SEQ ID NO: 691 was substituted by valine (9V);
- peptide "1I9A" (SEQ ID NO: 897), wherein the tryptophan at position 1 of SEQ ID NO: 691 was substituted by isoleucine (1I) and the isoleucine at position 9 of SEQ ID NO: 691 was substituted by alanine (9A); and
- peptide "1F9M" (SEQ ID NO: 898), wherein the tryptophan at position 1 of SEQ ID NO: 691 was substituted by phenylalanine (1F) and the isoleucine at position 9 of SEQ ID NO: 691 was substituted by methionine (9M).

A. Materials and Methods

The experimental protocol, materials and methods correspond to those outlined in Example 2, with the only difference that the above mentioned (poly)peptides were used.
B. Results The following in vitro binding affinities were obtained:

TABLE 7

| Peptide | In vitro binding affinity |
|---|---|
| IL13RA2-B (SEQ ID NO: 254) | 0.49 |
| 1A9V (SEQ ID NO: 896) | 3.06 |
| 1I9A (SEQ ID NO: 897) | 2.22 |
| 1F9M (SEQ ID NO: 898) | 2.62 |

Accordingly, the antigenic peptide according to the present invention (IL13RA2-B; SEQ ID NO: 254) showed considerably higher binding affinity to HLA-A*0201 than all other peptides tested, whereas the peptide "1A9V", as described by Eguchi Junichi et al., 2006, Identification of interleukin-13 receptor alpha 2 peptide analogues capable of inducing improved antiglioma CTL responses. Cancer Research 66(11): 5883-5891, showed the lowest affinity of the peptides tested.

Example 8: IL13RA2-L has Superior Affinity to the HLA-A*0201 Allele

This Example provides evidence that the antigenic peptide of the invention as set forth in SEQ ID NO: 255 (also referred to herein as IL13RA2-L) has a similarly high affinity to the HLA-A*0201 allele as the antigenic peptide of the invention as set forth in SEQ ID NO: 254 (FLPFGFILV, also referred to herein as IL13RA2-B)—and a higher affinity than the corresponding reference human peptide derived from IL13RA2 (IL13RA2-H, WLPFGFILI, SEQ ID NO: 691) and other sequence variants thereof. In this experiment, the antigenic peptide of sequence SEQ ID NO: 255 (IL13RA2-L) was compared to
- the comparative peptide "1A9V" (SEQ ID NO: 896), as described by Eguchi Junichi et al., 2006, Identification of interleukin-13 receptor alpha 2 peptide analogues capable of inducing improved antiglioma CTL responses. Cancer Research 66(11): 5883-5891, in which the tryptophan at position 1 of SEQ ID NO: 691 was substituted by alanine (1A) and the isoleucine at position 9 of SEQ ID NO: 691 was substituted by valine (9V);
- the antigenic peptide of the invention as set forth in SEQ ID NO: 254 (IL13RA2-B);
- the corresponding reference human peptide IL13RA2-H (SEQ ID NO: 691); and
- a positive control (HIV).

A. Materials and Methods

The experimental protocol, materials and methods correspond to those outlined in Example 2, with the only difference that the above mentioned (poly)peptides were used.

B. Results

The following in vitro binding affinities were obtained:

TABLE 8

| Peptide | SEQ ID NO | Concentration of peptide that induces 20% of HLA-A2 expression (μM) | In vitro binding affinity |
|---|---|---|---|
| IL13RA2-H | 691 | ND | ND |
| IL13RA2-B | 254 | 2.9 | 0.3 |
| IL13RA2-L | 255 | 3.2 | 0.3 |
| 1A9V | 896 | 36.5 | 3.6 |

Figure 12:
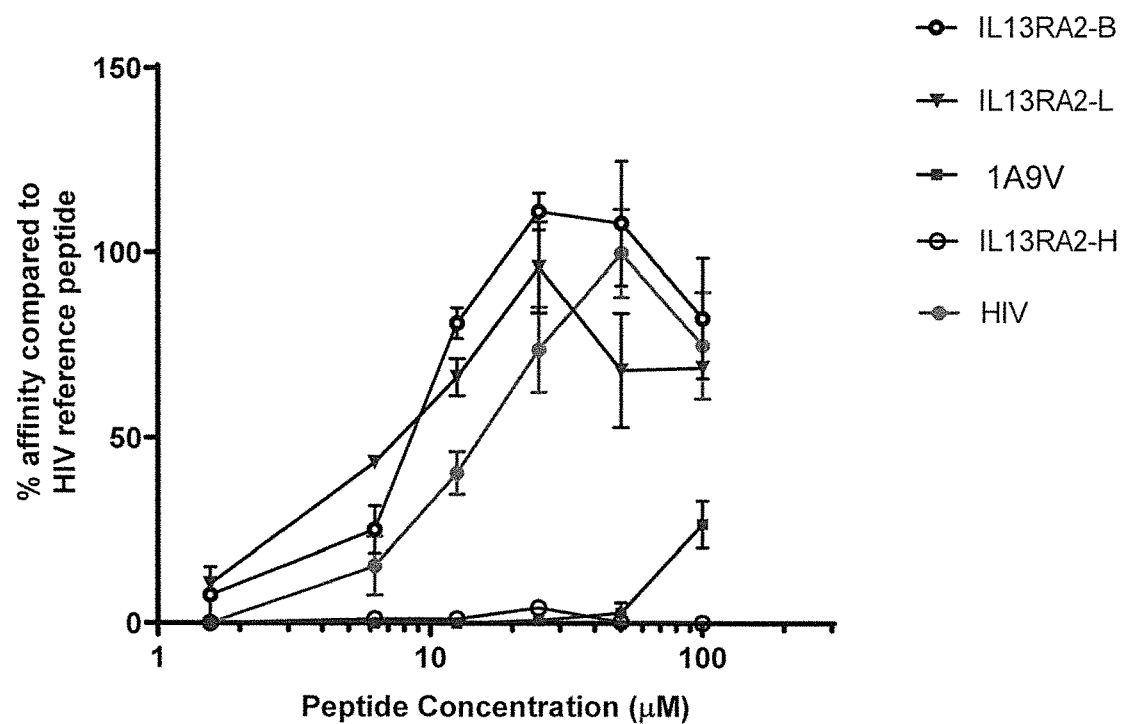
FIG. 12: shows for Example 8 in vitro affinity for antigenic peptides IL13RA2-B and IL13RA2-L in comparison to the corresponding human IL13RA2 epitope IL13RA2-H, to the comparative peptide 1A9V and to the positive control HIV.

Accordingly, the antigenic peptides according to the present invention (IL13RA2-B; SEQ ID NO: 254 and IL13RA2-L; SEQ ID NO: 255) showed considerably higher binding affinity to HLA-A*0201 than the corresponding human epitope (IL13RA2-H) and the comparative peptide "1A9V", as described by Eguchi Junichi et al., 2006, Identification of interleukin-13 receptor alpha 2 peptide analogues capable of inducing improved antiglioma CTL responses. Cancer Research 66(11): 5883-5891. In particular, the antigenic peptide IL13RA2-L (SEQ ID NO: 255) shows a strong binding affinity to HLA-A*0201, namely, 69% of maximum HIV pol 589-597 binding activity at 100 μM; 96% at 25 μM and 43% at 6.25 μM. Results are also shown in FIG. 12.

Example 9: BIRC5-B1 has Superior Affinity to the HLA-A*0201 Allele

This Example provides evidence that the antigenic peptide of the invention as set forth in SEQ ID NO: 32 (also referred to herein as BIRC5-B1) has a higher affinity than the corresponding reference human peptide derived from BIRC5 (BIRC5-H, SEQ ID NO: 593) and a comparative sequence variant thereof ("2M"; SEQ ID NO: 899). In this experiment, the antigenic peptide of sequence SEQ ID NO: 32 (BIRC5-B1) was compared to the peptide "2M" (LMLGEFLKL; SEQ ID NO: 899), in which the threonine at position 2 of SEQ ID NO: 593 was substituted by methionine (2M);

the corresponding reference human peptide BIRC5-H (SEQ ID NO: 593); and a positive control (HIV).

A. Materials and Methods

The experimental protocol, materials and methods correspond to those outlined in Example 2, with the only difference that the above mentioned (poly)peptides were used.

B. Results

The following in vitro binding affinities were obtained:

TABLE 9

| Peptide | SEQ ID NO | Concentration of peptide that induces 20% of HLA-A2 expression (μM) | In vitro binding affinity |
|---|---|---|---|
| BIRC5-H | 593 | 95.9 | 112.82 |
| BIRC5-B1 | 32 | 1.24 | 1.46 |
| 2M | 899 | 2.87 | 3.38 |
| HIV | | 0.85 | 1.00 |

TABLE 10

| Peptide | | Peptide concentration (μM) | | | |
|---|---|---|---|---|---|
| Name | SEQ ID NO. | 100 | 10 | 1 | 0.1 |
| HIV | | 100 | 84.725 | 22.14 | 2.405 |
| BIRC5-H | 593 | 20.545 | 3.515 | 0 | 0 |
| BIRC5-B | 32 | 101.845 | 65.06 | 17.42 | 1.07 |
| 2M | 899 | 75.22 | 48.465 | 8.37 | 0.76 |

Figure 13:
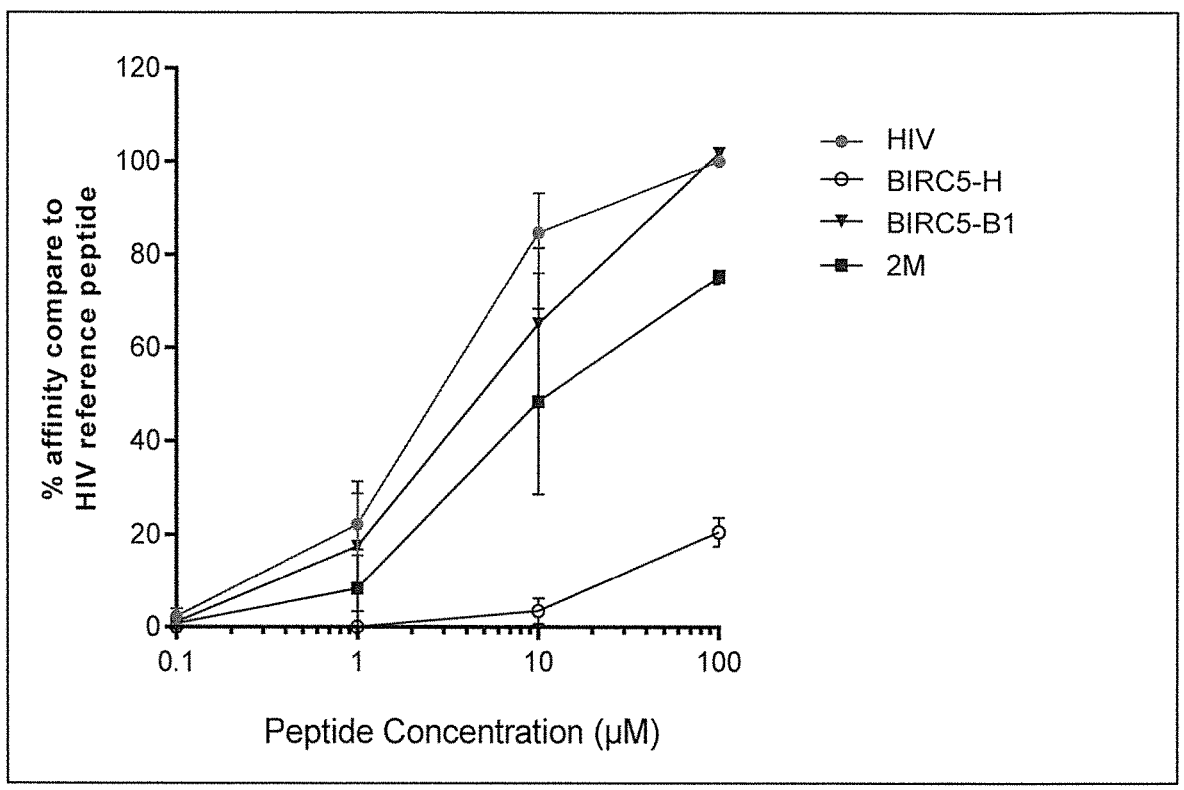
FIG. 13: shows for Example 9 in vitro affinity for the antigenic peptides BIRC5-B1 in comparison to the corresponding human BIRC5 epitope B1RC5-H, to the comparative peptide 2M and to the positive control HIV.

In summary, the antigenic peptide according to the present invention (BIRC5-B1; SEQ ID NO: 32) showed considerably higher in vitro binding affinity to HLA-A*0201 than the corresponding human epitope (BIRC5-H) and the comparative peptide "2M". Results are also shown in FIG. 13.

The invention claimed is:

1. An antigenic peptide comprising or consisting of the amino acid sequence as set forth in SEQ ID NO: 32.

2. The antigenic peptide according to claim 1, wherein the length of the antigenic peptide does not exceed 30 amino acids.

3. The antigenic peptide according to claim 1, wherein the antigenic peptide is not a full-length (microbiota) protein.

4. An immunogenic compound comprising the antigenic peptide according to claim 1.

5. A nanoparticle loaded with
(i) at least one antigenic peptide according to claim 1, or
(ii) at least one immunogenic compound comprising the antigenic peptide of (i);
and, optionally, with an adjuvant.

6. A cell loaded with the antigenic peptide according to claim 1 or with an immunogenic compound comprising the antigenic peptide.

7. A nucleic acid encoding:
(i) the antigenic peptide according to claim 1, or
(ii) an immunogenic compound comprising the antigenic peptide of (i), wherein the immunogenic compound is a peptide or a protein.

8. A host cell comprising the nucleic acid according to claim 7.

9. The host cell according to claim 8, wherein the host cell is a bacterial cell.

10. A pharmaceutical composition comprising,
(i) the antigenic peptide according to claim 1,
(ii) an immunogenic compound comprising the antigenic peptide of (i),
(iii) a nanoparticle loaded with the antigenic peptide of (i) or the immunogenic compound of (ii),
(iv) a cell loaded with the antigenic peptide of (i) or the immunogenic compound of (ii),
(v) a nucleic acid encoding the antigenic peptide of (i) or the immunogenic compound of (ii), wherein the immunogenic compound is a peptide or a protein, and/or
(vi) a host cell comprising the nucleic acid of (v),
and, optionally, one or more pharmaceutically acceptable excipients or carriers.

11. The pharmaceutical composition according to claim 10, wherein the composition further comprises:
(i) a distinct additional antigenic peptide;
(ii) a distinct additional immunogenic compound;
(iii) a distinct additional nanoparticle; and/or
(iv) a distinct additional nucleic acid.

12. The pharmaceutical composition according to claim 11, wherein the distinct additional antigenic peptide comprises or consists of the amino acid sequence as set forth in SEQ ID NO: 220.

13. A kit comprising:
(i) the antigenic peptide according to claim 1,
(ii) an immunogenic compound comprising the antigenic peptide of (i),
(iii) a nanoparticle loaded with the antigenic peptide of (i) or the immunogenic compound of (ii),
(iv) a cell loaded with the antigenic peptide of (i) or the immunogenic compound of (ii),
(v) a nucleic acid encoding the antigenic peptide of (i) or the immunogenic compound of (ii), wherein the immunogenic compound is a peptide or a protein,
(vi) a host cell comprising the nucleic acid of (v), and/or
(vii) a pharmaceutical composition comprising the antigenic peptide of (i), the immunogenic compound of (ii), the nanoparticle of (iii), the cell of (iv), the nucleic acid of (v) or the host cell of (vi).

14. The kit according to claim 13, wherein the kit further comprises a distinct additional antigenic peptide.

15. The kit according to claim 14, wherein the distinct additional antigenic peptide comprises or consists of the amino acid sequence as set forth in SEQ ID NO: 220.

16. A combination comprising the antigenic peptide according to claim 1 and a distinct additional antigenic peptide.

17. The combination according to claim 16, wherein the antigenic peptides are comprised in the same composition.

18. The combination according to claim 16, wherein the distinct additional antigenic peptide comprises or consists of the amino acid sequence as set forth in SEQ ID NO: 220.

19. A peptide-MHC (pMHC) multimer comprising the antigenic peptide according to claim 1.

20. A method for treating a cancer or initiating, enhancing or prolonging an anti-tumor-response in a subject in need thereof comprising administering to the subject:
   (i) the antigenic peptide according to claim 1,
   (ii) an immunogenic compound comprising the antigenic peptide of (i),
   (iii) a nanoparticle loaded with the antigenic peptide of (i) or the immunogenic compound of (ii),
   (iv) a cell loaded with the antigenic peptide of (i) or the immunogenic compound of (ii),
   (v) a nucleic acid encoding the antigenic peptide of (i) or the immunogenic compound of (ii), wherein the immunogenic compound is a peptide or a protein,
   (vi) a host cell comprising the nucleic acid of (v),
   (vii) a pharmaceutical composition comprising the antigenic peptide of (i), the immunogenic compound of (ii), the nanoparticle of (iii), the cell of (iv), the nucleic acid of (v) or the host cell of (vi), and/or
   (viii) a combination comprising at least two distinct antigenic peptides of (i).

21. The method according to claim 20, wherein the cancer is selected from glioma, kidney cancer, skin cancer, lung cancer, ovarian cancer, breast cancer, colorectal cancer, liver cancer, pancreatic cancer, head and neck cancer, urothelial cancer and prostate cancer.

22. The method according to claim 21, wherein the skin cancer is melanoma.

23. The antigenic peptide of claim 1, wherein the antigenic peptide consists of the amino acid sequence as set forth in SEQ ID NO: 32.

24. The pharmaceutical composition according to claim 10, wherein the antigenic peptide consists of the amino acid sequence as set forth in SEQ ID NO: 32.

25. The pharmaceutical composition according to claim 12, wherein the antigenic peptide consists of the amino acid sequence as set forth in SEQ ID NO: 32 and wherein the distinct additional antigenic peptide consists of the amino acid sequence as set forth in SEQ ID NO: 220.

26. The kit according to claim 15, wherein the antigenic peptide consists of the amino acid sequence as set forth in SEQ ID NO: 32 and wherein the distinct additional antigenic peptide consists of the amino acid sequence as set forth in SEQ ID NO: 220.

27. The combination according to claim 18, wherein the antigenic peptide consists of the amino acid sequence as set forth in SEQ ID NO: 32 and wherein the distinct additional antigenic peptide consists of the amino acid sequence as set forth in SEQ ID NO: 220.

28. A method for treating a glioma or initiating, enhancing or prolonging an anti-tumor-response in a subject in need thereof, the method comprising administering to the subject:
   (i) the antigenic peptide according to claim 23,
   (ii) a pharmaceutical composition comprising (i) and optionally a distinct additional antigenic peptide that consists of the amino acid sequence as set forth in SEQ ID NO: 220, and/or
   (iii) a combination comprising (i) and a distinct additional antigenic peptide that consists of the amino acid sequence as set forth in SEQ ID NO: 220.

29. A method for treating a colorectal cancer or initiating, enhancing or prolonging an anti-tumor-response in a subject in need thereof, the method comprising administering to the subject:
   (i) the antigenic peptide according to claim 23,
   (ii) a pharmaceutical composition comprising (i) and optionally a distinct additional antigenic peptide that consists of the amino acid sequence as set forth in SEQ ID NO: 220, and/or
   (iii) a combination comprising (i) and a distinct additional antigenic peptide that consists of the amino acid sequence as set forth in SEQ ID NO: 220.

30. A method for treating a breast cancer or initiating, enhancing or prolonging an anti-tumor-response in a subject in need thereof, the method comprising administering to the subject:
   (i) the antigenic peptide according to claim 23,
   (ii) a pharmaceutical composition comprising (i) and optionally a distinct additional antigenic peptide that consists of the amino acid sequence as set forth in SEQ ID NO: 220, and/or
   (iii) a combination comprising (i) and a distinct additional antigenic peptide that consists of the amino acid sequence as set forth in SEQ ID NO: 220.

\* \* \* \* \*

SEQUENCE LISTING

```
<160> NUMBER OF SEQ ID NOS: 899

<210> SEQ ID NO 1
<211> LENGTH: 9
<212> TYPE: PRT
<213> ORGANISM: Artificial Sequence
<220> FEATURE:
<223> OTHER INFORMATION: peptide

<400> SEQUENCE: 1

Val Leu Phe Leu Leu Phe Phe Pro Val
1               5

<210> SEQ ID NO 2
<211> LENGTH: 9
<212> TYPE: PRT
<213> ORGANISM: Artificial Sequence
<220> FEATURE:
<223> OTHER INFORMATION: peptide

<400> SEQUENCE: 2

Ser Met Ser Leu Gly Phe Leu Ser Val
1               5

<210> SEQ ID NO 3
<211> LENGTH: 9
```

-continued

```
<212> TYPE: PRT
<213> ORGANISM: Artificial Sequence
<220> FEATURE:
<223> OTHER INFORMATION: peptide

<400> SEQUENCE: 3

Phe Leu Ser Leu Gly Phe Leu Ala Val
1               5

<210> SEQ ID NO 4
<211> LENGTH: 9
<212> TYPE: PRT
<213> ORGANISM: Artificial Sequence
<220> FEATURE:
<223> OTHER INFORMATION: peptide

<400> SEQUENCE: 4

Leu Leu Leu Gly Phe Leu Phe Leu Ile
1               5

<210> SEQ ID NO 5
<211> LENGTH: 9
<212> TYPE: PRT
<213> ORGANISM: Artificial Sequence
<220> FEATURE:
<223> OTHER INFORMATION: peptide

<400> SEQUENCE: 5

Tyr Leu Ser Asn Asp Ser Tyr Arg Val
1               5

<210> SEQ ID NO 6
<211> LENGTH: 9
<212> TYPE: PRT
<213> ORGANISM: Artificial Sequence
<220> FEATURE:
<223> OTHER INFORMATION: peptide

<400> SEQUENCE: 6

Gly Leu Ile Asp Ser Gly Ala Phe Leu
1               5

<210> SEQ ID NO 7
<211> LENGTH: 9
<212> TYPE: PRT
<213> ORGANISM: Artificial Sequence
<220> FEATURE:
<223> OTHER INFORMATION: peptide

<400> SEQUENCE: 7

Leu Leu Ile Asp Ser Gly Ala Leu Val
1               5

<210> SEQ ID NO 8
<211> LENGTH: 9
<212> TYPE: PRT
<213> ORGANISM: Artificial Sequence
<220> FEATURE:
<223> OTHER INFORMATION: peptide

<400> SEQUENCE: 8

Arg Leu Ile Asp Ser Gly Ala Thr Val
1               5

<210> SEQ ID NO 9
<211> LENGTH: 9
<212> TYPE: PRT
```

```
<213> ORGANISM: Artificial Sequence
<220> FEATURE:
<223> OTHER INFORMATION: peptide

<400> SEQUENCE: 9

Lys Leu Phe Glu Ser Ser Ala Ala Leu
1               5

<210> SEQ ID NO 10
<211> LENGTH: 9
<212> TYPE: PRT
<213> ORGANISM: Artificial Sequence
<220> FEATURE:
<223> OTHER INFORMATION: peptide

<400> SEQUENCE: 10

Thr Leu Phe Glu Ser Ser Ala Phe Ala
1               5

<210> SEQ ID NO 11
<211> LENGTH: 9
<212> TYPE: PRT
<213> ORGANISM: Artificial Sequence
<220> FEATURE:
<223> OTHER INFORMATION: peptide

<400> SEQUENCE: 11

Met Leu Thr Pro Leu Leu Leu Gly Leu
1               5

<210> SEQ ID NO 12
<211> LENGTH: 9
<212> TYPE: PRT
<213> ORGANISM: Artificial Sequence
<220> FEATURE:
<223> OTHER INFORMATION: peptide

<400> SEQUENCE: 12

Tyr Leu Thr Pro Leu Leu Leu Ile Leu
1               5

<210> SEQ ID NO 13
<211> LENGTH: 9
<212> TYPE: PRT
<213> ORGANISM: Artificial Sequence
<220> FEATURE:
<223> OTHER INFORMATION: peptide

<400> SEQUENCE: 13

Ile Met Thr Pro Leu Leu Leu Pro Val
1               5

<210> SEQ ID NO 14
<211> LENGTH: 9
<212> TYPE: PRT
<213> ORGANISM: Artificial Sequence
<220> FEATURE:
<223> OTHER INFORMATION: peptide

<400> SEQUENCE: 14

Phe Met Thr Pro Leu Leu Leu Cys Leu
1               5

<210> SEQ ID NO 15
<211> LENGTH: 9
<212> TYPE: PRT
<213> ORGANISM: Artificial Sequence
```

```
<220> FEATURE:
<223> OTHER INFORMATION: peptide

<400> SEQUENCE: 15

Phe Leu Thr Pro Leu Leu Leu Trp Leu
1               5

<210> SEQ ID NO 16
<211> LENGTH: 9
<212> TYPE: PRT
<213> ORGANISM: Artificial Sequence
<220> FEATURE:
<223> OTHER INFORMATION: peptide

<400> SEQUENCE: 16

Trp Met Ala Val Ile Leu Thr Ala Leu
1               5

<210> SEQ ID NO 17
<211> LENGTH: 9
<212> TYPE: PRT
<213> ORGANISM: Artificial Sequence
<220> FEATURE:
<223> OTHER INFORMATION: peptide

<400> SEQUENCE: 17

Val Leu Ala Val Ile Leu Thr Ala Val
1               5

<210> SEQ ID NO 18
<211> LENGTH: 9
<212> TYPE: PRT
<213> ORGANISM: Artificial Sequence
<220> FEATURE:
<223> OTHER INFORMATION: peptide

<400> SEQUENCE: 18

Val Leu Ala Ala Ile Ala Ala Gly Val
1               5

<210> SEQ ID NO 19
<211> LENGTH: 9
<212> TYPE: PRT
<213> ORGANISM: Artificial Sequence
<220> FEATURE:
<223> OTHER INFORMATION: peptide

<400> SEQUENCE: 19

Leu Leu Ala Ala Ile Ala Ala Phe Leu
1               5

<210> SEQ ID NO 20
<211> LENGTH: 9
<212> TYPE: PRT
<213> ORGANISM: Artificial Sequence
<220> FEATURE:
<223> OTHER INFORMATION: peptide

<400> SEQUENCE: 20

Lys Leu Ala Ala Ile Ala Ala Ala Val
1               5

<210> SEQ ID NO 21
<211> LENGTH: 9
<212> TYPE: PRT
<213> ORGANISM: Artificial Sequence
<220> FEATURE:
```

<223> OTHER INFORMATION: peptide

<400> SEQUENCE: 21

Ile Leu Ala Ala Ile Ala Ala Ala Val
1               5

<210> SEQ ID NO 22
<211> LENGTH: 9
<212> TYPE: PRT
<213> ORGANISM: Artificial Sequence
<220> FEATURE:
<223> OTHER INFORMATION: peptide

<400> SEQUENCE: 22

Gly Met Ala Ala Ile Ala Ala Phe Leu
1               5

<210> SEQ ID NO 23
<211> LENGTH: 9
<212> TYPE: PRT
<213> ORGANISM: Artificial Sequence
<220> FEATURE:
<223> OTHER INFORMATION: peptide

<400> SEQUENCE: 23

Phe Leu Ala Ala Ile Ala Ala Val Leu
1               5

<210> SEQ ID NO 24
<211> LENGTH: 9
<212> TYPE: PRT
<213> ORGANISM: Artificial Sequence
<220> FEATURE:
<223> OTHER INFORMATION: peptide

<400> SEQUENCE: 24

Ala Leu Ala Ala Ile Ala Ala Leu Val
1               5

<210> SEQ ID NO 25
<211> LENGTH: 9
<212> TYPE: PRT
<213> ORGANISM: Artificial Sequence
<220> FEATURE:
<223> OTHER INFORMATION: peptide

<400> SEQUENCE: 25

Ala Leu Ala Ala Phe Gln Ala Gly Leu
1               5

<210> SEQ ID NO 26
<211> LENGTH: 9
<212> TYPE: PRT
<213> ORGANISM: Artificial Sequence
<220> FEATURE:
<223> OTHER INFORMATION: peptide

<400> SEQUENCE: 26

Ser Leu Val Asn Leu Gly Phe Ser Leu
1               5

<210> SEQ ID NO 27
<211> LENGTH: 9
<212> TYPE: PRT
<213> ORGANISM: Artificial Sequence
<220> FEATURE:
<223> OTHER INFORMATION: peptide

<400> SEQUENCE: 27

Gly Leu Val Asn Leu Gly Phe Ala Leu
1               5

<210> SEQ ID NO 28
<211> LENGTH: 9
<212> TYPE: PRT
<213> ORGANISM: Artificial Sequence
<220> FEATURE:
<223> OTHER INFORMATION: peptide

<400> SEQUENCE: 28

Gln Leu Leu Asp Phe Ser Ser Ser Leu
1               5

<210> SEQ ID NO 29
<211> LENGTH: 9
<212> TYPE: PRT
<213> ORGANISM: Artificial Sequence
<220> FEATURE:
<223> OTHER INFORMATION: peptide

<400> SEQUENCE: 29

Ile Leu Leu Asp Phe Ser Ser Val Val
1               5

<210> SEQ ID NO 30
<211> LENGTH: 9
<212> TYPE: PRT
<213> ORGANISM: Artificial Sequence
<220> FEATURE:
<223> OTHER INFORMATION: peptide

<400> SEQUENCE: 30

Tyr Thr Leu Gly Glu Phe Leu Tyr Ile
1               5

<210> SEQ ID NO 31
<211> LENGTH: 9
<212> TYPE: PRT
<213> ORGANISM: Artificial Sequence
<220> FEATURE:
<223> OTHER INFORMATION: peptide

<400> SEQUENCE: 31

Gly Leu Leu Gly Glu Phe Leu Gln Ile
1               5

<210> SEQ ID NO 32
<211> LENGTH: 9
<212> TYPE: PRT
<213> ORGANISM: Artificial Sequence
<220> FEATURE:
<223> OTHER INFORMATION: peptide

<400> SEQUENCE: 32

Phe Met Leu Gly Glu Phe Leu Lys Leu
1               5

<210> SEQ ID NO 33
<211> LENGTH: 9
<212> TYPE: PRT
<213> ORGANISM: Artificial Sequence
<220> FEATURE:
<223> OTHER INFORMATION: peptide

```
<400> SEQUENCE: 33

Val Leu Gly Asp Ile Leu Ala Leu Leu
1               5

<210> SEQ ID NO 34
<211> LENGTH: 9
<212> TYPE: PRT
<213> ORGANISM: Artificial Sequence
<220> FEATURE:
<223> OTHER INFORMATION: peptide

<400> SEQUENCE: 34

Lys Val Gly Asp Ile Leu Ala Leu Val
1               5

<210> SEQ ID NO 35
<211> LENGTH: 9
<212> TYPE: PRT
<213> ORGANISM: Artificial Sequence
<220> FEATURE:
<223> OTHER INFORMATION: peptide

<400> SEQUENCE: 35

Asn Leu Val Phe Gly Leu Leu Pro Val
1               5

<210> SEQ ID NO 36
<211> LENGTH: 9
<212> TYPE: PRT
<213> ORGANISM: Artificial Sequence
<220> FEATURE:
<223> OTHER INFORMATION: peptide

<400> SEQUENCE: 36

Phe Leu Val Phe Gly Leu Leu Gly Leu
1               5

<210> SEQ ID NO 37
<211> LENGTH: 9
<212> TYPE: PRT
<213> ORGANISM: Artificial Sequence
<220> FEATURE:
<223> OTHER INFORMATION: peptide

<400> SEQUENCE: 37

Ala Leu Val Phe Gly Leu Leu Arg Val
1               5

<210> SEQ ID NO 38
<211> LENGTH: 9
<212> TYPE: PRT
<213> ORGANISM: Artificial Sequence
<220> FEATURE:
<223> OTHER INFORMATION: peptide

<400> SEQUENCE: 38

Gly Val Tyr Glu Gly Ser Leu Thr Val
1               5

<210> SEQ ID NO 39
<211> LENGTH: 9
<212> TYPE: PRT
<213> ORGANISM: Artificial Sequence
<220> FEATURE:
<223> OTHER INFORMATION: peptide

<400> SEQUENCE: 39
```

Val Leu Ser Thr Ala Phe Ala Leu Val
1               5

<210> SEQ ID NO 40
<211> LENGTH: 9
<212> TYPE: PRT
<213> ORGANISM: Artificial Sequence
<220> FEATURE:
<223> OTHER INFORMATION: peptide

<400> SEQUENCE: 40

Gly Leu Ser Thr Ala Phe Ala Ala Val
1               5

<210> SEQ ID NO 41
<211> LENGTH: 9
<212> TYPE: PRT
<213> ORGANISM: Artificial Sequence
<220> FEATURE:
<223> OTHER INFORMATION: peptide

<400> SEQUENCE: 41

Ala Leu Ser Thr Ala Phe Ala Val Val
1               5

<210> SEQ ID NO 42
<211> LENGTH: 9
<212> TYPE: PRT
<213> ORGANISM: Artificial Sequence
<220> FEATURE:
<223> OTHER INFORMATION: peptide

<400> SEQUENCE: 42

Met Leu Leu Leu Leu Leu Val Pro Val
1               5

<210> SEQ ID NO 43
<211> LENGTH: 9
<212> TYPE: PRT
<213> ORGANISM: Artificial Sequence
<220> FEATURE:
<223> OTHER INFORMATION: peptide

<400> SEQUENCE: 43

Leu Leu Leu Leu Leu Leu Val Pro Val
1               5

<210> SEQ ID NO 44
<211> LENGTH: 9
<212> TYPE: PRT
<213> ORGANISM: Artificial Sequence
<220> FEATURE:
<223> OTHER INFORMATION: peptide

<400> SEQUENCE: 44

Ala Ile Leu Leu Leu Leu Val Pro Val
1               5

<210> SEQ ID NO 45
<211> LENGTH: 9
<212> TYPE: PRT
<213> ORGANISM: Artificial Sequence
<220> FEATURE:
<223> OTHER INFORMATION: peptide

<400> SEQUENCE: 45

```
Tyr Leu Leu Leu Ser Leu Leu Arg Leu
1               5

<210> SEQ ID NO 46
<211> LENGTH: 9
<212> TYPE: PRT
<213> ORGANISM: Artificial Sequence
<220> FEATURE:
<223> OTHER INFORMATION: peptide

<400> SEQUENCE: 46

Phe Leu Leu Leu Ser Leu Leu Thr Leu
1               5

<210> SEQ ID NO 47
<211> LENGTH: 9
<212> TYPE: PRT
<213> ORGANISM: Artificial Sequence
<220> FEATURE:
<223> OTHER INFORMATION: peptide

<400> SEQUENCE: 47

Ala Leu Leu Leu Ser Leu Leu Pro Leu
1               5

<210> SEQ ID NO 48
<211> LENGTH: 9
<212> TYPE: PRT
<213> ORGANISM: Artificial Sequence
<220> FEATURE:
<223> OTHER INFORMATION: peptide

<400> SEQUENCE: 48

Arg Leu Leu Leu Leu Ser Leu Leu Val
1               5

<210> SEQ ID NO 49
<211> LENGTH: 9
<212> TYPE: PRT
<213> ORGANISM: Artificial Sequence
<220> FEATURE:
<223> OTHER INFORMATION: peptide

<400> SEQUENCE: 49

Lys Leu Leu Leu Leu Ser Leu Leu Leu
1               5

<210> SEQ ID NO 50
<211> LENGTH: 9
<212> TYPE: PRT
<213> ORGANISM: Artificial Sequence
<220> FEATURE:
<223> OTHER INFORMATION: peptide

<400> SEQUENCE: 50

Phe Leu Leu Leu Leu Ser Leu Leu Ile
1               5

<210> SEQ ID NO 51
<211> LENGTH: 9
<212> TYPE: PRT
<213> ORGANISM: Artificial Sequence
<220> FEATURE:
<223> OTHER INFORMATION: peptide

<400> SEQUENCE: 51

Arg Leu Ala Lys Tyr Val Ala Leu Val
```

```
1               5
```

<210> SEQ ID NO 52
<211> LENGTH: 9
<212> TYPE: PRT
<213> ORGANISM: Artificial Sequence
<220> FEATURE:
<223> OTHER INFORMATION: peptide

<400> SEQUENCE: 52

```
Leu Ile Ala Ala Ala Ala Phe Thr Val
1               5
```

<210> SEQ ID NO 53
<211> LENGTH: 9
<212> TYPE: PRT
<213> ORGANISM: Artificial Sequence
<220> FEATURE:
<223> OTHER INFORMATION: peptide

<400> SEQUENCE: 53

```
Gly Met Ala Ala Ala Ala Phe Cys Leu
1               5
```

<210> SEQ ID NO 54
<211> LENGTH: 9
<212> TYPE: PRT
<213> ORGANISM: Artificial Sequence
<220> FEATURE:
<223> OTHER INFORMATION: peptide

<400> SEQUENCE: 54

```
Gly Leu Ala Ala Ala Ala Phe Cys Ile
1               5
```

<210> SEQ ID NO 55
<211> LENGTH: 9
<212> TYPE: PRT
<213> ORGANISM: Artificial Sequence
<220> FEATURE:
<223> OTHER INFORMATION: peptide

<400> SEQUENCE: 55

```
Phe Leu Ala Ala Ala Ala Phe Cys Leu
1               5
```

<210> SEQ ID NO 56
<211> LENGTH: 9
<212> TYPE: PRT
<213> ORGANISM: Artificial Sequence
<220> FEATURE:
<223> OTHER INFORMATION: peptide

<400> SEQUENCE: 56

```
Trp Leu Asn Asp Arg Val Leu Gln Leu
1               5
```

<210> SEQ ID NO 57
<211> LENGTH: 9
<212> TYPE: PRT
<213> ORGANISM: Artificial Sequence
<220> FEATURE:
<223> OTHER INFORMATION: peptide

<400> SEQUENCE: 57

```
Lys Leu Leu Leu Thr Thr Leu Leu Val
1               5
```

```
<210> SEQ ID NO 58
<211> LENGTH: 9
<212> TYPE: PRT
<213> ORGANISM: Artificial Sequence
<220> FEATURE:
<223> OTHER INFORMATION: peptide

<400> SEQUENCE: 58

Gly Met Ala Val Val Phe Ile Asn Val
1               5

<210> SEQ ID NO 59
<211> LENGTH: 9
<212> TYPE: PRT
<213> ORGANISM: Artificial Sequence
<220> FEATURE:
<223> OTHER INFORMATION: peptide

<400> SEQUENCE: 59

Gly Met Ala Val Val Phe Ile Glu Val
1               5

<210> SEQ ID NO 60
<211> LENGTH: 9
<212> TYPE: PRT
<213> ORGANISM: Artificial Sequence
<220> FEATURE:
<223> OTHER INFORMATION: peptide

<400> SEQUENCE: 60

Leu Leu Leu Thr Thr Leu Leu Ala Val
1               5

<210> SEQ ID NO 61
<211> LENGTH: 9
<212> TYPE: PRT
<213> ORGANISM: Artificial Sequence
<220> FEATURE:
<223> OTHER INFORMATION: peptide

<400> SEQUENCE: 61

Ala Leu Leu Thr Thr Leu Leu Leu Val
1               5

<210> SEQ ID NO 62
<211> LENGTH: 9
<212> TYPE: PRT
<213> ORGANISM: Artificial Sequence
<220> FEATURE:
<223> OTHER INFORMATION: peptide

<400> SEQUENCE: 62

Ala Leu Leu Thr Thr Leu Leu Gly Leu
1               5

<210> SEQ ID NO 63
<211> LENGTH: 9
<212> TYPE: PRT
<213> ORGANISM: Artificial Sequence
<220> FEATURE:
<223> OTHER INFORMATION: peptide

<400> SEQUENCE: 63

Lys Ile Ile Gly Ile Ile Leu Ala Val
1               5
```

<210> SEQ ID NO 64
<211> LENGTH: 9
<212> TYPE: PRT
<213> ORGANISM: Artificial Sequence
<220> FEATURE:
<223> OTHER INFORMATION: peptide

<400> SEQUENCE: 64

Tyr Leu Val Ala Ile Leu Leu Leu Val
1               5

<210> SEQ ID NO 65
<211> LENGTH: 9
<212> TYPE: PRT
<213> ORGANISM: Artificial Sequence
<220> FEATURE:
<223> OTHER INFORMATION: peptide

<400> SEQUENCE: 65

Thr Leu Val Ala Ile Leu Leu Asn Val
1               5

<210> SEQ ID NO 66
<211> LENGTH: 9
<212> TYPE: PRT
<213> ORGANISM: Artificial Sequence
<220> FEATURE:
<223> OTHER INFORMATION: peptide

<400> SEQUENCE: 66

Met Leu Val Ala Ile Leu Leu Ala Val
1               5

<210> SEQ ID NO 67
<211> LENGTH: 9
<212> TYPE: PRT
<213> ORGANISM: Artificial Sequence
<220> FEATURE:
<223> OTHER INFORMATION: peptide

<400> SEQUENCE: 67

Leu Leu Val Ala Ile Leu Leu Ser Val
1               5

<210> SEQ ID NO 68
<211> LENGTH: 9
<212> TYPE: PRT
<213> ORGANISM: Artificial Sequence
<220> FEATURE:
<223> OTHER INFORMATION: peptide

<400> SEQUENCE: 68

Phe Leu Val Ala Ile Leu Leu Asn Leu
1               5

<210> SEQ ID NO 69
<211> LENGTH: 9
<212> TYPE: PRT
<213> ORGANISM: Artificial Sequence
<220> FEATURE:
<223> OTHER INFORMATION: peptide

<400> SEQUENCE: 69

Ala Met Val Ala Ile Leu Leu Asn Ile
1               5

```
<210> SEQ ID NO 70
<211> LENGTH: 9
<212> TYPE: PRT
<213> ORGANISM: Artificial Sequence
<220> FEATURE:
<223> OTHER INFORMATION: peptide

<400> SEQUENCE: 70

Ala Leu Val Ala Ile Leu Leu Ala Ile
1               5

<210> SEQ ID NO 71
<211> LENGTH: 9
<212> TYPE: PRT
<213> ORGANISM: Artificial Sequence
<220> FEATURE:
<223> OTHER INFORMATION: peptide

<400> SEQUENCE: 71

Leu Leu Ser Asp Val Gly Thr Leu Leu
1               5

<210> SEQ ID NO 72
<211> LENGTH: 9
<212> TYPE: PRT
<213> ORGANISM: Artificial Sequence
<220> FEATURE:
<223> OTHER INFORMATION: peptide

<400> SEQUENCE: 72

Phe Leu Ser Thr Tyr Leu Leu Pro Met
1               5

<210> SEQ ID NO 73
<211> LENGTH: 9
<212> TYPE: PRT
<213> ORGANISM: Artificial Sequence
<220> FEATURE:
<223> OTHER INFORMATION: peptide

<400> SEQUENCE: 73

Ala Leu Leu Glu Glu Tyr Thr Gly Ile
1               5

<210> SEQ ID NO 74
<211> LENGTH: 9
<212> TYPE: PRT
<213> ORGANISM: Artificial Sequence
<220> FEATURE:
<223> OTHER INFORMATION: peptide

<400> SEQUENCE: 74

Ser Leu Leu Cys Ile Val Ile Gly Leu
1               5

<210> SEQ ID NO 75
<211> LENGTH: 9
<212> TYPE: PRT
<213> ORGANISM: Artificial Sequence
<220> FEATURE:
<223> OTHER INFORMATION: peptide

<400> SEQUENCE: 75

Ile Leu Leu Cys Ile Val Ile Gly Leu
1               5

<210> SEQ ID NO 76
```

```
<211> LENGTH: 9
<212> TYPE: PRT
<213> ORGANISM: Artificial Sequence
<220> FEATURE:
<223> OTHER INFORMATION: peptide

<400> SEQUENCE: 76

Met Leu Val Thr Val Val Leu Thr Val
1               5

<210> SEQ ID NO 77
<211> LENGTH: 9
<212> TYPE: PRT
<213> ORGANISM: Artificial Sequence
<220> FEATURE:
<223> OTHER INFORMATION: peptide

<400> SEQUENCE: 77

Met Leu Val Thr Val Val Leu Leu Val
1               5

<210> SEQ ID NO 78
<211> LENGTH: 9
<212> TYPE: PRT
<213> ORGANISM: Artificial Sequence
<220> FEATURE:
<223> OTHER INFORMATION: peptide

<400> SEQUENCE: 78

Leu Leu Val Thr Val Val Leu Pro Val
1               5

<210> SEQ ID NO 79
<211> LENGTH: 9
<212> TYPE: PRT
<213> ORGANISM: Artificial Sequence
<220> FEATURE:
<223> OTHER INFORMATION: peptide

<400> SEQUENCE: 79

Leu Leu Val Thr Val Val Leu Ala Val
1               5

<210> SEQ ID NO 80
<211> LENGTH: 9
<212> TYPE: PRT
<213> ORGANISM: Artificial Sequence
<220> FEATURE:
<223> OTHER INFORMATION: peptide

<400> SEQUENCE: 80

Lys Leu Val Thr Val Val Leu Ala Val
1               5

<210> SEQ ID NO 81
<211> LENGTH: 9
<212> TYPE: PRT
<213> ORGANISM: Artificial Sequence
<220> FEATURE:
<223> OTHER INFORMATION: peptide

<400> SEQUENCE: 81

Ile Leu Val Thr Val Val Leu Gly Ile
1               5

<210> SEQ ID NO 82
<211> LENGTH: 9
```

```
<212> TYPE: PRT
<213> ORGANISM: Artificial Sequence
<220> FEATURE:
<223> OTHER INFORMATION: peptide

<400> SEQUENCE: 82

Leu Met Ala Leu Val Leu Met Leu Val
1               5

<210> SEQ ID NO 83
<211> LENGTH: 9
<212> TYPE: PRT
<213> ORGANISM: Artificial Sequence
<220> FEATURE:
<223> OTHER INFORMATION: peptide

<400> SEQUENCE: 83

Gly Leu Thr Phe Trp Asn Pro Asn Val
1               5

<210> SEQ ID NO 84
<211> LENGTH: 9
<212> TYPE: PRT
<213> ORGANISM: Artificial Sequence
<220> FEATURE:
<223> OTHER INFORMATION: peptide

<400> SEQUENCE: 84

Phe Met Leu Leu Leu Ser Ala Ala Ala
1               5

<210> SEQ ID NO 85
<211> LENGTH: 9
<212> TYPE: PRT
<213> ORGANISM: Artificial Sequence
<220> FEATURE:
<223> OTHER INFORMATION: peptide

<400> SEQUENCE: 85

Phe Leu Leu Leu Leu Ser Ala Ala Leu
1               5

<210> SEQ ID NO 86
<211> LENGTH: 9
<212> TYPE: PRT
<213> ORGANISM: Artificial Sequence
<220> FEATURE:
<223> OTHER INFORMATION: peptide

<400> SEQUENCE: 86

Tyr Leu Leu Ser Ala Ala Leu Thr Leu
1               5

<210> SEQ ID NO 87
<211> LENGTH: 9
<212> TYPE: PRT
<213> ORGANISM: Artificial Sequence
<220> FEATURE:
<223> OTHER INFORMATION: peptide

<400> SEQUENCE: 87

Tyr Leu Leu Ser Ala Ala Leu Thr Ile
1               5

<210> SEQ ID NO 88
<211> LENGTH: 9
<212> TYPE: PRT
```

```
<213> ORGANISM: Artificial Sequence
<220> FEATURE:
<223> OTHER INFORMATION: peptide

<400> SEQUENCE: 88

Val Leu Leu Ser Ala Ala Leu Leu Leu
1               5

<210> SEQ ID NO 89
<211> LENGTH: 9
<212> TYPE: PRT
<213> ORGANISM: Artificial Sequence
<220> FEATURE:
<223> OTHER INFORMATION: peptide

<400> SEQUENCE: 89

Val Leu Leu Ser Ala Ala Leu Phe Leu
1               5

<210> SEQ ID NO 90
<211> LENGTH: 9
<212> TYPE: PRT
<213> ORGANISM: Artificial Sequence
<220> FEATURE:
<223> OTHER INFORMATION: peptide

<400> SEQUENCE: 90

Ser Leu Leu Ser Ala Ala Leu Thr Val
1               5

<210> SEQ ID NO 91
<211> LENGTH: 9
<212> TYPE: PRT
<213> ORGANISM: Artificial Sequence
<220> FEATURE:
<223> OTHER INFORMATION: peptide

<400> SEQUENCE: 91

Arg Leu Leu Ser Ala Ala Leu Ala Leu
1               5

<210> SEQ ID NO 92
<211> LENGTH: 9
<212> TYPE: PRT
<213> ORGANISM: Artificial Sequence
<220> FEATURE:
<223> OTHER INFORMATION: peptide

<400> SEQUENCE: 92

Leu Met Leu Ser Ala Ala Leu Leu Leu
1               5

<210> SEQ ID NO 93
<211> LENGTH: 9
<212> TYPE: PRT
<213> ORGANISM: Artificial Sequence
<220> FEATURE:
<223> OTHER INFORMATION: peptide

<400> SEQUENCE: 93

Leu Met Leu Ser Ala Ala Leu Cys Val
1               5

<210> SEQ ID NO 94
<211> LENGTH: 9
<212> TYPE: PRT
<213> ORGANISM: Artificial Sequence
```

```
<220> FEATURE:
<223> OTHER INFORMATION: peptide

<400> SEQUENCE: 94

Leu Met Leu Ser Ala Ala Leu Ala Val
1               5

<210> SEQ ID NO 95
<211> LENGTH: 9
<212> TYPE: PRT
<213> ORGANISM: Artificial Sequence
<220> FEATURE:
<223> OTHER INFORMATION: peptide

<400> SEQUENCE: 95

Leu Leu Leu Ser Ala Ala Leu Trp Val
1               5

<210> SEQ ID NO 96
<211> LENGTH: 9
<212> TYPE: PRT
<213> ORGANISM: Artificial Sequence
<220> FEATURE:
<223> OTHER INFORMATION: peptide

<400> SEQUENCE: 96

Leu Leu Leu Ser Ala Ala Leu Thr Val
1               5

<210> SEQ ID NO 97
<211> LENGTH: 9
<212> TYPE: PRT
<213> ORGANISM: Artificial Sequence
<220> FEATURE:
<223> OTHER INFORMATION: peptide

<400> SEQUENCE: 97

Leu Leu Leu Ser Ala Ala Leu Ser Val
1               5

<210> SEQ ID NO 98
<211> LENGTH: 9
<212> TYPE: PRT
<213> ORGANISM: Artificial Sequence
<220> FEATURE:
<223> OTHER INFORMATION: peptide

<400> SEQUENCE: 98

Leu Leu Leu Ser Ala Ala Leu Met Ile
1               5

<210> SEQ ID NO 99
<211> LENGTH: 9
<212> TYPE: PRT
<213> ORGANISM: Artificial Sequence
<220> FEATURE:
<223> OTHER INFORMATION: peptide

<400> SEQUENCE: 99

Leu Leu Leu Ser Ala Ala Leu Leu Leu
1               5

<210> SEQ ID NO 100
<211> LENGTH: 9
<212> TYPE: PRT
<213> ORGANISM: Artificial Sequence
<220> FEATURE:
```

<223> OTHER INFORMATION: peptide

<400> SEQUENCE: 100

Leu Leu Leu Ser Ala Ala Leu Cys Val
1               5

<210> SEQ ID NO 101
<211> LENGTH: 9
<212> TYPE: PRT
<213> ORGANISM: Artificial Sequence
<220> FEATURE:
<223> OTHER INFORMATION: peptide

<400> SEQUENCE: 101

Leu Leu Leu Ser Ala Ala Leu Ala Leu
1               5

<210> SEQ ID NO 102
<211> LENGTH: 9
<212> TYPE: PRT
<213> ORGANISM: Artificial Sequence
<220> FEATURE:
<223> OTHER INFORMATION: peptide

<400> SEQUENCE: 102

Lys Leu Leu Ser Ala Ala Leu Ser Val
1               5

<210> SEQ ID NO 103
<211> LENGTH: 9
<212> TYPE: PRT
<213> ORGANISM: Artificial Sequence
<220> FEATURE:
<223> OTHER INFORMATION: peptide

<400> SEQUENCE: 103

Ile Leu Leu Ser Ala Ala Leu Leu Leu
1               5

<210> SEQ ID NO 104
<211> LENGTH: 9
<212> TYPE: PRT
<213> ORGANISM: Artificial Sequence
<220> FEATURE:
<223> OTHER INFORMATION: peptide

<400> SEQUENCE: 104

Ile Leu Leu Ser Ala Ala Leu Gly Ile
1               5

<210> SEQ ID NO 105
<211> LENGTH: 9
<212> TYPE: PRT
<213> ORGANISM: Artificial Sequence
<220> FEATURE:
<223> OTHER INFORMATION: peptide

<400> SEQUENCE: 105

Phe Leu Leu Ser Ala Ala Leu Val Val
1               5

<210> SEQ ID NO 106
<211> LENGTH: 9
<212> TYPE: PRT
<213> ORGANISM: Artificial Sequence
<220> FEATURE:
<223> OTHER INFORMATION: peptide

```
<400> SEQUENCE: 106

Phe Leu Leu Ser Ala Ala Leu Ile Leu
1               5

<210> SEQ ID NO 107
<211> LENGTH: 9
<212> TYPE: PRT
<213> ORGANISM: Artificial Sequence
<220> FEATURE:
<223> OTHER INFORMATION: peptide

<400> SEQUENCE: 107

Ala Leu Leu Ser Ala Ala Leu Met Leu
1               5

<210> SEQ ID NO 108
<211> LENGTH: 9
<212> TYPE: PRT
<213> ORGANISM: Artificial Sequence
<220> FEATURE:
<223> OTHER INFORMATION: peptide

<400> SEQUENCE: 108

Ala Leu Leu Ser Ala Ala Leu Leu Val
1               5

<210> SEQ ID NO 109
<211> LENGTH: 9
<212> TYPE: PRT
<213> ORGANISM: Artificial Sequence
<220> FEATURE:
<223> OTHER INFORMATION: peptide

<400> SEQUENCE: 109

Ala Leu Leu Ser Ala Ala Leu Leu Leu
1               5

<210> SEQ ID NO 110
<211> LENGTH: 9
<212> TYPE: PRT
<213> ORGANISM: Artificial Sequence
<220> FEATURE:
<223> OTHER INFORMATION: peptide

<400> SEQUENCE: 110

Tyr Met Ala Gly Ala Met Val Gln Leu
1               5

<210> SEQ ID NO 111
<211> LENGTH: 9
<212> TYPE: PRT
<213> ORGANISM: Artificial Sequence
<220> FEATURE:
<223> OTHER INFORMATION: peptide

<400> SEQUENCE: 111

Arg Met Ala Gly Ala Met Val Pro Val
1               5

<210> SEQ ID NO 112
<211> LENGTH: 9
<212> TYPE: PRT
<213> ORGANISM: Artificial Sequence
<220> FEATURE:
<223> OTHER INFORMATION: peptide
```

```
<400> SEQUENCE: 112

Arg Leu Ala Gly Ala Met Val Asp Val
1               5

<210> SEQ ID NO 113
<211> LENGTH: 9
<212> TYPE: PRT
<213> ORGANISM: Artificial Sequence
<220> FEATURE:
<223> OTHER INFORMATION: peptide

<400> SEQUENCE: 113

Met Met Thr Gly Phe Val Val Leu Met
1               5

<210> SEQ ID NO 114
<211> LENGTH: 9
<212> TYPE: PRT
<213> ORGANISM: Artificial Sequence
<220> FEATURE:
<223> OTHER INFORMATION: peptide

<400> SEQUENCE: 114

Tyr Leu Ala Ser Ser Glu Thr His Val
1               5

<210> SEQ ID NO 115
<211> LENGTH: 9
<212> TYPE: PRT
<213> ORGANISM: Artificial Sequence
<220> FEATURE:
<223> OTHER INFORMATION: peptide

<400> SEQUENCE: 115

Ser Met Leu Ser Ile Gly Gly Tyr Val
1               5

<210> SEQ ID NO 116
<211> LENGTH: 9
<212> TYPE: PRT
<213> ORGANISM: Artificial Sequence
<220> FEATURE:
<223> OTHER INFORMATION: peptide

<400> SEQUENCE: 116

Leu Leu Ile Tyr Ser Phe Ala Arg Val
1               5

<210> SEQ ID NO 117
<211> LENGTH: 9
<212> TYPE: PRT
<213> ORGANISM: Artificial Sequence
<220> FEATURE:
<223> OTHER INFORMATION: peptide

<400> SEQUENCE: 117

Lys Leu Ile His Glu Leu Ala Glu Val
1               5

<210> SEQ ID NO 118
<211> LENGTH: 9
<212> TYPE: PRT
<213> ORGANISM: Artificial Sequence
<220> FEATURE:
<223> OTHER INFORMATION: peptide

<400> SEQUENCE: 118
```

Ile Leu Ile His Glu Leu Ala His Ile
1               5

<210> SEQ ID NO 119
<211> LENGTH: 9
<212> TYPE: PRT
<213> ORGANISM: Artificial Sequence
<220> FEATURE:
<223> OTHER INFORMATION: peptide

<400> SEQUENCE: 119

His Leu Trp Ala Gly Val Val Leu Val
1               5

<210> SEQ ID NO 120
<211> LENGTH: 9
<212> TYPE: PRT
<213> ORGANISM: Artificial Sequence
<220> FEATURE:
<223> OTHER INFORMATION: peptide

<400> SEQUENCE: 120

Arg Leu Trp Asp Phe Thr Val Gly Val
1               5

<210> SEQ ID NO 121
<211> LENGTH: 9
<212> TYPE: PRT
<213> ORGANISM: Artificial Sequence
<220> FEATURE:
<223> OTHER INFORMATION: peptide

<400> SEQUENCE: 121

Val Leu Ala Ser Ser Ile Leu Tyr Ile
1               5

<210> SEQ ID NO 122
<211> LENGTH: 9
<212> TYPE: PRT
<213> ORGANISM: Artificial Sequence
<220> FEATURE:
<223> OTHER INFORMATION: peptide

<400> SEQUENCE: 122

Ser Leu Ala Ser Ser Ile Leu Gln Leu
1               5

<210> SEQ ID NO 123
<211> LENGTH: 9
<212> TYPE: PRT
<213> ORGANISM: Artificial Sequence
<220> FEATURE:
<223> OTHER INFORMATION: peptide

<400> SEQUENCE: 123

Ala Leu Ala Ser Ser Ile Leu Gln Leu
1               5

<210> SEQ ID NO 124
<211> LENGTH: 9
<212> TYPE: PRT
<213> ORGANISM: Artificial Sequence
<220> FEATURE:
<223> OTHER INFORMATION: peptide

<400> SEQUENCE: 124

```
Phe Leu Ala Val Ser Leu Ala Pro Leu
1               5

<210> SEQ ID NO 125
<211> LENGTH: 9
<212> TYPE: PRT
<213> ORGANISM: Artificial Sequence
<220> FEATURE:
<223> OTHER INFORMATION: peptide

<400> SEQUENCE: 125

Ile Leu Val Gly Leu Phe Val Pro Val
1               5

<210> SEQ ID NO 126
<211> LENGTH: 9
<212> TYPE: PRT
<213> ORGANISM: Artificial Sequence
<220> FEATURE:
<223> OTHER INFORMATION: peptide

<400> SEQUENCE: 126

Ile Leu Val Gly Leu Phe Val Ala Val
1               5

<210> SEQ ID NO 127
<211> LENGTH: 9
<212> TYPE: PRT
<213> ORGANISM: Artificial Sequence
<220> FEATURE:
<223> OTHER INFORMATION: peptide

<400> SEQUENCE: 127

Tyr Leu Phe Val Leu Leu Ala Gly Ile
1               5

<210> SEQ ID NO 128
<211> LENGTH: 9
<212> TYPE: PRT
<213> ORGANISM: Artificial Sequence
<220> FEATURE:
<223> OTHER INFORMATION: peptide

<400> SEQUENCE: 128

Ser Leu Phe Val Leu Leu Ala Ala Val
1               5

<210> SEQ ID NO 129
<211> LENGTH: 9
<212> TYPE: PRT
<213> ORGANISM: Artificial Sequence
<220> FEATURE:
<223> OTHER INFORMATION: peptide

<400> SEQUENCE: 129

Lys Leu Phe Val Leu Leu Ala Leu Val
1               5

<210> SEQ ID NO 130
<211> LENGTH: 9
<212> TYPE: PRT
<213> ORGANISM: Artificial Sequence
<220> FEATURE:
<223> OTHER INFORMATION: peptide

<400> SEQUENCE: 130

Gly Ile Tyr Asp Phe Phe Val Lys Val
```

```
1               5

<210> SEQ ID NO 131
<211> LENGTH: 9
<212> TYPE: PRT
<213> ORGANISM: Artificial Sequence
<220> FEATURE:
<223> OTHER INFORMATION: peptide

<400> SEQUENCE: 131

Thr Ile Met Gly Thr Leu Val Ser Val
1               5

<210> SEQ ID NO 132
<211> LENGTH: 9
<212> TYPE: PRT
<213> ORGANISM: Artificial Sequence
<220> FEATURE:
<223> OTHER INFORMATION: peptide

<400> SEQUENCE: 132

Arg Val Met Gly Thr Leu Val Gly Ile
1               5

<210> SEQ ID NO 133
<211> LENGTH: 9
<212> TYPE: PRT
<213> ORGANISM: Artificial Sequence
<220> FEATURE:
<223> OTHER INFORMATION: peptide

<400> SEQUENCE: 133

Thr Leu Ala Glu Gly Leu Ala Leu Ala
1               5

<210> SEQ ID NO 134
<211> LENGTH: 9
<212> TYPE: PRT
<213> ORGANISM: Artificial Sequence
<220> FEATURE:
<223> OTHER INFORMATION: peptide

<400> SEQUENCE: 134

Phe Leu Ala Ala Gly Leu Gly Gln Val
1               5

<210> SEQ ID NO 135
<211> LENGTH: 9
<212> TYPE: PRT
<213> ORGANISM: Artificial Sequence
<220> FEATURE:
<223> OTHER INFORMATION: peptide

<400> SEQUENCE: 135

Val Leu Glu Ser Ile Leu His Pro Val
1               5

<210> SEQ ID NO 136
<211> LENGTH: 9
<212> TYPE: PRT
<213> ORGANISM: Artificial Sequence
<220> FEATURE:
<223> OTHER INFORMATION: peptide

<400> SEQUENCE: 136

Arg Met Glu Ser Ile Leu His Glu Val
1               5
```

```
<210> SEQ ID NO 137
<211> LENGTH: 9
<212> TYPE: PRT
<213> ORGANISM: Artificial Sequence
<220> FEATURE:
<223> OTHER INFORMATION: peptide

<400> SEQUENCE: 137

Ala Leu Leu Ala Ala Leu Cys Tyr Val
1               5

<210> SEQ ID NO 138
<211> LENGTH: 9
<212> TYPE: PRT
<213> ORGANISM: Artificial Sequence
<220> FEATURE:
<223> OTHER INFORMATION: peptide

<400> SEQUENCE: 138

Tyr Leu Leu Ala Leu Leu Ala Trp Leu
1               5

<210> SEQ ID NO 139
<211> LENGTH: 9
<212> TYPE: PRT
<213> ORGANISM: Artificial Sequence
<220> FEATURE:
<223> OTHER INFORMATION: peptide

<400> SEQUENCE: 139

Val Leu Leu Ala Leu Leu Ala Glu Val
1               5

<210> SEQ ID NO 140
<211> LENGTH: 9
<212> TYPE: PRT
<213> ORGANISM: Artificial Sequence
<220> FEATURE:
<223> OTHER INFORMATION: peptide

<400> SEQUENCE: 140

Ser Leu Leu Ala Leu Leu Ala Phe Val
1               5

<210> SEQ ID NO 141
<211> LENGTH: 9
<212> TYPE: PRT
<213> ORGANISM: Artificial Sequence
<220> FEATURE:
<223> OTHER INFORMATION: peptide

<400> SEQUENCE: 141

Arg Leu Leu Ala Leu Leu Ala Ser Val
1               5

<210> SEQ ID NO 142
<211> LENGTH: 9
<212> TYPE: PRT
<213> ORGANISM: Artificial Sequence
<220> FEATURE:
<223> OTHER INFORMATION: peptide

<400> SEQUENCE: 142

Arg Leu Leu Ala Leu Leu Ala Ala Val
1               5
```

<210> SEQ ID NO 143
<211> LENGTH: 9
<212> TYPE: PRT
<213> ORGANISM: Artificial Sequence
<220> FEATURE:
<223> OTHER INFORMATION: peptide

<400> SEQUENCE: 143

Leu Leu Leu Ala Leu Leu Ala Pro Val
1               5

<210> SEQ ID NO 144
<211> LENGTH: 9
<212> TYPE: PRT
<213> ORGANISM: Artificial Sequence
<220> FEATURE:
<223> OTHER INFORMATION: peptide

<400> SEQUENCE: 144

Ala Leu Leu Ala Leu Leu Ala Ser Val
1               5

<210> SEQ ID NO 145
<211> LENGTH: 9
<212> TYPE: PRT
<213> ORGANISM: Artificial Sequence
<220> FEATURE:
<223> OTHER INFORMATION: peptide

<400> SEQUENCE: 145

Ile Leu Asp Glu Ala Tyr Val Arg Val
1               5

<210> SEQ ID NO 146
<211> LENGTH: 9
<212> TYPE: PRT
<213> ORGANISM: Artificial Sequence
<220> FEATURE:
<223> OTHER INFORMATION: peptide

<400> SEQUENCE: 146

Ala Leu Leu Leu Leu Val Val Gly Val
1               5

<210> SEQ ID NO 147
<211> LENGTH: 9
<212> TYPE: PRT
<213> ORGANISM: Artificial Sequence
<220> FEATURE:
<223> OTHER INFORMATION: peptide

<400> SEQUENCE: 147

Gly Leu Gly Ala Leu Leu Leu Leu Val
1               5

<210> SEQ ID NO 148
<211> LENGTH: 9
<212> TYPE: PRT
<213> ORGANISM: Artificial Sequence
<220> FEATURE:
<223> OTHER INFORMATION: peptide

<400> SEQUENCE: 148

Tyr Met Gln Glu Ile Leu His Arg Leu
1               5

```
<210> SEQ ID NO 149
<211> LENGTH: 9
<212> TYPE: PRT
<213> ORGANISM: Artificial Sequence
<220> FEATURE:
<223> OTHER INFORMATION: peptide

<400> SEQUENCE: 149

Thr Leu Ala Val Val Ser Leu Ala Val
1               5

<210> SEQ ID NO 150
<211> LENGTH: 9
<212> TYPE: PRT
<213> ORGANISM: Artificial Sequence
<220> FEATURE:
<223> OTHER INFORMATION: peptide

<400> SEQUENCE: 150

Leu Leu Ala Val Val Ser Leu Phe Val
1               5

<210> SEQ ID NO 151
<211> LENGTH: 9
<212> TYPE: PRT
<213> ORGANISM: Artificial Sequence
<220> FEATURE:
<223> OTHER INFORMATION: peptide

<400> SEQUENCE: 151

Tyr Leu Val Gly Ile Leu Leu Val Leu
1               5

<210> SEQ ID NO 152
<211> LENGTH: 9
<212> TYPE: PRT
<213> ORGANISM: Artificial Sequence
<220> FEATURE:
<223> OTHER INFORMATION: peptide

<400> SEQUENCE: 152

Lys Val Val Gly Ile Leu Leu Pro Ile
1               5

<210> SEQ ID NO 153
<211> LENGTH: 9
<212> TYPE: PRT
<213> ORGANISM: Artificial Sequence
<220> FEATURE:
<223> OTHER INFORMATION: peptide

<400> SEQUENCE: 153

Ile Leu Val Gly Ile Leu Leu Val Val
1               5

<210> SEQ ID NO 154
<211> LENGTH: 9
<212> TYPE: PRT
<213> ORGANISM: Artificial Sequence
<220> FEATURE:
<223> OTHER INFORMATION: peptide

<400> SEQUENCE: 154

Phe Val Val Gly Ile Leu Leu Gln Val
1               5

<210> SEQ ID NO 155
```

```
<211> LENGTH: 9
<212> TYPE: PRT
<213> ORGANISM: Artificial Sequence
<220> FEATURE:
<223> OTHER INFORMATION: peptide

<400> SEQUENCE: 155

Ile Leu Asp Glu Ala Tyr Val Arg Val
1               5

<210> SEQ ID NO 156
<211> LENGTH: 9
<212> TYPE: PRT
<213> ORGANISM: Artificial Sequence
<220> FEATURE:
<223> OTHER INFORMATION: peptide

<400> SEQUENCE: 156

Leu Leu Ala Leu Leu Pro Pro Glu Val
1               5

<210> SEQ ID NO 157
<211> LENGTH: 9
<212> TYPE: PRT
<213> ORGANISM: Artificial Sequence
<220> FEATURE:
<223> OTHER INFORMATION: peptide

<400> SEQUENCE: 157

Leu Leu Ala Leu Leu Pro Pro Glu Leu
1               5

<210> SEQ ID NO 158
<211> LENGTH: 9
<212> TYPE: PRT
<213> ORGANISM: Artificial Sequence
<220> FEATURE:
<223> OTHER INFORMATION: peptide

<400> SEQUENCE: 158

Ala Met Ala Leu Leu Pro Pro Glu Val
1               5

<210> SEQ ID NO 159
<211> LENGTH: 9
<212> TYPE: PRT
<213> ORGANISM: Artificial Sequence
<220> FEATURE:
<223> OTHER INFORMATION: peptide

<400> SEQUENCE: 159

Ala Leu Ala Leu Leu Pro Pro Pro Val
1               5

<210> SEQ ID NO 160
<211> LENGTH: 9
<212> TYPE: PRT
<213> ORGANISM: Artificial Sequence
<220> FEATURE:
<223> OTHER INFORMATION: peptide

<400> SEQUENCE: 160

Ile Leu Ile Ser Ala Val Val Gly Leu
1               5

<210> SEQ ID NO 161
<211> LENGTH: 9
```

```
<212> TYPE: PRT
<213> ORGANISM: Artificial Sequence
<220> FEATURE:
<223> OTHER INFORMATION: peptide

<400> SEQUENCE: 161

Ile Val Leu Gly Val Val Phe Gly Val
1               5

<210> SEQ ID NO 162
<211> LENGTH: 9
<212> TYPE: PRT
<213> ORGANISM: Artificial Sequence
<220> FEATURE:
<223> OTHER INFORMATION: peptide

<400> SEQUENCE: 162

Ile Ile Leu Gly Val Val Phe Gly Leu
1               5

<210> SEQ ID NO 163
<211> LENGTH: 9
<212> TYPE: PRT
<213> ORGANISM: Artificial Sequence
<220> FEATURE:
<223> OTHER INFORMATION: peptide

<400> SEQUENCE: 163

Tyr Leu Leu Glu Leu Leu Ser Ala Leu
1               5

<210> SEQ ID NO 164
<211> LENGTH: 9
<212> TYPE: PRT
<213> ORGANISM: Artificial Sequence
<220> FEATURE:
<223> OTHER INFORMATION: peptide

<400> SEQUENCE: 164

Ile Met Trp Gln Phe Leu Leu Glu Leu
1               5

<210> SEQ ID NO 165
<211> LENGTH: 9
<212> TYPE: PRT
<213> ORGANISM: Artificial Sequence
<220> FEATURE:
<223> OTHER INFORMATION: peptide

<400> SEQUENCE: 165

Tyr Leu Leu Asp Ala Glu Pro Gln Leu
1               5

<210> SEQ ID NO 166
<211> LENGTH: 9
<212> TYPE: PRT
<213> ORGANISM: Artificial Sequence
<220> FEATURE:
<223> OTHER INFORMATION: peptide

<400> SEQUENCE: 166

Lys Leu Thr Asp Thr Leu Ile Pro Leu
1               5

<210> SEQ ID NO 167
<211> LENGTH: 9
<212> TYPE: PRT
```

```
<213> ORGANISM: Artificial Sequence
<220> FEATURE:
<223> OTHER INFORMATION: peptide

<400> SEQUENCE: 167

Lys Leu Thr Asp Thr Leu Ile Glu Leu
1               5

<210> SEQ ID NO 168
<211> LENGTH: 9
<212> TYPE: PRT
<213> ORGANISM: Artificial Sequence
<220> FEATURE:
<223> OTHER INFORMATION: peptide

<400> SEQUENCE: 168

Tyr Leu Leu Phe Ala Pro Asn Ala Val
1               5

<210> SEQ ID NO 169
<211> LENGTH: 9
<212> TYPE: PRT
<213> ORGANISM: Artificial Sequence
<220> FEATURE:
<223> OTHER INFORMATION: peptide

<400> SEQUENCE: 169

Phe Leu Leu Phe Ala Pro Asn Ser Ala
1               5

<210> SEQ ID NO 170
<211> LENGTH: 9
<212> TYPE: PRT
<213> ORGANISM: Artificial Sequence
<220> FEATURE:
<223> OTHER INFORMATION: peptide

<400> SEQUENCE: 170

Tyr Leu Asp Ala Glu Pro Pro Ala Val
1               5

<210> SEQ ID NO 171
<211> LENGTH: 9
<212> TYPE: PRT
<213> ORGANISM: Artificial Sequence
<220> FEATURE:
<223> OTHER INFORMATION: peptide

<400> SEQUENCE: 171

Thr Leu Asn Ser Gly Val Tyr Leu Ile
1               5

<210> SEQ ID NO 172
<211> LENGTH: 9
<212> TYPE: PRT
<213> ORGANISM: Artificial Sequence
<220> FEATURE:
<223> OTHER INFORMATION: peptide

<400> SEQUENCE: 172

Lys Met Asn Ser Gly Val Tyr Val Ile
1               5

<210> SEQ ID NO 173
<211> LENGTH: 9
<212> TYPE: PRT
<213> ORGANISM: Artificial Sequence
```

```
<220> FEATURE:
<223> OTHER INFORMATION: peptide

<400> SEQUENCE: 173

Leu Leu Ile Gly Leu Val Trp Ser Leu
1               5

<210> SEQ ID NO 174
<211> LENGTH: 9
<212> TYPE: PRT
<213> ORGANISM: Artificial Sequence
<220> FEATURE:
<223> OTHER INFORMATION: peptide

<400> SEQUENCE: 174

Tyr Leu Tyr Asp Leu Leu Leu Thr Val
1               5

<210> SEQ ID NO 175
<211> LENGTH: 9
<212> TYPE: PRT
<213> ORGANISM: Artificial Sequence
<220> FEATURE:
<223> OTHER INFORMATION: peptide

<400> SEQUENCE: 175

Val Leu Tyr Asp Leu Leu Leu Glu Val
1               5

<210> SEQ ID NO 176
<211> LENGTH: 9
<212> TYPE: PRT
<213> ORGANISM: Artificial Sequence
<220> FEATURE:
<223> OTHER INFORMATION: peptide

<400> SEQUENCE: 176

Thr Leu Tyr Asp Leu Leu Leu Ser Leu
1               5

<210> SEQ ID NO 177
<211> LENGTH: 9
<212> TYPE: PRT
<213> ORGANISM: Artificial Sequence
<220> FEATURE:
<223> OTHER INFORMATION: peptide

<400> SEQUENCE: 177

Gln Leu Tyr Asp Leu Leu Leu Val Ala
1               5

<210> SEQ ID NO 178
<211> LENGTH: 9
<212> TYPE: PRT
<213> ORGANISM: Artificial Sequence
<220> FEATURE:
<223> OTHER INFORMATION: peptide

<400> SEQUENCE: 178

Gln Leu Tyr Asp Leu Leu Leu Ser Leu
1               5

<210> SEQ ID NO 179
<211> LENGTH: 9
<212> TYPE: PRT
<213> ORGANISM: Artificial Sequence
<220> FEATURE:
```

```
<223> OTHER INFORMATION: peptide

<400> SEQUENCE: 179

Gly Leu Tyr Asp Leu Leu Leu Arg Ile
1               5

<210> SEQ ID NO 180
<211> LENGTH: 9
<212> TYPE: PRT
<213> ORGANISM: Artificial Sequence
<220> FEATURE:
<223> OTHER INFORMATION: peptide

<400> SEQUENCE: 180

Ala Val Tyr Asp Leu Leu Leu Glu Val
1               5

<210> SEQ ID NO 181
<211> LENGTH: 9
<212> TYPE: PRT
<213> ORGANISM: Artificial Sequence
<220> FEATURE:
<223> OTHER INFORMATION: peptide

<400> SEQUENCE: 181

Ala Leu Tyr Asp Leu Leu Leu Glu Val
1               5

<210> SEQ ID NO 182
<211> LENGTH: 9
<212> TYPE: PRT
<213> ORGANISM: Artificial Sequence
<220> FEATURE:
<223> OTHER INFORMATION: peptide

<400> SEQUENCE: 182

Val Leu Leu Leu Ile Leu Ser Gly Val
1               5

<210> SEQ ID NO 183
<211> LENGTH: 9
<212> TYPE: PRT
<213> ORGANISM: Artificial Sequence
<220> FEATURE:
<223> OTHER INFORMATION: peptide

<400> SEQUENCE: 183

Val Leu Leu Leu Ile Leu Ser Glu Val
1               5

<210> SEQ ID NO 184
<211> LENGTH: 9
<212> TYPE: PRT
<213> ORGANISM: Artificial Sequence
<220> FEATURE:
<223> OTHER INFORMATION: peptide

<400> SEQUENCE: 184

Ser Leu Leu Leu Ile Leu Ser Phe Val
1               5

<210> SEQ ID NO 185
<211> LENGTH: 9
<212> TYPE: PRT
<213> ORGANISM: Artificial Sequence
<220> FEATURE:
<223> OTHER INFORMATION: peptide
```

<400> SEQUENCE: 185

Met Leu Leu Leu Ile Leu Ser Tyr Leu
1               5

<210> SEQ ID NO 186
<211> LENGTH: 9
<212> TYPE: PRT
<213> ORGANISM: Artificial Sequence
<220> FEATURE:
<223> OTHER INFORMATION: peptide

<400> SEQUENCE: 186

Ile Leu Leu Leu Ile Leu Ser Gly Ile
1               5

<210> SEQ ID NO 187
<211> LENGTH: 9
<212> TYPE: PRT
<213> ORGANISM: Artificial Sequence
<220> FEATURE:
<223> OTHER INFORMATION: peptide

<400> SEQUENCE: 187

Phe Leu Leu Leu Ile Leu Ser Leu Leu
1               5

<210> SEQ ID NO 188
<211> LENGTH: 9
<212> TYPE: PRT
<213> ORGANISM: Artificial Sequence
<220> FEATURE:
<223> OTHER INFORMATION: peptide

<400> SEQUENCE: 188

Phe Leu Leu Leu Ile Leu Ser Phe Leu
1               5

<210> SEQ ID NO 189
<211> LENGTH: 9
<212> TYPE: PRT
<213> ORGANISM: Artificial Sequence
<220> FEATURE:
<223> OTHER INFORMATION: peptide

<400> SEQUENCE: 189

Ser Leu Ala Gln Leu Leu Leu Ala Ile
1               5

<210> SEQ ID NO 190
<211> LENGTH: 9
<212> TYPE: PRT
<213> ORGANISM: Artificial Sequence
<220> FEATURE:
<223> OTHER INFORMATION: peptide

<400> SEQUENCE: 190

Met Leu Ala Gln Leu Leu Leu Thr Val
1               5

<210> SEQ ID NO 191
<211> LENGTH: 9
<212> TYPE: PRT
<213> ORGANISM: Artificial Sequence
<220> FEATURE:
<223> OTHER INFORMATION: peptide

<400> SEQUENCE: 191

Lys Leu Ile His Leu Met Ala Ala Val
1               5

<210> SEQ ID NO 192
<211> LENGTH: 9
<212> TYPE: PRT
<213> ORGANISM: Artificial Sequence
<220> FEATURE:
<223> OTHER INFORMATION: peptide

<400> SEQUENCE: 192

Phe Leu Asp Lys Ile Thr Asp Leu Val
1               5

<210> SEQ ID NO 193
<211> LENGTH: 9
<212> TYPE: PRT
<213> ORGANISM: Artificial Sequence
<220> FEATURE:
<223> OTHER INFORMATION: peptide

<400> SEQUENCE: 193

Phe Leu Val Glu Asp Glu Thr Val Ile
1               5

<210> SEQ ID NO 194
<211> LENGTH: 9
<212> TYPE: PRT
<213> ORGANISM: Artificial Sequence
<220> FEATURE:
<223> OTHER INFORMATION: peptide

<400> SEQUENCE: 194

Ala Val Phe Arg Val Leu Ile Pro Val
1               5

<210> SEQ ID NO 195
<211> LENGTH: 9
<212> TYPE: PRT
<213> ORGANISM: Artificial Sequence
<220> FEATURE:
<223> OTHER INFORMATION: peptide

<400> SEQUENCE: 195

Leu Leu Ser Ala Val Leu Ala Leu Val
1               5

<210> SEQ ID NO 196
<211> LENGTH: 9
<212> TYPE: PRT
<213> ORGANISM: Artificial Sequence
<220> FEATURE:
<223> OTHER INFORMATION: peptide

<400> SEQUENCE: 196

Leu Leu Ser Ala Val Leu Ala Leu Ala
1               5

<210> SEQ ID NO 197
<211> LENGTH: 9
<212> TYPE: PRT
<213> ORGANISM: Artificial Sequence
<220> FEATURE:
<223> OTHER INFORMATION: peptide

<400> SEQUENCE: 197

Gly Ile Ser Ala Val Leu Ala Leu Val
1               5

<210> SEQ ID NO 198
<211> LENGTH: 9
<212> TYPE: PRT
<213> ORGANISM: Artificial Sequence
<220> FEATURE:
<223> OTHER INFORMATION: peptide

<400> SEQUENCE: 198

Asn Leu Trp Ala Gly Gly Phe Phe Leu
1               5

<210> SEQ ID NO 199
<211> LENGTH: 9
<212> TYPE: PRT
<213> ORGANISM: Artificial Sequence
<220> FEATURE:
<223> OTHER INFORMATION: peptide

<400> SEQUENCE: 199

Tyr Leu Ala Leu Leu Val Met Leu Leu
1               5

<210> SEQ ID NO 200
<211> LENGTH: 9
<212> TYPE: PRT
<213> ORGANISM: Artificial Sequence
<220> FEATURE:
<223> OTHER INFORMATION: peptide

<400> SEQUENCE: 200

Leu Leu Ala Leu Leu Val Met Ala Val
1               5

<210> SEQ ID NO 201
<211> LENGTH: 9
<212> TYPE: PRT
<213> ORGANISM: Artificial Sequence
<220> FEATURE:
<223> OTHER INFORMATION: peptide

<400> SEQUENCE: 201

Ala Leu Ala Leu Leu Val Met Ala Val
1               5

<210> SEQ ID NO 202
<211> LENGTH: 9
<212> TYPE: PRT
<213> ORGANISM: Artificial Sequence
<220> FEATURE:
<223> OTHER INFORMATION: peptide

<400> SEQUENCE: 202

Thr Met Leu Ser Cys Leu Leu His Leu
1               5

<210> SEQ ID NO 203
<211> LENGTH: 9
<212> TYPE: PRT
<213> ORGANISM: Artificial Sequence
<220> FEATURE:
<223> OTHER INFORMATION: peptide

<400> SEQUENCE: 203

Met Leu Leu Ser Cys Leu Leu Phe Met
1               5

<210> SEQ ID NO 204
<211> LENGTH: 9
<212> TYPE: PRT
<213> ORGANISM: Artificial Sequence
<220> FEATURE:
<223> OTHER INFORMATION: peptide

<400> SEQUENCE: 204

Leu Leu Leu Ser Cys Leu Leu Pro Leu
1               5

<210> SEQ ID NO 205
<211> LENGTH: 9
<212> TYPE: PRT
<213> ORGANISM: Artificial Sequence
<220> FEATURE:
<223> OTHER INFORMATION: peptide

<400> SEQUENCE: 205

Leu Leu Leu Ser Cys Leu Leu His Leu
1               5

<210> SEQ ID NO 206
<211> LENGTH: 9
<212> TYPE: PRT
<213> ORGANISM: Artificial Sequence
<220> FEATURE:
<223> OTHER INFORMATION: peptide

<400> SEQUENCE: 206

Ile Leu Leu Ser Cys Leu Leu Leu Leu
1               5

<210> SEQ ID NO 207
<211> LENGTH: 9
<212> TYPE: PRT
<213> ORGANISM: Artificial Sequence
<220> FEATURE:
<223> OTHER INFORMATION: peptide

<400> SEQUENCE: 207

Phe Leu Leu Ser Cys Leu Leu Cys Leu
1               5

<210> SEQ ID NO 208
<211> LENGTH: 9
<212> TYPE: PRT
<213> ORGANISM: Artificial Sequence
<220> FEATURE:
<223> OTHER INFORMATION: peptide

<400> SEQUENCE: 208

Ala Leu Leu Ser Cys Leu Leu Met Leu
1               5

<210> SEQ ID NO 209
<211> LENGTH: 9
<212> TYPE: PRT
<213> ORGANISM: Artificial Sequence
<220> FEATURE:
<223> OTHER INFORMATION: peptide

<400> SEQUENCE: 209

Tyr Val Ala Ala Thr Leu Phe Ala Leu

```
1               5
```

<210> SEQ ID NO 210
<211> LENGTH: 9
<212> TYPE: PRT
<213> ORGANISM: Artificial Sequence
<220> FEATURE:
<223> OTHER INFORMATION: peptide

<400> SEQUENCE: 210

```
Tyr Leu Tyr Ser Glu Ile Pro Asp Ile
1               5
```

<210> SEQ ID NO 211
<211> LENGTH: 9
<212> TYPE: PRT
<213> ORGANISM: Artificial Sequence
<220> FEATURE:
<223> OTHER INFORMATION: peptide

<400> SEQUENCE: 211

```
Tyr Met Ala Ser Thr Leu Val His Leu
1               5
```

<210> SEQ ID NO 212
<211> LENGTH: 9
<212> TYPE: PRT
<213> ORGANISM: Artificial Sequence
<220> FEATURE:
<223> OTHER INFORMATION: peptide

<400> SEQUENCE: 212

```
Gln Met Ala Ser Thr Leu Val Tyr Leu
1               5
```

<210> SEQ ID NO 213
<211> LENGTH: 9
<212> TYPE: PRT
<213> ORGANISM: Artificial Sequence
<220> FEATURE:
<223> OTHER INFORMATION: peptide

<400> SEQUENCE: 213

```
Tyr Gln Phe Asp Lys Ile Tyr Ser Ile
1               5
```

<210> SEQ ID NO 214
<211> LENGTH: 9
<212> TYPE: PRT
<213> ORGANISM: Artificial Sequence
<220> FEATURE:
<223> OTHER INFORMATION: peptide

<400> SEQUENCE: 214

```
Met Met Phe Trp Leu Leu Leu Val Val
1               5
```

<210> SEQ ID NO 215
<211> LENGTH: 9
<212> TYPE: PRT
<213> ORGANISM: Artificial Sequence
<220> FEATURE:
<223> OTHER INFORMATION: peptide

<400> SEQUENCE: 215

```
Gly Met Leu Trp Glu Ile Phe Gly Val
1               5
```

<210> SEQ ID NO 216
<211> LENGTH: 9
<212> TYPE: PRT
<213> ORGANISM: Artificial Sequence
<220> FEATURE:
<223> OTHER INFORMATION: peptide

<400> SEQUENCE: 216

Ala Met Lys Asp Gly Leu Pro Glu Val
1               5

<210> SEQ ID NO 217
<211> LENGTH: 9
<212> TYPE: PRT
<213> ORGANISM: Artificial Sequence
<220> FEATURE:
<223> OTHER INFORMATION: peptide

<400> SEQUENCE: 217

Thr Leu Leu Asp Ile Ser Phe Ala Ala
1               5

<210> SEQ ID NO 218
<211> LENGTH: 9
<212> TYPE: PRT
<213> ORGANISM: Artificial Sequence
<220> FEATURE:
<223> OTHER INFORMATION: peptide

<400> SEQUENCE: 218

Asn Met Leu Asp Ile Ser Phe Tyr Leu
1               5

<210> SEQ ID NO 219
<211> LENGTH: 9
<212> TYPE: PRT
<213> ORGANISM: Artificial Sequence
<220> FEATURE:
<223> OTHER INFORMATION: peptide

<400> SEQUENCE: 219

Ile Leu Asp Ile Ser Phe Pro Leu Val
1               5

<210> SEQ ID NO 220
<211> LENGTH: 9
<212> TYPE: PRT
<213> ORGANISM: Artificial Sequence
<220> FEATURE:
<223> OTHER INFORMATION: peptide

<400> SEQUENCE: 220

Leu Met Asp Leu Ser Thr Thr Glu Val
1               5

<210> SEQ ID NO 221
<211> LENGTH: 9
<212> TYPE: PRT
<213> ORGANISM: Artificial Sequence
<220> FEATURE:
<223> OTHER INFORMATION: peptide

<400> SEQUENCE: 221

Arg Leu Ser Ser Tyr Leu Val Glu Ile
1               5

<210> SEQ ID NO 222
<211> LENGTH: 9
<212> TYPE: PRT
<213> ORGANISM: Artificial Sequence
<220> FEATURE:
<223> OTHER INFORMATION: peptide

<400> SEQUENCE: 222

Met Val Ser Ser Tyr Leu Val Glu Val
1               5

<210> SEQ ID NO 223
<211> LENGTH: 9
<212> TYPE: PRT
<213> ORGANISM: Artificial Sequence
<220> FEATURE:
<223> OTHER INFORMATION: peptide

<400> SEQUENCE: 223

Lys Val Ser Ser Tyr Leu Val Glu Val
1               5

<210> SEQ ID NO 224
<211> LENGTH: 9
<212> TYPE: PRT
<213> ORGANISM: Artificial Sequence
<220> FEATURE:
<223> OTHER INFORMATION: peptide

<400> SEQUENCE: 224

Ile Leu Ser Lys Ile Leu Leu Phe Ala
1               5

<210> SEQ ID NO 225
<211> LENGTH: 9
<212> TYPE: PRT
<213> ORGANISM: Artificial Sequence
<220> FEATURE:
<223> OTHER INFORMATION: peptide

<400> SEQUENCE: 225

Tyr Gln Leu Ser Tyr Ser Gln Met Val
1               5

<210> SEQ ID NO 226
<211> LENGTH: 9
<212> TYPE: PRT
<213> ORGANISM: Artificial Sequence
<220> FEATURE:
<223> OTHER INFORMATION: peptide

<400> SEQUENCE: 226

Lys Leu Leu Ser Tyr Ser Gln Glu Leu
1               5

<210> SEQ ID NO 227
<211> LENGTH: 9
<212> TYPE: PRT
<213> ORGANISM: Artificial Sequence
<220> FEATURE:
<223> OTHER INFORMATION: peptide

<400> SEQUENCE: 227

Lys Ile Ala Glu Leu Pro Phe Pro Leu
1               5

```
<210> SEQ ID NO 228
<211> LENGTH: 9
<212> TYPE: PRT
<213> ORGANISM: Artificial Sequence
<220> FEATURE:
<223> OTHER INFORMATION: peptide

<400> SEQUENCE: 228

Tyr Leu Asn Glu Ser Glu Thr Val Leu
1               5

<210> SEQ ID NO 229
<211> LENGTH: 9
<212> TYPE: PRT
<213> ORGANISM: Artificial Sequence
<220> FEATURE:
<223> OTHER INFORMATION: peptide

<400> SEQUENCE: 229

Met Leu Val Glu Leu Leu Lys Lys Val
1               5

<210> SEQ ID NO 230
<211> LENGTH: 9
<212> TYPE: PRT
<213> ORGANISM: Artificial Sequence
<220> FEATURE:
<223> OTHER INFORMATION: peptide

<400> SEQUENCE: 230

Lys Leu Val Glu Leu Leu Lys Leu Leu
1               5

<210> SEQ ID NO 231
<211> LENGTH: 9
<212> TYPE: PRT
<213> ORGANISM: Artificial Sequence
<220> FEATURE:
<223> OTHER INFORMATION: peptide

<400> SEQUENCE: 231

Ala Leu Val Glu Leu Leu Lys Pro Leu
1               5

<210> SEQ ID NO 232
<211> LENGTH: 9
<212> TYPE: PRT
<213> ORGANISM: Artificial Sequence
<220> FEATURE:
<223> OTHER INFORMATION: peptide

<400> SEQUENCE: 232

Phe Leu Ala Ser Thr Thr Pro Thr Ala
1               5

<210> SEQ ID NO 233
<211> LENGTH: 9
<212> TYPE: PRT
<213> ORGANISM: Artificial Sequence
<220> FEATURE:
<223> OTHER INFORMATION: peptide

<400> SEQUENCE: 233

Ser Leu Ala Arg Glu Val Ala Ala Val
1               5

<210> SEQ ID NO 234
```

```
<211> LENGTH: 9
<212> TYPE: PRT
<213> ORGANISM: Artificial Sequence
<220> FEATURE:
<223> OTHER INFORMATION: peptide

<400> SEQUENCE: 234

Gly Met Ala Arg Glu Val Ala Ala Val
1               5

<210> SEQ ID NO 235
<211> LENGTH: 9
<212> TYPE: PRT
<213> ORGANISM: Artificial Sequence
<220> FEATURE:
<223> OTHER INFORMATION: peptide

<400> SEQUENCE: 235

Trp Leu Leu Ser Leu Ala Phe Leu Leu
1               5

<210> SEQ ID NO 236
<211> LENGTH: 9
<212> TYPE: PRT
<213> ORGANISM: Artificial Sequence
<220> FEATURE:
<223> OTHER INFORMATION: peptide

<400> SEQUENCE: 236

Ser Leu Leu Ser Leu Ala Phe Ser Ala
1               5

<210> SEQ ID NO 237
<211> LENGTH: 9
<212> TYPE: PRT
<213> ORGANISM: Artificial Sequence
<220> FEATURE:
<223> OTHER INFORMATION: peptide

<400> SEQUENCE: 237

Leu Leu Leu Ser Leu Ala Phe Ile Leu
1               5

<210> SEQ ID NO 238
<211> LENGTH: 9
<212> TYPE: PRT
<213> ORGANISM: Artificial Sequence
<220> FEATURE:
<223> OTHER INFORMATION: peptide

<400> SEQUENCE: 238

Lys Leu Asn Pro Ala Gln Gly Tyr Val
1               5

<210> SEQ ID NO 239
<211> LENGTH: 9
<212> TYPE: PRT
<213> ORGANISM: Artificial Sequence
<220> FEATURE:
<223> OTHER INFORMATION: peptide

<400> SEQUENCE: 239

Lys Leu Trp Gly Leu Ala Thr Leu Ile
1               5

<210> SEQ ID NO 240
<211> LENGTH: 9
```

-continued

```
<212> TYPE: PRT
<213> ORGANISM: Artificial Sequence
<220> FEATURE:
<223> OTHER INFORMATION: peptide

<400> SEQUENCE: 240

Val Leu Ala Leu Gly Leu Leu Ala Val
1               5

<210> SEQ ID NO 241
<211> LENGTH: 9
<212> TYPE: PRT
<213> ORGANISM: Artificial Sequence
<220> FEATURE:
<223> OTHER INFORMATION: peptide

<400> SEQUENCE: 241

Ser Leu Ala Leu Gly Leu Leu Gln Val
1               5

<210> SEQ ID NO 242
<211> LENGTH: 9
<212> TYPE: PRT
<213> ORGANISM: Artificial Sequence
<220> FEATURE:
<223> OTHER INFORMATION: peptide

<400> SEQUENCE: 242

Ser Leu Ala Leu Gly Leu Leu Leu Val
1               5

<210> SEQ ID NO 243
<211> LENGTH: 9
<212> TYPE: PRT
<213> ORGANISM: Artificial Sequence
<220> FEATURE:
<223> OTHER INFORMATION: peptide

<400> SEQUENCE: 243

Met Leu Ala Leu Gly Leu Leu Glu Val
1               5

<210> SEQ ID NO 244
<211> LENGTH: 9
<212> TYPE: PRT
<213> ORGANISM: Artificial Sequence
<220> FEATURE:
<223> OTHER INFORMATION: peptide

<400> SEQUENCE: 244

Gly Leu Ala Leu Gly Leu Leu Phe Val
1               5

<210> SEQ ID NO 245
<211> LENGTH: 9
<212> TYPE: PRT
<213> ORGANISM: Artificial Sequence
<220> FEATURE:
<223> OTHER INFORMATION: peptide

<400> SEQUENCE: 245

Gly Leu Ala Leu Gly Leu Leu Ala Val
1               5

<210> SEQ ID NO 246
<211> LENGTH: 9
<212> TYPE: PRT
```

<213> ORGANISM: Artificial Sequence
<220> FEATURE:
<223> OTHER INFORMATION: peptide

<400> SEQUENCE: 246

Phe Leu Ala Leu Gly Leu Leu Phe Leu
1               5

<210> SEQ ID NO 247
<211> LENGTH: 9
<212> TYPE: PRT
<213> ORGANISM: Artificial Sequence
<220> FEATURE:
<223> OTHER INFORMATION: peptide

<400> SEQUENCE: 247

Ala Leu Ala Leu Gly Leu Leu Met Val
1               5

<210> SEQ ID NO 248
<211> LENGTH: 9
<212> TYPE: PRT
<213> ORGANISM: Artificial Sequence
<220> FEATURE:
<223> OTHER INFORMATION: peptide

<400> SEQUENCE: 248

Val Leu Leu Leu Ala Gly Ala Tyr Val
1               5

<210> SEQ ID NO 249
<211> LENGTH: 9
<212> TYPE: PRT
<213> ORGANISM: Artificial Sequence
<220> FEATURE:
<223> OTHER INFORMATION: peptide

<400> SEQUENCE: 249

Tyr Leu Tyr Thr Phe Leu Ile Val Leu
1               5

<210> SEQ ID NO 250
<211> LENGTH: 9
<212> TYPE: PRT
<213> ORGANISM: Artificial Sequence
<220> FEATURE:
<223> OTHER INFORMATION: peptide

<400> SEQUENCE: 250

Gly Met Tyr Thr Phe Leu Ile Pro Met
1               5

<210> SEQ ID NO 251
<211> LENGTH: 9
<212> TYPE: PRT
<213> ORGANISM: Artificial Sequence
<220> FEATURE:
<223> OTHER INFORMATION: peptide

<400> SEQUENCE: 251

Gly Leu Tyr Thr Phe Leu Ile Pro Met
1               5

<210> SEQ ID NO 252
<211> LENGTH: 9
<212> TYPE: PRT
<213> ORGANISM: Artificial Sequence

```
<220> FEATURE:
<223> OTHER INFORMATION: peptide

<400> SEQUENCE: 252

Phe Leu Ile Ser Thr Thr Phe Ala Ala
1               5

<210> SEQ ID NO 253
<211> LENGTH: 9
<212> TYPE: PRT
<213> ORGANISM: Artificial Sequence
<220> FEATURE:
<223> OTHER INFORMATION: peptide

<400> SEQUENCE: 253

Ile Leu Leu Asp Thr Asn Tyr Glu Ile
1               5

<210> SEQ ID NO 254
<211> LENGTH: 9
<212> TYPE: PRT
<213> ORGANISM: Artificial Sequence
<220> FEATURE:
<223> OTHER INFORMATION: peptide

<400> SEQUENCE: 254

Phe Leu Pro Phe Gly Phe Ile Leu Val
1               5

<210> SEQ ID NO 255
<211> LENGTH: 10
<212> TYPE: PRT
<213> ORGANISM: Artificial Sequence
<220> FEATURE:
<223> OTHER INFORMATION: peptide

<400> SEQUENCE: 255

Phe Leu Pro Phe Gly Phe Ile Leu Pro Val
1               5                   10

<210> SEQ ID NO 256
<211> LENGTH: 9
<212> TYPE: PRT
<213> ORGANISM: Artificial Sequence
<220> FEATURE:
<223> OTHER INFORMATION: peptide

<400> SEQUENCE: 256

Met Leu Tyr Leu Leu Pro Leu Ser Leu
1               5

<210> SEQ ID NO 257
<211> LENGTH: 9
<212> TYPE: PRT
<213> ORGANISM: Artificial Sequence
<220> FEATURE:
<223> OTHER INFORMATION: peptide

<400> SEQUENCE: 257

Met Leu Tyr Leu Leu Pro Leu Ala Leu
1               5

<210> SEQ ID NO 258
<211> LENGTH: 9
<212> TYPE: PRT
<213> ORGANISM: Artificial Sequence
<220> FEATURE:
```

<223> OTHER INFORMATION: peptide

<400> SEQUENCE: 258

Leu Leu Tyr Leu Leu Pro Leu Phe Leu
1               5

<210> SEQ ID NO 259
<211> LENGTH: 9
<212> TYPE: PRT
<213> ORGANISM: Artificial Sequence
<220> FEATURE:
<223> OTHER INFORMATION: peptide

<400> SEQUENCE: 259

Ser Met Leu Tyr Asn Leu Leu Ala Leu
1               5

<210> SEQ ID NO 260
<211> LENGTH: 9
<212> TYPE: PRT
<213> ORGANISM: Artificial Sequence
<220> FEATURE:
<223> OTHER INFORMATION: peptide

<400> SEQUENCE: 260

Ala Met Leu Tyr Asn Leu Leu Ala Leu
1               5

<210> SEQ ID NO 261
<211> LENGTH: 9
<212> TYPE: PRT
<213> ORGANISM: Artificial Sequence
<220> FEATURE:
<223> OTHER INFORMATION: peptide

<400> SEQUENCE: 261

Ala Leu Leu Tyr Asn Leu Leu Ala Leu
1               5

<210> SEQ ID NO 262
<211> LENGTH: 9
<212> TYPE: PRT
<213> ORGANISM: Artificial Sequence
<220> FEATURE:
<223> OTHER INFORMATION: peptide

<400> SEQUENCE: 262

Ile Leu Phe Leu Val Leu Gln Arg Val
1               5

<210> SEQ ID NO 263
<211> LENGTH: 9
<212> TYPE: PRT
<213> ORGANISM: Artificial Sequence
<220> FEATURE:
<223> OTHER INFORMATION: peptide

<400> SEQUENCE: 263

Tyr Leu Val Ala Ala Val Val Leu Leu
1               5

<210> SEQ ID NO 264
<211> LENGTH: 9
<212> TYPE: PRT
<213> ORGANISM: Artificial Sequence
<220> FEATURE:
<223> OTHER INFORMATION: peptide

<400> SEQUENCE: 264

Tyr Leu Ala Glu Arg Ala Gly His Val
1               5

<210> SEQ ID NO 265
<211> LENGTH: 9
<212> TYPE: PRT
<213> ORGANISM: Artificial Sequence
<220> FEATURE:
<223> OTHER INFORMATION: peptide

<400> SEQUENCE: 265

Ile Leu Val Pro Leu Phe Phe Thr Leu
1               5

<210> SEQ ID NO 266
<211> LENGTH: 9
<212> TYPE: PRT
<213> ORGANISM: Artificial Sequence
<220> FEATURE:
<223> OTHER INFORMATION: peptide

<400> SEQUENCE: 266

Gly Leu Val Pro Leu Phe Phe Ala Leu
1               5

<210> SEQ ID NO 267
<211> LENGTH: 9
<212> TYPE: PRT
<213> ORGANISM: Artificial Sequence
<220> FEATURE:
<223> OTHER INFORMATION: peptide

<400> SEQUENCE: 267

Phe Leu Val Pro Leu Phe Phe Val Val
1               5

<210> SEQ ID NO 268
<211> LENGTH: 9
<212> TYPE: PRT
<213> ORGANISM: Artificial Sequence
<220> FEATURE:
<223> OTHER INFORMATION: peptide

<400> SEQUENCE: 268

Phe Leu Val Pro Leu Phe Phe Leu Leu
1               5

<210> SEQ ID NO 269
<211> LENGTH: 9
<212> TYPE: PRT
<213> ORGANISM: Artificial Sequence
<220> FEATURE:
<223> OTHER INFORMATION: peptide

<400> SEQUENCE: 269

Ala Leu Val Pro Leu Phe Phe Ala Leu
1               5

<210> SEQ ID NO 270
<211> LENGTH: 9
<212> TYPE: PRT
<213> ORGANISM: Artificial Sequence
<220> FEATURE:
<223> OTHER INFORMATION: peptide

```
<400> SEQUENCE: 270

Tyr Met Leu Pro Leu Leu Ala Gly Ala
1               5

<210> SEQ ID NO 271
<211> LENGTH: 9
<212> TYPE: PRT
<213> ORGANISM: Artificial Sequence
<220> FEATURE:
<223> OTHER INFORMATION: peptide

<400> SEQUENCE: 271

Tyr Leu Leu Pro Leu Leu Ala Leu Ala
1               5

<210> SEQ ID NO 272
<211> LENGTH: 9
<212> TYPE: PRT
<213> ORGANISM: Artificial Sequence
<220> FEATURE:
<223> OTHER INFORMATION: peptide

<400> SEQUENCE: 272

Trp Leu Leu Pro Leu Leu Ala Val Val
1               5

<210> SEQ ID NO 273
<211> LENGTH: 9
<212> TYPE: PRT
<213> ORGANISM: Artificial Sequence
<220> FEATURE:
<223> OTHER INFORMATION: peptide

<400> SEQUENCE: 273

Trp Leu Leu Pro Leu Leu Ala Cys Leu
1               5

<210> SEQ ID NO 274
<211> LENGTH: 9
<212> TYPE: PRT
<213> ORGANISM: Artificial Sequence
<220> FEATURE:
<223> OTHER INFORMATION: peptide

<400> SEQUENCE: 274

Trp Leu Leu Pro Leu Leu Ala Ala Leu
1               5

<210> SEQ ID NO 275
<211> LENGTH: 9
<212> TYPE: PRT
<213> ORGANISM: Artificial Sequence
<220> FEATURE:
<223> OTHER INFORMATION: peptide

<400> SEQUENCE: 275

Thr Leu Leu Pro Leu Leu Ala Ala Val
1               5

<210> SEQ ID NO 276
<211> LENGTH: 9
<212> TYPE: PRT
<213> ORGANISM: Artificial Sequence
<220> FEATURE:
<223> OTHER INFORMATION: peptide

<400> SEQUENCE: 276
```

Thr Leu Leu Pro Leu Leu Ala Ala Ala
1               5

<210> SEQ ID NO 277
<211> LENGTH: 9
<212> TYPE: PRT
<213> ORGANISM: Artificial Sequence
<220> FEATURE:
<223> OTHER INFORMATION: peptide

<400> SEQUENCE: 277

Ser Leu Leu Pro Leu Leu Ala Gly Val
1               5

<210> SEQ ID NO 278
<211> LENGTH: 9
<212> TYPE: PRT
<213> ORGANISM: Artificial Sequence
<220> FEATURE:
<223> OTHER INFORMATION: peptide

<400> SEQUENCE: 278

Arg Leu Leu Pro Leu Leu Ala Val Leu
1               5

<210> SEQ ID NO 279
<211> LENGTH: 9
<212> TYPE: PRT
<213> ORGANISM: Artificial Sequence
<220> FEATURE:
<223> OTHER INFORMATION: peptide

<400> SEQUENCE: 279

Arg Leu Leu Pro Leu Leu Ala Ala Ile
1               5

<210> SEQ ID NO 280
<211> LENGTH: 9
<212> TYPE: PRT
<213> ORGANISM: Artificial Sequence
<220> FEATURE:
<223> OTHER INFORMATION: peptide

<400> SEQUENCE: 280

Gln Leu Leu Pro Leu Leu Ala Tyr Val
1               5

<210> SEQ ID NO 281
<211> LENGTH: 9
<212> TYPE: PRT
<213> ORGANISM: Artificial Sequence
<220> FEATURE:
<223> OTHER INFORMATION: peptide

<400> SEQUENCE: 281

Leu Leu Leu Pro Leu Leu Ala Gly Leu
1               5

<210> SEQ ID NO 282
<211> LENGTH: 9
<212> TYPE: PRT
<213> ORGANISM: Artificial Sequence
<220> FEATURE:
<223> OTHER INFORMATION: peptide

<400> SEQUENCE: 282

-continued

Leu Leu Leu Pro Leu Leu Ala Asp Leu
1               5

<210> SEQ ID NO 283
<211> LENGTH: 9
<212> TYPE: PRT
<213> ORGANISM: Artificial Sequence
<220> FEATURE:
<223> OTHER INFORMATION: peptide

<400> SEQUENCE: 283

Leu Leu Leu Pro Leu Leu Ala Ala Ala
1               5

<210> SEQ ID NO 284
<211> LENGTH: 9
<212> TYPE: PRT
<213> ORGANISM: Artificial Sequence
<220> FEATURE:
<223> OTHER INFORMATION: peptide

<400> SEQUENCE: 284

His Val Leu Pro Leu Leu Ala Thr Val
1               5

<210> SEQ ID NO 285
<211> LENGTH: 9
<212> TYPE: PRT
<213> ORGANISM: Artificial Sequence
<220> FEATURE:
<223> OTHER INFORMATION: peptide

<400> SEQUENCE: 285

His Leu Leu Pro Leu Leu Ala Glu Val
1               5

<210> SEQ ID NO 286
<211> LENGTH: 9
<212> TYPE: PRT
<213> ORGANISM: Artificial Sequence
<220> FEATURE:
<223> OTHER INFORMATION: peptide

<400> SEQUENCE: 286

Gly Leu Leu Pro Leu Leu Ala Lys Ile
1               5

<210> SEQ ID NO 287
<211> LENGTH: 9
<212> TYPE: PRT
<213> ORGANISM: Artificial Sequence
<220> FEATURE:
<223> OTHER INFORMATION: peptide

<400> SEQUENCE: 287

Gly Ile Leu Pro Leu Leu Ala Thr Val
1               5

<210> SEQ ID NO 288
<211> LENGTH: 9
<212> TYPE: PRT
<213> ORGANISM: Artificial Sequence
<220> FEATURE:
<223> OTHER INFORMATION: peptide

<400> SEQUENCE: 288

Tyr Leu Ser Asp Ala Val Glu Ala Val

```
<210> SEQ ID NO 289
<211> LENGTH: 9
<212> TYPE: PRT
<213> ORGANISM: Artificial Sequence
<220> FEATURE:
<223> OTHER INFORMATION: peptide

<400> SEQUENCE: 289

Ile Leu Arg Glu Ala Ala Met Pro Val
1               5

<210> SEQ ID NO 290
<211> LENGTH: 9
<212> TYPE: PRT
<213> ORGANISM: Artificial Sequence
<220> FEATURE:
<223> OTHER INFORMATION: peptide

<400> SEQUENCE: 290

Phe Leu Ile Pro Ala Pro Glu Ser Leu
1               5

<210> SEQ ID NO 291
<211> LENGTH: 9
<212> TYPE: PRT
<213> ORGANISM: Artificial Sequence
<220> FEATURE:
<223> OTHER INFORMATION: peptide

<400> SEQUENCE: 291

Phe Leu Leu His Gly Leu Asn Leu Met
1               5

<210> SEQ ID NO 292
<211> LENGTH: 9
<212> TYPE: PRT
<213> ORGANISM: Artificial Sequence
<220> FEATURE:
<223> OTHER INFORMATION: peptide

<400> SEQUENCE: 292

Tyr Met Ser Ser Leu Pro Gln Gly Leu
1               5

<210> SEQ ID NO 293
<211> LENGTH: 9
<212> TYPE: PRT
<213> ORGANISM: Artificial Sequence
<220> FEATURE:
<223> OTHER INFORMATION: peptide

<400> SEQUENCE: 293

Tyr Met Ile Leu Gly Val Ala Met Ile
1               5

<210> SEQ ID NO 294
<211> LENGTH: 9
<212> TYPE: PRT
<213> ORGANISM: Artificial Sequence
<220> FEATURE:
<223> OTHER INFORMATION: peptide

<400> SEQUENCE: 294

Val Leu Ile Leu Gly Val Ala Ala Val
1               5
```

```
<210> SEQ ID NO 295
<211> LENGTH: 9
<212> TYPE: PRT
<213> ORGANISM: Artificial Sequence
<220> FEATURE:
<223> OTHER INFORMATION: peptide

<400> SEQUENCE: 295

Ser Leu Ile Leu Gly Val Ala Ala Val
1               5

<210> SEQ ID NO 296
<211> LENGTH: 9
<212> TYPE: PRT
<213> ORGANISM: Artificial Sequence
<220> FEATURE:
<223> OTHER INFORMATION: peptide

<400> SEQUENCE: 296

Ile Leu Ile Leu Gly Val Ala Gly Ile
1               5

<210> SEQ ID NO 297
<211> LENGTH: 9
<212> TYPE: PRT
<213> ORGANISM: Artificial Sequence
<220> FEATURE:
<223> OTHER INFORMATION: peptide

<400> SEQUENCE: 297

Leu Leu Asp Cys Ile Ile Ala Phe Leu
1               5

<210> SEQ ID NO 298
<211> LENGTH: 9
<212> TYPE: PRT
<213> ORGANISM: Artificial Sequence
<220> FEATURE:
<223> OTHER INFORMATION: peptide

<400> SEQUENCE: 298

Leu Ile Leu Gly Ile Phe Ile Ser Val
1               5

<210> SEQ ID NO 299
<211> LENGTH: 9
<212> TYPE: PRT
<213> ORGANISM: Artificial Sequence
<220> FEATURE:
<223> OTHER INFORMATION: peptide

<400> SEQUENCE: 299

Tyr Leu Ala Val Leu Gly Ile Ser Leu
1               5

<210> SEQ ID NO 300
<211> LENGTH: 9
<212> TYPE: PRT
<213> ORGANISM: Artificial Sequence
<220> FEATURE:
<223> OTHER INFORMATION: peptide

<400> SEQUENCE: 300

Val Leu Ala Ala Ile Val Ile Gly Val
1               5
```

<210> SEQ ID NO 301
<211> LENGTH: 9
<212> TYPE: PRT
<213> ORGANISM: Artificial Sequence
<220> FEATURE:
<223> OTHER INFORMATION: peptide

<400> SEQUENCE: 301

Leu Leu Ala Cys Ser Leu Ala Met Leu
1               5

<210> SEQ ID NO 302
<211> LENGTH: 9
<212> TYPE: PRT
<213> ORGANISM: Artificial Sequence
<220> FEATURE:
<223> OTHER INFORMATION: peptide

<400> SEQUENCE: 302

Phe Val Ile Gly Ile Val Ala Leu Val
1               5

<210> SEQ ID NO 303
<211> LENGTH: 9
<212> TYPE: PRT
<213> ORGANISM: Artificial Sequence
<220> FEATURE:
<223> OTHER INFORMATION: peptide

<400> SEQUENCE: 303

Tyr Val Val Ala Val Pro Thr Pro Val
1               5

<210> SEQ ID NO 304
<211> LENGTH: 9
<212> TYPE: PRT
<213> ORGANISM: Artificial Sequence
<220> FEATURE:
<223> OTHER INFORMATION: peptide

<400> SEQUENCE: 304

Tyr Ile Val Ala Val Pro Thr Pro Val
1               5

<210> SEQ ID NO 305
<211> LENGTH: 9
<212> TYPE: PRT
<213> ORGANISM: Artificial Sequence
<220> FEATURE:
<223> OTHER INFORMATION: peptide

<400> SEQUENCE: 305

Phe Ile Val Ala Val Pro Thr Pro Ile
1               5

<210> SEQ ID NO 306
<211> LENGTH: 9
<212> TYPE: PRT
<213> ORGANISM: Artificial Sequence
<220> FEATURE:
<223> OTHER INFORMATION: peptide

<400> SEQUENCE: 306

Met Leu Lys Glu Leu Ser Pro Glu Leu
1               5

```
<210> SEQ ID NO 307
<211> LENGTH: 9
<212> TYPE: PRT
<213> ORGANISM: Artificial Sequence
<220> FEATURE:
<223> OTHER INFORMATION: peptide

<400> SEQUENCE: 307

Phe Leu Lys Glu Leu Ser Pro Gly Leu
1               5

<210> SEQ ID NO 308
<211> LENGTH: 9
<212> TYPE: PRT
<213> ORGANISM: Artificial Sequence
<220> FEATURE:
<223> OTHER INFORMATION: peptide

<400> SEQUENCE: 308

Phe Val Ala Asp Leu Val Gly His Val
1               5

<210> SEQ ID NO 309
<211> LENGTH: 9
<212> TYPE: PRT
<213> ORGANISM: Artificial Sequence
<220> FEATURE:
<223> OTHER INFORMATION: peptide

<400> SEQUENCE: 309

Ser Leu Leu Gly Thr Leu Glu Glu Leu
1               5

<210> SEQ ID NO 310
<211> LENGTH: 9
<212> TYPE: PRT
<213> ORGANISM: Artificial Sequence
<220> FEATURE:
<223> OTHER INFORMATION: peptide

<400> SEQUENCE: 310

Val Met Leu Ser Asp Val Gln Ser Val
1               5

<210> SEQ ID NO 311
<211> LENGTH: 9
<212> TYPE: PRT
<213> ORGANISM: Artificial Sequence
<220> FEATURE:
<223> OTHER INFORMATION: peptide

<400> SEQUENCE: 311

Arg Leu Leu Ser Asp Val Gln Gly Leu
1               5

<210> SEQ ID NO 312
<211> LENGTH: 9
<212> TYPE: PRT
<213> ORGANISM: Artificial Sequence
<220> FEATURE:
<223> OTHER INFORMATION: peptide

<400> SEQUENCE: 312

Ser Leu Ile Leu Ile Leu Ser Ser Val
1               5

<210> SEQ ID NO 313
```

```
<211> LENGTH: 9
<212> TYPE: PRT
<213> ORGANISM: Artificial Sequence
<220> FEATURE:
<223> OTHER INFORMATION: peptide

<400> SEQUENCE: 313

Lys Leu Ile Leu Ile Leu Ser Tyr Leu
1               5

<210> SEQ ID NO 314
<211> LENGTH: 9
<212> TYPE: PRT
<213> ORGANISM: Artificial Sequence
<220> FEATURE:
<223> OTHER INFORMATION: peptide

<400> SEQUENCE: 314

Ala Leu Asp Ala Ile Phe Gly Gly Val
1               5

<210> SEQ ID NO 315
<211> LENGTH: 9
<212> TYPE: PRT
<213> ORGANISM: Artificial Sequence
<220> FEATURE:
<223> OTHER INFORMATION: peptide

<400> SEQUENCE: 315

Phe Leu Ile Thr Lys Ala Glu Glu Leu
1               5

<210> SEQ ID NO 316
<211> LENGTH: 9
<212> TYPE: PRT
<213> ORGANISM: Artificial Sequence
<220> FEATURE:
<223> OTHER INFORMATION: peptide

<400> SEQUENCE: 316

Ser Leu Leu Glu Glu Leu Pro Ala Leu
1               5

<210> SEQ ID NO 317
<211> LENGTH: 9
<212> TYPE: PRT
<213> ORGANISM: Artificial Sequence
<220> FEATURE:
<223> OTHER INFORMATION: peptide

<400> SEQUENCE: 317

Met Thr Leu Glu Glu Leu Pro Phe Leu
1               5

<210> SEQ ID NO 318
<211> LENGTH: 9
<212> TYPE: PRT
<213> ORGANISM: Artificial Sequence
<220> FEATURE:
<223> OTHER INFORMATION: peptide

<400> SEQUENCE: 318

Ile Ile Leu Glu Tyr Ile Ala Leu Leu
1               5

<210> SEQ ID NO 319
<211> LENGTH: 9
```

```
<212> TYPE: PRT
<213> ORGANISM: Artificial Sequence
<220> FEATURE:
<223> OTHER INFORMATION: peptide

<400> SEQUENCE: 319

Tyr Met Val Phe Gly Ile Glu Gly Ile
1               5

<210> SEQ ID NO 320
<211> LENGTH: 9
<212> TYPE: PRT
<213> ORGANISM: Artificial Sequence
<220> FEATURE:
<223> OTHER INFORMATION: peptide

<400> SEQUENCE: 320

Ser Leu Ser Ser Ser Ser Pro Leu Val
1               5

<210> SEQ ID NO 321
<211> LENGTH: 9
<212> TYPE: PRT
<213> ORGANISM: Artificial Sequence
<220> FEATURE:
<223> OTHER INFORMATION: peptide

<400> SEQUENCE: 321

Lys Leu Asp Glu Leu Ala His Phe Leu
1               5

<210> SEQ ID NO 322
<211> LENGTH: 9
<212> TYPE: PRT
<213> ORGANISM: Artificial Sequence
<220> FEATURE:
<223> OTHER INFORMATION: peptide

<400> SEQUENCE: 322

Phe Val Leu Glu His Val Val Pro Leu
1               5

<210> SEQ ID NO 323
<211> LENGTH: 9
<212> TYPE: PRT
<213> ORGANISM: Artificial Sequence
<220> FEATURE:
<223> OTHER INFORMATION: peptide

<400> SEQUENCE: 323

Tyr Leu Leu Gly Val Leu Leu Leu Leu
1               5

<210> SEQ ID NO 324
<211> LENGTH: 9
<212> TYPE: PRT
<213> ORGANISM: Artificial Sequence
<220> FEATURE:
<223> OTHER INFORMATION: peptide

<400> SEQUENCE: 324

Tyr Ile Leu Gly Val Leu Leu Thr Ala
1               5

<210> SEQ ID NO 325
<211> LENGTH: 9
<212> TYPE: PRT
```

```
<213> ORGANISM: Artificial Sequence
<220> FEATURE:
<223> OTHER INFORMATION: peptide

<400> SEQUENCE: 325

Met Leu Leu Gly Val Leu Leu Leu Leu
1               5

<210> SEQ ID NO 326
<211> LENGTH: 9
<212> TYPE: PRT
<213> ORGANISM: Artificial Sequence
<220> FEATURE:
<223> OTHER INFORMATION: peptide

<400> SEQUENCE: 326

Met Ile Leu Gly Val Leu Leu Phe Leu
1               5

<210> SEQ ID NO 327
<211> LENGTH: 9
<212> TYPE: PRT
<213> ORGANISM: Artificial Sequence
<220> FEATURE:
<223> OTHER INFORMATION: peptide

<400> SEQUENCE: 327

Leu Met Leu Gly Val Leu Leu Leu Ala
1               5

<210> SEQ ID NO 328
<211> LENGTH: 9
<212> TYPE: PRT
<213> ORGANISM: Artificial Sequence
<220> FEATURE:
<223> OTHER INFORMATION: peptide

<400> SEQUENCE: 328

Leu Leu Leu Gly Val Leu Leu Leu Leu
1               5

<210> SEQ ID NO 329
<211> LENGTH: 9
<212> TYPE: PRT
<213> ORGANISM: Artificial Sequence
<220> FEATURE:
<223> OTHER INFORMATION: peptide

<400> SEQUENCE: 329

Lys Leu Leu Gly Val Leu Leu Leu Val
1               5

<210> SEQ ID NO 330
<211> LENGTH: 9
<212> TYPE: PRT
<213> ORGANISM: Artificial Sequence
<220> FEATURE:
<223> OTHER INFORMATION: peptide

<400> SEQUENCE: 330

Ile Ile Leu Gly Val Leu Leu Ala Val
1               5

<210> SEQ ID NO 331
<211> LENGTH: 9
<212> TYPE: PRT
<213> ORGANISM: Artificial Sequence
```

```
<220> FEATURE:
<223> OTHER INFORMATION: peptide

<400> SEQUENCE: 331

Phe Ile Leu Gly Val Leu Leu Ser Leu
1               5

<210> SEQ ID NO 332
<211> LENGTH: 9
<212> TYPE: PRT
<213> ORGANISM: Artificial Sequence
<220> FEATURE:
<223> OTHER INFORMATION: peptide

<400> SEQUENCE: 332

Ala Leu Leu Gly Val Leu Leu Leu Leu
1               5

<210> SEQ ID NO 333
<211> LENGTH: 9
<212> TYPE: PRT
<213> ORGANISM: Artificial Sequence
<220> FEATURE:
<223> OTHER INFORMATION: peptide

<400> SEQUENCE: 333

Ala Leu Leu Gly Val Leu Leu Leu Ala
1               5

<210> SEQ ID NO 334
<211> LENGTH: 9
<212> TYPE: PRT
<213> ORGANISM: Artificial Sequence
<220> FEATURE:
<223> OTHER INFORMATION: peptide

<400> SEQUENCE: 334

Ala Ile Leu Gly Val Leu Leu Leu Val
1               5

<210> SEQ ID NO 335
<211> LENGTH: 9
<212> TYPE: PRT
<213> ORGANISM: Artificial Sequence
<220> FEATURE:
<223> OTHER INFORMATION: peptide

<400> SEQUENCE: 335

Ile Leu Ala Ala Gly Val Pro Glu Leu
1               5

<210> SEQ ID NO 336
<211> LENGTH: 9
<212> TYPE: PRT
<213> ORGANISM: Artificial Sequence
<220> FEATURE:
<223> OTHER INFORMATION: peptide

<400> SEQUENCE: 336

Tyr Val Ser Asp Ile Leu Ser Tyr Val
1               5

<210> SEQ ID NO 337
<211> LENGTH: 9
<212> TYPE: PRT
<213> ORGANISM: Artificial Sequence
<220> FEATURE:
```

<223> OTHER INFORMATION: peptide

<400> SEQUENCE: 337

Tyr Ile Ser Asp Ile Leu Ser Tyr Val
1               5

<210> SEQ ID NO 338
<211> LENGTH: 9
<212> TYPE: PRT
<213> ORGANISM: Artificial Sequence
<220> FEATURE:
<223> OTHER INFORMATION: peptide

<400> SEQUENCE: 338

Val Ile Ser Asp Ile Leu Ser Phe Leu
1               5

<210> SEQ ID NO 339
<211> LENGTH: 9
<212> TYPE: PRT
<213> ORGANISM: Artificial Sequence
<220> FEATURE:
<223> OTHER INFORMATION: peptide

<400> SEQUENCE: 339

Ser Met Ser Asp Ile Leu Ser Arg Leu
1               5

<210> SEQ ID NO 340
<211> LENGTH: 9
<212> TYPE: PRT
<213> ORGANISM: Artificial Sequence
<220> FEATURE:
<223> OTHER INFORMATION: peptide

<400> SEQUENCE: 340

Phe Val Ser Asp Ile Leu Ser Ala Ala
1               5

<210> SEQ ID NO 341
<211> LENGTH: 9
<212> TYPE: PRT
<213> ORGANISM: Artificial Sequence
<220> FEATURE:
<223> OTHER INFORMATION: peptide

<400> SEQUENCE: 341

Trp Leu Leu Ala Ala Ser Val Thr Val
1               5

<210> SEQ ID NO 342
<211> LENGTH: 9
<212> TYPE: PRT
<213> ORGANISM: Artificial Sequence
<220> FEATURE:
<223> OTHER INFORMATION: peptide

<400> SEQUENCE: 342

Ile Leu Leu Ala Ala Ser Val Leu Val
1               5

<210> SEQ ID NO 343
<211> LENGTH: 9
<212> TYPE: PRT
<213> ORGANISM: Artificial Sequence
<220> FEATURE:
<223> OTHER INFORMATION: peptide

<400> SEQUENCE: 343

Phe Leu Leu Ala Ala Ser Val Met Met
1               5

<210> SEQ ID NO 344
<211> LENGTH: 9
<212> TYPE: PRT
<213> ORGANISM: Artificial Sequence
<220> FEATURE:
<223> OTHER INFORMATION: peptide

<400> SEQUENCE: 344

Ala Leu Leu Ala Ala Ser Val Leu Val
1               5

<210> SEQ ID NO 345
<211> LENGTH: 9
<212> TYPE: PRT
<213> ORGANISM: Artificial Sequence
<220> FEATURE:
<223> OTHER INFORMATION: peptide

<400> SEQUENCE: 345

Leu Leu Ala Ala Ser Val Ala Leu Leu
1               5

<210> SEQ ID NO 346
<211> LENGTH: 9
<212> TYPE: PRT
<213> ORGANISM: Artificial Sequence
<220> FEATURE:
<223> OTHER INFORMATION: peptide

<400> SEQUENCE: 346

Leu Leu Ala Ala Ser Val Ala Gly Val
1               5

<210> SEQ ID NO 347
<211> LENGTH: 9
<212> TYPE: PRT
<213> ORGANISM: Artificial Sequence
<220> FEATURE:
<223> OTHER INFORMATION: peptide

<400> SEQUENCE: 347

Ile Leu Ala Ala Ser Val Ala Ala Val
1               5

<210> SEQ ID NO 348
<211> LENGTH: 9
<212> TYPE: PRT
<213> ORGANISM: Artificial Sequence
<220> FEATURE:
<223> OTHER INFORMATION: peptide

<400> SEQUENCE: 348

Gly Leu Ala Ala Ser Val Ala Pro Val
1               5

<210> SEQ ID NO 349
<211> LENGTH: 9
<212> TYPE: PRT
<213> ORGANISM: Artificial Sequence
<220> FEATURE:
<223> OTHER INFORMATION: peptide

```
<400> SEQUENCE: 349

Ala Leu Leu Arg Lys Val Ala Glu Val
1               5

<210> SEQ ID NO 350
<211> LENGTH: 9
<212> TYPE: PRT
<213> ORGANISM: Artificial Sequence
<220> FEATURE:
<223> OTHER INFORMATION: peptide

<400> SEQUENCE: 350

Ser Leu Pro Glu Leu Tyr Ala Trp Ile
1               5

<210> SEQ ID NO 351
<211> LENGTH: 9
<212> TYPE: PRT
<213> ORGANISM: Artificial Sequence
<220> FEATURE:
<223> OTHER INFORMATION: peptide

<400> SEQUENCE: 351

Ile Leu Tyr Gly Lys Ile Lys Tyr Leu
1               5

<210> SEQ ID NO 352
<211> LENGTH: 9
<212> TYPE: PRT
<213> ORGANISM: Artificial Sequence
<220> FEATURE:
<223> OTHER INFORMATION: peptide

<400> SEQUENCE: 352

Met Leu Leu Gly Leu Ala Ala Phe Leu
1               5

<210> SEQ ID NO 353
<211> LENGTH: 9
<212> TYPE: PRT
<213> ORGANISM: Artificial Sequence
<220> FEATURE:
<223> OTHER INFORMATION: peptide

<400> SEQUENCE: 353

Gly Leu Leu Gly Leu Ala Ala Phe Leu
1               5

<210> SEQ ID NO 354
<211> LENGTH: 9
<212> TYPE: PRT
<213> ORGANISM: Artificial Sequence
<220> FEATURE:
<223> OTHER INFORMATION: peptide

<400> SEQUENCE: 354

Ala Leu Leu Gly Leu Ala Ala Phe Leu
1               5

<210> SEQ ID NO 355
<211> LENGTH: 9
<212> TYPE: PRT
<213> ORGANISM: Artificial Sequence
<220> FEATURE:
<223> OTHER INFORMATION: peptide

<400> SEQUENCE: 355
```

```
Tyr Leu Asp Glu Val Lys Ser Leu Val
1               5

<210> SEQ ID NO 356
<211> LENGTH: 9
<212> TYPE: PRT
<213> ORGANISM: Artificial Sequence
<220> FEATURE:
<223> OTHER INFORMATION: peptide

<400> SEQUENCE: 356

Tyr Leu Asp Glu Val Lys Ser Leu Ile
1               5

<210> SEQ ID NO 357
<211> LENGTH: 9
<212> TYPE: PRT
<213> ORGANISM: Artificial Sequence
<220> FEATURE:
<223> OTHER INFORMATION: peptide

<400> SEQUENCE: 357

Tyr Leu Asp Glu Val Lys Ser Ile Leu
1               5

<210> SEQ ID NO 358
<211> LENGTH: 9
<212> TYPE: PRT
<213> ORGANISM: Artificial Sequence
<220> FEATURE:
<223> OTHER INFORMATION: peptide

<400> SEQUENCE: 358

Leu Leu Asp Glu Val Lys Ser Leu Val
1               5

<210> SEQ ID NO 359
<211> LENGTH: 9
<212> TYPE: PRT
<213> ORGANISM: Artificial Sequence
<220> FEATURE:
<223> OTHER INFORMATION: peptide

<400> SEQUENCE: 359

Phe Ile Leu Leu Ser Leu Ser Pro Val
1               5

<210> SEQ ID NO 360
<211> LENGTH: 9
<212> TYPE: PRT
<213> ORGANISM: Artificial Sequence
<220> FEATURE:
<223> OTHER INFORMATION: peptide

<400> SEQUENCE: 360

Arg Leu Phe Leu Phe Ser Val Leu Val
1               5

<210> SEQ ID NO 361
<211> LENGTH: 9
<212> TYPE: PRT
<213> ORGANISM: Artificial Sequence
<220> FEATURE:
<223> OTHER INFORMATION: peptide

<400> SEQUENCE: 361
```

-continued

Ala Leu Thr Val Tyr Leu Val Tyr Leu
1               5

<210> SEQ ID NO 362
<211> LENGTH: 9
<212> TYPE: PRT
<213> ORGANISM: Artificial Sequence
<220> FEATURE:
<223> OTHER INFORMATION: peptide

<400> SEQUENCE: 362

Arg Leu Leu Phe Val Ala Val Pro Ile
1               5

<210> SEQ ID NO 363
<211> LENGTH: 9
<212> TYPE: PRT
<213> ORGANISM: Artificial Sequence
<220> FEATURE:
<223> OTHER INFORMATION: peptide

<400> SEQUENCE: 363

Arg Leu Leu Phe Val Ala Val Gly Leu
1               5

<210> SEQ ID NO 364
<211> LENGTH: 9
<212> TYPE: PRT
<213> ORGANISM: Artificial Sequence
<220> FEATURE:
<223> OTHER INFORMATION: peptide

<400> SEQUENCE: 364

Phe Leu Leu Phe Val Ala Val Ser Val
1               5

<210> SEQ ID NO 365
<211> LENGTH: 9
<212> TYPE: PRT
<213> ORGANISM: Artificial Sequence
<220> FEATURE:
<223> OTHER INFORMATION: peptide

<400> SEQUENCE: 365

Phe Ile Ser Leu Phe Leu Phe Ser Val
1               5

<210> SEQ ID NO 366
<211> LENGTH: 9
<212> TYPE: PRT
<213> ORGANISM: Artificial Sequence
<220> FEATURE:
<223> OTHER INFORMATION: peptide

<400> SEQUENCE: 366

Leu Ile Ala Gly Phe Val Ala Leu Val
1               5

<210> SEQ ID NO 367
<211> LENGTH: 9
<212> TYPE: PRT
<213> ORGANISM: Artificial Sequence
<220> FEATURE:
<223> OTHER INFORMATION: peptide

<400> SEQUENCE: 367

Tyr Leu Leu Val Leu Met Ala Ser Ile

```
1               5

<210> SEQ ID NO 368
<211> LENGTH: 9
<212> TYPE: PRT
<213> ORGANISM: Artificial Sequence
<220> FEATURE:
<223> OTHER INFORMATION: peptide

<400> SEQUENCE: 368

Tyr Leu Val Gly Ile Leu Leu Val Leu
1               5

<210> SEQ ID NO 369
<211> LENGTH: 9
<212> TYPE: PRT
<213> ORGANISM: Artificial Sequence
<220> FEATURE:
<223> OTHER INFORMATION: peptide

<400> SEQUENCE: 369

Lys Ile Val Gly Ile Leu Leu Gly Ile
1               5

<210> SEQ ID NO 370
<211> LENGTH: 9
<212> TYPE: PRT
<213> ORGANISM: Artificial Sequence
<220> FEATURE:
<223> OTHER INFORMATION: peptide

<400> SEQUENCE: 370

Lys Ile Val Gly Ile Leu Leu Ala Val
1               5

<210> SEQ ID NO 371
<211> LENGTH: 9
<212> TYPE: PRT
<213> ORGANISM: Artificial Sequence
<220> FEATURE:
<223> OTHER INFORMATION: peptide

<400> SEQUENCE: 371

Ile Leu Val Gly Ile Leu Leu Val Val
1               5

<210> SEQ ID NO 372
<211> LENGTH: 9
<212> TYPE: PRT
<213> ORGANISM: Artificial Sequence
<220> FEATURE:
<223> OTHER INFORMATION: peptide

<400> SEQUENCE: 372

Gly Ile Val Gly Ile Leu Leu Asn Val
1               5

<210> SEQ ID NO 373
<211> LENGTH: 9
<212> TYPE: PRT
<213> ORGANISM: Artificial Sequence
<220> FEATURE:
<223> OTHER INFORMATION: peptide

<400> SEQUENCE: 373

Gly Ile Val Gly Ile Leu Leu Ala Val
1               5
```

```
<210> SEQ ID NO 374
<211> LENGTH: 9
<212> TYPE: PRT
<213> ORGANISM: Artificial Sequence
<220> FEATURE:
<223> OTHER INFORMATION: peptide

<400> SEQUENCE: 374

Leu Leu Ala Val Val Leu Ala Phe Val
1               5

<210> SEQ ID NO 375
<211> LENGTH: 9
<212> TYPE: PRT
<213> ORGANISM: Artificial Sequence
<220> FEATURE:
<223> OTHER INFORMATION: peptide

<400> SEQUENCE: 375

Leu Leu Ala Val Val Leu Ala Ala Val
1               5

<210> SEQ ID NO 376
<211> LENGTH: 9
<212> TYPE: PRT
<213> ORGANISM: Artificial Sequence
<220> FEATURE:
<223> OTHER INFORMATION: peptide

<400> SEQUENCE: 376

Gly Val Leu Asp Gly Thr Ala Thr Val
1               5

<210> SEQ ID NO 377
<211> LENGTH: 9
<212> TYPE: PRT
<213> ORGANISM: Artificial Sequence
<220> FEATURE:
<223> OTHER INFORMATION: peptide

<400> SEQUENCE: 377

Ala Leu Ala Asp Thr Asn Ser Tyr Val
1               5

<210> SEQ ID NO 378
<211> LENGTH: 9
<212> TYPE: PRT
<213> ORGANISM: Artificial Sequence
<220> FEATURE:
<223> OTHER INFORMATION: peptide

<400> SEQUENCE: 378

Ala Leu Ala Asp Thr Asn Ser Tyr Leu
1               5

<210> SEQ ID NO 379
<211> LENGTH: 9
<212> TYPE: PRT
<213> ORGANISM: Artificial Sequence
<220> FEATURE:
<223> OTHER INFORMATION: peptide

<400> SEQUENCE: 379

Ala Met Gln Ala Ala Ile Pro Met Leu
1               5
```

```
<210> SEQ ID NO 380
<211> LENGTH: 9
<212> TYPE: PRT
<213> ORGANISM: Artificial Sequence
<220> FEATURE:
<223> OTHER INFORMATION: peptide

<400> SEQUENCE: 380

Ile Val Leu Asp Gly Leu Asp Leu Val
1               5

<210> SEQ ID NO 381
<211> LENGTH: 9
<212> TYPE: PRT
<213> ORGANISM: Artificial Sequence
<220> FEATURE:
<223> OTHER INFORMATION: peptide

<400> SEQUENCE: 381

Ala Val Leu Asp Gly Leu Asp Pro Val
1               5

<210> SEQ ID NO 382
<211> LENGTH: 9
<212> TYPE: PRT
<213> ORGANISM: Artificial Sequence
<220> FEATURE:
<223> OTHER INFORMATION: peptide

<400> SEQUENCE: 382

Tyr Leu Leu Ala Leu Leu Pro Leu Leu
1               5

<210> SEQ ID NO 383
<211> LENGTH: 9
<212> TYPE: PRT
<213> ORGANISM: Artificial Sequence
<220> FEATURE:
<223> OTHER INFORMATION: peptide

<400> SEQUENCE: 383

Tyr Leu Leu Ala Leu Leu Pro Ile Leu
1               5

<210> SEQ ID NO 384
<211> LENGTH: 9
<212> TYPE: PRT
<213> ORGANISM: Artificial Sequence
<220> FEATURE:
<223> OTHER INFORMATION: peptide

<400> SEQUENCE: 384

Gln Leu Leu Ala Leu Leu Pro Gly Val
1               5

<210> SEQ ID NO 385
<211> LENGTH: 9
<212> TYPE: PRT
<213> ORGANISM: Artificial Sequence
<220> FEATURE:
<223> OTHER INFORMATION: peptide

<400> SEQUENCE: 385

Leu Leu Leu Ala Leu Leu Pro Thr Val
1               5
```

```
<210> SEQ ID NO 386
<211> LENGTH: 9
<212> TYPE: PRT
<213> ORGANISM: Artificial Sequence
<220> FEATURE:
<223> OTHER INFORMATION: peptide

<400> SEQUENCE: 386

Phe Leu Arg Glu Leu Leu Cys Gln Leu
1               5

<210> SEQ ID NO 387
<211> LENGTH: 9
<212> TYPE: PRT
<213> ORGANISM: Artificial Sequence
<220> FEATURE:
<223> OTHER INFORMATION: peptide

<400> SEQUENCE: 387

Leu Leu Tyr Pro Val Pro Leu Gly Val
1               5

<210> SEQ ID NO 388
<211> LENGTH: 9
<212> TYPE: PRT
<213> ORGANISM: Artificial Sequence
<220> FEATURE:
<223> OTHER INFORMATION: peptide

<400> SEQUENCE: 388

Ala Leu Phe Leu Leu Ser Tyr Thr Val
1               5

<210> SEQ ID NO 389
<211> LENGTH: 9
<212> TYPE: PRT
<213> ORGANISM: Artificial Sequence
<220> FEATURE:
<223> OTHER INFORMATION: peptide

<400> SEQUENCE: 389

Tyr Val Leu Ser Leu Leu Leu Thr Leu
1               5

<210> SEQ ID NO 390
<211> LENGTH: 9
<212> TYPE: PRT
<213> ORGANISM: Artificial Sequence
<220> FEATURE:
<223> OTHER INFORMATION: peptide

<400> SEQUENCE: 390

Val Leu Leu Ser Leu Leu Leu Ile Val
1               5

<210> SEQ ID NO 391
<211> LENGTH: 9
<212> TYPE: PRT
<213> ORGANISM: Artificial Sequence
<220> FEATURE:
<223> OTHER INFORMATION: peptide

<400> SEQUENCE: 391

Ser Leu Leu Ser Leu Leu Leu Ile Leu
1               5

<210> SEQ ID NO 392
```

```
<211> LENGTH: 9
<212> TYPE: PRT
<213> ORGANISM: Artificial Sequence
<220> FEATURE:
<223> OTHER INFORMATION: peptide

<400> SEQUENCE: 392

Arg Leu Leu Ser Leu Leu Leu Val Leu
1               5

<210> SEQ ID NO 393
<211> LENGTH: 9
<212> TYPE: PRT
<213> ORGANISM: Artificial Sequence
<220> FEATURE:
<223> OTHER INFORMATION: peptide

<400> SEQUENCE: 393

Leu Val Leu Ser Leu Leu Leu Leu Val
1               5

<210> SEQ ID NO 394
<211> LENGTH: 9
<212> TYPE: PRT
<213> ORGANISM: Artificial Sequence
<220> FEATURE:
<223> OTHER INFORMATION: peptide

<400> SEQUENCE: 394

Lys Leu Leu Ser Leu Leu Leu Val Leu
1               5

<210> SEQ ID NO 395
<211> LENGTH: 9
<212> TYPE: PRT
<213> ORGANISM: Artificial Sequence
<220> FEATURE:
<223> OTHER INFORMATION: peptide

<400> SEQUENCE: 395

Ile Leu Leu Ser Leu Leu Leu Val Leu
1               5

<210> SEQ ID NO 396
<211> LENGTH: 9
<212> TYPE: PRT
<213> ORGANISM: Artificial Sequence
<220> FEATURE:
<223> OTHER INFORMATION: peptide

<400> SEQUENCE: 396

Phe Thr Leu Ser Leu Leu Leu Thr Leu
1               5

<210> SEQ ID NO 397
<211> LENGTH: 9
<212> TYPE: PRT
<213> ORGANISM: Artificial Sequence
<220> FEATURE:
<223> OTHER INFORMATION: peptide

<400> SEQUENCE: 397

Ala Leu Leu Ser Leu Leu Leu Ile Leu
1               5

<210> SEQ ID NO 398
<211> LENGTH: 9
```

```
<212> TYPE: PRT
<213> ORGANISM: Artificial Sequence
<220> FEATURE:
<223> OTHER INFORMATION: peptide

<400> SEQUENCE: 398

Val Leu Phe Val Leu Ser Leu Phe Leu
1               5

<210> SEQ ID NO 399
<211> LENGTH: 9
<212> TYPE: PRT
<213> ORGANISM: Artificial Sequence
<220> FEATURE:
<223> OTHER INFORMATION: peptide

<400> SEQUENCE: 399

Ile Leu Phe Val Leu Ser Leu Gln Leu
1               5

<210> SEQ ID NO 400
<211> LENGTH: 9
<212> TYPE: PRT
<213> ORGANISM: Artificial Sequence
<220> FEATURE:
<223> OTHER INFORMATION: peptide

<400> SEQUENCE: 400

Leu Leu Leu Glu Lys Gln Ala Glu Val
1               5

<210> SEQ ID NO 401
<211> LENGTH: 9
<212> TYPE: PRT
<213> ORGANISM: Artificial Sequence
<220> FEATURE:
<223> OTHER INFORMATION: peptide

<400> SEQUENCE: 401

Val Leu Ser Glu Leu Lys Leu Ala Val
1               5

<210> SEQ ID NO 402
<211> LENGTH: 9
<212> TYPE: PRT
<213> ORGANISM: Artificial Sequence
<220> FEATURE:
<223> OTHER INFORMATION: peptide

<400> SEQUENCE: 402

Arg Met Ile Glu His Val Leu Thr Val
1               5

<210> SEQ ID NO 403
<211> LENGTH: 9
<212> TYPE: PRT
<213> ORGANISM: Artificial Sequence
<220> FEATURE:
<223> OTHER INFORMATION: peptide

<400> SEQUENCE: 403

Gln Ile Phe Asp Arg Leu Ile Pro Ile
1               5

<210> SEQ ID NO 404
<211> LENGTH: 9
<212> TYPE: PRT
```

```
<213> ORGANISM: Artificial Sequence
<220> FEATURE:
<223> OTHER INFORMATION: peptide

<400> SEQUENCE: 404

Gly Val Phe Asp Arg Leu Ile Pro Ile
1               5

<210> SEQ ID NO 405
<211> LENGTH: 9
<212> TYPE: PRT
<213> ORGANISM: Artificial Sequence
<220> FEATURE:
<223> OTHER INFORMATION: peptide

<400> SEQUENCE: 405

Tyr Leu Lys Glu Gln Phe Gln Thr Leu
1               5

<210> SEQ ID NO 406
<211> LENGTH: 9
<212> TYPE: PRT
<213> ORGANISM: Artificial Sequence
<220> FEATURE:
<223> OTHER INFORMATION: peptide

<400> SEQUENCE: 406

Ser Leu Leu Asp Ser Ala Phe Leu Leu
1               5

<210> SEQ ID NO 407
<211> LENGTH: 9
<212> TYPE: PRT
<213> ORGANISM: Artificial Sequence
<220> FEATURE:
<223> OTHER INFORMATION: peptide

<400> SEQUENCE: 407

Met Leu Ser Leu Val Phe Ser Leu Ile
1               5

<210> SEQ ID NO 408
<211> LENGTH: 9
<212> TYPE: PRT
<213> ORGANISM: Artificial Sequence
<220> FEATURE:
<223> OTHER INFORMATION: peptide

<400> SEQUENCE: 408

Leu Met Ser Leu Val Phe Ser Leu Val
1               5

<210> SEQ ID NO 409
<211> LENGTH: 9
<212> TYPE: PRT
<213> ORGANISM: Artificial Sequence
<220> FEATURE:
<223> OTHER INFORMATION: peptide

<400> SEQUENCE: 409

Trp Met Gln Ile Leu Pro Tyr Gln Val
1               5

<210> SEQ ID NO 410
<211> LENGTH: 9
<212> TYPE: PRT
<213> ORGANISM: Artificial Sequence
```

```
<220> FEATURE:
<223> OTHER INFORMATION: peptide

<400> SEQUENCE: 410

Met Met Thr Gly Phe Thr Phe Gly Val
1               5

<210> SEQ ID NO 411
<211> LENGTH: 9
<212> TYPE: PRT
<213> ORGANISM: Artificial Sequence
<220> FEATURE:
<223> OTHER INFORMATION: peptide

<400> SEQUENCE: 411

Met Leu Leu Leu Leu Val Asn Leu Val
1               5

<210> SEQ ID NO 412
<211> LENGTH: 9
<212> TYPE: PRT
<213> ORGANISM: Artificial Sequence
<220> FEATURE:
<223> OTHER INFORMATION: peptide

<400> SEQUENCE: 412

Val Leu Phe Gly Leu Leu Thr Phe Leu
1               5

<210> SEQ ID NO 413
<211> LENGTH: 9
<212> TYPE: PRT
<213> ORGANISM: Artificial Sequence
<220> FEATURE:
<223> OTHER INFORMATION: peptide

<400> SEQUENCE: 413

Gln Leu Phe Gly Leu Leu Thr Asp Val
1               5

<210> SEQ ID NO 414
<211> LENGTH: 9
<212> TYPE: PRT
<213> ORGANISM: Artificial Sequence
<220> FEATURE:
<223> OTHER INFORMATION: peptide

<400> SEQUENCE: 414

Phe Leu Phe Gly Leu Leu Thr Met Ile
1               5

<210> SEQ ID NO 415
<211> LENGTH: 9
<212> TYPE: PRT
<213> ORGANISM: Artificial Sequence
<220> FEATURE:
<223> OTHER INFORMATION: peptide

<400> SEQUENCE: 415

Phe Leu Phe Gly Leu Leu Thr Asp Ala
1               5

<210> SEQ ID NO 416
<211> LENGTH: 9
<212> TYPE: PRT
<213> ORGANISM: Artificial Sequence
<220> FEATURE:
```

<223> OTHER INFORMATION: peptide

<400> SEQUENCE: 416

Thr Leu Leu Leu Ser Leu Phe Leu Leu
1               5

<210> SEQ ID NO 417
<211> LENGTH: 9
<212> TYPE: PRT
<213> ORGANISM: Artificial Sequence
<220> FEATURE:
<223> OTHER INFORMATION: peptide

<400> SEQUENCE: 417

Phe Ile Leu Leu Ser Leu Phe Met Leu
1               5

<210> SEQ ID NO 418
<211> LENGTH: 9
<212> TYPE: PRT
<213> ORGANISM: Artificial Sequence
<220> FEATURE:
<223> OTHER INFORMATION: peptide

<400> SEQUENCE: 418

Ile Leu Leu Pro Pro Pro Pro Val Val
1               5

<210> SEQ ID NO 419
<211> LENGTH: 9
<212> TYPE: PRT
<213> ORGANISM: Artificial Sequence
<220> FEATURE:
<223> OTHER INFORMATION: peptide

<400> SEQUENCE: 419

Val Leu Leu Thr Leu Ile Phe Ala Leu
1               5

<210> SEQ ID NO 420
<211> LENGTH: 9
<212> TYPE: PRT
<213> ORGANISM: Artificial Sequence
<220> FEATURE:
<223> OTHER INFORMATION: peptide

<400> SEQUENCE: 420

Arg Leu Leu Thr Leu Ile Phe Thr Leu
1               5

<210> SEQ ID NO 421
<211> LENGTH: 9
<212> TYPE: PRT
<213> ORGANISM: Artificial Sequence
<220> FEATURE:
<223> OTHER INFORMATION: peptide

<400> SEQUENCE: 421

Gln Leu Leu Thr Leu Ile Phe Tyr Leu
1               5

<210> SEQ ID NO 422
<211> LENGTH: 9
<212> TYPE: PRT
<213> ORGANISM: Artificial Sequence
<220> FEATURE:
<223> OTHER INFORMATION: peptide

<400> SEQUENCE: 422

Leu Leu Leu Thr Leu Ile Phe Pro Ile
1               5

<210> SEQ ID NO 423
<211> LENGTH: 9
<212> TYPE: PRT
<213> ORGANISM: Artificial Sequence
<220> FEATURE:
<223> OTHER INFORMATION: peptide

<400> SEQUENCE: 423

Phe Leu Leu Thr Leu Ile Phe Ser Leu
1               5

<210> SEQ ID NO 424
<211> LENGTH: 9
<212> TYPE: PRT
<213> ORGANISM: Artificial Sequence
<220> FEATURE:
<223> OTHER INFORMATION: peptide

<400> SEQUENCE: 424

Val Met Val Ala Ile Tyr Phe Thr Leu
1               5

<210> SEQ ID NO 425
<211> LENGTH: 9
<212> TYPE: PRT
<213> ORGANISM: Artificial Sequence
<220> FEATURE:
<223> OTHER INFORMATION: peptide

<400> SEQUENCE: 425

Leu Leu Gly Ala Leu Leu Pro Ala Val
1               5

<210> SEQ ID NO 426
<211> LENGTH: 9
<212> TYPE: PRT
<213> ORGANISM: Artificial Sequence
<220> FEATURE:
<223> OTHER INFORMATION: peptide

<400> SEQUENCE: 426

Ile Leu Gly Ala Leu Leu Pro Leu Leu
1               5

<210> SEQ ID NO 427
<211> LENGTH: 9
<212> TYPE: PRT
<213> ORGANISM: Artificial Sequence
<220> FEATURE:
<223> OTHER INFORMATION: peptide

<400> SEQUENCE: 427

Ser Val Ala Ala Phe Pro Val Thr Val
1               5

<210> SEQ ID NO 428
<211> LENGTH: 9
<212> TYPE: PRT
<213> ORGANISM: Artificial Sequence
<220> FEATURE:
<223> OTHER INFORMATION: peptide

```
<400> SEQUENCE: 428

Leu Leu Leu Ser Leu Phe Cys Leu Ile
1               5

<210> SEQ ID NO 429
<211> LENGTH: 9
<212> TYPE: PRT
<213> ORGANISM: Artificial Sequence
<220> FEATURE:
<223> OTHER INFORMATION: peptide

<400> SEQUENCE: 429

Lys Leu Leu Ser Leu Phe Cys Thr Leu
1               5

<210> SEQ ID NO 430
<211> LENGTH: 9
<212> TYPE: PRT
<213> ORGANISM: Artificial Sequence
<220> FEATURE:
<223> OTHER INFORMATION: peptide

<400> SEQUENCE: 430

Phe Leu Leu Ser Leu Phe Cys Ile Ala
1               5

<210> SEQ ID NO 431
<211> LENGTH: 9
<212> TYPE: PRT
<213> ORGANISM: Artificial Sequence
<220> FEATURE:
<223> OTHER INFORMATION: peptide

<400> SEQUENCE: 431

Ile Leu Leu Gly Val Gly Phe Gly Ile
1               5

<210> SEQ ID NO 432
<211> LENGTH: 9
<212> TYPE: PRT
<213> ORGANISM: Artificial Sequence
<220> FEATURE:
<223> OTHER INFORMATION: peptide

<400> SEQUENCE: 432

Ala Leu Leu Gly Val Gly Phe Gly Ile
1               5

<210> SEQ ID NO 433
<211> LENGTH: 9
<212> TYPE: PRT
<213> ORGANISM: Artificial Sequence
<220> FEATURE:
<223> OTHER INFORMATION: peptide

<400> SEQUENCE: 433

Arg Leu Ile Asp Glu Phe Gln Ser Val
1               5

<210> SEQ ID NO 434
<211> LENGTH: 9
<212> TYPE: PRT
<213> ORGANISM: Artificial Sequence
<220> FEATURE:
<223> OTHER INFORMATION: peptide

<400> SEQUENCE: 434
```

```
Phe Leu Glu Ser Val Ile Thr Thr Val
1               5

<210> SEQ ID NO 435
<211> LENGTH: 9
<212> TYPE: PRT
<213> ORGANISM: Artificial Sequence
<220> FEATURE:
<223> OTHER INFORMATION: peptide

<400> SEQUENCE: 435

Gly Leu Phe Gly Val Leu Ile Gly Val
1               5

<210> SEQ ID NO 436
<211> LENGTH: 9
<212> TYPE: PRT
<213> ORGANISM: Artificial Sequence
<220> FEATURE:
<223> OTHER INFORMATION: peptide

<400> SEQUENCE: 436

Ala Met Phe Gly Val Leu Ile Ser Val
1               5

<210> SEQ ID NO 437
<211> LENGTH: 9
<212> TYPE: PRT
<213> ORGANISM: Artificial Sequence
<220> FEATURE:
<223> OTHER INFORMATION: peptide

<400> SEQUENCE: 437

Phe Ile Asp Phe Leu Leu Ser Glu Val
1               5

<210> SEQ ID NO 438
<211> LENGTH: 9
<212> TYPE: PRT
<213> ORGANISM: Artificial Sequence
<220> FEATURE:
<223> OTHER INFORMATION: peptide

<400> SEQUENCE: 438

Gly Leu Phe Met Val Ile Ala Gly Val
1               5

<210> SEQ ID NO 439
<211> LENGTH: 9
<212> TYPE: PRT
<213> ORGANISM: Artificial Sequence
<220> FEATURE:
<223> OTHER INFORMATION: peptide

<400> SEQUENCE: 439

Phe Leu Phe Met Val Ile Ala Phe Ala
1               5

<210> SEQ ID NO 440
<211> LENGTH: 9
<212> TYPE: PRT
<213> ORGANISM: Artificial Sequence
<220> FEATURE:
<223> OTHER INFORMATION: peptide

<400> SEQUENCE: 440
```

```
His Leu Pro Tyr Leu Leu Phe Leu Leu
1               5

<210> SEQ ID NO 441
<211> LENGTH: 9
<212> TYPE: PRT
<213> ORGANISM: Artificial Sequence
<220> FEATURE:
<223> OTHER INFORMATION: peptide

<400> SEQUENCE: 441

Thr Leu Thr Ala Cys Leu Val Gly Val
1               5

<210> SEQ ID NO 442
<211> LENGTH: 9
<212> TYPE: PRT
<213> ORGANISM: Artificial Sequence
<220> FEATURE:
<223> OTHER INFORMATION: peptide

<400> SEQUENCE: 442

Met Leu Ser Glu Lys Met Val Gln Leu
1               5

<210> SEQ ID NO 443
<211> LENGTH: 9
<212> TYPE: PRT
<213> ORGANISM: Artificial Sequence
<220> FEATURE:
<223> OTHER INFORMATION: peptide

<400> SEQUENCE: 443

Asn Leu Phe Asp Leu Ser Leu Val Ala
1               5

<210> SEQ ID NO 444
<211> LENGTH: 9
<212> TYPE: PRT
<213> ORGANISM: Artificial Sequence
<220> FEATURE:
<223> OTHER INFORMATION: peptide

<400> SEQUENCE: 444

Gly Leu Phe Asp Leu Ser Leu Arg Val
1               5

<210> SEQ ID NO 445
<211> LENGTH: 9
<212> TYPE: PRT
<213> ORGANISM: Artificial Sequence
<220> FEATURE:
<223> OTHER INFORMATION: peptide

<400> SEQUENCE: 445

Ala Leu Phe Asp Leu Ser Leu Pro Ile
1               5

<210> SEQ ID NO 446
<211> LENGTH: 9
<212> TYPE: PRT
<213> ORGANISM: Artificial Sequence
<220> FEATURE:
<223> OTHER INFORMATION: peptide

<400> SEQUENCE: 446

Thr Leu Pro Ala Val Met Ala Glu Val
```

<210> SEQ ID NO 447
<211> LENGTH: 9
<212> TYPE: PRT
<213> ORGANISM: Artificial Sequence
<220> FEATURE:
<223> OTHER INFORMATION: peptide

<400> SEQUENCE: 447

Leu Leu Ala Glu Pro Gln Ala Ser Leu
1               5

<210> SEQ ID NO 448
<211> LENGTH: 9
<212> TYPE: PRT
<213> ORGANISM: Artificial Sequence
<220> FEATURE:
<223> OTHER INFORMATION: peptide

<400> SEQUENCE: 448

Ile Leu Ala Glu Pro Gln Ala Leu Val
1               5

<210> SEQ ID NO 449
<211> LENGTH: 9
<212> TYPE: PRT
<213> ORGANISM: Artificial Sequence
<220> FEATURE:
<223> OTHER INFORMATION: peptide

<400> SEQUENCE: 449

Phe Ile Ala Glu Pro Gln Ala Ala Leu
1               5

<210> SEQ ID NO 450
<211> LENGTH: 9
<212> TYPE: PRT
<213> ORGANISM: Artificial Sequence
<220> FEATURE:
<223> OTHER INFORMATION: peptide

<400> SEQUENCE: 450

Leu Leu Phe Leu Leu Ser Ala Leu Leu
1               5

<210> SEQ ID NO 451
<211> LENGTH: 9
<212> TYPE: PRT
<213> ORGANISM: Artificial Sequence
<220> FEATURE:
<223> OTHER INFORMATION: peptide

<400> SEQUENCE: 451

Lys Met Leu Thr Phe Leu Tyr Thr Ala
1               5

<210> SEQ ID NO 452
<211> LENGTH: 9
<212> TYPE: PRT
<213> ORGANISM: Artificial Sequence
<220> FEATURE:
<223> OTHER INFORMATION: peptide

<400> SEQUENCE: 452

Ala Val Leu His Ala Ile Tyr Gly Val
1               5

<210> SEQ ID NO 453
<211> LENGTH: 9
<212> TYPE: PRT
<213> ORGANISM: Artificial Sequence
<220> FEATURE:
<223> OTHER INFORMATION: peptide

<400> SEQUENCE: 453

His Leu Phe Ala Val Leu His Ala Val
1               5

<210> SEQ ID NO 454
<211> LENGTH: 9
<212> TYPE: PRT
<213> ORGANISM: Artificial Sequence
<220> FEATURE:
<223> OTHER INFORMATION: peptide

<400> SEQUENCE: 454

Ser Val Ile Ala Ala Ile Val Leu Val
1               5

<210> SEQ ID NO 455
<211> LENGTH: 9
<212> TYPE: PRT
<213> ORGANISM: Artificial Sequence
<220> FEATURE:
<223> OTHER INFORMATION: peptide

<400> SEQUENCE: 455

Phe Val Ile Ala Ala Ile Val Cys Val
1               5

<210> SEQ ID NO 456
<211> LENGTH: 9
<212> TYPE: PRT
<213> ORGANISM: Artificial Sequence
<220> FEATURE:
<223> OTHER INFORMATION: peptide

<400> SEQUENCE: 456

Phe Ile Ile Ala Ala Ile Val Ala Val
1               5

<210> SEQ ID NO 457
<211> LENGTH: 9
<212> TYPE: PRT
<213> ORGANISM: Artificial Sequence
<220> FEATURE:
<223> OTHER INFORMATION: peptide

<400> SEQUENCE: 457

Ala Val Ile Ala Ala Ile Val Gly Val
1               5

<210> SEQ ID NO 458
<211> LENGTH: 9
<212> TYPE: PRT
<213> ORGANISM: Artificial Sequence
<220> FEATURE:
<223> OTHER INFORMATION: peptide

<400> SEQUENCE: 458

Tyr Ile Ala Ala Ile Ile Ala Glu Ala
1               5

<210> SEQ ID NO 459
<211> LENGTH: 9
<212> TYPE: PRT
<213> ORGANISM: Artificial Sequence
<220> FEATURE:
<223> OTHER INFORMATION: peptide

<400> SEQUENCE: 459

Phe Val Ala Ala Ile Ile Ala Ser Leu
1               5

<210> SEQ ID NO 460
<211> LENGTH: 9
<212> TYPE: PRT
<213> ORGANISM: Artificial Sequence
<220> FEATURE:
<223> OTHER INFORMATION: peptide

<400> SEQUENCE: 460

Phe Ile Ala Ala Ile Ile Ala Pro Ile
1               5

<210> SEQ ID NO 461
<211> LENGTH: 9
<212> TYPE: PRT
<213> ORGANISM: Artificial Sequence
<220> FEATURE:
<223> OTHER INFORMATION: peptide

<400> SEQUENCE: 461

Gly Leu Phe Lys Ser Ile Leu Phe Leu
1               5

<210> SEQ ID NO 462
<211> LENGTH: 9
<212> TYPE: PRT
<213> ORGANISM: Artificial Sequence
<220> FEATURE:
<223> OTHER INFORMATION: peptide

<400> SEQUENCE: 462

Met Leu Leu Gly Thr Ile His Gly Val
1               5

<210> SEQ ID NO 463
<211> LENGTH: 9
<212> TYPE: PRT
<213> ORGANISM: Artificial Sequence
<220> FEATURE:
<223> OTHER INFORMATION: peptide

<400> SEQUENCE: 463

Leu Leu Ser Phe Phe Phe Ala Met Leu
1               5

<210> SEQ ID NO 464
<211> LENGTH: 9
<212> TYPE: PRT
<213> ORGANISM: Artificial Sequence
<220> FEATURE:
<223> OTHER INFORMATION: peptide

<400> SEQUENCE: 464

Leu Leu Ser Phe Phe Phe Ala Ala Leu
1               5

```
<210> SEQ ID NO 465
<211> LENGTH: 9
<212> TYPE: PRT
<213> ORGANISM: Artificial Sequence
<220> FEATURE:
<223> OTHER INFORMATION: peptide

<400> SEQUENCE: 465

Phe Leu Ser Phe Phe Phe Ala Ala Met
1               5

<210> SEQ ID NO 466
<211> LENGTH: 9
<212> TYPE: PRT
<213> ORGANISM: Artificial Sequence
<220> FEATURE:
<223> OTHER INFORMATION: peptide

<400> SEQUENCE: 466

Phe Leu Ala Val Phe Leu Pro Val Leu
1               5

<210> SEQ ID NO 467
<211> LENGTH: 9
<212> TYPE: PRT
<213> ORGANISM: Artificial Sequence
<220> FEATURE:
<223> OTHER INFORMATION: peptide

<400> SEQUENCE: 467

Ser Leu Leu Leu Gly Thr Ile Leu Val
1               5

<210> SEQ ID NO 468
<211> LENGTH: 9
<212> TYPE: PRT
<213> ORGANISM: Artificial Sequence
<220> FEATURE:
<223> OTHER INFORMATION: peptide

<400> SEQUENCE: 468

Ile Leu Leu Leu Gly Thr Ile Leu Leu
1               5

<210> SEQ ID NO 469
<211> LENGTH: 9
<212> TYPE: PRT
<213> ORGANISM: Artificial Sequence
<220> FEATURE:
<223> OTHER INFORMATION: peptide

<400> SEQUENCE: 469

Arg Leu Ser Leu Ile Val Ala Leu Val
1               5

<210> SEQ ID NO 470
<211> LENGTH: 9
<212> TYPE: PRT
<213> ORGANISM: Artificial Sequence
<220> FEATURE:
<223> OTHER INFORMATION: peptide

<400> SEQUENCE: 470

Arg Leu Ser Leu Ile Val Ala Phe Val
1               5

<210> SEQ ID NO 471
```

```
<211> LENGTH: 9
<212> TYPE: PRT
<213> ORGANISM: Artificial Sequence
<220> FEATURE:
<223> OTHER INFORMATION: peptide

<400> SEQUENCE: 471

Met Ile Ser Pro Asn Leu Phe Arg Val
1               5

<210> SEQ ID NO 472
<211> LENGTH: 9
<212> TYPE: PRT
<213> ORGANISM: Artificial Sequence
<220> FEATURE:
<223> OTHER INFORMATION: peptide

<400> SEQUENCE: 472

Leu Leu Asp His Val Leu Ile Ala Val
1               5

<210> SEQ ID NO 473
<211> LENGTH: 9
<212> TYPE: PRT
<213> ORGANISM: Artificial Sequence
<220> FEATURE:
<223> OTHER INFORMATION: peptide

<400> SEQUENCE: 473

Arg Leu Ile Asp Glu His Leu Val Val
1               5

<210> SEQ ID NO 474
<211> LENGTH: 9
<212> TYPE: PRT
<213> ORGANISM: Artificial Sequence
<220> FEATURE:
<223> OTHER INFORMATION: peptide

<400> SEQUENCE: 474

Thr Leu Ser Glu Val Leu Glu Tyr Leu
1               5

<210> SEQ ID NO 475
<211> LENGTH: 9
<212> TYPE: PRT
<213> ORGANISM: Artificial Sequence
<220> FEATURE:
<223> OTHER INFORMATION: peptide

<400> SEQUENCE: 475

Phe Leu Leu Arg Pro Asp Thr Phe Leu
1               5

<210> SEQ ID NO 476
<211> LENGTH: 9
<212> TYPE: PRT
<213> ORGANISM: Artificial Sequence
<220> FEATURE:
<223> OTHER INFORMATION: peptide

<400> SEQUENCE: 476

Leu Met Met Thr Ile Ile Asn Gln Val
1               5

<210> SEQ ID NO 477
<211> LENGTH: 9
```

```
<212> TYPE: PRT
<213> ORGANISM: Artificial Sequence
<220> FEATURE:
<223> OTHER INFORMATION: peptide

<400> SEQUENCE: 477

Leu Leu Met Thr Ile Ile Asn Gln Val
1               5

<210> SEQ ID NO 478
<211> LENGTH: 9
<212> TYPE: PRT
<213> ORGANISM: Artificial Sequence
<220> FEATURE:
<223> OTHER INFORMATION: peptide

<400> SEQUENCE: 478

Phe Leu Met Thr Ile Ile Asn Gln Val
1               5

<210> SEQ ID NO 479
<211> LENGTH: 9
<212> TYPE: PRT
<213> ORGANISM: Artificial Sequence
<220> FEATURE:
<223> OTHER INFORMATION: peptide

<400> SEQUENCE: 479

Arg Leu Ala Gly Ser Val Ala Gly Val
1               5

<210> SEQ ID NO 480
<211> LENGTH: 9
<212> TYPE: PRT
<213> ORGANISM: Artificial Sequence
<220> FEATURE:
<223> OTHER INFORMATION: peptide

<400> SEQUENCE: 480

Lys Leu Ala Gly Ser Val Ala Gly Val
1               5

<210> SEQ ID NO 481
<211> LENGTH: 9
<212> TYPE: PRT
<213> ORGANISM: Artificial Sequence
<220> FEATURE:
<223> OTHER INFORMATION: peptide

<400> SEQUENCE: 481

Leu Leu Met Met Thr Ile Ile Thr Val
1               5

<210> SEQ ID NO 482
<211> LENGTH: 9
<212> TYPE: PRT
<213> ORGANISM: Artificial Sequence
<220> FEATURE:
<223> OTHER INFORMATION: peptide

<400> SEQUENCE: 482

Ala Met Leu Ser Ser Leu Ala Gly Val
1               5

<210> SEQ ID NO 483
<211> LENGTH: 9
<212> TYPE: PRT
```

```
<213> ORGANISM: Artificial Sequence
<220> FEATURE:
<223> OTHER INFORMATION: peptide

<400> SEQUENCE: 483

Tyr Val Phe Thr Met Leu Ser Ala Val
1               5

<210> SEQ ID NO 484
<211> LENGTH: 9
<212> TYPE: PRT
<213> ORGANISM: Artificial Sequence
<220> FEATURE:
<223> OTHER INFORMATION: peptide

<400> SEQUENCE: 484

Tyr Leu Ala Gly Val Ile Ile Leu Ile
1               5

<210> SEQ ID NO 485
<211> LENGTH: 9
<212> TYPE: PRT
<213> ORGANISM: Artificial Sequence
<220> FEATURE:
<223> OTHER INFORMATION: peptide

<400> SEQUENCE: 485

Met Leu Ala Gly Val Ile Ile Tyr Ile
1               5

<210> SEQ ID NO 486
<211> LENGTH: 9
<212> TYPE: PRT
<213> ORGANISM: Artificial Sequence
<220> FEATURE:
<223> OTHER INFORMATION: peptide

<400> SEQUENCE: 486

Met Leu Ala Gly Val Ile Ile Gly Ile
1               5

<210> SEQ ID NO 487
<211> LENGTH: 9
<212> TYPE: PRT
<213> ORGANISM: Artificial Sequence
<220> FEATURE:
<223> OTHER INFORMATION: peptide

<400> SEQUENCE: 487

Leu Leu Ala Gly Val Ile Ile Thr Ile
1               5

<210> SEQ ID NO 488
<211> LENGTH: 9
<212> TYPE: PRT
<213> ORGANISM: Artificial Sequence
<220> FEATURE:
<223> OTHER INFORMATION: peptide

<400> SEQUENCE: 488

Leu Leu Ala Gly Val Ile Ile Gly Ile
1               5

<210> SEQ ID NO 489
<211> LENGTH: 9
<212> TYPE: PRT
<213> ORGANISM: Artificial Sequence
```

```
<220> FEATURE:
<223> OTHER INFORMATION: peptide

<400> SEQUENCE: 489

Gly Leu Ala Gly Val Ile Ile Thr Ile
1               5

<210> SEQ ID NO 490
<211> LENGTH: 9
<212> TYPE: PRT
<213> ORGANISM: Artificial Sequence
<220> FEATURE:
<223> OTHER INFORMATION: peptide

<400> SEQUENCE: 490

Gly Leu Ala Gly Val Ile Ile Ala Val
1               5

<210> SEQ ID NO 491
<211> LENGTH: 9
<212> TYPE: PRT
<213> ORGANISM: Artificial Sequence
<220> FEATURE:
<223> OTHER INFORMATION: peptide

<400> SEQUENCE: 491

Val Met Leu Phe Gly Val Phe Met Val
1               5

<210> SEQ ID NO 492
<211> LENGTH: 9
<212> TYPE: PRT
<213> ORGANISM: Artificial Sequence
<220> FEATURE:
<223> OTHER INFORMATION: peptide

<400> SEQUENCE: 492

Val Leu Leu Phe Gly Val Phe Leu Val
1               5

<210> SEQ ID NO 493
<211> LENGTH: 9
<212> TYPE: PRT
<213> ORGANISM: Artificial Sequence
<220> FEATURE:
<223> OTHER INFORMATION: peptide

<400> SEQUENCE: 493

Ile Leu Leu Phe Gly Val Phe Met Val
1               5

<210> SEQ ID NO 494
<211> LENGTH: 9
<212> TYPE: PRT
<213> ORGANISM: Artificial Sequence
<220> FEATURE:
<223> OTHER INFORMATION: peptide

<400> SEQUENCE: 494

Phe Ile Leu Phe Gly Val Phe Met Leu
1               5

<210> SEQ ID NO 495
<211> LENGTH: 9
<212> TYPE: PRT
<213> ORGANISM: Artificial Sequence
<220> FEATURE:
```

<223> OTHER INFORMATION: peptide

<400> SEQUENCE: 495

Val Leu Phe Gly Val Phe Leu Gly Val
1               5

<210> SEQ ID NO 496
<211> LENGTH: 9
<212> TYPE: PRT
<213> ORGANISM: Artificial Sequence
<220> FEATURE:
<223> OTHER INFORMATION: peptide

<400> SEQUENCE: 496

Gly Met Phe Gly Val Phe Leu Thr Leu
1               5

<210> SEQ ID NO 497
<211> LENGTH: 9
<212> TYPE: PRT
<213> ORGANISM: Artificial Sequence
<220> FEATURE:
<223> OTHER INFORMATION: peptide

<400> SEQUENCE: 497

Phe Leu Phe Gly Val Phe Leu Ala Met
1               5

<210> SEQ ID NO 498
<211> LENGTH: 9
<212> TYPE: PRT
<213> ORGANISM: Artificial Sequence
<220> FEATURE:
<223> OTHER INFORMATION: peptide

<400> SEQUENCE: 498

Val Leu Asp Thr Ala Ile Ile Tyr Ile
1               5

<210> SEQ ID NO 499
<211> LENGTH: 9
<212> TYPE: PRT
<213> ORGANISM: Artificial Sequence
<220> FEATURE:
<223> OTHER INFORMATION: peptide

<400> SEQUENCE: 499

Lys Leu Asp Thr Ala Ile Ile His Val
1               5

<210> SEQ ID NO 500
<211> LENGTH: 9
<212> TYPE: PRT
<213> ORGANISM: Artificial Sequence
<220> FEATURE:
<223> OTHER INFORMATION: peptide

<400> SEQUENCE: 500

Leu Ile Ser Ser Phe Ala Phe Leu Val
1               5

<210> SEQ ID NO 501
<211> LENGTH: 9
<212> TYPE: PRT
<213> ORGANISM: Artificial Sequence
<220> FEATURE:
<223> OTHER INFORMATION: peptide

<400> SEQUENCE: 501

Leu Ile Ser Ser Phe Ala Phe Leu Leu
1               5

<210> SEQ ID NO 502
<211> LENGTH: 9
<212> TYPE: PRT
<213> ORGANISM: Artificial Sequence
<220> FEATURE:
<223> OTHER INFORMATION: peptide

<400> SEQUENCE: 502

Phe Met Leu Arg Leu Ile Ile Asn Leu
1               5

<210> SEQ ID NO 503
<211> LENGTH: 9
<212> TYPE: PRT
<213> ORGANISM: Artificial Sequence
<220> FEATURE:
<223> OTHER INFORMATION: peptide

<400> SEQUENCE: 503

Ala Leu Ala Ile Ala Leu Phe Pro Val
1               5

<210> SEQ ID NO 504
<211> LENGTH: 9
<212> TYPE: PRT
<213> ORGANISM: Artificial Sequence
<220> FEATURE:
<223> OTHER INFORMATION: peptide

<400> SEQUENCE: 504

Ala Leu Trp Leu His Thr Ser Phe Ala
1               5

<210> SEQ ID NO 505
<211> LENGTH: 9
<212> TYPE: PRT
<213> ORGANISM: Artificial Sequence
<220> FEATURE:
<223> OTHER INFORMATION: peptide

<400> SEQUENCE: 505

Thr Met Phe Gly Tyr Thr Val Phe Leu
1               5

<210> SEQ ID NO 506
<211> LENGTH: 9
<212> TYPE: PRT
<213> ORGANISM: Artificial Sequence
<220> FEATURE:
<223> OTHER INFORMATION: peptide

<400> SEQUENCE: 506

Tyr Leu Ala Gly Ile Val Phe Thr Leu
1               5

<210> SEQ ID NO 507
<211> LENGTH: 9
<212> TYPE: PRT
<213> ORGANISM: Artificial Sequence
<220> FEATURE:
<223> OTHER INFORMATION: peptide

```
<400> SEQUENCE: 507

Leu Met Leu Leu Phe Ala Tyr Tyr Leu
1               5

<210> SEQ ID NO 508
<211> LENGTH: 9
<212> TYPE: PRT
<213> ORGANISM: Artificial Sequence
<220> FEATURE:
<223> OTHER INFORMATION: peptide

<400> SEQUENCE: 508

Tyr Leu Phe Ala Tyr Val Leu Ile Val
1               5

<210> SEQ ID NO 509
<211> LENGTH: 9
<212> TYPE: PRT
<213> ORGANISM: Artificial Sequence
<220> FEATURE:
<223> OTHER INFORMATION: peptide

<400> SEQUENCE: 509

Thr Leu Phe Ala Tyr Val Leu Gly Leu
1               5

<210> SEQ ID NO 510
<211> LENGTH: 9
<212> TYPE: PRT
<213> ORGANISM: Artificial Sequence
<220> FEATURE:
<223> OTHER INFORMATION: peptide

<400> SEQUENCE: 510

Gly Leu Leu Phe Ala Tyr Val Glu Val
1               5

<210> SEQ ID NO 511
<211> LENGTH: 9
<212> TYPE: PRT
<213> ORGANISM: Artificial Sequence
<220> FEATURE:
<223> OTHER INFORMATION: peptide

<400> SEQUENCE: 511

Lys Ile Leu Tyr Ser Leu Val Glu Val
1               5

<210> SEQ ID NO 512
<211> LENGTH: 9
<212> TYPE: PRT
<213> ORGANISM: Artificial Sequence
<220> FEATURE:
<223> OTHER INFORMATION: peptide

<400> SEQUENCE: 512

Phe Leu Leu Leu Val Asn Leu Leu Val
1               5

<210> SEQ ID NO 513
<211> LENGTH: 9
<212> TYPE: PRT
<213> ORGANISM: Artificial Sequence
<220> FEATURE:
<223> OTHER INFORMATION: peptide

<400> SEQUENCE: 513
```

Val Ile Ala Asp Val Ile Ala Leu Leu
1               5

<210> SEQ ID NO 514
<211> LENGTH: 9
<212> TYPE: PRT
<213> ORGANISM: Artificial Sequence
<220> FEATURE:
<223> OTHER INFORMATION: peptide

<400> SEQUENCE: 514

Gln Ile Ala Asp Val Ile Ala Phe Leu
1               5

<210> SEQ ID NO 515
<211> LENGTH: 9
<212> TYPE: PRT
<213> ORGANISM: Artificial Sequence
<220> FEATURE:
<223> OTHER INFORMATION: peptide

<400> SEQUENCE: 515

Leu Val Ala Asp Val Ile Ala Ser Val
1               5

<210> SEQ ID NO 516
<211> LENGTH: 9
<212> TYPE: PRT
<213> ORGANISM: Artificial Sequence
<220> FEATURE:
<223> OTHER INFORMATION: peptide

<400> SEQUENCE: 516

Leu Ile Ala Asp Val Ile Ala Leu Leu
1               5

<210> SEQ ID NO 517
<211> LENGTH: 9
<212> TYPE: PRT
<213> ORGANISM: Artificial Sequence
<220> FEATURE:
<223> OTHER INFORMATION: peptide

<400> SEQUENCE: 517

Leu Leu Tyr Ser Leu Val Phe Phe Leu
1               5

<210> SEQ ID NO 518
<211> LENGTH: 9
<212> TYPE: PRT
<213> ORGANISM: Artificial Sequence
<220> FEATURE:
<223> OTHER INFORMATION: peptide

<400> SEQUENCE: 518

Phe Leu Val Lys Ile Asn Thr Asn Ile
1               5

<210> SEQ ID NO 519
<211> LENGTH: 9
<212> TYPE: PRT
<213> ORGANISM: Artificial Sequence
<220> FEATURE:
<223> OTHER INFORMATION: peptide

<400> SEQUENCE: 519

Lys Leu Asp Ser Leu Gly Phe Thr Leu
1               5

<210> SEQ ID NO 520
<211> LENGTH: 9
<212> TYPE: PRT
<213> ORGANISM: Artificial Sequence
<220> FEATURE:
<223> OTHER INFORMATION: peptide

<400> SEQUENCE: 520

Lys Leu Asp Ser Leu Gly Phe Ser Leu
1               5

<210> SEQ ID NO 521
<211> LENGTH: 9
<212> TYPE: PRT
<213> ORGANISM: Artificial Sequence
<220> FEATURE:
<223> OTHER INFORMATION: peptide

<400> SEQUENCE: 521

Phe Leu Asp Ser Leu Gly Phe Ser Leu
1               5

<210> SEQ ID NO 522
<211> LENGTH: 9
<212> TYPE: PRT
<213> ORGANISM: Artificial Sequence
<220> FEATURE:
<223> OTHER INFORMATION: peptide

<400> SEQUENCE: 522

Phe Met Arg Asp Glu Phe Pro Asp Val
1               5

<210> SEQ ID NO 523
<211> LENGTH: 9
<212> TYPE: PRT
<213> ORGANISM: Artificial Sequence
<220> FEATURE:
<223> OTHER INFORMATION: peptide

<400> SEQUENCE: 523

Phe Leu Arg Asp Glu Phe Pro Glu Ala
1               5

<210> SEQ ID NO 524
<211> LENGTH: 9
<212> TYPE: PRT
<213> ORGANISM: Artificial Sequence
<220> FEATURE:
<223> OTHER INFORMATION: peptide

<400> SEQUENCE: 524

Ser Met Glu Glu Leu Leu Trp Phe Val
1               5

<210> SEQ ID NO 525
<211> LENGTH: 9
<212> TYPE: PRT
<213> ORGANISM: Artificial Sequence
<220> FEATURE:
<223> OTHER INFORMATION: peptide

<400> SEQUENCE: 525

Tyr Leu Leu Ala Gly Leu Val Leu Leu

```
1               5

<210> SEQ ID NO 526
<211> LENGTH: 9
<212> TYPE: PRT
<213> ORGANISM: Artificial Sequence
<220> FEATURE:
<223> OTHER INFORMATION: peptide

<400> SEQUENCE: 526

Tyr Leu Leu Ala Gly Leu Val Leu Ile
1               5

<210> SEQ ID NO 527
<211> LENGTH: 9
<212> TYPE: PRT
<213> ORGANISM: Artificial Sequence
<220> FEATURE:
<223> OTHER INFORMATION: peptide

<400> SEQUENCE: 527

Trp Leu Val Gly Ala Val Leu Thr Leu
1               5

<210> SEQ ID NO 528
<211> LENGTH: 9
<212> TYPE: PRT
<213> ORGANISM: Artificial Sequence
<220> FEATURE:
<223> OTHER INFORMATION: peptide

<400> SEQUENCE: 528

Leu Leu Val Gly Ala Val Leu Thr Val
1               5

<210> SEQ ID NO 529
<211> LENGTH: 9
<212> TYPE: PRT
<213> ORGANISM: Artificial Sequence
<220> FEATURE:
<223> OTHER INFORMATION: peptide

<400> SEQUENCE: 529

Ala Leu Val Gly Ala Val Leu Thr Val
1               5

<210> SEQ ID NO 530
<211> LENGTH: 9
<212> TYPE: PRT
<213> ORGANISM: Artificial Sequence
<220> FEATURE:
<223> OTHER INFORMATION: peptide

<400> SEQUENCE: 530

Ala Leu Val Gly Ala Val Leu Leu Val
1               5

<210> SEQ ID NO 531
<211> LENGTH: 9
<212> TYPE: PRT
<213> ORGANISM: Artificial Sequence
<220> FEATURE:
<223> OTHER INFORMATION: peptide

<400> SEQUENCE: 531

Cys Leu Ser Asp Tyr Val Ile Pro Val
1               5
```

<210> SEQ ID NO 532
<211> LENGTH: 9
<212> TYPE: PRT
<213> ORGANISM: Artificial Sequence
<220> FEATURE:
<223> OTHER INFORMATION: peptide

<400> SEQUENCE: 532

Lys Leu Ala Gly Leu Val Ser Ser Val
1               5

<210> SEQ ID NO 533
<211> LENGTH: 9
<212> TYPE: PRT
<213> ORGANISM: Artificial Sequence
<220> FEATURE:
<223> OTHER INFORMATION: peptide

<400> SEQUENCE: 533

Gly Met Ser Pro Ala Ser Phe Phe Ala
1               5

<210> SEQ ID NO 534
<211> LENGTH: 9
<212> TYPE: PRT
<213> ORGANISM: Artificial Sequence
<220> FEATURE:
<223> OTHER INFORMATION: peptide

<400> SEQUENCE: 534

Ala Leu Gly Ala Val Leu Thr Ala Val
1               5

<210> SEQ ID NO 535
<211> LENGTH: 9
<212> TYPE: PRT
<213> ORGANISM: Artificial Sequence
<220> FEATURE:
<223> OTHER INFORMATION: peptide

<400> SEQUENCE: 535

Tyr Leu Thr Ala Leu Leu Ala Glu Met
1               5

<210> SEQ ID NO 536
<211> LENGTH: 9
<212> TYPE: PRT
<213> ORGANISM: Artificial Sequence
<220> FEATURE:
<223> OTHER INFORMATION: peptide

<400> SEQUENCE: 536

Val Leu Thr Ala Leu Leu Ala Ala Val
1               5

<210> SEQ ID NO 537
<211> LENGTH: 9
<212> TYPE: PRT
<213> ORGANISM: Artificial Sequence
<220> FEATURE:
<223> OTHER INFORMATION: peptide

<400> SEQUENCE: 537

Arg Leu Thr Ala Leu Leu Ala Ala Val
1               5

<210> SEQ ID NO 538
<211> LENGTH: 9
<212> TYPE: PRT
<213> ORGANISM: Artificial Sequence
<220> FEATURE:
<223> OTHER INFORMATION: peptide

<400> SEQUENCE: 538

Gly Leu Thr Ala Leu Leu Ala Pro Val
1               5

<210> SEQ ID NO 539
<211> LENGTH: 9
<212> TYPE: PRT
<213> ORGANISM: Artificial Sequence
<220> FEATURE:
<223> OTHER INFORMATION: peptide

<400> SEQUENCE: 539

Phe Leu Thr Ala Leu Leu Ala Thr Val
1               5

<210> SEQ ID NO 540
<211> LENGTH: 9
<212> TYPE: PRT
<213> ORGANISM: Artificial Sequence
<220> FEATURE:
<223> OTHER INFORMATION: peptide

<400> SEQUENCE: 540

Thr Leu Thr Glu Ser Leu Leu Tyr Leu
1               5

<210> SEQ ID NO 541
<211> LENGTH: 9
<212> TYPE: PRT
<213> ORGANISM: Artificial Sequence
<220> FEATURE:
<223> OTHER INFORMATION: peptide

<400> SEQUENCE: 541

Lys Leu Thr Glu Ser Leu Leu Thr Ile
1               5

<210> SEQ ID NO 542
<211> LENGTH: 9
<212> TYPE: PRT
<213> ORGANISM: Artificial Sequence
<220> FEATURE:
<223> OTHER INFORMATION: peptide

<400> SEQUENCE: 542

Ile Leu Thr Glu Ser Leu Leu Phe Leu
1               5

<210> SEQ ID NO 543
<211> LENGTH: 9
<212> TYPE: PRT
<213> ORGANISM: Artificial Sequence
<220> FEATURE:
<223> OTHER INFORMATION: peptide

<400> SEQUENCE: 543

Arg Leu Ala Leu Leu Ser Pro Tyr Ile
1               5

```
<210> SEQ ID NO 544
<211> LENGTH: 9
<212> TYPE: PRT
<213> ORGANISM: Artificial Sequence
<220> FEATURE:
<223> OTHER INFORMATION: peptide

<400> SEQUENCE: 544

Ser Ile Leu Gly Phe Ile Ile Ala Ala
1               5

<210> SEQ ID NO 545
<211> LENGTH: 9
<212> TYPE: PRT
<213> ORGANISM: Artificial Sequence
<220> FEATURE:
<223> OTHER INFORMATION: peptide

<400> SEQUENCE: 545

Leu Ile Leu Gly Phe Ile Ile Ala Val
1               5

<210> SEQ ID NO 546
<211> LENGTH: 9
<212> TYPE: PRT
<213> ORGANISM: Artificial Sequence
<220> FEATURE:
<223> OTHER INFORMATION: peptide

<400> SEQUENCE: 546

Phe Val Leu Gly Phe Ile Ile Thr Ile
1               5

<210> SEQ ID NO 547
<211> LENGTH: 9
<212> TYPE: PRT
<213> ORGANISM: Artificial Sequence
<220> FEATURE:
<223> OTHER INFORMATION: peptide

<400> SEQUENCE: 547

Phe Ile Leu Gly Phe Ile Ile Thr Ile
1               5

<210> SEQ ID NO 548
<211> LENGTH: 9
<212> TYPE: PRT
<213> ORGANISM: Artificial Sequence
<220> FEATURE:
<223> OTHER INFORMATION: peptide

<400> SEQUENCE: 548

Ser Leu Ser Gly Leu Leu Ser Gly Val
1               5

<210> SEQ ID NO 549
<211> LENGTH: 9
<212> TYPE: PRT
<213> ORGANISM: Artificial Sequence
<220> FEATURE:
<223> OTHER INFORMATION: peptide

<400> SEQUENCE: 549

Phe Leu Ser Gly Leu Leu Ser Ala Leu
1               5

<210> SEQ ID NO 550
```

```
<211> LENGTH: 9
<212> TYPE: PRT
<213> ORGANISM: Artificial Sequence
<220> FEATURE:
<223> OTHER INFORMATION: peptide

<400> SEQUENCE: 550

Ile Leu Pro Leu Ile Leu Ile Thr Val
1               5

<210> SEQ ID NO 551
<211> LENGTH: 9
<212> TYPE: PRT
<213> ORGANISM: Artificial Sequence
<220> FEATURE:
<223> OTHER INFORMATION: peptide

<400> SEQUENCE: 551

Met Leu Gly Phe Ile Ile Ala Phe Leu
1               5

<210> SEQ ID NO 552
<211> LENGTH: 9
<212> TYPE: PRT
<213> ORGANISM: Artificial Sequence
<220> FEATURE:
<223> OTHER INFORMATION: peptide

<400> SEQUENCE: 552

Leu Leu Gly Phe Ile Ile Ala Glu Val
1               5

<210> SEQ ID NO 553
<211> LENGTH: 9
<212> TYPE: PRT
<213> ORGANISM: Artificial Sequence
<220> FEATURE:
<223> OTHER INFORMATION: peptide

<400> SEQUENCE: 553

Ile Leu Gly Phe Ile Ile Ala Ala Val
1               5

<210> SEQ ID NO 554
<211> LENGTH: 9
<212> TYPE: PRT
<213> ORGANISM: Artificial Sequence
<220> FEATURE:
<223> OTHER INFORMATION: peptide

<400> SEQUENCE: 554

Phe Leu Gly Phe Ile Ile Ala Asp Val
1               5

<210> SEQ ID NO 555
<211> LENGTH: 9
<212> TYPE: PRT
<213> ORGANISM: Artificial Sequence
<220> FEATURE:
<223> OTHER INFORMATION: peptide

<400> SEQUENCE: 555

Met Ile Ile Thr Val Leu Leu Leu Val
1               5

<210> SEQ ID NO 556
<211> LENGTH: 9
```

```
<212> TYPE: PRT
<213> ORGANISM: Artificial Sequence
<220> FEATURE:
<223> OTHER INFORMATION: peptide

<400> SEQUENCE: 556

Phe Ile Ile Thr Val Leu Leu Gly Leu
1               5

<210> SEQ ID NO 557
<211> LENGTH: 9
<212> TYPE: PRT
<213> ORGANISM: Artificial Sequence
<220> FEATURE:
<223> OTHER INFORMATION: peptide

<400> SEQUENCE: 557

Tyr Gln Ile Gly Asp Ser Val Leu Leu
1               5

<210> SEQ ID NO 558
<211> LENGTH: 9
<212> TYPE: PRT
<213> ORGANISM: Artificial Sequence
<220> FEATURE:
<223> OTHER INFORMATION: peptide

<400> SEQUENCE: 558

Met Leu Ser Ser Leu Ile Ile Pro Leu
1               5

<210> SEQ ID NO 559
<211> LENGTH: 9
<212> TYPE: PRT
<213> ORGANISM: Artificial Sequence
<220> FEATURE:
<223> OTHER INFORMATION: peptide

<400> SEQUENCE: 559

Ile Leu Ile Asp Gly Ala Tyr Thr Val
1               5

<210> SEQ ID NO 560
<211> LENGTH: 9
<212> TYPE: PRT
<213> ORGANISM: Artificial Sequence
<220> FEATURE:
<223> OTHER INFORMATION: peptide

<400> SEQUENCE: 560

Tyr Leu Leu Glu Glu Gly Ser Ser Val
1               5

<210> SEQ ID NO 561
<211> LENGTH: 9
<212> TYPE: PRT
<213> ORGANISM: Artificial Sequence
<220> FEATURE:
<223> OTHER INFORMATION: peptide

<400> SEQUENCE: 561

Tyr Met Phe Gly Phe Thr Leu Thr Met
1               5

<210> SEQ ID NO 562
<211> LENGTH: 9
<212> TYPE: PRT
```

```
<213> ORGANISM: Artificial Sequence
<220> FEATURE:
<223> OTHER INFORMATION: peptide

<400> SEQUENCE: 562

Tyr Leu Phe Gly Phe Thr Leu Gly Met
1               5

<210> SEQ ID NO 563
<211> LENGTH: 9
<212> TYPE: PRT
<213> ORGANISM: Artificial Sequence
<220> FEATURE:
<223> OTHER INFORMATION: peptide

<400> SEQUENCE: 563

Val Leu Phe Gly Phe Thr Leu Ser Ile
1               5

<210> SEQ ID NO 564
<211> LENGTH: 9
<212> TYPE: PRT
<213> ORGANISM: Artificial Sequence
<220> FEATURE:
<223> OTHER INFORMATION: peptide

<400> SEQUENCE: 564

Arg Met Phe Gly Phe Thr Leu Met Leu
1               5

<210> SEQ ID NO 565
<211> LENGTH: 9
<212> TYPE: PRT
<213> ORGANISM: Artificial Sequence
<220> FEATURE:
<223> OTHER INFORMATION: peptide

<400> SEQUENCE: 565

Leu Met Phe Gly Phe Thr Leu Arg Thr
1               5

<210> SEQ ID NO 566
<211> LENGTH: 9
<212> TYPE: PRT
<213> ORGANISM: Artificial Sequence
<220> FEATURE:
<223> OTHER INFORMATION: peptide

<400> SEQUENCE: 566

Tyr Leu Leu Phe Gly Phe Thr Arg Val
1               5

<210> SEQ ID NO 567
<211> LENGTH: 9
<212> TYPE: PRT
<213> ORGANISM: Artificial Sequence
<220> FEATURE:
<223> OTHER INFORMATION: peptide

<400> SEQUENCE: 567

Val Leu Gly Pro Leu Ala Ala Leu Val
1               5

<210> SEQ ID NO 568
<211> LENGTH: 9
<212> TYPE: PRT
<213> ORGANISM: Artificial Sequence
```

```
<220> FEATURE:
<223> OTHER INFORMATION: peptide

<400> SEQUENCE: 568

Ile Leu Gly Pro Leu Ala Ala Trp Leu
1               5

<210> SEQ ID NO 569
<211> LENGTH: 9
<212> TYPE: PRT
<213> ORGANISM: Artificial Sequence
<220> FEATURE:
<223> OTHER INFORMATION: peptide

<400> SEQUENCE: 569

Ser Leu Asn Ala Leu Leu Pro Tyr Val
1               5

<210> SEQ ID NO 570
<211> LENGTH: 9
<212> TYPE: PRT
<213> ORGANISM: Artificial Sequence
<220> FEATURE:
<223> OTHER INFORMATION: peptide

<400> SEQUENCE: 570

Met Met Ile Pro Gln Val Ala Thr Leu
1               5

<210> SEQ ID NO 571
<211> LENGTH: 9
<212> TYPE: PRT
<213> ORGANISM: Artificial Sequence
<220> FEATURE:
<223> OTHER INFORMATION: peptide

<400> SEQUENCE: 571

Met Met Ile Pro Gln Val Ala Thr Ile
1               5

<210> SEQ ID NO 572
<211> LENGTH: 9
<212> TYPE: PRT
<213> ORGANISM: Artificial Sequence
<220> FEATURE:
<223> OTHER INFORMATION: peptide

<400> SEQUENCE: 572

Tyr Leu Ser Asp Ile Gln Asn Ala Ile
1               5

<210> SEQ ID NO 573
<211> LENGTH: 9
<212> TYPE: PRT
<213> ORGANISM: Artificial Sequence
<220> FEATURE:
<223> OTHER INFORMATION: peptide

<400> SEQUENCE: 573

Val Met Ser Asp Ile Gln Asn Arg Val
1               5

<210> SEQ ID NO 574
<211> LENGTH: 9
<212> TYPE: PRT
<213> ORGANISM: Artificial Sequence
<220> FEATURE:
```

```
<223> OTHER INFORMATION: peptide

<400> SEQUENCE: 574

Tyr Gln Ala Val Val Leu Pro Gly Leu
1               5

<210> SEQ ID NO 575
<211> LENGTH: 9
<212> TYPE: PRT
<213> ORGANISM: Artificial Sequence
<220> FEATURE:
<223> OTHER INFORMATION: peptide

<400> SEQUENCE: 575

Leu Leu Leu Glu Gln Phe Leu Ser Val
1               5

<210> SEQ ID NO 576
<211> LENGTH: 9
<212> TYPE: PRT
<213> ORGANISM: Artificial Sequence
<220> FEATURE:
<223> OTHER INFORMATION: peptide

<400> SEQUENCE: 576

Leu Leu Leu Glu Gln Phe Leu Ala Ile
1               5

<210> SEQ ID NO 577
<211> LENGTH: 9
<212> TYPE: PRT
<213> ORGANISM: Artificial Sequence
<220> FEATURE:
<223> OTHER INFORMATION: peptide

<400> SEQUENCE: 577

Ala Leu Leu Glu Gln Phe Leu Thr Ala
1               5

<210> SEQ ID NO 578
<211> LENGTH: 9
<212> TYPE: PRT
<213> ORGANISM: Artificial Sequence
<220> FEATURE:
<223> OTHER INFORMATION: peptide

<400> SEQUENCE: 578

Gly Val Ser Gly Tyr Ile Ser Pro Val
1               5

<210> SEQ ID NO 579
<211> LENGTH: 9
<212> TYPE: PRT
<213> ORGANISM: Artificial Sequence
<220> FEATURE:
<223> OTHER INFORMATION: peptide

<400> SEQUENCE: 579

Lys Leu Thr Asp Ile Ser Ser Leu Val
1               5

<210> SEQ ID NO 580
<211> LENGTH: 9
<212> TYPE: PRT
<213> ORGANISM: Artificial Sequence
<220> FEATURE:
<223> OTHER INFORMATION: peptide
```

<400> SEQUENCE: 580

Tyr Leu Leu Ser Asn Phe Tyr Thr Val
1               5

<210> SEQ ID NO 581
<211> LENGTH: 9
<212> TYPE: PRT
<213> ORGANISM: Homo sapiens

<400> SEQUENCE: 581

Phe Leu Phe Leu Leu Phe Phe Trp Leu
1               5

<210> SEQ ID NO 582
<211> LENGTH: 9
<212> TYPE: PRT
<213> ORGANISM: Homo sapiens

<400> SEQUENCE: 582

Ser Leu Ser Leu Gly Phe Leu Phe Leu
1               5

<210> SEQ ID NO 583
<211> LENGTH: 9
<212> TYPE: PRT
<213> ORGANISM: Homo sapiens

<400> SEQUENCE: 583

Leu Ser Leu Gly Phe Leu Phe Leu Leu
1               5

<210> SEQ ID NO 584
<211> LENGTH: 9
<212> TYPE: PRT
<213> ORGANISM: Homo sapiens

<400> SEQUENCE: 584

Tyr Thr Ser Asn Asp Ser Tyr Ile Val
1               5

<210> SEQ ID NO 585
<211> LENGTH: 9
<212> TYPE: PRT
<213> ORGANISM: Homo sapiens

<400> SEQUENCE: 585

Ile Leu Ile Asp Ser Gly Ala Asp Ile
1               5

<210> SEQ ID NO 586
<211> LENGTH: 9
<212> TYPE: PRT
<213> ORGANISM: Homo sapiens

<400> SEQUENCE: 586

Ser Leu Phe Glu Ser Ser Ala Lys Ile
1               5

<210> SEQ ID NO 587
<211> LENGTH: 9
<212> TYPE: PRT
<213> ORGANISM: Homo sapiens

<400> SEQUENCE: 587

```
Ser Leu Thr Pro Leu Leu Leu Ser Ile
1               5
```

<210> SEQ ID NO 588
<211> LENGTH: 9
<212> TYPE: PRT
<213> ORGANISM: Homo sapiens

<400> SEQUENCE: 588

```
Met Ser Ala Val Ile Leu Thr Ala Val
1               5
```

<210> SEQ ID NO 589
<211> LENGTH: 9
<212> TYPE: PRT
<213> ORGANISM: Homo sapiens

<400> SEQUENCE: 589

```
Ala Leu Ala Ala Ile Ala Ala Phe Met
1               5
```

<210> SEQ ID NO 590
<211> LENGTH: 9
<212> TYPE: PRT
<213> ORGANISM: Homo sapiens

<400> SEQUENCE: 590

```
Val Ser Ala Ala Phe Gln Ala Gly Val
1               5
```

<210> SEQ ID NO 591
<211> LENGTH: 9
<212> TYPE: PRT
<213> ORGANISM: Homo sapiens

<400> SEQUENCE: 591

```
Lys Leu Val Asn Leu Gly Phe Gln Ala
1               5
```

<210> SEQ ID NO 592
<211> LENGTH: 9
<212> TYPE: PRT
<213> ORGANISM: Homo sapiens

<400> SEQUENCE: 592

```
Glu Leu Leu Asp Phe Ser Ser Trp Leu
1               5
```

<210> SEQ ID NO 593
<211> LENGTH: 9
<212> TYPE: PRT
<213> ORGANISM: Homo sapiens

<400> SEQUENCE: 593

```
Leu Thr Leu Gly Glu Phe Leu Lys Leu
1               5
```

<210> SEQ ID NO 594
<211> LENGTH: 9
<212> TYPE: PRT
<213> ORGANISM: Homo sapiens

<400> SEQUENCE: 594

```
Ala Ala Gly Asp Ile Leu Ala Leu Val
```

```
1               5

<210> SEQ ID NO 595
<211> LENGTH: 9
<212> TYPE: PRT
<213> ORGANISM: Homo sapiens

<400> SEQUENCE: 595

Ala Leu Val Phe Gly Leu Leu Phe Ala
1               5

<210> SEQ ID NO 596
<211> LENGTH: 9
<212> TYPE: PRT
<213> ORGANISM: Homo sapiens

<400> SEQUENCE: 596

Phe Gln Tyr Glu Gly Ser Leu Thr Thr
1               5

<210> SEQ ID NO 597
<211> LENGTH: 9
<212> TYPE: PRT
<213> ORGANISM: Homo sapiens

<400> SEQUENCE: 597

His Leu Ser Thr Ala Phe Ala Arg Val
1               5

<210> SEQ ID NO 598
<211> LENGTH: 9
<212> TYPE: PRT
<213> ORGANISM: Homo sapiens

<400> SEQUENCE: 598

Leu Ser Leu Leu Leu Leu Val Pro Val
1               5

<210> SEQ ID NO 599
<211> LENGTH: 9
<212> TYPE: PRT
<213> ORGANISM: Homo sapiens

<400> SEQUENCE: 599

Gln Leu Leu Leu Ser Leu Leu Leu Leu
1               5

<210> SEQ ID NO 600
<211> LENGTH: 9
<212> TYPE: PRT
<213> ORGANISM: Homo sapiens

<400> SEQUENCE: 600

Val Gln Leu Leu Leu Ser Leu Leu Leu
1               5

<210> SEQ ID NO 601
<211> LENGTH: 9
<212> TYPE: PRT
<213> ORGANISM: Homo sapiens

<400> SEQUENCE: 601

Asn Leu Ala Lys Tyr Val Ala Glu Leu
1               5
```

<210> SEQ ID NO 602
<211> LENGTH: 9
<212> TYPE: PRT
<213> ORGANISM: Homo sapiens

<400> SEQUENCE: 602

Leu Ile Ala Ala Ala Ala Phe Cys Leu
1               5

<210> SEQ ID NO 603
<211> LENGTH: 9
<212> TYPE: PRT
<213> ORGANISM: Homo sapiens

<400> SEQUENCE: 603

Leu Leu Asn Asp Arg Val Leu Arg Ala
1               5

<210> SEQ ID NO 604
<211> LENGTH: 9
<212> TYPE: PRT
<213> ORGANISM: Homo sapiens

<400> SEQUENCE: 604

Gly Ile Leu Leu Thr Thr Leu Leu Val
1               5

<210> SEQ ID NO 605
<211> LENGTH: 9
<212> TYPE: PRT
<213> ORGANISM: Homo sapiens

<400> SEQUENCE: 605

Ile Leu Ala Val Val Phe Ile Arg Ile
1               5

<210> SEQ ID NO 606
<211> LENGTH: 9
<212> TYPE: PRT
<213> ORGANISM: Homo sapiens

<400> SEQUENCE: 606

Ile Leu Leu Thr Thr Leu Leu Val Ile
1               5

<210> SEQ ID NO 607
<211> LENGTH: 9
<212> TYPE: PRT
<213> ORGANISM: Homo sapiens

<400> SEQUENCE: 607

Leu Val Ile Gly Ile Ile Leu Ala Val
1               5

<210> SEQ ID NO 608
<211> LENGTH: 9
<212> TYPE: PRT
<213> ORGANISM: Homo sapiens

<400> SEQUENCE: 608

Ala Leu Val Ala Ile Leu Leu Cys Ile
1               5

<210> SEQ ID NO 609

```
<211> LENGTH: 9
<212> TYPE: PRT
<213> ORGANISM: Homo sapiens

<400> SEQUENCE: 609

Glu Met Ser Asp Val Gly Thr Phe Val
1               5

<210> SEQ ID NO 610
<211> LENGTH: 9
<212> TYPE: PRT
<213> ORGANISM: Homo sapiens

<400> SEQUENCE: 610

Glu Met Ser Thr Tyr Leu Leu Pro Val
1               5

<210> SEQ ID NO 611
<211> LENGTH: 9
<212> TYPE: PRT
<213> ORGANISM: Homo sapiens

<400> SEQUENCE: 611

Phe Leu Leu Glu Glu Tyr Thr Gly Ser
1               5

<210> SEQ ID NO 612
<211> LENGTH: 9
<212> TYPE: PRT
<213> ORGANISM: Homo sapiens

<400> SEQUENCE: 612

Ile Leu Leu Cys Ile Val Ile Leu Leu
1               5

<210> SEQ ID NO 613
<211> LENGTH: 9
<212> TYPE: PRT
<213> ORGANISM: Homo sapiens

<400> SEQUENCE: 613

Leu Leu Val Thr Val Val Leu Phe Ala
1               5

<210> SEQ ID NO 614
<211> LENGTH: 9
<212> TYPE: PRT
<213> ORGANISM: Homo sapiens

<400> SEQUENCE: 614

Ala Val Ala Leu Val Leu Met Leu Leu
1               5

<210> SEQ ID NO 615
<211> LENGTH: 9
<212> TYPE: PRT
<213> ORGANISM: Homo sapiens

<400> SEQUENCE: 615

Leu Leu Thr Phe Trp Asn Pro Pro Thr
1               5

<210> SEQ ID NO 616
<211> LENGTH: 9
<212> TYPE: PRT
```

-continued

<213> ORGANISM: Homo sapiens

<400> SEQUENCE: 616

Lys Gln Leu Leu Leu Ser Ala Ala Leu
1               5

<210> SEQ ID NO 617
<211> LENGTH: 9
<212> TYPE: PRT
<213> ORGANISM: Homo sapiens

<400> SEQUENCE: 617

Leu Leu Leu Ser Ala Ala Leu Ser Ala
1               5

<210> SEQ ID NO 618
<211> LENGTH: 9
<212> TYPE: PRT
<213> ORGANISM: Homo sapiens

<400> SEQUENCE: 618

Gln Leu Ala Gly Ala Met Val Trp Ala
1               5

<210> SEQ ID NO 619
<211> LENGTH: 9
<212> TYPE: PRT
<213> ORGANISM: Homo sapiens

<400> SEQUENCE: 619

Ser Gln Thr Gly Phe Val Val Leu Val
1               5

<210> SEQ ID NO 620
<211> LENGTH: 9
<212> TYPE: PRT
<213> ORGANISM: Homo sapiens

<400> SEQUENCE: 620

Thr Leu Ala Ser Ser Glu Thr Gly Val
1               5

<210> SEQ ID NO 621
<211> LENGTH: 9
<212> TYPE: PRT
<213> ORGANISM: Homo sapiens

<400> SEQUENCE: 621

Ile Leu Leu Ser Ile Gly Gly Tyr Leu
1               5

<210> SEQ ID NO 622
<211> LENGTH: 9
<212> TYPE: PRT
<213> ORGANISM: Homo sapiens

<400> SEQUENCE: 622

His Leu Ile Tyr Ser Phe Ala Ser Ile
1               5

<210> SEQ ID NO 623
<211> LENGTH: 9
<212> TYPE: PRT
<213> ORGANISM: Homo sapiens

<400> SEQUENCE: 623

Val Leu Ile His Glu Leu Ala Glu Ala
1               5

<210> SEQ ID NO 624
<211> LENGTH: 9
<212> TYPE: PRT
<213> ORGANISM: Homo sapiens

<400> SEQUENCE: 624

Ser Leu Trp Ala Gly Val Val Val Leu
1               5

<210> SEQ ID NO 625
<211> LENGTH: 9
<212> TYPE: PRT
<213> ORGANISM: Homo sapiens

<400> SEQUENCE: 625

Trp Leu Trp Asp Phe Thr Val Thr Thr
1               5

<210> SEQ ID NO 626
<211> LENGTH: 9
<212> TYPE: PRT
<213> ORGANISM: Homo sapiens

<400> SEQUENCE: 626

Leu Leu Ala Ser Ser Ile Leu Cys Ala
1               5

<210> SEQ ID NO 627
<211> LENGTH: 9
<212> TYPE: PRT
<213> ORGANISM: Homo sapiens

<400> SEQUENCE: 627

Lys Leu Ala Val Ser Leu Ala Glu Thr
1               5

<210> SEQ ID NO 628
<211> LENGTH: 9
<212> TYPE: PRT
<213> ORGANISM: Homo sapiens

<400> SEQUENCE: 628

Ala Leu Val Gly Leu Phe Val Leu Leu
1               5

<210> SEQ ID NO 629
<211> LENGTH: 9
<212> TYPE: PRT
<213> ORGANISM: Homo sapiens

<400> SEQUENCE: 629

Gly Leu Phe Val Leu Leu Ala Phe Leu
1               5

<210> SEQ ID NO 630
<211> LENGTH: 9
<212> TYPE: PRT
<213> ORGANISM: Homo sapiens

<400> SEQUENCE: 630

```
Ser Val Tyr Asp Phe Phe Val Trp Leu
1               5

<210> SEQ ID NO 631
<211> LENGTH: 9
<212> TYPE: PRT
<213> ORGANISM: Homo sapiens

<400> SEQUENCE: 631

Val Val Met Gly Thr Leu Val Ala Leu
1               5

<210> SEQ ID NO 632
<211> LENGTH: 9
<212> TYPE: PRT
<213> ORGANISM: Homo sapiens

<400> SEQUENCE: 632

Gly Thr Ala Glu Gly Leu Ala Leu Ala
1               5

<210> SEQ ID NO 633
<211> LENGTH: 9
<212> TYPE: PRT
<213> ORGANISM: Homo sapiens

<400> SEQUENCE: 633

Gly Leu Ala Ala Gly Leu Gly Pro Ala
1               5

<210> SEQ ID NO 634
<211> LENGTH: 9
<212> TYPE: PRT
<213> ORGANISM: Homo sapiens

<400> SEQUENCE: 634

Ala Leu Glu Ser Ile Leu His Arg Ile
1               5

<210> SEQ ID NO 635
<211> LENGTH: 9
<212> TYPE: PRT
<213> ORGANISM: Homo sapiens

<400> SEQUENCE: 635

Ala Leu Leu Ala Ala Leu Cys Pro Ala
1               5

<210> SEQ ID NO 636
<211> LENGTH: 9
<212> TYPE: PRT
<213> ORGANISM: Homo sapiens

<400> SEQUENCE: 636

Ala Leu Leu Ala Leu Leu Ala Ala Leu
1               5

<210> SEQ ID NO 637
<211> LENGTH: 9
<212> TYPE: PRT
<213> ORGANISM: Homo sapiens

<400> SEQUENCE: 637

Ile Leu Asp Glu Ala Tyr Val Met Ala
1               5
```

```
<210> SEQ ID NO 638
<211> LENGTH: 9
<212> TYPE: PRT
<213> ORGANISM: Homo sapiens

<400> SEQUENCE: 638

Leu Leu Leu Leu Val Val Ala Leu
1               5

<210> SEQ ID NO 639
<211> LENGTH: 9
<212> TYPE: PRT
<213> ORGANISM: Homo sapiens

<400> SEQUENCE: 639

Met Val Gly Ala Leu Leu Leu Leu
1               5

<210> SEQ ID NO 640
<211> LENGTH: 9
<212> TYPE: PRT
<213> ORGANISM: Homo sapiens

<400> SEQUENCE: 640

Asn Leu Gln Glu Ile Leu His Gly Ala
1               5

<210> SEQ ID NO 641
<211> LENGTH: 9
<212> TYPE: PRT
<213> ORGANISM: Homo sapiens

<400> SEQUENCE: 641

Ser Leu Ala Val Val Ser Leu Asn Ile
1               5

<210> SEQ ID NO 642
<211> LENGTH: 9
<212> TYPE: PRT
<213> ORGANISM: Homo sapiens

<400> SEQUENCE: 642

Ala Val Val Gly Ile Leu Leu Val Val
1               5

<210> SEQ ID NO 643
<211> LENGTH: 9
<212> TYPE: PRT
<213> ORGANISM: Homo sapiens

<400> SEQUENCE: 643

Ile Leu Asp Glu Ala Tyr Val Met Ala
1               5

<210> SEQ ID NO 644
<211> LENGTH: 9
<212> TYPE: PRT
<213> ORGANISM: Homo sapiens

<400> SEQUENCE: 644

Leu Leu Ala Leu Leu Pro Pro Gly Ala
1               5
```

<210> SEQ ID NO 645
<211> LENGTH: 9
<212> TYPE: PRT
<213> ORGANISM: Homo sapiens

<400> SEQUENCE: 645

Ser Ile Ile Ser Ala Val Val Gly Ile
1               5

<210> SEQ ID NO 646
<211> LENGTH: 9
<212> TYPE: PRT
<213> ORGANISM: Homo sapiens

<400> SEQUENCE: 646

Val Val Leu Gly Val Val Phe Gly Ile
1               5

<210> SEQ ID NO 647
<211> LENGTH: 9
<212> TYPE: PRT
<213> ORGANISM: Homo sapiens

<400> SEQUENCE: 647

Phe Leu Leu Glu Leu Leu Ser Asp Ser
1               5

<210> SEQ ID NO 648
<211> LENGTH: 9
<212> TYPE: PRT
<213> ORGANISM: Homo sapiens

<400> SEQUENCE: 648

Ala Leu Leu Asp Ala Glu Pro Pro Ile
1               5

<210> SEQ ID NO 649
<211> LENGTH: 9
<212> TYPE: PRT
<213> ORGANISM: Homo sapiens

<400> SEQUENCE: 649

Lys Ile Thr Asp Thr Leu Ile His Leu
1               5

<210> SEQ ID NO 650
<211> LENGTH: 9
<212> TYPE: PRT
<213> ORGANISM: Homo sapiens

<400> SEQUENCE: 650

Lys Leu Leu Phe Ala Pro Asn Leu Leu
1               5

<210> SEQ ID NO 651
<211> LENGTH: 9
<212> TYPE: PRT
<213> ORGANISM: Homo sapiens

<400> SEQUENCE: 651

Leu Leu Asp Ala Glu Pro Pro Ile Leu
1               5

<210> SEQ ID NO 652
<211> LENGTH: 9

```
<212> TYPE: PRT
<213> ORGANISM: Homo sapiens

<400> SEQUENCE: 652

Leu Leu Asn Ser Gly Val Tyr Thr Phe
1               5

<210> SEQ ID NO 653
<211> LENGTH: 9
<212> TYPE: PRT
<213> ORGANISM: Homo sapiens

<400> SEQUENCE: 653

Leu Met Ile Gly Leu Val Trp Arg Ser
1               5

<210> SEQ ID NO 654
<211> LENGTH: 9
<212> TYPE: PRT
<213> ORGANISM: Homo sapiens

<400> SEQUENCE: 654

Pro Leu Tyr Asp Leu Leu Leu Glu Met
1               5

<210> SEQ ID NO 655
<211> LENGTH: 9
<212> TYPE: PRT
<213> ORGANISM: Homo sapiens

<400> SEQUENCE: 655

Gln Leu Leu Leu Ile Leu Ser His Ile
1               5

<210> SEQ ID NO 656
<211> LENGTH: 9
<212> TYPE: PRT
<213> ORGANISM: Homo sapiens

<400> SEQUENCE: 656

Arg Leu Ala Gln Leu Leu Leu Ile Leu
1               5

<210> SEQ ID NO 657
<211> LENGTH: 9
<212> TYPE: PRT
<213> ORGANISM: Homo sapiens

<400> SEQUENCE: 657

Thr Leu Ile His Leu Met Ala Lys Ala
1               5

<210> SEQ ID NO 658
<211> LENGTH: 9
<212> TYPE: PRT
<213> ORGANISM: Homo sapiens

<400> SEQUENCE: 658

Val Leu Asp Lys Ile Thr Asp Thr Leu
1               5

<210> SEQ ID NO 659
<211> LENGTH: 9
<212> TYPE: PRT
<213> ORGANISM: Homo sapiens
```

```
<400> SEQUENCE: 659

Phe Met Val Glu Asp Glu Thr Val Leu
1               5

<210> SEQ ID NO 660
<211> LENGTH: 9
<212> TYPE: PRT
<213> ORGANISM: Homo sapiens

<400> SEQUENCE: 660

Ser Met Phe Arg Val Leu Ile Gly Thr
1               5

<210> SEQ ID NO 661
<211> LENGTH: 9
<212> TYPE: PRT
<213> ORGANISM: Homo sapiens

<400> SEQUENCE: 661

Ala Thr Ser Ala Val Leu Ala Leu Leu
1               5

<210> SEQ ID NO 662
<211> LENGTH: 9
<212> TYPE: PRT
<213> ORGANISM: Homo sapiens

<400> SEQUENCE: 662

Thr Gly Trp Ala Gly Gly Phe Phe Val
1               5

<210> SEQ ID NO 663
<211> LENGTH: 9
<212> TYPE: PRT
<213> ORGANISM: Homo sapiens

<400> SEQUENCE: 663

Val Leu Ala Leu Leu Val Met Cys Ile
1               5

<210> SEQ ID NO 664
<211> LENGTH: 9
<212> TYPE: PRT
<213> ORGANISM: Homo sapiens

<400> SEQUENCE: 664

Ala Leu Leu Ser Cys Leu Leu Leu Thr
1               5

<210> SEQ ID NO 665
<211> LENGTH: 9
<212> TYPE: PRT
<213> ORGANISM: Homo sapiens

<400> SEQUENCE: 665

Cys Val Ala Ala Thr Leu Phe Trp Leu
1               5

<210> SEQ ID NO 666
<211> LENGTH: 9
<212> TYPE: PRT
<213> ORGANISM: Homo sapiens

<400> SEQUENCE: 666
```

```
Glu Met Tyr Ser Glu Ile Pro Glu Ile
1               5

<210> SEQ ID NO 667
<211> LENGTH: 9
<212> TYPE: PRT
<213> ORGANISM: Homo sapiens

<400> SEQUENCE: 667

Lys Met Ala Ser Thr Leu Val Val Ala
1               5

<210> SEQ ID NO 668
<211> LENGTH: 9
<212> TYPE: PRT
<213> ORGANISM: Homo sapiens

<400> SEQUENCE: 668

Ser Ile Phe Asp Lys Ile Tyr Ser Thr
1               5

<210> SEQ ID NO 669
<211> LENGTH: 9
<212> TYPE: PRT
<213> ORGANISM: Homo sapiens

<400> SEQUENCE: 669

Thr Leu Phe Trp Leu Leu Leu Thr Leu
1               5

<210> SEQ ID NO 670
<211> LENGTH: 9
<212> TYPE: PRT
<213> ORGANISM: Homo sapiens

<400> SEQUENCE: 670

Val Leu Leu Trp Glu Ile Phe Ser Leu
1               5

<210> SEQ ID NO 671
<211> LENGTH: 9
<212> TYPE: PRT
<213> ORGANISM: Homo sapiens

<400> SEQUENCE: 671

Trp Leu Lys Asp Gly Leu Pro Ala Thr
1               5

<210> SEQ ID NO 672
<211> LENGTH: 9
<212> TYPE: PRT
<213> ORGANISM: Homo sapiens

<400> SEQUENCE: 672

Ile Leu Leu Asp Ile Ser Phe Pro Gly
1               5

<210> SEQ ID NO 673
<211> LENGTH: 9
<212> TYPE: PRT
<213> ORGANISM: Homo sapiens

<400> SEQUENCE: 673

Leu Leu Asp Ile Ser Phe Pro Gly Leu
```

```
1               5

<210> SEQ ID NO 674
<211> LENGTH: 9
<212> TYPE: PRT
<213> ORGANISM: Homo sapiens

<400> SEQUENCE: 674

Leu Met Asp Leu Ser Thr Thr Pro Leu
1               5

<210> SEQ ID NO 675
<211> LENGTH: 9
<212> TYPE: PRT
<213> ORGANISM: Homo sapiens

<400> SEQUENCE: 675

Arg Val Ser Ser Tyr Leu Val Pro Ile
1               5

<210> SEQ ID NO 676
<211> LENGTH: 9
<212> TYPE: PRT
<213> ORGANISM: Homo sapiens

<400> SEQUENCE: 676

Ser Leu Ser Lys Ile Leu Leu Asp Ile
1               5

<210> SEQ ID NO 677
<211> LENGTH: 9
<212> TYPE: PRT
<213> ORGANISM: Homo sapiens

<400> SEQUENCE: 677

Ser Gln Leu Ser Tyr Ser Gln Glu Val
1               5

<210> SEQ ID NO 678
<211> LENGTH: 9
<212> TYPE: PRT
<213> ORGANISM: Homo sapiens

<400> SEQUENCE: 678

Trp Ala Ala Glu Leu Pro Phe Pro Ala
1               5

<210> SEQ ID NO 679
<211> LENGTH: 9
<212> TYPE: PRT
<213> ORGANISM: Homo sapiens

<400> SEQUENCE: 679

Leu Leu Asn Glu Ser Glu Thr Lys Val
1               5

<210> SEQ ID NO 680
<211> LENGTH: 9
<212> TYPE: PRT
<213> ORGANISM: Homo sapiens

<400> SEQUENCE: 680

Arg Leu Val Glu Leu Leu Lys Asp Leu
1               5
```

```
<210> SEQ ID NO 681
<211> LENGTH: 9
<212> TYPE: PRT
<213> ORGANISM: Homo sapiens

<400> SEQUENCE: 681

Gly Leu Ala Ser Thr Thr Pro Glu Ala
1               5

<210> SEQ ID NO 682
<211> LENGTH: 9
<212> TYPE: PRT
<213> ORGANISM: Homo sapiens

<400> SEQUENCE: 682

Arg Met Ala Arg Glu Val Ala Ala Leu
1               5

<210> SEQ ID NO 683
<211> LENGTH: 9
<212> TYPE: PRT
<213> ORGANISM: Homo sapiens

<400> SEQUENCE: 683

Phe Leu Leu Ser Leu Ala Phe Tyr Gly
1               5

<210> SEQ ID NO 684
<211> LENGTH: 9
<212> TYPE: PRT
<213> ORGANISM: Homo sapiens

<400> SEQUENCE: 684

Ile Leu Asn Pro Ala Gln Gly Phe Leu
1               5

<210> SEQ ID NO 685
<211> LENGTH: 9
<212> TYPE: PRT
<213> ORGANISM: Homo sapiens

<400> SEQUENCE: 685

Met Ala Trp Gly Leu Ala Thr Leu Leu
1               5

<210> SEQ ID NO 686
<211> LENGTH: 9
<212> TYPE: PRT
<213> ORGANISM: Homo sapiens

<400> SEQUENCE: 686

Arg Leu Ala Leu Gly Leu Leu Gln Leu
1               5

<210> SEQ ID NO 687
<211> LENGTH: 9
<212> TYPE: PRT
<213> ORGANISM: Homo sapiens

<400> SEQUENCE: 687

Arg Leu Leu Leu Ala Gly Ala Glu Val
1               5

<210> SEQ ID NO 688
```

```
<210> SEQ ID NO 688
<211> LENGTH: 9
<212> TYPE: PRT
<213> ORGANISM: Homo sapiens

<400> SEQUENCE: 688

Cys Leu Tyr Thr Phe Leu Ile Ser Thr
1               5

<210> SEQ ID NO 689
<211> LENGTH: 9
<212> TYPE: PRT
<213> ORGANISM: Homo sapiens

<400> SEQUENCE: 689

Phe Leu Ile Ser Thr Thr Phe Gly Cys
1               5

<210> SEQ ID NO 690
<211> LENGTH: 9
<212> TYPE: PRT
<213> ORGANISM: Homo sapiens

<400> SEQUENCE: 690

Val Leu Leu Asp Thr Asn Tyr Asn Leu
1               5

<210> SEQ ID NO 691
<211> LENGTH: 9
<212> TYPE: PRT
<213> ORGANISM: Homo sapiens

<400> SEQUENCE: 691

Trp Leu Pro Phe Gly Phe Ile Leu Ile
1               5

<210> SEQ ID NO 692
<211> LENGTH: 10
<212> TYPE: PRT
<213> ORGANISM: Homo sapiens

<400> SEQUENCE: 692

Trp Leu Pro Phe Gly Phe Ile Leu Ile Leu
1               5                   10

<210> SEQ ID NO 693
<211> LENGTH: 9
<212> TYPE: PRT
<213> ORGANISM: Homo sapiens

<400> SEQUENCE: 693

Ala Leu Tyr Leu Leu Pro Leu Leu Ala
1               5

<210> SEQ ID NO 694
<211> LENGTH: 9
<212> TYPE: PRT
<213> ORGANISM: Homo sapiens

<400> SEQUENCE: 694

Phe Ala Leu Tyr Asn Leu Leu Ala Leu
1               5

<210> SEQ ID NO 695
<211> LENGTH: 9
<212> TYPE: PRT
```

-continued

<213> ORGANISM: Homo sapiens

<400> SEQUENCE: 695

Gln Leu Phe Leu Val Leu Gln Ala Leu
1               5

<210> SEQ ID NO 696
<211> LENGTH: 9
<212> TYPE: PRT
<213> ORGANISM: Homo sapiens

<400> SEQUENCE: 696

Arg Leu Val Ala Ala Val Val Leu Leu
1               5

<210> SEQ ID NO 697
<211> LENGTH: 9
<212> TYPE: PRT
<213> ORGANISM: Homo sapiens

<400> SEQUENCE: 697

Val Leu Ala Glu Arg Ala Gly Ala Val
1               5

<210> SEQ ID NO 698
<211> LENGTH: 9
<212> TYPE: PRT
<213> ORGANISM: Homo sapiens

<400> SEQUENCE: 698

Trp Leu Val Pro Leu Phe Phe Ala Ala
1               5

<210> SEQ ID NO 699
<211> LENGTH: 9
<212> TYPE: PRT
<213> ORGANISM: Homo sapiens

<400> SEQUENCE: 699

Tyr Leu Leu Pro Leu Leu Ala Thr Cys
1               5

<210> SEQ ID NO 700
<211> LENGTH: 9
<212> TYPE: PRT
<213> ORGANISM: Homo sapiens

<400> SEQUENCE: 700

Gly Leu Ser Asp Ala Val Glu Ala Leu
1               5

<210> SEQ ID NO 701
<211> LENGTH: 9
<212> TYPE: PRT
<213> ORGANISM: Homo sapiens

<400> SEQUENCE: 701

Met Leu Arg Glu Ala Ala Met Gly Ile
1               5

<210> SEQ ID NO 702
<211> LENGTH: 9
<212> TYPE: PRT
<213> ORGANISM: Homo sapiens

```
<400> SEQUENCE: 702

Ala Leu Ile Pro Ala Pro Glu Leu Val
1               5

<210> SEQ ID NO 703
<211> LENGTH: 9
<212> TYPE: PRT
<213> ORGANISM: Homo sapiens

<400> SEQUENCE: 703

Asn Leu Leu His Gly Leu Asn Leu Leu
1               5

<210> SEQ ID NO 704
<211> LENGTH: 9
<212> TYPE: PRT
<213> ORGANISM: Homo sapiens

<400> SEQUENCE: 704

Tyr Val Ser Ser Leu Pro Gln Pro Leu
1               5

<210> SEQ ID NO 705
<211> LENGTH: 9
<212> TYPE: PRT
<213> ORGANISM: Homo sapiens

<400> SEQUENCE: 705

Tyr Leu Ile Leu Gly Val Ala Gly Ser
1               5

<210> SEQ ID NO 706
<211> LENGTH: 9
<212> TYPE: PRT
<213> ORGANISM: Homo sapiens

<400> SEQUENCE: 706

Asn Met Asp Cys Ile Ile Ala Glu Ile
1               5

<210> SEQ ID NO 707
<211> LENGTH: 9
<212> TYPE: PRT
<213> ORGANISM: Homo sapiens

<400> SEQUENCE: 707

Ala Val Leu Gly Ile Phe Ile Ile Val
1               5

<210> SEQ ID NO 708
<211> LENGTH: 9
<212> TYPE: PRT
<213> ORGANISM: Homo sapiens

<400> SEQUENCE: 708

Lys Leu Ala Val Leu Gly Ile Phe Ile
1               5

<210> SEQ ID NO 709
<211> LENGTH: 9
<212> TYPE: PRT
<213> ORGANISM: Homo sapiens

<400> SEQUENCE: 709
```

```
Ala Ile Ala Ala Ile Val Ile Gly Ile
1               5

<210> SEQ ID NO 710
<211> LENGTH: 9
<212> TYPE: PRT
<213> ORGANISM: Homo sapiens

<400> SEQUENCE: 710

Ala Leu Ala Cys Ser Leu Ala Ala Cys
1               5

<210> SEQ ID NO 711
<211> LENGTH: 9
<212> TYPE: PRT
<213> ORGANISM: Homo sapiens

<400> SEQUENCE: 711

Ile Val Ile Gly Ile Val Ala Leu Ala
1               5

<210> SEQ ID NO 712
<211> LENGTH: 9
<212> TYPE: PRT
<213> ORGANISM: Homo sapiens

<400> SEQUENCE: 712

Arg Ile Val Ala Val Pro Thr Pro Leu
1               5

<210> SEQ ID NO 713
<211> LENGTH: 9
<212> TYPE: PRT
<213> ORGANISM: Homo sapiens

<400> SEQUENCE: 713

Ser Leu Lys Glu Leu Ser Pro Gly Ile
1               5

<210> SEQ ID NO 714
<211> LENGTH: 9
<212> TYPE: PRT
<213> ORGANISM: Homo sapiens

<400> SEQUENCE: 714

Lys Val Ala Asp Leu Val Gly Phe Leu
1               5

<210> SEQ ID NO 715
<211> LENGTH: 9
<212> TYPE: PRT
<213> ORGANISM: Homo sapiens

<400> SEQUENCE: 715

Gly Met Leu Ser Asp Val Gln Ser Met
1               5

<210> SEQ ID NO 716
<211> LENGTH: 9
<212> TYPE: PRT
<213> ORGANISM: Homo sapiens

<400> SEQUENCE: 716

Ile Leu Ile Leu Ile Leu Ser Ile Val
1               5
```

<210> SEQ ID NO 717
<211> LENGTH: 9
<212> TYPE: PRT
<213> ORGANISM: Homo sapiens

<400> SEQUENCE: 717

Ala Met Asp Ala Ile Phe Gly Ser Leu
1               5

<210> SEQ ID NO 718
<211> LENGTH: 9
<212> TYPE: PRT
<213> ORGANISM: Homo sapiens

<400> SEQUENCE: 718

Gly Leu Ile Thr Lys Ala Glu Met Leu
1               5

<210> SEQ ID NO 719
<211> LENGTH: 9
<212> TYPE: PRT
<213> ORGANISM: Homo sapiens

<400> SEQUENCE: 719

Gly Thr Leu Glu Glu Leu Pro Ala Ala
1               5

<210> SEQ ID NO 720
<211> LENGTH: 9
<212> TYPE: PRT
<213> ORGANISM: Homo sapiens

<400> SEQUENCE: 720

Lys Val Leu Glu Tyr Ile Ala Asn Ala
1               5

<210> SEQ ID NO 721
<211> LENGTH: 9
<212> TYPE: PRT
<213> ORGANISM: Homo sapiens

<400> SEQUENCE: 721

Gln Leu Val Phe Gly Ile Glu Val Val
1               5

<210> SEQ ID NO 722
<211> LENGTH: 9
<212> TYPE: PRT
<213> ORGANISM: Homo sapiens

<400> SEQUENCE: 722

Ala Val Ser Ser Ser Ser Pro Leu Val
1               5

<210> SEQ ID NO 723
<211> LENGTH: 9
<212> TYPE: PRT
<213> ORGANISM: Homo sapiens

<400> SEQUENCE: 723

Lys Val Asp Glu Leu Ala His Phe Leu
1               5

-continued

<210> SEQ ID NO 724
<211> LENGTH: 9
<212> TYPE: PRT
<213> ORGANISM: Homo sapiens

<400> SEQUENCE: 724

Lys Val Leu Glu His Val Val Arg Val
1               5

<210> SEQ ID NO 725
<211> LENGTH: 9
<212> TYPE: PRT
<213> ORGANISM: Homo sapiens

<400> SEQUENCE: 725

Val Ile Leu Gly Val Leu Leu Leu Ile
1               5

<210> SEQ ID NO 726
<211> LENGTH: 9
<212> TYPE: PRT
<213> ORGANISM: Homo sapiens

<400> SEQUENCE: 726

Met Thr Ala Ala Gly Val Pro Gln Leu
1               5

<210> SEQ ID NO 727
<211> LENGTH: 9
<212> TYPE: PRT
<213> ORGANISM: Homo sapiens

<400> SEQUENCE: 727

Ser Val Ser Asp Ile Leu Ser Pro Leu
1               5

<210> SEQ ID NO 728
<211> LENGTH: 9
<212> TYPE: PRT
<213> ORGANISM: Homo sapiens

<400> SEQUENCE: 728

Ala Leu Leu Ala Ala Ser Val Ala Leu
1               5

<210> SEQ ID NO 729
<211> LENGTH: 9
<212> TYPE: PRT
<213> ORGANISM: Homo sapiens

<400> SEQUENCE: 729

Leu Leu Ala Ala Ser Val Ala Leu Ala
1               5

<210> SEQ ID NO 730
<211> LENGTH: 9
<212> TYPE: PRT
<213> ORGANISM: Homo sapiens

<400> SEQUENCE: 730

Gln Leu Leu Arg Lys Val Ala Glu Leu
1               5

<210> SEQ ID NO 731
<211> LENGTH: 9

```
<212> TYPE: PRT
<213> ORGANISM: Homo sapiens

<400> SEQUENCE: 731

Thr Leu Pro Glu Leu Tyr Ala Phe Thr
1               5

<210> SEQ ID NO 732
<211> LENGTH: 9
<212> TYPE: PRT
<213> ORGANISM: Homo sapiens

<400> SEQUENCE: 732

Tyr Leu Tyr Gly Lys Ile Lys Lys Thr
1               5

<210> SEQ ID NO 733
<211> LENGTH: 9
<212> TYPE: PRT
<213> ORGANISM: Homo sapiens

<400> SEQUENCE: 733

Gln Val Leu Gly Leu Ala Ala Tyr Leu
1               5

<210> SEQ ID NO 734
<211> LENGTH: 9
<212> TYPE: PRT
<213> ORGANISM: Homo sapiens

<400> SEQUENCE: 734

Gly Leu Asp Glu Val Lys Ser Ser Leu
1               5

<210> SEQ ID NO 735
<211> LENGTH: 9
<212> TYPE: PRT
<213> ORGANISM: Homo sapiens

<400> SEQUENCE: 735

Phe Val Leu Leu Ser Leu Ser Gly Ala
1               5

<210> SEQ ID NO 736
<211> LENGTH: 9
<212> TYPE: PRT
<213> ORGANISM: Homo sapiens

<400> SEQUENCE: 736

Ser Leu Phe Leu Phe Ser Val Leu Leu
1               5

<210> SEQ ID NO 737
<211> LENGTH: 9
<212> TYPE: PRT
<213> ORGANISM: Homo sapiens

<400> SEQUENCE: 737

Ser Leu Thr Val Tyr Leu Val Val Ala
1               5

<210> SEQ ID NO 738
<211> LENGTH: 9
<212> TYPE: PRT
<213> ORGANISM: Homo sapiens
```

<400> SEQUENCE: 738

Val Leu Leu Phe Val Ala Val Arg Leu
1               5

<210> SEQ ID NO 739
<211> LENGTH: 9
<212> TYPE: PRT
<213> ORGANISM: Homo sapiens

<400> SEQUENCE: 739

Val Ser Ser Leu Phe Leu Phe Ser Val
1               5

<210> SEQ ID NO 740
<211> LENGTH: 9
<212> TYPE: PRT
<213> ORGANISM: Homo sapiens

<400> SEQUENCE: 740

Ser Ile Ala Gly Phe Val Ala Ser Ile
1               5

<210> SEQ ID NO 741
<211> LENGTH: 9
<212> TYPE: PRT
<213> ORGANISM: Homo sapiens

<400> SEQUENCE: 741

Ile Leu Leu Val Leu Met Ala Val Val
1               5

<210> SEQ ID NO 742
<211> LENGTH: 9
<212> TYPE: PRT
<213> ORGANISM: Homo sapiens

<400> SEQUENCE: 742

Leu Ile Val Gly Ile Leu Leu Val Leu
1               5

<210> SEQ ID NO 743
<211> LENGTH: 9
<212> TYPE: PRT
<213> ORGANISM: Homo sapiens

<400> SEQUENCE: 743

Leu Met Ala Val Val Leu Ala Ser Leu
1               5

<210> SEQ ID NO 744
<211> LENGTH: 9
<212> TYPE: PRT
<213> ORGANISM: Homo sapiens

<400> SEQUENCE: 744

Pro Leu Leu Asp Gly Thr Ala Thr Leu
1               5

<210> SEQ ID NO 745
<211> LENGTH: 9
<212> TYPE: PRT
<213> ORGANISM: Homo sapiens

<400> SEQUENCE: 745

Ser Leu Ala Asp Thr Asn Ser Leu Ala
1               5

<210> SEQ ID NO 746
<211> LENGTH: 9
<212> TYPE: PRT
<213> ORGANISM: Homo sapiens

<400> SEQUENCE: 746

Val Leu Gln Ala Ala Ile Pro Leu Thr
1               5

<210> SEQ ID NO 747
<211> LENGTH: 9
<212> TYPE: PRT
<213> ORGANISM: Homo sapiens

<400> SEQUENCE: 747

Ala Val Leu Asp Gly Leu Asp Val Leu
1               5

<210> SEQ ID NO 748
<211> LENGTH: 9
<212> TYPE: PRT
<213> ORGANISM: Homo sapiens

<400> SEQUENCE: 748

Gln Leu Leu Ala Leu Leu Pro Ser Leu
1               5

<210> SEQ ID NO 749
<211> LENGTH: 9
<212> TYPE: PRT
<213> ORGANISM: Homo sapiens

<400> SEQUENCE: 749

Arg Leu Arg Glu Leu Leu Cys Glu Leu
1               5

<210> SEQ ID NO 750
<211> LENGTH: 9
<212> TYPE: PRT
<213> ORGANISM: Homo sapiens

<400> SEQUENCE: 750

Val Leu Tyr Pro Val Pro Leu Glu Ser
1               5

<210> SEQ ID NO 751
<211> LENGTH: 9
<212> TYPE: PRT
<213> ORGANISM: Homo sapiens

<400> SEQUENCE: 751

Ala Val Phe Leu Leu Ser Tyr Ala Val
1               5

<210> SEQ ID NO 752
<211> LENGTH: 9
<212> TYPE: PRT
<213> ORGANISM: Homo sapiens

<400> SEQUENCE: 752

Phe Val Leu Ser Leu Leu Leu Ile Leu

<210> SEQ ID NO 753
<211> LENGTH: 9
<212> TYPE: PRT
<213> ORGANISM: Homo sapiens

<400> SEQUENCE: 753

Ile Ile Phe Val Leu Ser Leu Leu Leu
1               5

<210> SEQ ID NO 754
<211> LENGTH: 9
<212> TYPE: PRT
<213> ORGANISM: Homo sapiens

<400> SEQUENCE: 754

Leu Ile Leu Glu Lys Gln Ala Ala Val
1               5

<210> SEQ ID NO 755
<211> LENGTH: 9
<212> TYPE: PRT
<213> ORGANISM: Homo sapiens

<400> SEQUENCE: 755

Leu Ile Ser Glu Leu Lys Leu Ala Val
1               5

<210> SEQ ID NO 756
<211> LENGTH: 9
<212> TYPE: PRT
<213> ORGANISM: Homo sapiens

<400> SEQUENCE: 756

Arg Ala Ile Glu His Val Leu Gln Val
1               5

<210> SEQ ID NO 757
<211> LENGTH: 9
<212> TYPE: PRT
<213> ORGANISM: Homo sapiens

<400> SEQUENCE: 757

Ser Ser Phe Asp Arg Leu Ile Pro Leu
1               5

<210> SEQ ID NO 758
<211> LENGTH: 9
<212> TYPE: PRT
<213> ORGANISM: Homo sapiens

<400> SEQUENCE: 758

Thr Leu Lys Glu Gln Phe Gln Phe Val
1               5

<210> SEQ ID NO 759
<211> LENGTH: 9
<212> TYPE: PRT
<213> ORGANISM: Homo sapiens

<400> SEQUENCE: 759

Ala Ile Leu Asp Ser Ala Phe Leu Leu
1               5

```
<210> SEQ ID NO 760
<211> LENGTH: 9
<212> TYPE: PRT
<213> ORGANISM: Homo sapiens

<400> SEQUENCE: 760

Ala Ile Ser Leu Val Phe Ser Leu Val
1               5

<210> SEQ ID NO 761
<211> LENGTH: 9
<212> TYPE: PRT
<213> ORGANISM: Homo sapiens

<400> SEQUENCE: 761

Ala Leu Gln Ile Leu Pro Tyr Thr Leu
1               5

<210> SEQ ID NO 762
<211> LENGTH: 9
<212> TYPE: PRT
<213> ORGANISM: Homo sapiens

<400> SEQUENCE: 762

Ala Leu Thr Gly Phe Thr Phe Ser Ala
1               5

<210> SEQ ID NO 763
<211> LENGTH: 9
<212> TYPE: PRT
<213> ORGANISM: Homo sapiens

<400> SEQUENCE: 763

Ala Gln Leu Leu Leu Val Asn Leu Leu
1               5

<210> SEQ ID NO 764
<211> LENGTH: 9
<212> TYPE: PRT
<213> ORGANISM: Homo sapiens

<400> SEQUENCE: 764

Cys Leu Phe Gly Leu Leu Thr Leu Ile
1               5

<210> SEQ ID NO 765
<211> LENGTH: 9
<212> TYPE: PRT
<213> ORGANISM: Homo sapiens

<400> SEQUENCE: 765

Gly Ile Leu Leu Ser Leu Phe Leu Ile
1               5

<210> SEQ ID NO 766
<211> LENGTH: 9
<212> TYPE: PRT
<213> ORGANISM: Homo sapiens

<400> SEQUENCE: 766

Gly Leu Leu Pro Pro Pro Ala Leu
1               5

<210> SEQ ID NO 767
```

```
<211> LENGTH: 9
<212> TYPE: PRT
<213> ORGANISM: Homo sapiens

<400> SEQUENCE: 767

Gly Leu Leu Thr Leu Ile Phe Leu Thr
1               5

<210> SEQ ID NO 768
<211> LENGTH: 9
<212> TYPE: PRT
<213> ORGANISM: Homo sapiens

<400> SEQUENCE: 768

Gly Leu Val Ala Ile Tyr Phe Ala Thr
1               5

<210> SEQ ID NO 769
<211> LENGTH: 9
<212> TYPE: PRT
<213> ORGANISM: Homo sapiens

<400> SEQUENCE: 769

Asn Leu Gly Ala Leu Leu Pro Arg Leu
1               5

<210> SEQ ID NO 770
<211> LENGTH: 9
<212> TYPE: PRT
<213> ORGANISM: Homo sapiens

<400> SEQUENCE: 770

Ser Val Ala Ala Phe Pro Val Ala Ala
1               5

<210> SEQ ID NO 771
<211> LENGTH: 9
<212> TYPE: PRT
<213> ORGANISM: Homo sapiens

<400> SEQUENCE: 771

Phe Leu Leu Ser Leu Phe Cys Val Thr
1               5

<210> SEQ ID NO 772
<211> LENGTH: 9
<212> TYPE: PRT
<213> ORGANISM: Homo sapiens

<400> SEQUENCE: 772

Phe Ser Leu Gly Val Gly Phe Gly Val
1               5

<210> SEQ ID NO 773
<211> LENGTH: 9
<212> TYPE: PRT
<213> ORGANISM: Homo sapiens

<400> SEQUENCE: 773

Gly Leu Ile Asp Glu Phe Gln Leu Leu
1               5

<210> SEQ ID NO 774
<211> LENGTH: 9
<212> TYPE: PRT
```

```
<213> ORGANISM: Homo sapiens

<400> SEQUENCE: 774

Gly Met Glu Ser Val Ile Thr Gly Leu
1               5

<210> SEQ ID NO 775
<211> LENGTH: 9
<212> TYPE: PRT
<213> ORGANISM: Homo sapiens

<400> SEQUENCE: 775

Ile Leu Phe Gly Val Leu Ile Glu Ala
1               5

<210> SEQ ID NO 776
<211> LENGTH: 9
<212> TYPE: PRT
<213> ORGANISM: Homo sapiens

<400> SEQUENCE: 776

Lys Ile Asp Phe Leu Leu Ser Val Ile
1               5

<210> SEQ ID NO 777
<211> LENGTH: 9
<212> TYPE: PRT
<213> ORGANISM: Homo sapiens

<400> SEQUENCE: 777

Leu Leu Phe Met Val Ile Ala Gly Met
1               5

<210> SEQ ID NO 778
<211> LENGTH: 9
<212> TYPE: PRT
<213> ORGANISM: Homo sapiens

<400> SEQUENCE: 778

Leu Val Pro Tyr Leu Leu Phe Met Val
1               5

<210> SEQ ID NO 779
<211> LENGTH: 9
<212> TYPE: PRT
<213> ORGANISM: Homo sapiens

<400> SEQUENCE: 779

Gln Leu Thr Ala Cys Leu Val Leu Val
1               5

<210> SEQ ID NO 780
<211> LENGTH: 9
<212> TYPE: PRT
<213> ORGANISM: Homo sapiens

<400> SEQUENCE: 780

Met Ile Ser Glu Lys Met Val Lys Leu
1               5

<210> SEQ ID NO 781
<211> LENGTH: 9
<212> TYPE: PRT
<213> ORGANISM: Homo sapiens
```

```
<400> SEQUENCE: 781

Leu Met Phe Asp Leu Ser Leu Asn Phe
1               5

<210> SEQ ID NO 782
<211> LENGTH: 9
<212> TYPE: PRT
<213> ORGANISM: Homo sapiens

<400> SEQUENCE: 782

Ala Leu Pro Ala Val Met Ala Gly Leu
1               5

<210> SEQ ID NO 783
<211> LENGTH: 9
<212> TYPE: PRT
<213> ORGANISM: Homo sapiens

<400> SEQUENCE: 783

Gly Leu Ala Glu Pro Gln Ala Ala Ala
1               5

<210> SEQ ID NO 784
<211> LENGTH: 9
<212> TYPE: PRT
<213> ORGANISM: Homo sapiens

<400> SEQUENCE: 784

Gly Ile Phe Leu Leu Ser Ala Leu Ala
1               5

<210> SEQ ID NO 785
<211> LENGTH: 9
<212> TYPE: PRT
<213> ORGANISM: Homo sapiens

<400> SEQUENCE: 785

Ala Ser Leu Thr Phe Leu Tyr Thr Leu
1               5

<210> SEQ ID NO 786
<211> LENGTH: 9
<212> TYPE: PRT
<213> ORGANISM: Homo sapiens

<400> SEQUENCE: 786

Ala Val Leu His Ala Ile Tyr Ser Leu
1               5

<210> SEQ ID NO 787
<211> LENGTH: 9
<212> TYPE: PRT
<213> ORGANISM: Homo sapiens

<400> SEQUENCE: 787

Phe Phe Phe Ala Val Leu His Ala Ile
1               5

<210> SEQ ID NO 788
<211> LENGTH: 9
<212> TYPE: PRT
<213> ORGANISM: Homo sapiens

<400> SEQUENCE: 788
```

Gly Val Ile Ala Ala Ile Val Gln Leu
1               5

<210> SEQ ID NO 789
<211> LENGTH: 9
<212> TYPE: PRT
<213> ORGANISM: Homo sapiens

<400> SEQUENCE: 789

Lys Ile Ala Ala Ile Ile Ala Ser Leu
1               5

<210> SEQ ID NO 790
<211> LENGTH: 9
<212> TYPE: PRT
<213> ORGANISM: Homo sapiens

<400> SEQUENCE: 790

Leu Ile Phe Lys Ser Ile Leu Phe Leu
1               5

<210> SEQ ID NO 791
<211> LENGTH: 9
<212> TYPE: PRT
<213> ORGANISM: Homo sapiens

<400> SEQUENCE: 791

Leu Leu Leu Gly Thr Ile His Ala Leu
1               5

<210> SEQ ID NO 792
<211> LENGTH: 9
<212> TYPE: PRT
<213> ORGANISM: Homo sapiens

<400> SEQUENCE: 792

Leu Leu Ser Phe Phe Phe Ala Val Leu
1               5

<210> SEQ ID NO 793
<211> LENGTH: 9
<212> TYPE: PRT
<213> ORGANISM: Homo sapiens

<400> SEQUENCE: 793

Met Ile Ala Val Phe Leu Pro Ile Val
1               5

<210> SEQ ID NO 794
<211> LENGTH: 9
<212> TYPE: PRT
<213> ORGANISM: Homo sapiens

<400> SEQUENCE: 794

Ser Leu Leu Leu Gly Thr Ile His Ala
1               5

<210> SEQ ID NO 795
<211> LENGTH: 9
<212> TYPE: PRT
<213> ORGANISM: Homo sapiens

<400> SEQUENCE: 795

Ser Leu Ser Leu Ile Val Ala Val Ile
1               5

```
<210> SEQ ID NO 796
<211> LENGTH: 9
<212> TYPE: PRT
<213> ORGANISM: Homo sapiens

<400> SEQUENCE: 796

Ile Ile Ser Pro Asn Leu Phe Tyr Ala
1               5

<210> SEQ ID NO 797
<211> LENGTH: 9
<212> TYPE: PRT
<213> ORGANISM: Homo sapiens

<400> SEQUENCE: 797

Leu Leu Asp His Val Leu Ile Glu Met
1               5

<210> SEQ ID NO 798
<211> LENGTH: 9
<212> TYPE: PRT
<213> ORGANISM: Homo sapiens

<400> SEQUENCE: 798

Val Leu Ile Asp Glu His Leu Val Leu
1               5

<210> SEQ ID NO 799
<211> LENGTH: 9
<212> TYPE: PRT
<213> ORGANISM: Homo sapiens

<400> SEQUENCE: 799

Tyr Ser Ser Glu Val Leu Glu Tyr Met
1               5

<210> SEQ ID NO 800
<211> LENGTH: 9
<212> TYPE: PRT
<213> ORGANISM: Homo sapiens

<400> SEQUENCE: 800

Ile Leu Leu Arg Pro Asp Thr Tyr Ile
1               5

<210> SEQ ID NO 801
<211> LENGTH: 9
<212> TYPE: PRT
<213> ORGANISM: Homo sapiens

<400> SEQUENCE: 801

Leu Met Met Thr Ile Ile Asn Leu Ala
1               5

<210> SEQ ID NO 802
<211> LENGTH: 9
<212> TYPE: PRT
<213> ORGANISM: Homo sapiens

<400> SEQUENCE: 802

Gln Leu Ala Gly Ser Val Ala Glu Met
1               5
```

```
<210> SEQ ID NO 803
<211> LENGTH: 9
<212> TYPE: PRT
<213> ORGANISM: Homo sapiens

<400> SEQUENCE: 803

Ser Leu Met Met Thr Ile Ile Asn Leu
1               5

<210> SEQ ID NO 804
<211> LENGTH: 9
<212> TYPE: PRT
<213> ORGANISM: Homo sapiens

<400> SEQUENCE: 804

Thr Met Leu Ser Ser Leu Ala Arg Leu
1               5

<210> SEQ ID NO 805
<211> LENGTH: 9
<212> TYPE: PRT
<213> ORGANISM: Homo sapiens

<400> SEQUENCE: 805

Tyr Ile Phe Thr Met Leu Ser Ser Leu
1               5

<210> SEQ ID NO 806
<211> LENGTH: 9
<212> TYPE: PRT
<213> ORGANISM: Homo sapiens

<400> SEQUENCE: 806

Asp Leu Ala Gly Val Ile Ile Glu Leu
1               5

<210> SEQ ID NO 807
<211> LENGTH: 9
<212> TYPE: PRT
<213> ORGANISM: Homo sapiens

<400> SEQUENCE: 807

Phe Gly Leu Phe Gly Val Phe Leu Val
1               5

<210> SEQ ID NO 808
<211> LENGTH: 9
<212> TYPE: PRT
<213> ORGANISM: Homo sapiens

<400> SEQUENCE: 808

Gly Leu Phe Gly Val Phe Leu Val Leu
1               5

<210> SEQ ID NO 809
<211> LENGTH: 9
<212> TYPE: PRT
<213> ORGANISM: Homo sapiens

<400> SEQUENCE: 809

Ile Leu Asp Thr Ala Ile Ile Val Ile
1               5

<210> SEQ ID NO 810
<211> LENGTH: 9
```

<212> TYPE: PRT
<213> ORGANISM: Homo sapiens

<400> SEQUENCE: 810

Ile Val Ser Ser Phe Ala Phe Gly Leu
1               5

<210> SEQ ID NO 811
<211> LENGTH: 9
<212> TYPE: PRT
<213> ORGANISM: Homo sapiens

<400> SEQUENCE: 811

Arg Leu Leu Arg Leu Ile Ile Leu Leu
1               5

<210> SEQ ID NO 812
<211> LENGTH: 9
<212> TYPE: PRT
<213> ORGANISM: Homo sapiens

<400> SEQUENCE: 812

Ser Leu Ala Ile Ala Leu Phe Phe Leu
1               5

<210> SEQ ID NO 813
<211> LENGTH: 9
<212> TYPE: PRT
<213> ORGANISM: Homo sapiens

<400> SEQUENCE: 813

Tyr Phe Trp Leu His Thr Ser Phe Ile
1               5

<210> SEQ ID NO 814
<211> LENGTH: 9
<212> TYPE: PRT
<213> ORGANISM: Homo sapiens

<400> SEQUENCE: 814

Ala Met Phe Gly Tyr Thr Val Gly Thr
1               5

<210> SEQ ID NO 815
<211> LENGTH: 9
<212> TYPE: PRT
<213> ORGANISM: Homo sapiens

<400> SEQUENCE: 815

Phe Ile Ala Gly Ile Val Phe Arg Leu
1               5

<210> SEQ ID NO 816
<211> LENGTH: 9
<212> TYPE: PRT
<213> ORGANISM: Homo sapiens

<400> SEQUENCE: 816

Phe Leu Leu Leu Phe Ala Tyr Val Leu
1               5

<210> SEQ ID NO 817
<211> LENGTH: 9
<212> TYPE: PRT
<213> ORGANISM: Homo sapiens

<400> SEQUENCE: 817

Leu Leu Phe Ala Tyr Val Leu Leu Met
1               5

<210> SEQ ID NO 818
<211> LENGTH: 9
<212> TYPE: PRT
<213> ORGANISM: Homo sapiens

<400> SEQUENCE: 818

Leu Leu Leu Phe Ala Tyr Val Leu Leu
1               5

<210> SEQ ID NO 819
<211> LENGTH: 9
<212> TYPE: PRT
<213> ORGANISM: Homo sapiens

<400> SEQUENCE: 819

Leu Val Leu Tyr Ser Leu Val Phe Val
1               5

<210> SEQ ID NO 820
<211> LENGTH: 9
<212> TYPE: PRT
<213> ORGANISM: Homo sapiens

<400> SEQUENCE: 820

Asn Ile Leu Leu Val Asn Leu Leu Val
1               5

<210> SEQ ID NO 821
<211> LENGTH: 9
<212> TYPE: PRT
<213> ORGANISM: Homo sapiens

<400> SEQUENCE: 821

Gln Ile Ala Asp Val Ile Ala Ser Leu
1               5

<210> SEQ ID NO 822
<211> LENGTH: 9
<212> TYPE: PRT
<213> ORGANISM: Homo sapiens

<400> SEQUENCE: 822

Val Leu Tyr Ser Leu Val Phe Val Leu
1               5

<210> SEQ ID NO 823
<211> LENGTH: 9
<212> TYPE: PRT
<213> ORGANISM: Homo sapiens

<400> SEQUENCE: 823

Tyr Leu Val Lys Ile Asn Thr Lys Ala
1               5

<210> SEQ ID NO 824
<211> LENGTH: 9
<212> TYPE: PRT
<213> ORGANISM: Homo sapiens

<400> SEQUENCE: 824

Phe Leu Asp Ser Leu Gly Phe Ser Thr
1               5

<210> SEQ ID NO 825
<211> LENGTH: 9
<212> TYPE: PRT
<213> ORGANISM: Homo sapiens

<400> SEQUENCE: 825

Ser Leu Arg Asp Glu Phe Pro Leu Leu
1               5

<210> SEQ ID NO 826
<211> LENGTH: 9
<212> TYPE: PRT
<213> ORGANISM: Homo sapiens

<400> SEQUENCE: 826

Val Leu Glu Glu Leu Leu Trp Phe Ile
1               5

<210> SEQ ID NO 827
<211> LENGTH: 9
<212> TYPE: PRT
<213> ORGANISM: Homo sapiens

<400> SEQUENCE: 827

Ala Leu Leu Ala Gly Leu Val Ser Leu
1               5

<210> SEQ ID NO 828
<211> LENGTH: 9
<212> TYPE: PRT
<213> ORGANISM: Homo sapiens

<400> SEQUENCE: 828

Ala Met Val Gly Ala Val Leu Thr Ala
1               5

<210> SEQ ID NO 829
<211> LENGTH: 9
<212> TYPE: PRT
<213> ORGANISM: Homo sapiens

<400> SEQUENCE: 829

Ile Ser Ser Asp Tyr Val Ile Pro Ile
1               5

<210> SEQ ID NO 830
<211> LENGTH: 9
<212> TYPE: PRT
<213> ORGANISM: Homo sapiens

<400> SEQUENCE: 830

Leu Leu Ala Gly Leu Val Ser Leu Leu
1               5

<210> SEQ ID NO 831
<211> LENGTH: 9
<212> TYPE: PRT
<213> ORGANISM: Homo sapiens

<400> SEQUENCE: 831

Leu Leu Ser Pro Ala Ser Phe Phe Ser

```
1               5

<210> SEQ ID NO 832
<211> LENGTH: 9
<212> TYPE: PRT
<213> ORGANISM: Homo sapiens

<400> SEQUENCE: 832

Met Val Gly Ala Val Leu Thr Ala Leu
1               5

<210> SEQ ID NO 833
<211> LENGTH: 9
<212> TYPE: PRT
<213> ORGANISM: Homo sapiens

<400> SEQUENCE: 833

Val Leu Thr Ala Leu Leu Ala Gly Leu
1               5

<210> SEQ ID NO 834
<211> LENGTH: 9
<212> TYPE: PRT
<213> ORGANISM: Homo sapiens

<400> SEQUENCE: 834

Ala Leu Thr Glu Ser Leu Leu Val Ala
1               5

<210> SEQ ID NO 835
<211> LENGTH: 9
<212> TYPE: PRT
<213> ORGANISM: Homo sapiens

<400> SEQUENCE: 835

Leu Leu Ala Leu Leu Ser Pro Gly Ala
1               5

<210> SEQ ID NO 836
<211> LENGTH: 9
<212> TYPE: PRT
<213> ORGANISM: Homo sapiens

<400> SEQUENCE: 836

Leu Val Leu Gly Phe Ile Ile Ala Leu
1               5

<210> SEQ ID NO 837
<211> LENGTH: 9
<212> TYPE: PRT
<213> ORGANISM: Homo sapiens

<400> SEQUENCE: 837

Ser Leu Ser Gly Leu Leu Ser Pro Ala
1               5

<210> SEQ ID NO 838
<211> LENGTH: 9
<212> TYPE: PRT
<213> ORGANISM: Homo sapiens

<400> SEQUENCE: 838

Thr Leu Pro Leu Ile Leu Ile Leu Leu
1               5
```

<210> SEQ ID NO 839
<211> LENGTH: 9
<212> TYPE: PRT
<213> ORGANISM: Homo sapiens

<400> SEQUENCE: 839

Val Leu Gly Phe Ile Ile Ala Leu Ala
1               5

<210> SEQ ID NO 840
<211> LENGTH: 9
<212> TYPE: PRT
<213> ORGANISM: Homo sapiens

<400> SEQUENCE: 840

Val Val Ile Thr Val Leu Leu Ser Val
1               5

<210> SEQ ID NO 841
<211> LENGTH: 9
<212> TYPE: PRT
<213> ORGANISM: Homo sapiens

<400> SEQUENCE: 841

Ala Gln Ile Gly Asp Ser Val Met Leu
1               5

<210> SEQ ID NO 842
<211> LENGTH: 9
<212> TYPE: PRT
<213> ORGANISM: Homo sapiens

<400> SEQUENCE: 842

Phe Ala Ser Ser Leu Ile Ile Pro Ala
1               5

<210> SEQ ID NO 843
<211> LENGTH: 9
<212> TYPE: PRT
<213> ORGANISM: Homo sapiens

<400> SEQUENCE: 843

Lys Ser Ile Asp Gly Ala Tyr Thr Ile
1               5

<210> SEQ ID NO 844
<211> LENGTH: 9
<212> TYPE: PRT
<213> ORGANISM: Homo sapiens

<400> SEQUENCE: 844

Ser Ile Leu Glu Glu Gly Ser Ser Val
1               5

<210> SEQ ID NO 845
<211> LENGTH: 9
<212> TYPE: PRT
<213> ORGANISM: Homo sapiens

<400> SEQUENCE: 845

Leu Leu Phe Gly Phe Thr Leu Val Ser
1               5

<210> SEQ ID NO 846

```
<211> LENGTH: 9
<212> TYPE: PRT
<213> ORGANISM: Homo sapiens

<400> SEQUENCE: 846

Leu Leu Leu Phe Gly Phe Thr Leu Val
1               5

<210> SEQ ID NO 847
<211> LENGTH: 9
<212> TYPE: PRT
<213> ORGANISM: Homo sapiens

<400> SEQUENCE: 847

Arg Leu Gly Pro Leu Ala Ala Ala Leu
1               5

<210> SEQ ID NO 848
<211> LENGTH: 9
<212> TYPE: PRT
<213> ORGANISM: Homo sapiens

<400> SEQUENCE: 848

Asp Leu Asn Ala Leu Leu Pro Ala Val
1               5

<210> SEQ ID NO 849
<211> LENGTH: 9
<212> TYPE: PRT
<213> ORGANISM: Homo sapiens

<400> SEQUENCE: 849

Ile Leu Ile Pro Gln Val Ala Tyr Thr
1               5

<210> SEQ ID NO 850
<211> LENGTH: 9
<212> TYPE: PRT
<213> ORGANISM: Homo sapiens

<400> SEQUENCE: 850

Asn Leu Ser Asp Ile Gln Asn Val Leu
1               5

<210> SEQ ID NO 851
<211> LENGTH: 9
<212> TYPE: PRT
<213> ORGANISM: Homo sapiens

<400> SEQUENCE: 851

Val Gln Ala Val Val Leu Pro Thr Val
1               5

<210> SEQ ID NO 852
<211> LENGTH: 9
<212> TYPE: PRT
<213> ORGANISM: Homo sapiens

<400> SEQUENCE: 852

Leu Val Leu Glu Gln Phe Leu Thr Ile
1               5

<210> SEQ ID NO 853
<211> LENGTH: 9
<212> TYPE: PRT
```

-continued

<213> ORGANISM: Homo sapiens

<400> SEQUENCE: 853

Arg Ile Ser Gly Tyr Ile Ser Glu Ala
1               5

<210> SEQ ID NO 854
<211> LENGTH: 9
<212> TYPE: PRT
<213> ORGANISM: Homo sapiens

<400> SEQUENCE: 854

Ala Met Thr Asp Ile Ser Ser Leu Ala
1               5

<210> SEQ ID NO 855
<211> LENGTH: 9
<212> TYPE: PRT
<213> ORGANISM: Homo sapiens

<400> SEQUENCE: 855

Val Leu Leu Ser Asn Phe Tyr Tyr Gly
1               5

<210> SEQ ID NO 856
<211> LENGTH: 20
<212> TYPE: PRT
<213> ORGANISM: Artificial Sequence
<220> FEATURE:
<223> OTHER INFORMATION: peptide

<400> SEQUENCE: 856

Met Ala Lys Thr Ile Ala Tyr Asp Glu Glu Ala Arg Arg Gly Leu Glu
1               5                   10                  15

Arg Gly Leu Asn
            20

<210> SEQ ID NO 857
<211> LENGTH: 9
<212> TYPE: PRT
<213> ORGANISM: Homo sapiens

<400> SEQUENCE: 857

Gln Leu Trp Gln Phe Leu Leu Glu Leu
1               5

<210> SEQ ID NO 858
<211> LENGTH: 9
<212> TYPE: PRT
<213> ORGANISM: Homo sapiens

<400> SEQUENCE: 858

Leu Val Leu Gly Thr Leu Glu Glu Val
1               5

<210> SEQ ID NO 859
<211> LENGTH: 15
<212> TYPE: PRT
<213> ORGANISM: Artificial Sequence
<220> FEATURE:
<223> OTHER INFORMATION: peptide

<400> SEQUENCE: 859

Lys Ser Val Trp Ser Lys Leu Gln Ser Ile Gly Ile Arg Gln His
1               5                   10                  15

```
<210> SEQ ID NO 860
<211> LENGTH: 13
<212> TYPE: PRT
<213> ORGANISM: Artificial Sequence
<220> FEATURE:
<223> OTHER INFORMATION: peptide

<400> SEQUENCE: 860

Thr Pro Pro Ala Tyr Arg Pro Pro Asn Ala Pro Ile Leu
1               5                   10

<210> SEQ ID NO 861
<211> LENGTH: 9
<212> TYPE: PRT
<213> ORGANISM: Artificial Sequence
<220> FEATURE:
<223> OTHER INFORMATION: peptide

<400> SEQUENCE: 861

Trp Leu Leu Asp Ile Ser Phe Pro Leu
1               5

<210> SEQ ID NO 862
<211> LENGTH: 9
<212> TYPE: PRT
<213> ORGANISM: Artificial Sequence
<220> FEATURE:
<223> OTHER INFORMATION: peptide

<400> SEQUENCE: 862

His Leu Leu Asp Ile Ser Phe Pro Ala
1               5

<210> SEQ ID NO 863
<211> LENGTH: 9
<212> TYPE: PRT
<213> ORGANISM: Artificial Sequence
<220> FEATURE:
<223> OTHER INFORMATION: peptide

<400> SEQUENCE: 863

Glu Leu Leu Asp Ile Ser Phe Pro Ala
1               5

<210> SEQ ID NO 864
<211> LENGTH: 9
<212> TYPE: PRT
<213> ORGANISM: Artificial Sequence
<220> FEATURE:
<223> OTHER INFORMATION: peptide

<400> SEQUENCE: 864

Val Leu Leu Asp Ile Ser Phe Glu Leu
1               5

<210> SEQ ID NO 865
<211> LENGTH: 9
<212> TYPE: PRT
<213> ORGANISM: Artificial Sequence
<220> FEATURE:
<223> OTHER INFORMATION: peptide

<400> SEQUENCE: 865

Val Leu Leu Asp Ile Ser Phe Lys Val
1               5
```

```
<210> SEQ ID NO 866
<211> LENGTH: 9
<212> TYPE: PRT
<213> ORGANISM: Artificial Sequence
<220> FEATURE:
<223> OTHER INFORMATION: peptide

<400> SEQUENCE: 866

Ile Met Leu Asp Ile Ser Phe Leu Leu
1               5

<210> SEQ ID NO 867
<211> LENGTH: 9
<212> TYPE: PRT
<213> ORGANISM: Artificial Sequence
<220> FEATURE:
<223> OTHER INFORMATION: peptide

<400> SEQUENCE: 867

Leu Leu Asp Ile Ser Phe Pro Ser Leu
1               5

<210> SEQ ID NO 868
<211> LENGTH: 9
<212> TYPE: PRT
<213> ORGANISM: Artificial Sequence
<220> FEATURE:
<223> OTHER INFORMATION: peptide

<400> SEQUENCE: 868

Leu Met Asp Leu Ser Thr Thr Asn Val
1               5

<210> SEQ ID NO 869
<211> LENGTH: 9
<212> TYPE: PRT
<213> ORGANISM: Artificial Sequence
<220> FEATURE:
<223> OTHER INFORMATION: peptide

<400> SEQUENCE: 869

Met Leu Ser Ser Tyr Leu Val Pro Ile
1               5

<210> SEQ ID NO 870
<211> LENGTH: 9
<212> TYPE: PRT
<213> ORGANISM: Artificial Sequence
<220> FEATURE:
<223> OTHER INFORMATION: peptide

<400> SEQUENCE: 870

Leu Leu Ser Ser Tyr Leu Val Pro Ile
1               5

<210> SEQ ID NO 871
<211> LENGTH: 9
<212> TYPE: PRT
<213> ORGANISM: Artificial Sequence
<220> FEATURE:
<223> OTHER INFORMATION: peptide

<400> SEQUENCE: 871

Phe Val Ser Ser Tyr Leu Val Pro Thr
1               5
```

```
<210> SEQ ID NO 872
<211> LENGTH: 9
<212> TYPE: PRT
<213> ORGANISM: Artificial Sequence
<220> FEATURE:
<223> OTHER INFORMATION: peptide

<400> SEQUENCE: 872

Ser Leu Ser Leu His Asp Met Phe Leu
1               5

<210> SEQ ID NO 873
<211> LENGTH: 9
<212> TYPE: PRT
<213> ORGANISM: Artificial Sequence
<220> FEATURE:
<223> OTHER INFORMATION: peptide

<400> SEQUENCE: 873

Lys Leu Lys Pro Leu Leu Pro Trp Ile
1               5

<210> SEQ ID NO 874
<211> LENGTH: 9
<212> TYPE: PRT
<213> ORGANISM: Artificial Sequence
<220> FEATURE:
<223> OTHER INFORMATION: peptide

<400> SEQUENCE: 874

Lys Leu Lys Pro Leu Leu Pro Phe Leu
1               5

<210> SEQ ID NO 875
<211> LENGTH: 9
<212> TYPE: PRT
<213> ORGANISM: Artificial Sequence
<220> FEATURE:
<223> OTHER INFORMATION: peptide

<400> SEQUENCE: 875

Lys Val Val Pro Ile Gln Phe Pro Val
1               5

<210> SEQ ID NO 876
<211> LENGTH: 9
<212> TYPE: PRT
<213> ORGANISM: Artificial Sequence
<220> FEATURE:
<223> OTHER INFORMATION: peptide

<400> SEQUENCE: 876

Lys Ile Val Pro Ile Gln Phe Pro Ile
1               5

<210> SEQ ID NO 877
<211> LENGTH: 9
<212> TYPE: PRT
<213> ORGANISM: Artificial Sequence
<220> FEATURE:
<223> OTHER INFORMATION: peptide

<400> SEQUENCE: 877

Tyr Gln Ala Met Ile Gln Phe Leu Ile
1               5

<210> SEQ ID NO 878
```

```
<211> LENGTH: 10
<212> TYPE: PRT
<213> ORGANISM: Artificial Sequence
<220> FEATURE:
<223> OTHER INFORMATION: peptide

<400> SEQUENCE: 878

Phe Met Pro Phe Gly Phe Ile Leu Pro Ile
1               5                   10

<210> SEQ ID NO 879
<211> LENGTH: 10
<212> TYPE: PRT
<213> ORGANISM: Artificial Sequence
<220> FEATURE:
<223> OTHER INFORMATION: peptide

<400> SEQUENCE: 879

Phe Met Pro Phe Gly Phe Ile Leu Gly Val
1               5                   10

<210> SEQ ID NO 880
<211> LENGTH: 10
<212> TYPE: PRT
<213> ORGANISM: Artificial Sequence
<220> FEATURE:
<223> OTHER INFORMATION: peptide

<400> SEQUENCE: 880

Phe Leu Ile Ser Thr Thr Phe Thr Ile Asn
1               5                   10

<210> SEQ ID NO 881
<211> LENGTH: 10
<212> TYPE: PRT
<213> ORGANISM: Artificial Sequence
<220> FEATURE:
<223> OTHER INFORMATION: peptide

<400> SEQUENCE: 881

Phe Met Ile Ser Thr Thr Phe Met Arg Leu
1               5                   10

<210> SEQ ID NO 882
<211> LENGTH: 10
<212> TYPE: PRT
<213> ORGANISM: Artificial Sequence
<220> FEATURE:
<223> OTHER INFORMATION: peptide

<400> SEQUENCE: 882

Gln Met Ile Ser Thr Thr Phe Gly Asn Val
1               5                   10

<210> SEQ ID NO 883
<211> LENGTH: 10
<212> TYPE: PRT
<213> ORGANISM: Artificial Sequence
<220> FEATURE:
<223> OTHER INFORMATION: peptide

<400> SEQUENCE: 883

Trp Leu Tyr Leu Gln Trp Gln Pro Ser Val
1               5                   10

<210> SEQ ID NO 884
<211> LENGTH: 10
```

```
<212> TYPE: PRT
<213> ORGANISM: Artificial Sequence
<220> FEATURE:
<223> OTHER INFORMATION: peptide

<400> SEQUENCE: 884

Phe Val Leu Leu Asp Thr Asn Tyr Glu Ile
1               5                   10

<210> SEQ ID NO 885
<211> LENGTH: 10
<212> TYPE: PRT
<213> ORGANISM: Artificial Sequence
<220> FEATURE:
<223> OTHER INFORMATION: peptide

<400> SEQUENCE: 885

Phe Ile Leu Leu Asp Thr Asn Tyr Glu Ile
1               5                   10

<210> SEQ ID NO 886
<211> LENGTH: 10
<212> TYPE: PRT
<213> ORGANISM: Artificial Sequence
<220> FEATURE:
<223> OTHER INFORMATION: peptide

<400> SEQUENCE: 886

Tyr Glu Leu Gln Asn Ile Val Leu Pro Ile
1               5                   10

<210> SEQ ID NO 887
<211> LENGTH: 10
<212> TYPE: PRT
<213> ORGANISM: Artificial Sequence
<220> FEATURE:
<223> OTHER INFORMATION: peptide

<400> SEQUENCE: 887

Phe Met Leu Gln Asn Ile Val Lys Asn Leu
1               5                   10

<210> SEQ ID NO 888
<211> LENGTH: 9
<212> TYPE: PRT
<213> ORGANISM: Homo sapiens

<400> SEQUENCE: 888

Asn Leu Ser Leu His Asp Met Phe Val
1               5

<210> SEQ ID NO 889
<211> LENGTH: 9
<212> TYPE: PRT
<213> ORGANISM: Homo sapiens

<400> SEQUENCE: 889

Lys Met Lys Pro Leu Leu Pro Arg Val
1               5

<210> SEQ ID NO 890
<211> LENGTH: 9
<212> TYPE: PRT
<213> ORGANISM: Homo sapiens

<400> SEQUENCE: 890
```

Tyr Leu Val Pro Ile Gln Phe Pro Val
1               5

<210> SEQ ID NO 891
<211> LENGTH: 9
<212> TYPE: PRT
<213> ORGANISM: Homo sapiens

<400> SEQUENCE: 891

Tyr Met Ala Met Ile Gln Phe Ala Ile
1               5

<210> SEQ ID NO 892
<211> LENGTH: 10
<212> TYPE: PRT
<213> ORGANISM: Homo sapiens

<400> SEQUENCE: 892

Phe Leu Ile Ser Thr Thr Phe Gly Cys Thr
1               5                   10

<210> SEQ ID NO 893
<211> LENGTH: 10
<212> TYPE: PRT
<213> ORGANISM: Homo sapiens

<400> SEQUENCE: 893

Tyr Leu Tyr Leu Gln Trp Gln Pro Pro Leu
1               5                   10

<210> SEQ ID NO 894
<211> LENGTH: 10
<212> TYPE: PRT
<213> ORGANISM: Homo sapiens

<400> SEQUENCE: 894

Gly Val Leu Leu Asp Thr Asn Tyr Asn Leu
1               5                   10

<210> SEQ ID NO 895
<211> LENGTH: 10
<212> TYPE: PRT
<213> ORGANISM: Homo sapiens

<400> SEQUENCE: 895

Phe Gln Leu Gln Asn Ile Val Lys Pro Leu
1               5                   10

<210> SEQ ID NO 896
<211> LENGTH: 9
<212> TYPE: PRT
<213> ORGANISM: Artificial Sequence
<220> FEATURE:
<223> OTHER INFORMATION: comparative peptide

<400> SEQUENCE: 896

Ala Leu Pro Phe Gly Phe Ile Leu Val
1               5

<210> SEQ ID NO 897
<211> LENGTH: 9
<212> TYPE: PRT
<213> ORGANISM: Artificial Sequence
<220> FEATURE:
<223> OTHER INFORMATION: comparative peptide

```
<400> SEQUENCE: 897

Ile Leu Pro Phe Gly Phe Ile Leu Ala
1               5

<210> SEQ ID NO 898
<211> LENGTH: 9
<212> TYPE: PRT
<213> ORGANISM: Artificial Sequence
<220> FEATURE:
<223> OTHER INFORMATION: comparative peptide

<400> SEQUENCE: 898

Phe Leu Pro Phe Gly Phe Ile Leu Met
1               5

<210> SEQ ID NO 899
<211> LENGTH: 9
<212> TYPE: PRT
<213> ORGANISM: Artificial Sequence
<220> FEATURE:
<223> OTHER INFORMATION: comparative peptide

<400> SEQUENCE: 899

Leu Met Leu Gly Glu Phe Leu Lys Leu
1               5
```